United States Patent
Chasset et al.

(10) Patent No.: US 9,238,026 B2
(45) Date of Patent: Jan. 19, 2016

(54) INHIBITORS OF VIRAL REPLICATION, THEIR PROCESS OF PREPARATION AND THEIR THERAPEUTICAL USES

(75) Inventors: Sophie Chasset, Nandy (FR); Francis Chevreuil, Chantilly (FR); Benoit Ledoussal, Pommerit-Jaudy (FR); Frédéric Le Strat, Gagny (FR); Richard Benarous, Paris (FR)

(73) Assignee: LABORATOIRE BIODIM, Paris (FR)

( * ) Notice: Subject to any disclaimer, the term of this patent is extended or adjusted under 35 U.S.C. 154(b) by 0 days.

(21) Appl. No.: 14/110,391

(22) PCT Filed: Apr. 6, 2012

(86) PCT No.: PCT/IB2012/051722
§ 371 (c)(1),
(2), (4) Date: Oct. 7, 2013

(87) PCT Pub. No.: WO2012/137181
PCT Pub. Date: Oct. 11, 2012

(65) Prior Publication Data
US 2014/0128383 A1  May 8, 2014

Related U.S. Application Data

(60) Provisional application No. 61/472,809, filed on Apr. 7, 2011.

(30) Foreign Application Priority Data

Apr. 7, 2011  (EP) .................................... 11305406

(51) Int. Cl.
| | | |
|---|---|---|
| A61K 31/405 | (2006.01) | |
| C07D 209/18 | (2006.01) | |
| C07D 209/24 | (2006.01) | |
| C07D 333/24 | (2006.01) | |
| C07D 333/60 | (2006.01) | |
| C07D 407/04 | (2006.01) | |
| C07D 409/04 | (2006.01) | |
| C07D 417/04 | (2006.01) | |
| C07D 495/04 | (2006.01) | |
| A61K 31/427 | (2006.01) | |
| A61K 31/436 | (2006.01) | |
| A61K 31/4743 | (2006.01) | |
| A61K 31/538 | (2006.01) | |
| A61K 45/06 | (2006.01) | |
| C07D 413/04 | (2006.01) | |
| C07D 491/052 | (2006.01) | |
| A61K 31/4365 | (2006.01) | |

(52) U.S. Cl.
CPC ............. *A61K 31/405* (2013.01); *A61K 31/427* (2013.01); *A61K 31/436* (2013.01); *A61K 31/4365* (2013.01); *A61K 31/4743* (2013.01); *A61K 31/538* (2013.01); *A61K 45/06* (2013.01); *C07D 209/18* (2013.01); *C07D 209/24* (2013.01); *C07D 333/24* (2013.01); *C07D 333/60* (2013.01); *C07D 407/04* (2013.01); *C07D 413/04* (2013.01); *C07D 417/04* (2013.01); *C07D 491/052* (2013.01); *C07D 495/04* (2013.01)

(58) Field of Classification Search
CPC . A61K 31/405; A61K 31/427; A61K 31/436; A61K 31/4743; A61K 31/538; A61K 45/06; C07D 209/18; C07D 209/24; C07D 333/24; C07D 333/60; C07D 407/04; C07D 409/04; C07D 417/04; C07D 495/04; C07D 413/04; C07D 491/052
See application file for complete search history.

(56) References Cited

U.S. PATENT DOCUMENTS

| | | |
|---|---|---|
| 3,271,407 A | 9/1966 | Raap et al. |
| 4,152,440 A | 5/1979 | Gebert et al. |
| 4,272,507 A | 6/1981 | Figala |
| 5,268,378 A | 12/1993 | Baker et al. |
| 5,656,629 A | 8/1997 | Bacon et al. |
| 5,910,506 A | 6/1999 | Sugimoto et al. |
| 6,184,245 B1 | 2/2001 | Sugawara et al. |
| 2002/0193415 A1 | 12/2002 | LaColla et al. |
| 2004/0204407 A1 | 10/2004 | Tang et al. |
| 2006/0052426 A1 | 3/2006 | Despeyroux et al. |
| 2009/0099228 A1 | 4/2009 | Aissaoui et al. |

FOREIGN PATENT DOCUMENTS

| | | |
|---|---|---|
| DE | 2450617 | 4/1975 |
| EP | 1 382 607 | 1/2004 |
| EP | 1 958 948 | 8/2008 |
| FR | 1 482 844 | 6/1967 |
| GB | 1 128 607 | 9/1968 |
| GB | 1 481 465 | 7/1977 |
| WO | WO 99/32464 | 7/1999 |
| WO | WO 2004/058776 | 7/2004 |
| WO | WO 2004/074257 | 9/2004 |

(Continued)

OTHER PUBLICATIONS

International Search Report; issued Oct. 11, 2012, in International Application No. PCT/IB2012/051722 filed on Apr. 6, 2012.
Written Opinion of International Searching Authority, issued Oct. 7, 2013, in International Application No. PCT/IB2012/051722 filed on Apr. 6, 2012.
European Search Report, issued Feb. 14, 2012, in European Application EP 2508511, filed on Apr. 7, 2011.
European Search Opinion, issued Feb. 14, 2012, in European Application EP 2508511, filed on Apr. 7, 2011.

(Continued)

*Primary Examiner* — Samantha Shterengarts
(74) *Attorney, Agent, or Firm* — Hunton & Williams LLP

(57) ABSTRACT

The present invention relates to compounds, their use in the treatment or the prevention of viral disorders, including HIV.

8 Claims, No Drawings

(56) References Cited

FOREIGN PATENT DOCUMENTS

| WO | WO 2004/099192 | 11/2004 |
|----|----------------|---------|
| WO | WO 2007/141267 | 12/2007 |
| WO | WO 2008/100867 | 8/2008 |
| WO | WO 2008/137609 | 11/2008 |
| WO | WO 2008/141011 | 11/2008 |
| WO | WO 2009/045700 | 4/2009 |
| WO | WO 2009/062288 | 5/2009 |
| WO | WO 2009/072139 | 6/2009 |
| WO | WO 2010/126851 | 11/2010 |

OTHER PUBLICATIONS

Abdelhamid et al, "Synthesis and Reactivity of 1-Amino-4-methyl-3,4-dihydro-5H-pyrazolo[3', 4':4,5]pyrimodo[1,6-]benzoimidazolo-5-one", *J. Heterocyclic Chem.* (2007), vol. 44, pp. 701-705.

Alberola et al, "Production and Transformation of Carbanions Derived from C4a—Functionalized 3, 5-Dimethylisothiazoles", *Gazzetta Chimica Italiana* (1987), vol. 117, pp. 461-467.

Bérnardeau et al. , "Aleglitazar, a new, potent and balanced dual PPARα/γ agonist for the treatment of type II diabetes", *Bioorganic & Medicinal Chemistry Letters* (2009), vol. 19, pp. 2468-2473.

Berger et al., "Benzimidazole-type Glycine Antagonists: The Role of the Ring Nitrogen Atoms", *Arch. Pharm. Pharm. Med. Chem.* (1996), vol. 329, pp. 121-124.

Bowden et al, "The Synthesis of Pantherine and Related Compounds", *J. Chem. Soc. (C)* (1968), vol. 37, pp. 172-185.

Bowman et al., "Amides as precursors of imidoyl radicals in cyclisation reactions" *Tetrahedron* (2007), vol. 63, pp. 191-203.

Brown et al., "Synthesis of 4-substituted hex-4-enoic and hept-5-enoic acid derivatives of 3,4-dihydro-1H-pyrano[3,4,-b] benzofuran as analogues of the 1,3-dioxane thromboxane receptor antagonists", *Eur. J. Med. Chem.* (1992), vol. 27, pp. 723-727.

Chatterjea et al., "A Synthesis of 5-Hydroxy Benzo[b] Naphtho[1,2-d] Furan. Revision of Structures of Compounds Regarded Earlier as 5-Hydroxy Benzo[b]Naphtho[1,2- d]Furans", *Tetrahedron Letters* (1970), vol. 5, pp. 395-399.

Christ et al., "Rational design of small-molecule inhibitors of the LEDGF/p75-integrase interaction and HIV replication", *Nature Chem. Bio.* (2010), vol. 6, pp. 442-448.

Chua et al., "A novel and efficient synthesis of 3-carboxy-4-oxo-1,8-naphthyridines using magnesium chloride", *Tetrahedron Letters* (2008), vol. 49, pp. 4437-4442.

Dannhardt et al., "Inhibition of Bovine Cyclooxygenase and 5-Lipoxygenase by N- Alkyldiphenyl-pyrrolyl Acetic and Propionic Acid Derivatives", *Arch. Pharm. (Weinheim)* (1993), vol. 326, pp. 157-162.

Das et al., "Effects of positional and geometrical isomerism on the biological activity of some novel oxazolidinones", *Bioorganic & Medicinal Chemistry Letters* (2005), vol. 15, pp. 337-343.

De Clercq, "Emerging antiviral drugs", *Expert Opin. Emerging Drugs* (2008), vol. 13, No. 3, pp. 393-416.

Dubinina et al., "Novel 5,7-disubstituted 6-amino-5H-pyrrolo [3,2-b]pyrazine-2,3- dicarbonitriles, the promising protein kinase inhibitors with anitproliferative activity", *European Journal of Medicinal Chemistry* (2006), vol. 41, pp. 727-737.

Dykstra et al., "Estrogen receptor ligands. Part 16: 2-Aryl indoles as highly subtype selective ligands for ERα", *Bioorganic & Medicinal Chemistry Letters* (2007), vol. 17, pp. 2322-2328.

Gaertner, "Reactions of 3-Thianaphthenylmethylmagnesium Chloride", *J. Am. Chem. Soc.* (1952), vol. 74, pp. 2185-2188.

Genin et al., "Novel 1,5-Diphenylpyrazole Nonnucleoside HIV-1 Reverse Transcriptase Inhibitors with Enhanced Activity versus the Delavirdine-Resistant P236L Mutant: Lead Identification and SAR of 3- and 4-Substituted Derivatives", *J. Med. Chem.* (2000), vol. 43, pp. 1034-1040.

Gray et al., "Novel Indole-2-carboxylates as Ligands for the Strychnine-Insensitive N-Methyl-D-aspartate-Linked Glycine Receptor", *J. Med. Chem.* (1991), vol. 34, pp. 1283-1292.

Guercio et al., "Overall Synthesis of GSK356278: Quick Delivery of a PDE4 Inhibitor Using a Fit-for-Purpose Approach", *Organic Process Research & Development* (2010), vol. 14, pp. 1153-1161.

Gupta et al., "Synthesis of β—D-Ribo- and 2'-Deoxy—β—D-ribofuranosyl Derivatives of 6-Aminopyrazolo[4,3-c]pyridin-4-(5H)-one by a Ring Closure of Pyrazole Nucleoside Precursors", *J. Heterocyclic Chem.* (1986), vol. 23, pp. 59-64.

Gürtler et al., "[4+2]-Cycloaddition Reactions between β-Acceptor-Substituted Enamines and 2-Vinylindole Radical Cations Acting as Hetero-Dienes", *J. Org. Chem.* (1996), vol. 61, pp. 4136-4143.

El-Alali et al., "Reactions of 1,3-dipolar aldazines and ketazines with the dipolarophile dimethyl acetylenedicarboxylate", *Can. J. Chem.* (2002), vol. 80, pp. 1293-130.

Sayed et al., "Synthesis and Reactions of New Pyridazinone Derivatives of Expected Antimicrobial Activities", *Egypt. J. Chem.* (2002), vol. 45, No. 4, pp. 767-776.

Droste et al., "Hexahydropyrroloindole Versuche zur Synthese von 2-Indolylthioethern", *Liebigs Ann. Chem.* (1987), vol. 11, pp. 901-910.

Singh, "Small molecule HIV entry inhibitors: Part II. Attachment and fusion inhibitors: 2004-2010", *Expert Opin. Ther. Patents* (2011), vol. 21, No. 3, pp. 399-416.

Singh, "Small molecule HIV entry inhibitors: Part I. Chemokine receptor antagonists: 2004-2010", *Expert Opin. Ther. Patents* (2011), vol. 21, No. 2, pp. 227-269.

Cervello, "Copper and Cobalt Mediated Regioselective Alkylation of Polyketide Models: Methyl 3,5-Dioxohexanoate and Triacetic Acid Lactone", *Tetrahedron* (1990), vol. 46, No. 6, pp. 2035-2046.

Tejedor et al., "Tertiary Skipped Diynes: A Pluripotent Building Block for the Modular and Diversity-Oriented Synthesis of Nitrogen Heterocycles", *Chem Eur. J.* (2010), vol. 16, pp. 3276-3280.

Jørgensen et al., "Synthesis and pharmacology of glutamate receptor ligands: new isothiazole analogues of ibotenic acid", *Org. & Biomol. Chem.* (2007), vol. 5, pp. 463-471.

Kita et al., "Synthetic Anthracyclines: Regiospecific Total Synthesis of a D-Ring Indole Analogue of Daunomycin", *Chem. Pharm. Bull.* (1990), vol. 38, No. 3, pp. 585-589.

Monge et al., "Synthesis of Pyridazino[4,5-b]indole Derivatives from 2-(3-Carboxy-1- methylindole)acetic Acid Anhydride", *J. Heterocyclic Chem.* (1986), vol. 23, pp. 141-144.

Pevzner et al., "Reactions of Halomethyl Derivatives of Acylfurans and Furycarbonitriles with Sodium Diethyl Phosphite", *Russian Journal of General Chemistry* (1994), vol. 64, No. 1, Part 2, pp. 125-128.

Pevzner, "Synthesis of Isomeric Bromo(diethoxyphosphorylmethyl) furans", *Russian Journal of General Chemistry* (2009), vol. 79, No. 3, pp. 362-372.

Rosen et al., "Synthesis, in Vitro Binding Profile, and Central Nervous System Penetrability of the Highly Potent 5-HT$_3$ Receptor Antagonist [$^3$H]-4-(2-Methoxyphenly)-2-[4(5)-methyl-5(4)-imidazolylmethyl]thiazole", *J. Med. Chem.* (1990), vol. 33, pp. 3020-3023.

Oda et al., "Some Researches on the Chemistry of Dimethyl Sulfoxide and Related Compounds", *Bull. Inst. Chem. Res.* (1969), vol. 47, No. 5, pp. 480-521.

Schneller et al., "6-Amino-1H—Pyrrolo[3,2-c]Pyridin-4(5H)-One (3,7- Dideazaguanine)", *Tetrahedron Letters* (1980), vol. 21, pp. 3135-3138.

Scott, "Reaction of Phenylacetonitrile Anion with Sulphites: a Novel Isothiazole Synthesis", *J. Chem. Soc., Perkins Trans.* (1972), vol. 1, pp. 1432-1434.

Šoškić et al., "Binding of ring-substituted indole-3-acetic acids to human serum albumin", *Bioorganic & Medicinal Chemistry* (2007), vol. 15, pp. 4595-4600.

Leese et al., "An Intramolecular Alkyne Insertion/Carbonylation/Cyclization Sequence of Chromium Aminocarbene Complexes: A Novel Access to Indole and Indenoindole Skeletons", *Chem. Ber.* (1996), vol. 129, pp. 623-631.

(56) References Cited

OTHER PUBLICATIONS

Uchida et al., "Thermally Irreversible Photochromic Systems. Reversible Photocyclization of 1,2-Bis(benzo[b]thiophen-3-yl)ethene Derivatives", *Bull Chem. Soc. Jpn.* (1990), vol. 63, pp. 1311-1315.

Vice et al., "C-2-Side Chain Modification of 2-Methyl-3-Alkylindoles Via 3- Methylthioindolenines: A New Approach to Pyrrolo[1,2-a] Indoles", *Tetrahedron Letters* (1985), vol. 26, No. 2, pp. 165-168.

Galystan et al., "Indole derivatives: 1,2-Disubstituted tryptamines", *Armyanskii Khimicheskii Zhurnal* (1974), vol. 27, No. 9, pp. 776-780, XP-002682259 (Abstract Only).

Galystan, et al., "Indole derivatives: 5-R-6-benzyl- and 5-R-3, 6-dibenzyl-1,2,3,4,5,6-hexahydroazepino [4,5-b]indoles", *Armyanskii Khimicheskii Zhurnal* (1976), vol. 29, No. 3, pp. 255-258, XP-002682260 (Abstract Only).

Rodionov et al, "Hydrazones of alpha, gamma-diphenylacetoacetic ester", *Zhurnal Obshchei Khimii* (1950), vol. 20, pp. 1273-1284, XP-002682261 (Abstract Only).

Dow, "An Efficient Synthesis of Ethyl 5-oxazoleacetates", *J. Org. Chem.* (1990), vol. 55, pp. 386-388.

INHIBITORS OF VIRAL REPLICATION, THEIR PROCESS OF PREPARATION AND THEIR THERAPEUTICAL USES

CROSS-REFERENCE TO RELATED APPLICATIONS

This application is the U.S. National Phase of International Application No. PCT/IB2012/051722, filed Apr. 6, 2012, which claims priority to European Application No. EP 11305406.8, filed Apr. 7, 2011, and U.S. provisional Application No. 61/472,809, filed Apr. 7, 2011. The contents of each are hereby incorporated by reference in their entireties.

BACKGROUND OF THE INVENTION

The present invention relates to compounds, their use in the treatment or the prevention of viral disorders, including HIV. The present invention also relates to methods for the preparation of such compounds. The present invention also relates to pharmaceutical compositions comprising such compounds. The present invention also relates to the treatment of viral infections by the administration of a therapeutically efficient amount of such compounds.

The Acquired Immuno Deficiency Syndrome (AIDS) is a disease due to infection by the Human Immunodeficiency Virus (HIV). HIV is a retrovirus, belonging to the subclass of primate lentiviruses. Two types of HIV have been identified, HIV-1 and HIV-2. HIV-1 is responsible for the larger part of the AIDS global epidemic in the world, with virtually every country reporting cases.

Currently HIV infected patients are treated with Highly Active Anti Retroviral Therapies (HAART) that rely on a combination of several drugs belonging to different classes. Up to 2003, all approved anti-HIV drugs were inhibitors of the catalytic activity of two viral enzymes, Reverse Transcriptase (RT) inhibitors and Protease (PR) inhibitors. Reverse Transcriptase inhibitors include two different classes, Nucleoside/Nucleotide RT Inhibitors (NRTI) and Non Nucleoside RT Inhibitors (NNRTI). In 2003, a new class of Anti-retroviral drug (ARV), Fusion inhibitor (Enfuvirtide) was introduced (Cervia et al, Clin Infect Dis., 2003, 37(8): 1102-6). And lately, in 2007, two other classes of ARV were approved, Entry inhibitors (Maraviroc (Pfizer)) targeting the CCR5 co-receptor, and Integrase inhibitors (Raltegravir (Merck)) (Hughes et al, J Infect., 2008, 57(1):1-10). Although these three novel drugs were very useful to treat patients in therapeutic failure due to multiresistance to RT and PR inhibitors, resistance mutations against these drugs have already been reported.

Although the development of these potent anti-HIV drugs, has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response.

Thus, there is a continuous need for the development of novel anti-HIV therapies or agents to overcome the problems of resistance to the existing drugs and to improve treatment efficiency (Daar E S, *Top HIV Med,* 2008, 16(4):110-6; De Clercq E, *Expert Opin Emerg Drugs.* 2008, 13(3):393-416).

Document Christ et al (Christ et al, Nat. Chem. Biol., 2010, 6: 442) and documents WO 2007/131350, WO 2009/062285, WO 2009/062288, WO 2009/062289, WO 2009/062308, WO 2010/130034, WO 2010/130842 or WO 2011/015641 describe partially or totally unsaturated 6-membered heterocyclic derivatives as anti-HIV agents.

Document U.S. Pat. No. 5,910,506 describes imidazole derivatives as anti-HIV agents.

SUMMARY OF THE INVENTION

The present invention relates to compounds that are able to totally or partially solve the above-mentioned problems and drawbacks.

The present invention provides new antiviral agents, especially anti-retroviral agents, and more particularly anti-HIV compounds.

The compounds according the invention are inhibitors of HIV replication as assessed by HIV-1 replication assay as herein-detailed. These compounds are thus useful agents for treating or preventing virus, such as HIV, or other viral pathogenic diseases or disorders, by inhibiting replication of the virus into the host infected cells.

Therefore, the compounds according to the invention constitute a useful class of new potent antiviral compounds that can be used in the treatment and/or prevention of viral infections in animals, mammals and humans, more specifically for the treatment and/or prevention of HIV in humans.

The present invention further relates to such compounds for their use as a medicine, to the use of such compounds as medicines, more specifically as antiviral agents, and to their use for the manufacture of medicaments for treating and/or preventing viral infections, in particular retroviral infections such as, but not limited to, HIV in humans.

The invention also relates to pharmaceutical compositions comprising such compounds in an antiviral effective amount, optionally in combination with at least one further antiviral agent.

The present invention further relates to such pharmaceutical composition for its use for the treatment of an HIV infection in a mammal being infected or having a risk to be infected by the HIV.

The present invention also relates to a method of treatment or prevention of viral infections, in particular retroviral infections such as, but not limited to HIV in humans by the administration of one or more such compounds, optionally in combination with one or more other antiviral agents, to a patient in need thereof.

The present invention also relates to a method of inhibiting the replication of HIV comprising exposing the virus to an effective amount of one or more such compounds under conditions where replication of HIV is inhibited.

In a first aspect, the invention provides compounds comprising a five membered carbocycle or heterocycle, said compounds having a structure according to formula (1):

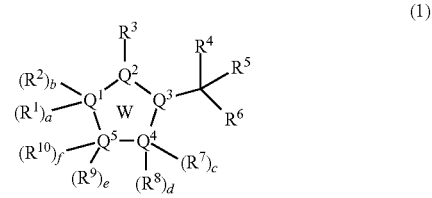

(1)

wherein:
W represents a substituted or non-substituted, partially or totally unsaturated, aromatic or non-aromatic carbo- or heterocycle;

a, b, c, d, e and f independently represent 0 or 1;

$Q^1$ represents $CR^1$, $CR^2$, $CR^1R^2$, N, $NR^1$, $NR^2$, S, O, C=O, C=S, N=O, S=O, $S(O)_2$;

$Q^2$ represents $CR^3$, $NR^3$;

$Q^3$ represents $CCR^4R^5R^6$, $NCR^4R^5R^6$; provided that $Q^2$-$Q^3$ represents N—C, C=C, N—N;

$Q^4$ represents $CR^7$, $CR^8$, $CR^7R^8$, N, $NR^7$, $NR^8$, S, O, C=O, C=S, N=O, S=O, $S(O)_2$;

$Q^5$ represents $CR^9$, $CR^{10}$, $CR^9R^{10}$, N, $NR^9$, $NR^{10}$, S, O, C=O, C=S, N=O, S=O, $S(O)_2$;

$R^1$, $R^2$, $R^7$, $R^8$, $R^9$ and $R^{10}$ independently represent hydrogen, —CN, —OH, —O-cycloalkyl, —O-cycloalkenyl, —O-cycloalkynyl, —$NH_2$, —$NR^{11}$-cycloalkyl, —$NR^{11}$-cycloalkenyl, —$NR^{11}$-cycloalkynyl, —S-cycloalkyl, —S-cycloalkenyl, —S-cycloalkynyl, —COOH, —C(O)$NH_2$, —$CF_3$, —$SO_2NH_2$, —$NHSO_2NH_2$, —NHC(O)$NH_2$, —OC(O)$NH_2$, halogen, alkyl, alkenyl, alkynyl, heteroalkyl, heteroalkenyl, heteroalkynyl, aryl, —O-aryl, —$NR^{11}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{11}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;

and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$R^3$ represents —O-cycloalkyl, —O-cycloalkenyl, —O-cycloalkynyl, —$NR^{11}$-cycloalkyl, —$NR^{11}$-cycloalkenyl, —$NR^{11}$-cycloalkynyl, —S-cycloalkyl, —S-cycloalkenyl, —S-cycloalkynyl, $C_4$-$C_{20}$ alkyl, $C_4$-$C_{20}$ alkenyl, $C_4$-$C_{20}$ alkynyl, heteroalkyl, heteroalkenyl, heteroalkynyl, aryl, —O-aryl, —$NR^{11}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{11}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocylyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be fused with at least one further cycle, and wherein alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$R^4$ or $R^5$ identical, or different, independently represent hydrogen, halogen, —CN, —O-cycloalkyl, —O-cycloalkenyl, —O-cycloalkynyl, —S-cycloalkyl, —S-cycloalkenyl, —S-cycloalkynyl, $C_3$-$C_{20}$ alkyl, alkenyl, alkynyl, heteroalkyl, heteroalkenyl, heteroalkynyl, aryl, —O-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^2$, and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety, $R^4$ and $R^5$ form with the carbon atom a 3- to 7-membered carbocycle or heterocycle, wherein the carbocycle or heterocycle is fused with at least one further cycle, or $R^4$ and $R^5$ form a group of formula (g)

wherein Z represents hydrogen, alkyl or heteroalkyl and wherein a carbon atom or heteroatom of said alkyl, can be oxidized to form a C=O, C=S, N=O, N=S, S=O or $S(O)_2$, provided that:
if $R^4$ represents a hydrogen atom or a halogen atom, $R^5$ does not represent a hydrogen atom or a halogen atom;

if $R^5$ represents a hydrogen atom or a halogen atom, $R^4$ does not represent a hydrogen atom or a halogen atom;

$R^4$ or $R^5$ does not represent a primary, secondary or tertiary amino group in the β-position of ring W;

if $R^4$ or $R^5$ represents O-alkyl, the alkyl group is a $C_2$-$C_{20}$ alkyl;

$R^6$ represents independently —C(O)OH, —C(O)$OR^{11}$;

$R^{11}$ represents hydrogen, alkyl or aryl, wherein a carbon atom of said alkyl or aryl can be oxidized to form a C=O, C=S, N=O, N=S, S=O or S(O)$_2$;

$R^1$, $Q^1$, $Q^5$ and $R^9$ form a saturated, partially or totally unsaturated 5-, 6- or 7-membered carbo- or hetero-cycle or a saturated, partially or totally unsaturated 10-, 11-, 12-, 13- or 14-membered polycarbo- or polyhetero-cycle;

$R^1$, $Q^1$, $Q^5$ and $R^{10}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^2$, $Q^1$, $Q^5$ and $R^9$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^2$, $Q^1$, $Q^5$ and $R^9$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^7$, $Q^4$, $Q^5$ and $R^9$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^7$, $Q^4$, $Q^5$ and $R^{10}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^8$, $Q^4$, $Q^5$ and $R^9$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^8$, $Q^4$, $Q^5$ and $R^{10}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$T^1$ represents hydrogen, halogen, —$OT^3$, —$OCF_3$, =O, —$ST^3$, =S, —S(O)$T^4$, —S(O)$_2T^4$, —S(O)$_2NT^5T^6$, $CF_3$, $NO_2$, —$NT^5T^6$, —$NT^3$S(O)$_2T^4$, CN, —$NT^3$C(O)$T^4$, —$NT^3$C(O)$NT^5T^6$, —C(O)$OT^3$, —C(O)$NT^5T^6$, —C(O)$T^4$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be substituted with one or more $T^7$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=, C=S, N=O, N=S, S=O or S(O)$_2$;

$T^2$ represents hydrogen, halogen, —$OT^8$, —$OCF_3$, =O, —$ST^8$, =S, —S(O)$T^9$, —S(O)$_2T^9$, —S(O)$_2NT^{10}T^{11}$, —$CF_3$, —$NO_2$, —$NT^{10}T^{11}$, —$NT^8$S(O)$_2T^9$, —CN, —$NT^8$C(O)$T^9$, —$NT^8$C(O)$NT^{10}T^{11}$, —C(O)$OT^8$, —C(O)$NT^{10}T^{11}$, —C(O)$T^9$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be substituted with one or more $T^7$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$;

$T^3$ represents hydrogen, alkyl, alkenyl, alkynyl, heteroalkyl, heteroalkenyl, heteroalkynyl, aryl, heterocycle, wherein said alkyl, alkenyl, alkynyl, heteroalkyl, heteroalkenyl, heteroalkynyl, aryl, heterocycle can be substituted or non substituted with one or more —OH, =O, halogen, —SH, =S, —$CF_3$, —O-alkyl, —$OCF_3$, —CN, —$NO_2$, —C(O)OH, —$NH_2$ or C(O)N $H_2$, and wherein a carbon atom or heteroatom of said alkyl, alkenyl, alkynyl, heteroalkyl, heteroalkenyl, heteroalkynyl, aryl, heterocycle can be oxidized to form a C=O, C=S, N=O, N=S, S=O or S(O)$_2$;

$T^4$ represents —OH, alkyl, alkenyl, alkynyl, heteroalkyl, heteroalkenyl, heteroalkynyl, aryl, heterocycle, wherein said alkyl, alkenyl, alkynyl, heteroalkyl, heteroalkenyl, heteroalkynyl, aryl, heterocycle, can be substituted or non substituted with one or more —OH, =O, halogen, —SH, =S, —$CF_3$, —O-alkyl, —$OCF_3$, —CN, —NO2, —C(O)OH, —$NH_2$ or C(O)$NH_2$, and wherein a carbon atom or heteroatom of said alkyl, alkenyl, alkynyl, heteroalkyl, heteroalkenyl, heteroalkynyl aryl, heterocycle can be oxidized to form a C=O, C=S, N=O, N=S, S=O or S(O)$_2$;

$T^5$ or $T^6$ independently represent hydrogen, alkyl, alkenyl, alkynyl, heteroalkyl, heteroalkenyl, heteroalkynyl, aryl, heterocycle wherein said alkyl, alkenyl, alkynyl, heteroalkyl, heteroalkenyl, heteroalkynyl, aryl, heterocycle can be substituted or non substituted with one or more —OH, =O, halogen, —SH, =S, —CF$_3$, —O-alkyl, —OCF$_3$, —CN, —NO$_2$, —C(O)OH, —NH$_2$ or C(O)NH$_2$, and wherein a carbon atom or heteroatom of said alkyl, alkenyl, alkynyl, heteroalkyl, heteroalkenyl, heteroalkynyl aryl, heterocycle can be oxidized to form a C=O, C=S, N=O, N=S, S=O or S(O)$_2$, or $T^5$ or $T^6$ can be taken together to form a 4, 5, 6 or 7 membered heterocycle substituted or non substituted with an alkyl, alkenyl, alkynyl, heteroalkyl, heteroalkenyl, heteroalkynyl, —OH, halogen, —SH, —CF$_3$, —O-alkyl, —OCF$_3$, —CN, —NO$_2$, —C(O)OH, —NH$_2$ or —C(O)NH$_2$;

$T^7$ represents an alkyl, alkenyl, alkynyl, heteroalkyl, heteroalkenyl, heteroalkynyl, —OH, =O, halogen, —SH, =S, —CF$_3$, —CN, —NO$_2$, —COOH, —NH$_2$, —C(O)NH$_2$;

$T^8$ represents hydrogen, alkyl, alkenyl, alkynyl, heteroalkyl, heteroalkenyl, heteroalkynyl, wherein said alkyl, alkenyl, alkynyl, heteroalkyl, heteroalkenyl, heteroalkynyl, can be substituted or non substituted with one or more —OH, =O, halogen, —SH, =S, —CF$_3$, —O-alkyl, —OCF$_3$, —CN, —NO2, —C(O)OH, —NH$_2$ or —C(O)NH$_2$, and wherein a carbon atom or heteroatom of said alkyl, alkenyl, alkynyl, heteroalkyl, heteroalkenyl, heteroalkynyl can be oxidized to form a C=O, C=S, N=O, N=S, S=O or S(O)$_2$;

$T^9$ represents —OH, alkyl, alkenyl, alkynyl, heteroalkyl, heteroalkenyl, heteroalkynyl, wherein said alkyl, alkenyl, alkynyl, heteroalkyl, heteroalkenyl, heteroalkynyl, can be substituted or non substituted with one or more —OH, =O, halogen, —SH, =S, —CF$_3$, —O-alkyl, —OCF$_3$, —CN, —NO$_2$, —C(O)OH, —NH$_2$ or —C(O)NH$_2$, and wherein a carbon atom or heteroatom of said alkyl, alkenyl, alkynyl, heteroalkyl, heteroalkenyl, heteroalkynyl can be oxidized to form a C=O, C=S, N=O, N=S, S=O or S(O)$_2$;

$T^{10}$ or $T^{11}$ independently represent hydrogen, alkyl, alkenyl, alkynyl, heteroalkyl, heteroalkenyl, heteroalkynyl, wherein said alkyl, alkenyl, alkynyl, heteroalkyl, heteroalkenyl, heteroalkynyl, can be substituted or non substituted with one or more —OH, =O, halogen, —SH, =S, —CF$_3$, —O-alkyl, —OCF$_3$, —CN, —NO$_2$, —C(O)OH, —NH$_2$ or —C(O)NH$_2$, and wherein a carbon atom or heteroatom of said alkyl, alkenyl, alkynyl, heteroalkyl, heteroalkenyl, heteroalkynyl can be oxidized to form a C=O, C=S, N=O, N=S, S=O or S(O)$_2$, or $T^{10}$ or $T^{11}$ can be taken together to form a 4, 5, 6 or 7 membered heterocycle substituted or non substituted with an alkyl, alkenyl, alkynyl, heteroalkyl, heteroalkenyl, heteroalkynyl, —OH, halogen, —SH, —CF_, O-alkyl, —OCF$_3$, —CN, —NO2, —C(O)OH, —NH$_2$ or —C(O)NH$_2$;

and a racemate, enantiomer, isomer, atropoisomer or diastereoisomer or a pharmaceutically acceptable salt thereof.

DETAILED DESCRIPTION OF THE INVENTION

Even if described in particular or preferred embodiments, the present invention is not to be understood as being limited to such particular or preferred embodiments.

According to the invention, $Q^2$ and $Q^3$ are defined such that the $Q^2$-$Q^3$ moiety represents N—C, C=C or N—N.

This definition requires that in case $Q^2$ or $Q^3$ represents a carbon atom, this carbon atom is a sp$^2$ hybridised carbon.

According to the invention, one of $R^4$ or $R^5$ does not represent a primary, a secondary or a tertiary amino group in the β-position of ring W. This definition requires that $R^4$ or $R^5$ does not represent a heteroalkyl group wherein a nitrogen atom is directly linked to the carbon atom bounding $R^7$.

The term "alkyl" as used herein, either alone or in combination with another radical, refers to acyclic, straight or branched chain alkyl radicals.

The term "alkenyl", as used herein, either alone or in combination with another radical, refers to an unsaturated, acyclic straight or branched chain hydrocarbon radicals, at least two of carbon atoms are bonded to each other by a double bond.

The term "alkynyl", as used herein, either alone or in combination with another radical, refers to an unsaturated, acyclic straight or branched chain hydrocarbon radicals, at least two of carbon atoms are bonded to each other by a triple bond.

The term "cycloalkyl", as used herein, either alone or in combination with another radical, refers to a monocyclic or polycyclic saturated hydrocarbon radical.

The term "cycloalkenyl", as used herein, alone or in combination with another radical, refers to a monocyclic or polycyclic non-aromatic hydrocarbon radical with at least one site of unsaturation, namely a carbon-carbon double bond The term "cycloalkynyl", as used herein, alone or in combination with another radical, refers to a monocyclic or polycyclic non-aromatic hydrocarbon radical with at least one site of unsaturation, namely a carbon-carbon triple bond The term "heteroalkyl" as used herein, alone or in combination with another radical, refers to an acyclic alkyl wherein one or more carbon atoms are replaced by an oxygen, nitrogen or sulphur atom.

The term "heteroalkenyl", as used herein, alone or in combination with another radical, refers to an acyclic alkenyl wherein one or more carbon atoms are replaced by an oxygen, nitrogen or sulphur atom.

The term "heteroalkynyl" as used herein, alone or in combination with another radical, refers to an acyclic alkynyl wherein one or more carbon atoms are replaced by an oxygen, nitrogen or sulphur atom.

The term "aryl", as used herein, either alone or in combination with another radical, refers to a carbocyclic aromatic monocyclic group containing 6 carbon atoms which can be fused with at least another saturated, unsaturated or aromatic carbocycle.

The term "arylakyl", as used herein, either alone or in combination with another radical, refers to an acyclic alkyl radical in which one of the hydrogen atoms bonded to a carbon atom is replaced with an aryl radical.

The term "arylalkenyl" as used herein, alone or in combination with another radical, refers to an acyclic alkenyl radical in which one of the hydrogen atoms bonded to a carbon atom, is replaced with an aryl radical.

The term "arylalkynyl" as used herein, alone or in combination with another radical, refers to an acyclic alkynyl radical in which one of the hydrogen atoms bonded to a carbon atom, is replaced with an aryl radical.

The term "arylheteroalkyl" as used herein, alone or in combination with another radical, refers to a heteroalkyl radical in which one of the hydrogen atoms bonded to a carbon atom is replaced with an aryl radical.

The term "arylheteroalkenyl" as used herein, alone or in combination with another radical, refers to a heteroalkenyl radical in which one of the hydrogen atoms bonded to a carbon atom, is replaced with an aryl radical.

The term "arylheteroalkynyl" as used herein, alone or in combination with another radical, refers to a heteroalkynyl radical in which one of the hydrogen atoms bonded to a carbon atom, is replaced with an aryl radical.

The term "carbocycle", as used herein and unless specified otherwise, either alone or in combination with another radical, refers to a 3- to 8 membered saturated, unsaturated or aromatic cyclic radical in which all of the ring members are carbon atoms and which can be fused with at least another carbocycle.

The term "heterocycle" as used herein means a saturated, unsaturated or aromatic ring system of 3 to 18 atoms including at least one N, O or S and which can be fused with at least another carbocycle or heterocycle.

The term "heterocyclyl-alkyl" as used herein, alone or in combination with another radical, refers to an acyclic alkyl radical in which one of the hydrogen atoms bonded to a carbon atom is replaced with an heterocycle radical.

The term "heterocyclyl-alkenyl" as used herein, alone or in combination with another radical, refers to an acyclic alkenyl radical in which one of the hydrogen atoms bonded to a carbon atom is replaced with an heterocycle radical.

The term "heterocyclyl-alkynyl" as used herein, alone or in combination with another radical, refers to an acyclic alkynyl radical in which one of the hydrogen atoms bonded to a carbon atom is replaced with an heterocycle radical.

The term "heterocyclyl-heteroalkyl" as used herein, alone or in combination with another radical, refers to a hetero alkyl radical in which one of the hydrogen atoms bonded to a carbon atom is replaced with an heterocycle radical.

The term "heterocycle-heteroalkenyl" as used herein, alone or in combination with another radical, refers to a heteroalkenyl radical in which one of the hydrogen atoms bonded to a carbon atom, is replaced with an heterocycle radical.

The term "heterocycle-heteroalkynyl" as used herein, alone or in combination with another radical, refers to a heteroalkynyl radical in which one of the hydrogen atoms bonded to a carbon atom, is replaced with an heterocycle radical.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic adds; and the like.

The pharmaceutically acceptable salts of the present invention can be synthesized from the parent compound which contains a basic or acidic moiety by conventional chemical methods.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV from mother to baby, by administration to the mother before giving birth and to the child within the first days of life.

The expression "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient Such a therapeutically effective amount can be determined routinely by one of ordinary skill in the art having regard to their own knowledge, the state of the art, and this disclosure The term "mammal" as used herein is intended to encompass humans, as well as non-human mammals which are susceptible to infection by HIV or non human equivalents of HIV. Non-human mammals include but are not limited to domestic animals, such as cows, pigs, dogs, cats, rabbits, rats and mice, and non domestic animals.

The compounds according to the invention are compounds of formula (1) as defined and including the embodiments described in the summary of the invention.

Particularly, the compounds according to the invention are compounds of formula (1) wherein $R^6$ represents C(O)OH.

More particularly, the compounds according to the invention are compounds of formula (1) wherein $R^5$ represents hydrogen.

Advantageously, the invention provides compounds of formulae (A) to (E):

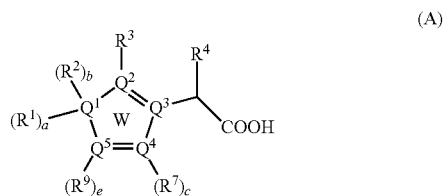

(A)

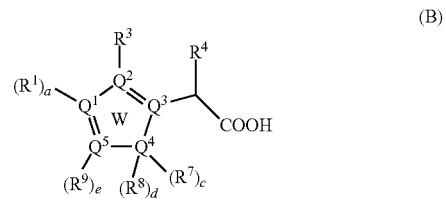

(B)

-continued

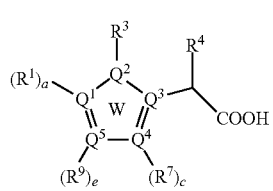
(C)

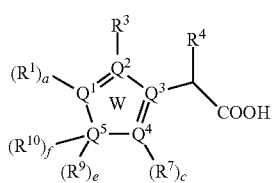
(D)

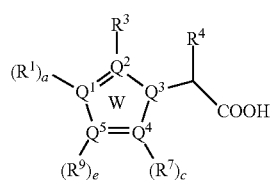
(E)

wherein:

$Q^3$ represents $CCR^4HC(O)OH$, $NCR^4HC(O)OH$;

$R^4$ represents independently —CN, —O-cycloalkyl, —O-cycloalkenyl, —O-cycloalkynyl, —S-cycloalkyl, —S-cycloalkenyl, —S-cycloalkynyl, $C_3$-$C_{20}$ alkyl, alkenyl, alkynyl, heteroalkyl, heteroalkenyl, heteroalkynyl, aryl, —O-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^2$, and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety, provided that:

$R^4$ does not represent a primary, secondary or tertiary amino group in the β-position of ring W;

if $R^4$ represents 0-alkyl, the alkyl group is a $C_2$-$C_{20}$ alkyl;

$Q^1$, $Q^2$, $Q^4$, $Q^5$, $R^1$, $R^2$, $R^3$, $R^7$, $R^8$, $R^9$, $R^{10}$, $R^{11}$, $T^1$, $T^2$, $T^3$, $T^4$, $T^5$, $T^6$, $T^7$, $T^8$, $T^9$ and $T^{10}$ are defined as for the compounds of formula (1).

Preferably, the invention provides compounds of formulae (A1) to (A9):

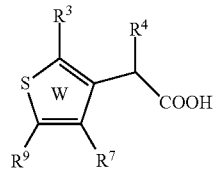
(A1)

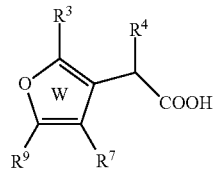
(A2)

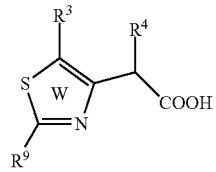
(A3)

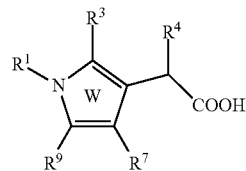
(A4)

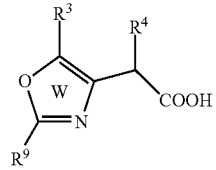
(A5)

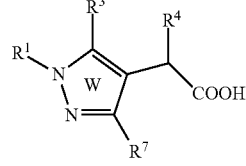
(A6)

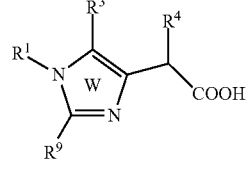
(A7)

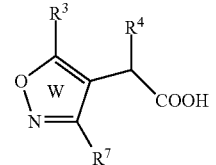
(A8)

(A9)

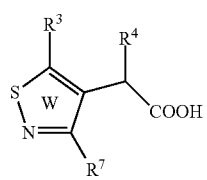

wherein:

W represents a substituted aromatic heterocycle;

R⁴ is defined as for the compounds of formula (A);

$R^1, R^3, R^7, R^9, R^{11}, T^1, T^2, T^3, T^4, T^5, T^6, T^7, T^8, T^9$ and $T^{10}$ are defined as for the compounds of formula (1).

As examples of compounds of formula (A), the invention provides compounds of formulae (A1a), (A3a), (A3b), (A6a), (A6b) or (A6c):

(A1-a)

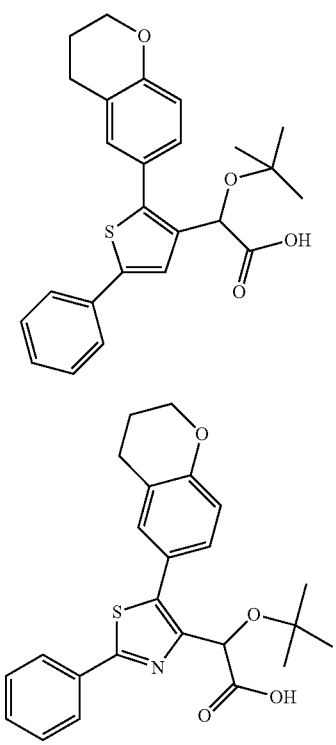

(A3a)

(A3b)

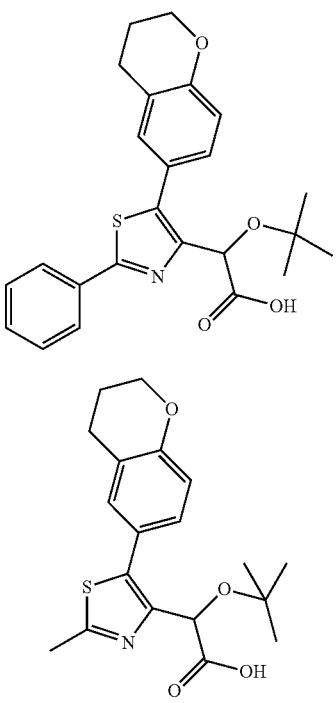

(A6a)

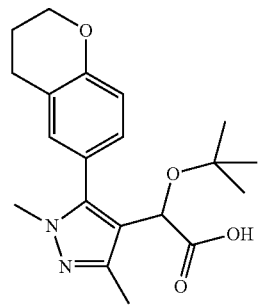

(A6b)

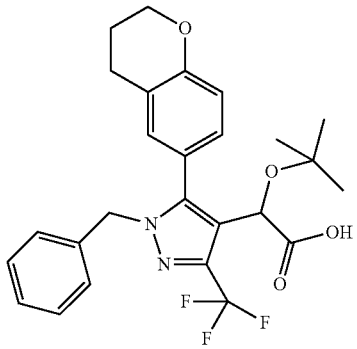

(A6c)

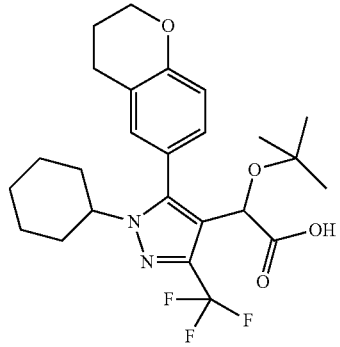

Preferably, the invention provides compounds of formulae (B1) to (B9):

(B1)

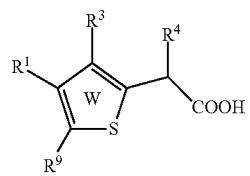

(B2)

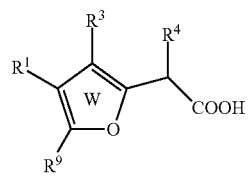

-continued (B3)
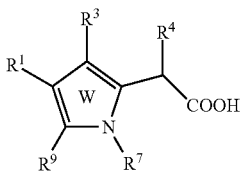

(B4)
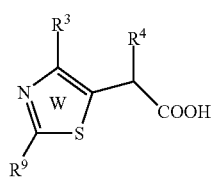

(B5)
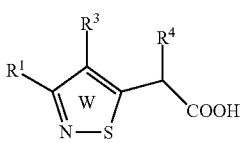

(B6)
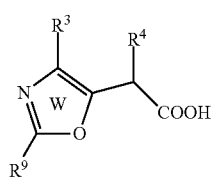

(B7)
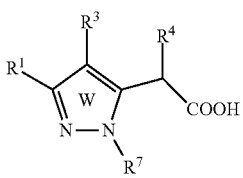

(B8)
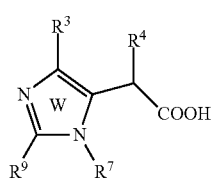

(B9)
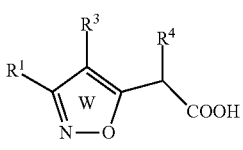

wherein:
W represents a substituted aromatic heterocycle;
$R^4$ is defined as for the compounds of formula (B);
$R^1, R^3, R^7, R^9, R^{11}, T^1, T^2, T^3, T^4, T^5, T^6, T^7, T^8, T^9$ and $T^{10}$ are defined as for the compounds of formula (1).

As examples of compounds of formula (B), the invention provides compounds of formulae (B1a), (B1b), (B4a) or (B4b):

(B1a)
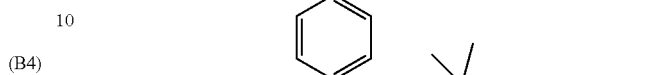
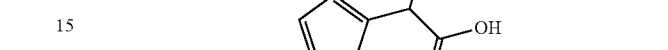

(B1b)
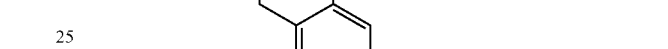
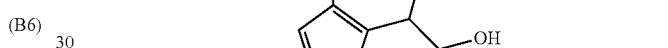

(B4a)
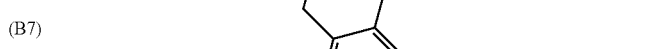
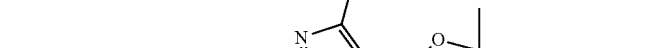

(B4b)
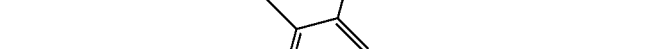

Preferably, the invention provides compounds of formulae (C1) to (C4):

(C1) 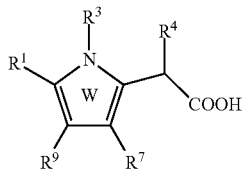

(C2) 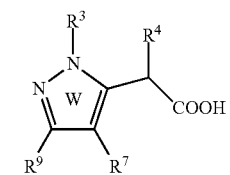

(C3) 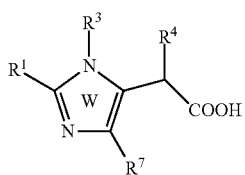

(C4) 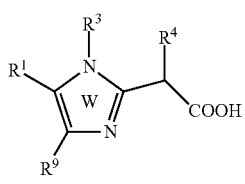

wherein:
W represents a substituted aromatic heterocycle;
$R^4$ is defined as for the compounds of formula (C);
$R^1, R^3, R^7, R^9, R^{11}, T^1, T^2, T^3, T^4, T^5, T^6, T^7, T^8, T^9$ and $T^{10}$ are defined as for the compounds of formula (1).

Preferably, the invention provides compounds of formulae (D1) to (D9):

(D1) 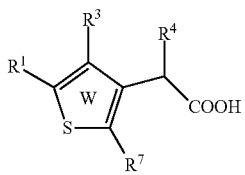

(D2) 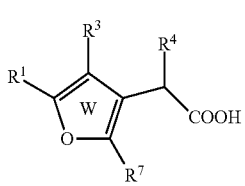

(D3) 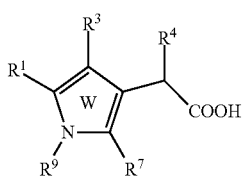

(D4) 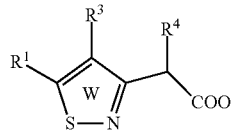

(D5) 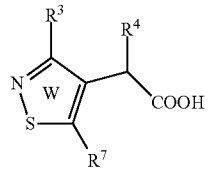

(D6) 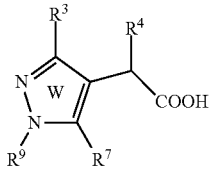

(D7) 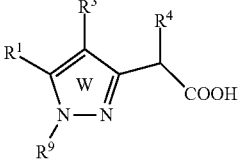

(D8) 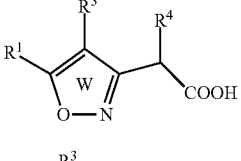

(D9) 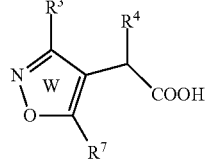

wherein:
W represents a substituted aromatic heterocycle;
$R^4$ is defined as for the compounds of formula (D);
$R^1, R^3, R^7, R^9, R^{11}, T^1, T^2, T^3, T^4, T^5, T^6, T^7, T^8, T^9, T^{10}$ are defined as for the compounds of formula (1).

As examples of compounds of formula (D), the invention provides compounds of formulae (D1a) to (D1z), (D1a') to (D1h'):

(D1a) 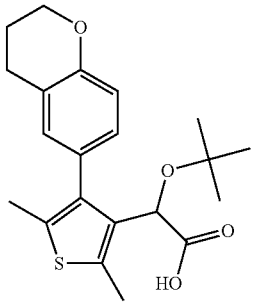

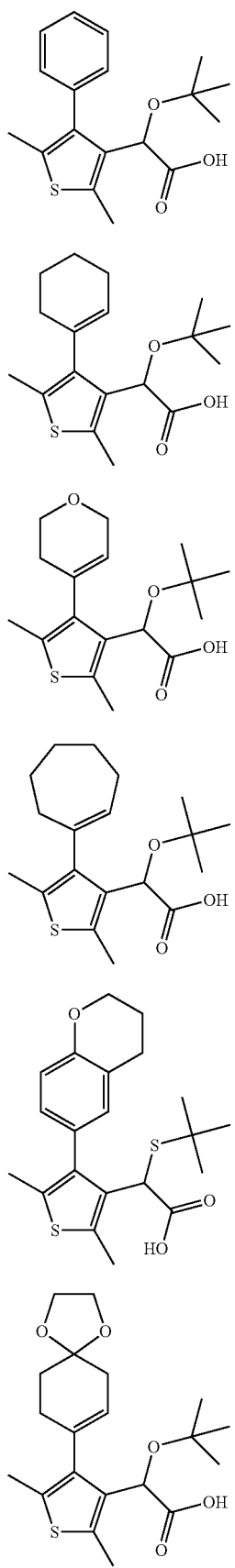
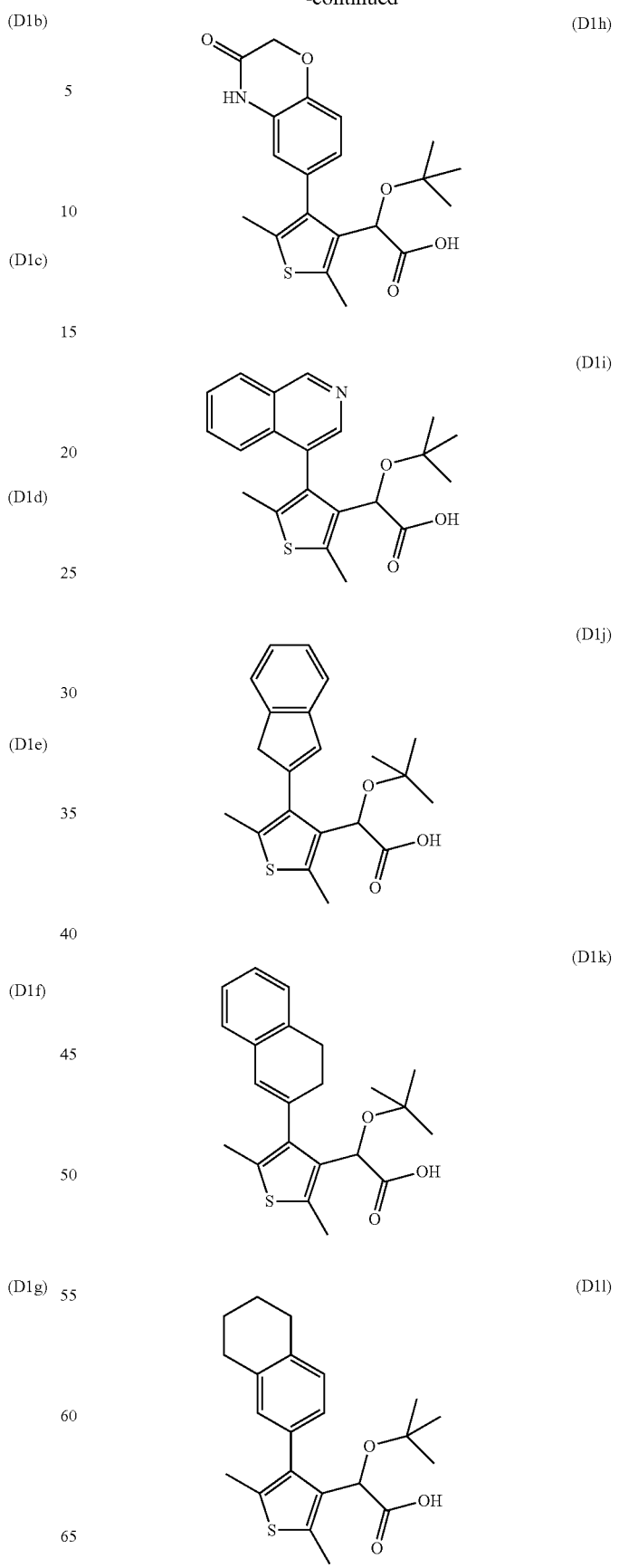

(D1m)
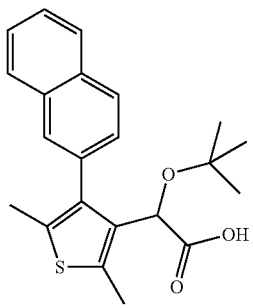
(D1n)
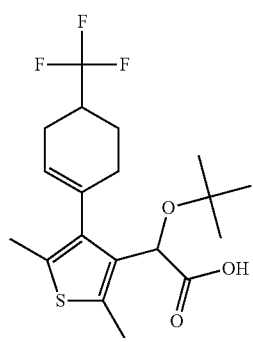
(D1o)
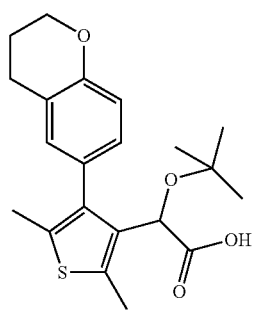
(D1p)
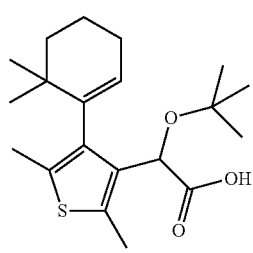
(D1q)
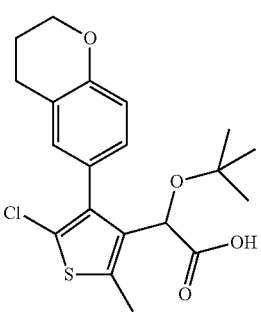
(D1r)
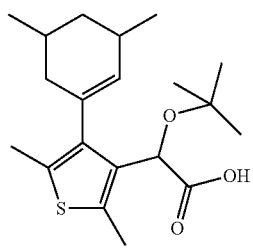
(D1s)
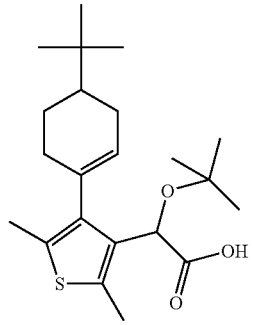
(D1t)
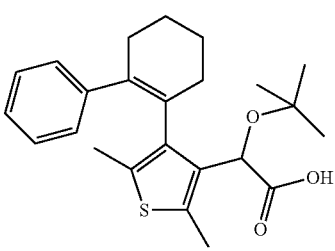
(D1u)
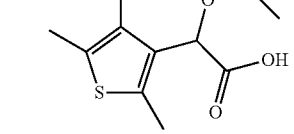
(D1v)
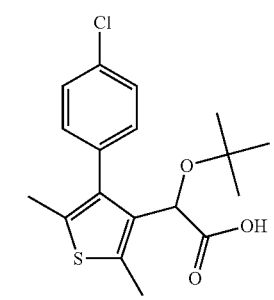
(D1w)
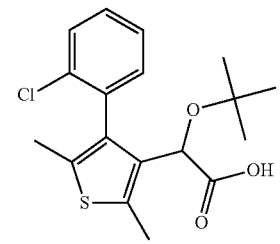

-continued
(D1x)
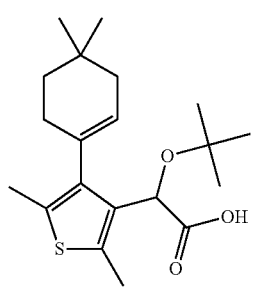
(D1y)
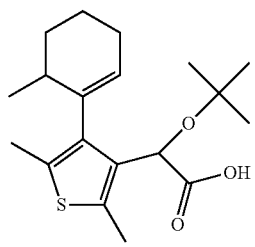
(D1z)
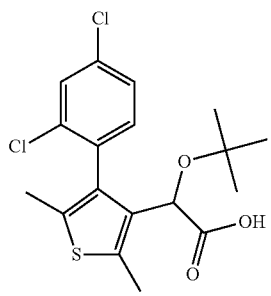
(D1a')
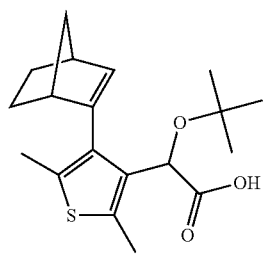
(D1b')
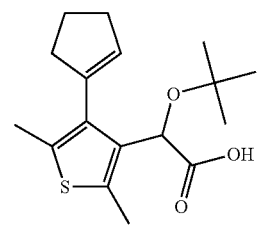
(D1c')
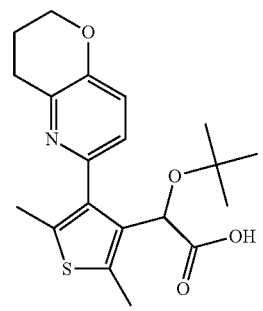
-continued
(D1d')
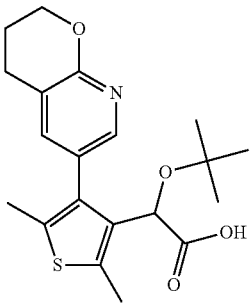
(D1e')
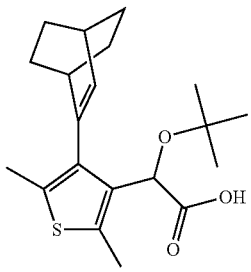
(D1f')
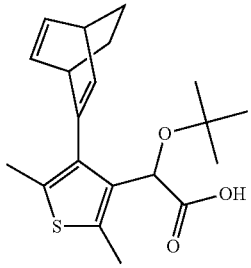
(D1g')
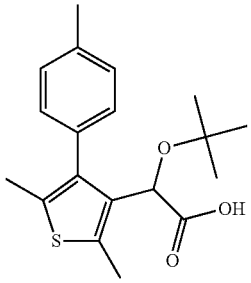
(D1h')
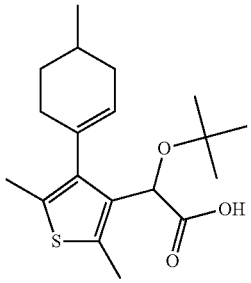
Preferably, the invention provides compounds of formulae (E1) to (E4):

(E1) 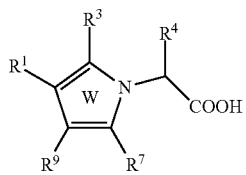
(E2) 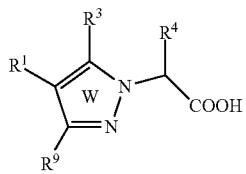
(E3) 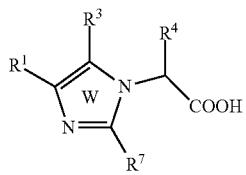
(E4) 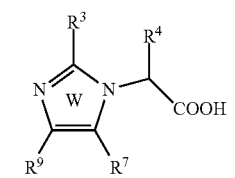
wherein:
W represents a substituted aromatic heterocycle;
$R^4$ is defined as for the compounds of formula (E);
$R^1$, $R^3$, $R^7$, $R^9$, $R^{11}$, $T^1$, $T^2$, $T^3$, $T^4$, $T^5$, $T^6$, $T^7$, $T^8$, $T^9$, and $T^{10}$ are defined as for the compounds of formula (1).
Also advantageously, the invention provides compounds of formulae (F) to (S):
(F) 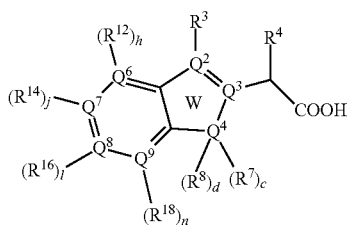
(G) 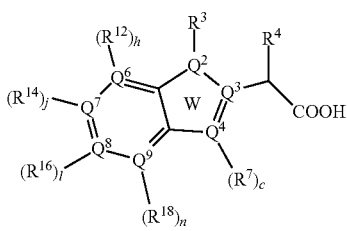
(H) 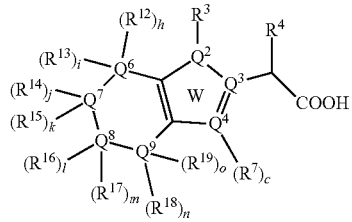
(I) 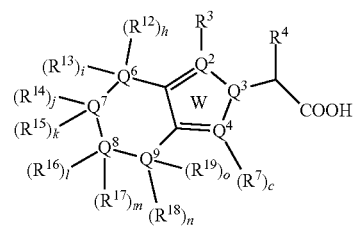
(J) 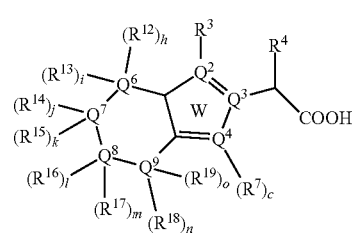
(K) 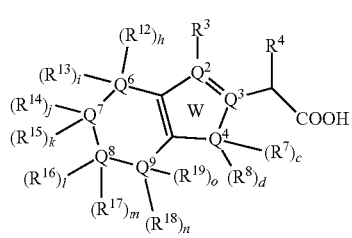
(L) 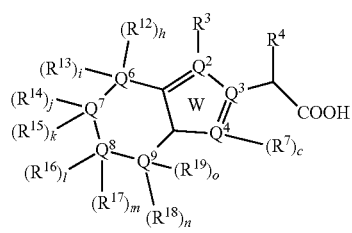
(M) 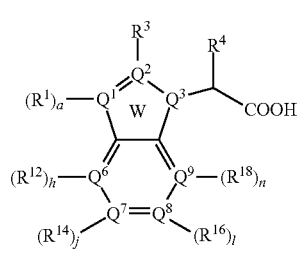

(N) 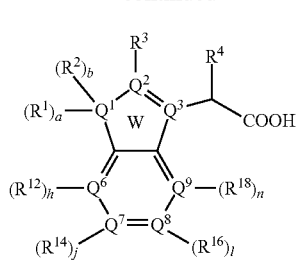

(O) 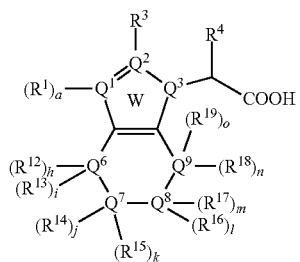

(P) 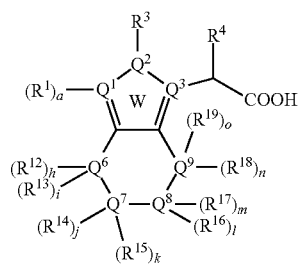

(Q) 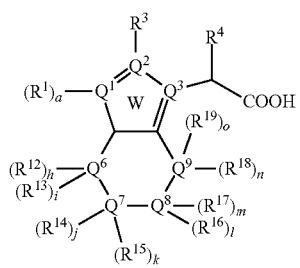

(R) 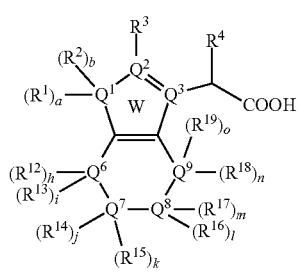

(S) 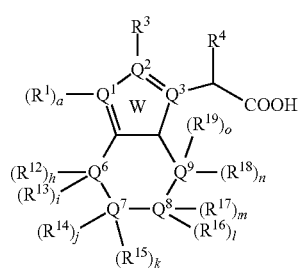

wherein:
W represents a fused, substituted, partially unsaturated or aromatic carbo- or heterocycle;
a, b, c, d, h, i, j, k, l, m, n and o independently represent 0 or 1;
$Q^3$ represents $CCR^4HC(O)OH$, $NCR^4HCOOH$;
$Q^6$ represents $CR^{12}$, $CR^{13}$, $CR^{12}R^{13}$, N, $NR^{12}$, $NR^{13}$, S, O, C=O, C=S, N=O, S=O, $S(O)_2$;
$Q^7$ represents $CR^{14}$, $CR^{15}$, $CR^{14}R^{15}$, N, $NR^{14}$, $NR^{15}$, S, O, C=O, C=S, N=O, S=O, $S(O)_2$;
$Q^8$ represents $CR^{16}$, $CR^{17}$, $CR^{16}R^{17}$, N, $NR^{16}$, $NR^{17}$, S, O, C=O, C=S, N=O, S=O, $S(O)_2$;
$Q^9$ represents $CR^{18}$, $CR^{19}$, $CR^{18}R^{19}$, N, $NR^{18}$, $NR^{19}$, S, O, C=O, C=S, N=O, S=O, $S(O)_2$;
$R^4$ represents independently —CN, —O-cycloalkyl, —O-cycloalkenyl, —O-cycloalkynyl, —S-cycloalkyl, —S-cycloalkenyl, —S-cycloalkynyl, $C_3$-$C_{20}$ alkyl, alkenyl, alkynyl, heteroalkyl, heteroalkenyl, heteroalkynyl, aryl, —O-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^2$,
and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$,
and wherein alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;
provided that:
$R^4$ does not represent a primary, secondary or tertiary amino group in the β-position of ring W;
if $R^4$ represents O-alkyl, the alkyl group is a $C_2$-$C_{20}$ alkyl;
$R^{12}$, $R^{13}$, $R^{14}$, $R^{15}$, $R^{16}$, $R^{17}$, $R^{18}$ and $R^{19}$ independently represent hydrogen, —CN, —OH, —O-cycloalkyl, —O-cycloalkenyl, —O-cycloalkynyl, —$NH_2$, —$NR^{11}$-cycloalkyl, —$NR^{11}$-cycloalkenyl, —$NR^{11}$-cycloalkynyl, —S-cycloalkyl, —S-cycloalkenyl, —S-cycloalkynyl, —COOH, —$C(O)NH_2$, —$CF_3$, —$SO_2NH_2$, —$NHSO_2NH_2$, —$NHC(O)NH_2$, —$OC(O)NH_2$, halogen, alkyl, alkenyl, alkynyl, heteroalkyl, heteroalkenyl, heteroalkynyl, aryl, —O-aryl, —$NR^{11}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{11}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$,
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$Q^1, Q^2, Q^4, R^1, R^2, R^3, R^7, R^8, R^{11}, T^1, T^2, T^3, T^4, T^5, T^6, T^7, T^8, T^9$ and $T^{10}$ are defined as for the compounds of formula (1).

Preferably, the invention provides compounds of formulae (F1) to (F3):

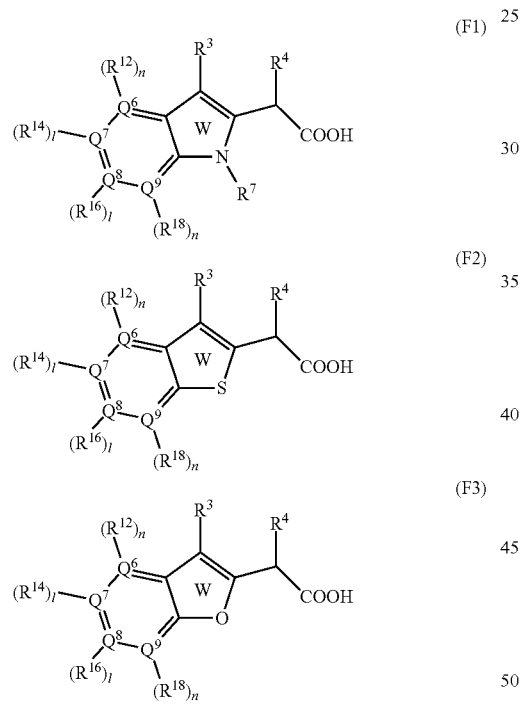

wherein:
W represents a fused, substituted, partially unsaturated heterocycle;
h, j, l and n independently represent 0 or 1;
$Q^6$ represents $CR^{12}$, N;
$Q^7$ represents $CR^{14}$, N;
$Q^8$ represents $CR^{16}$, N;
$Q^9$ represents $CR^{18}$, N;
$R^4, R^{12}, R^{14}, R^{16}, R^{18}$ are defined as for the compounds of formula (F);
$R^3, R^7, R^{11}, T^1, T^2, T^3, T^4, T^5, T^6, T^7, T^8, T^9$, and $T^{10}$ are defined as for the compounds of formula (1).

As examples of compounds of formula (F), the invention provides compounds of formulae (F1a), (F1b), (F2a) to (F2d), (F3a):

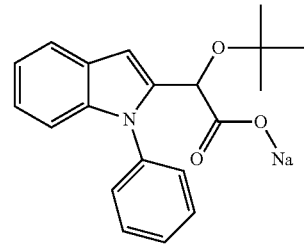

(F1a)

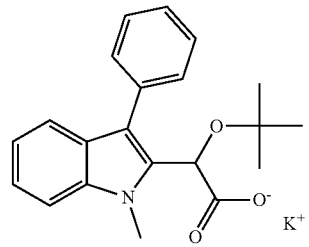

(F1b)

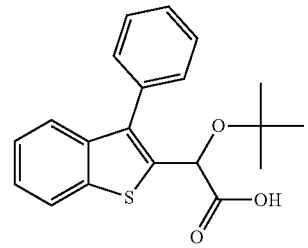

(F2a)

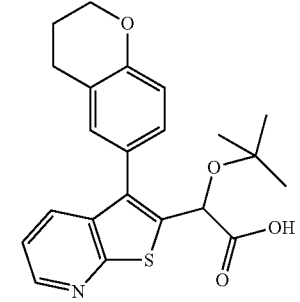

(F2b)

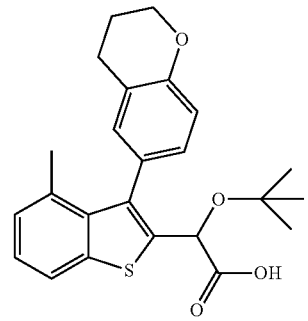

(F2c)

-continued

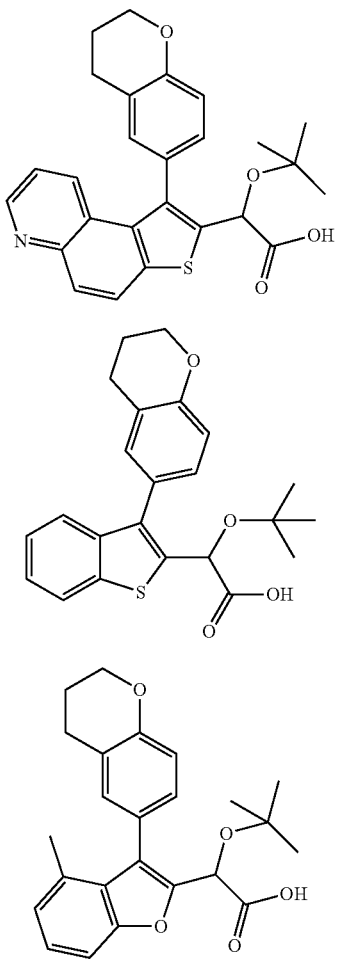

Preferably, the invention provides compounds of formula (G1) or (G2):

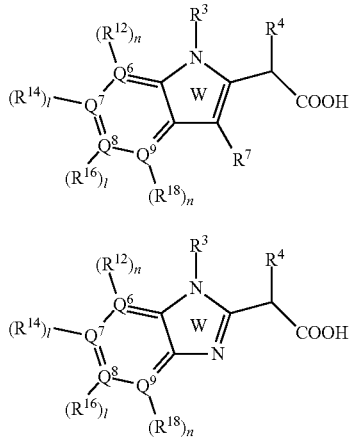

wherein:
W represents a fused, substituted, partially unsaturated heterocycle;
h, j, l and n independently represent 0 or 1;
$Q^6$ represents $CR^{12}$, N;
$Q^7$ represents $CR^{14}$, N;
$Q^8$ represents $CR^{16}$, N;
$Q^9$ represents $CR^{18}$, N;
$R^4, R^{12}, R^{14}, R^{16}, R^{18}$ are defined as for the compounds of formula (G);
$R^3, R^{11}, T^1, T^2, T^3, T^4, T^5, T^6, T^7, T^8, T^9$ and $T^{10}$ are defined as for the compounds of formula (1).

As an example of compounds of formula (G), the invention provides a compound of formula (G1a):

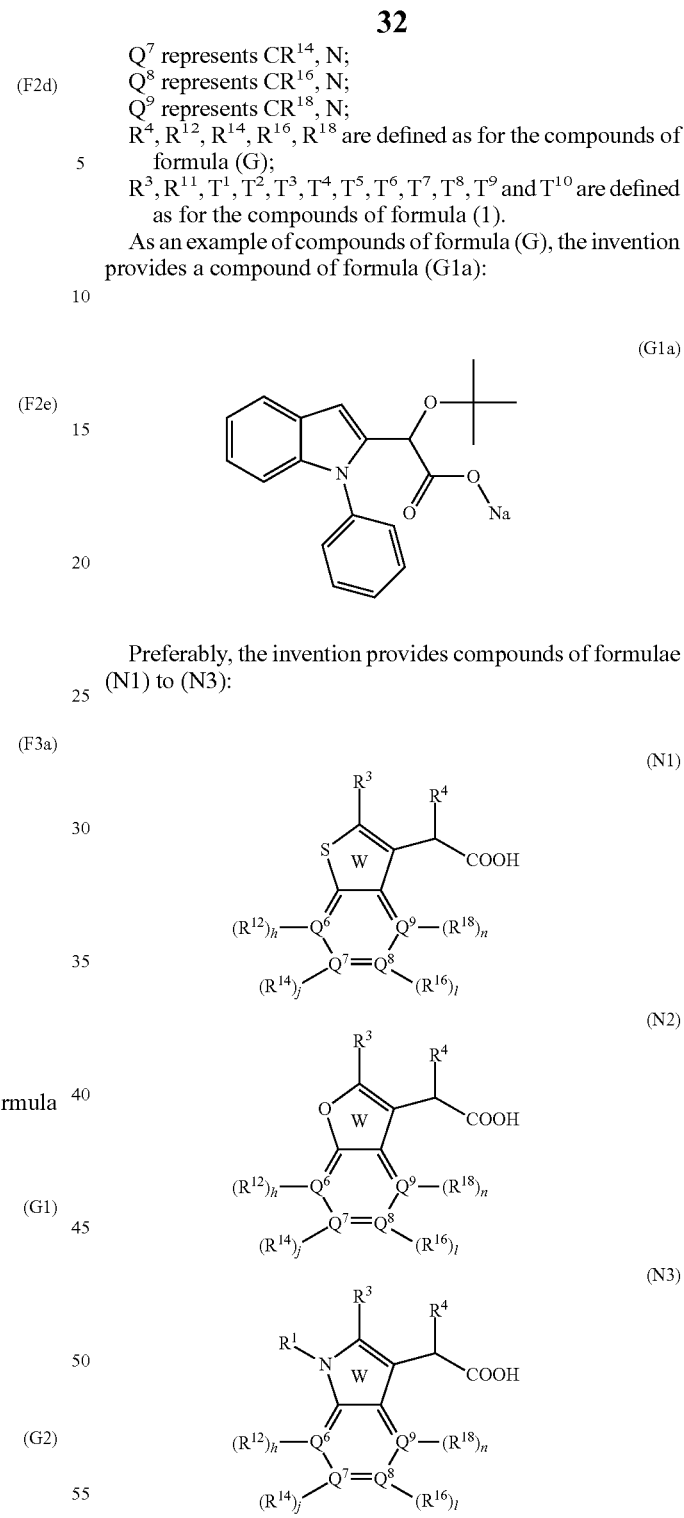

Preferably, the invention provides compounds of formulae (N1) to (N3):

wherein:
W represents a fused, substituted, partially unsaturated heterocycle;
h, j, l and n independently represent 0 or 1;
$Q^6$ represents $CR^{12}$, N;
$Q^7$ represents $CR^{14}$, N;
$Q^8$ represents $CR^{16}$, N;
$Q^9$ represents $CR^{18}$, N;
$R^4, R^{12}, R^{14}, R^{16}, R^{18}$ are defined as for the compounds of formula (G);

$R^1$, $R^3$, $R^{11}$, $T^1$, $T^2$, $T^3$, $T^4$, $T^5$, $T^6$, $T^7$, $T^8$, $T^9$ and $T^{10}$ are defined as for the compounds of formula (1).

As examples of compounds of formula (N), the invention provides compounds of formulae (N1a), (N1b), (N2a), (N3a) or (N3b):

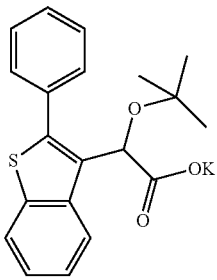

(N1a)

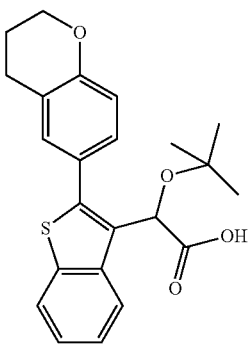

(N1b)

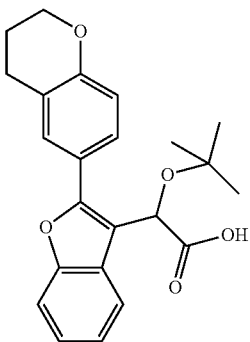

(N2a)

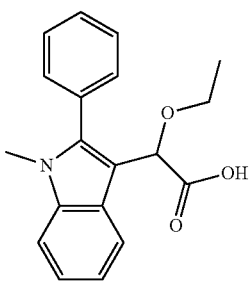

(N3a)

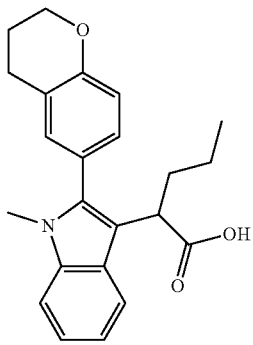

(N3b)

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antiviral activity of compounds according to the invention.

Preparation of the Compounds
Abbreviations or symbols used herein include:
DMSO: dimethylsulfoxide
MS: Mass Spectrometry
NMR: Nuclear Magnetic Resonance Spectroscopy
s: singlet
bs: broad singlet
d: doublet
t: triplet
q: quadruplet
dd: doubled doublet
ddd: doubled doubled doublet
dt: doubled triplet
m: massif
TLC: Thin Layer Chromatography

Example 1

Synthesis of potassium 2-(tert-butoxy)-2-(1-methyl-3-phenyl-1H-indol-2-yl)acetate

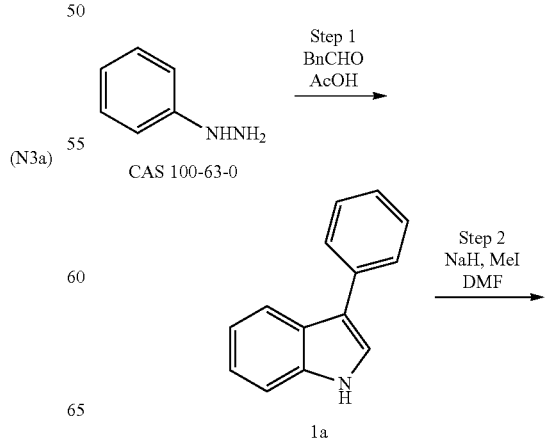

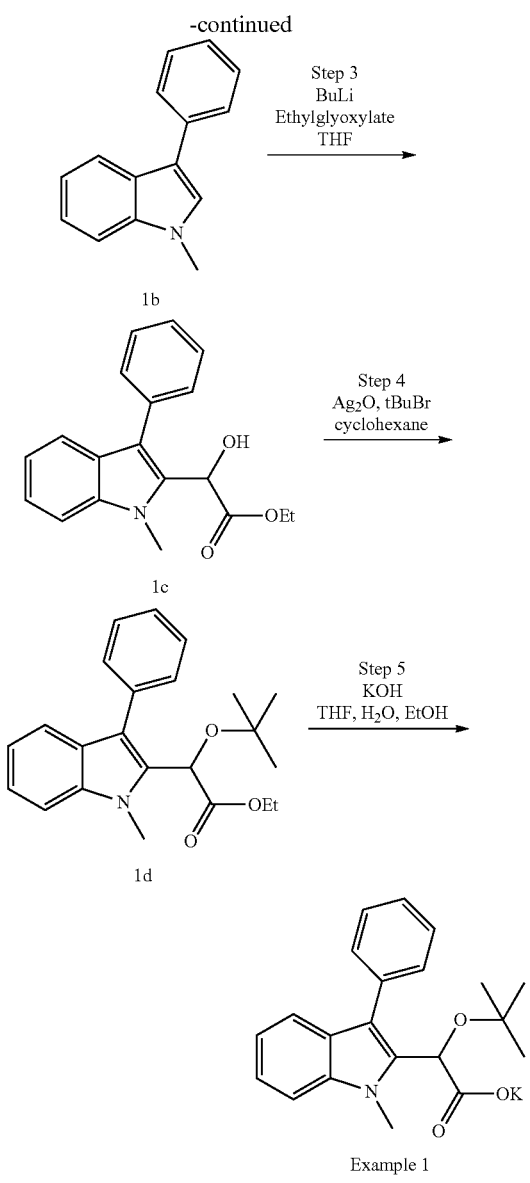

Step 2: Preparation of intermediate 1-methyl-3-phenyl-1H-indole (1b)

Sodium hydride (60% in mineral oil, 200 mg, 5 mmol) was added at 0° C. to a solution of 3-phenyl-1H-indole (1a) (940 mg, 4.86 mmol) in N,N-dimethylformamide (20 mL) under a nitrogen atmosphere. The suspension was stirred for 15 minutes at 0° C. and methyliodide (311 µL, 5 mmol) was then added. The reaction mixture was warmed to room temperature, stirred for 6 hours and then concentrated in vacuo. The residue was partitioned between ethyl acetate (30 mL) and water (10 mL). The organic layer was washed with water (2×10 mL), brine (10 mL), dried over sodium sulfate, filtered and evaporated to dryness to give the desired product (1b) as a yellow oil (1 g, 4.86 mmol, 100%) which was used without further purification.

$^1$H NMR (400 MHz, CDCl$_3$) δ 3.84 (s, 3H), 7.19-7.30 (m, 4H), 7.36 (d, J=8.1 Hz, 1H), 7.43 (t, J=7.6 Hz, 2H), 7.65 (d, J=7.1 Hz, 2H), 7.95 (d, J=8.0 Hz, 1H).

MS m/z ([M+H]$^+$) 208.

Step 3: Preparation of intermediate ethyl 2-hydroxy-2-(1-methyl-3-phenyl-1H-indol-2-yl)acetate (1c)

A solution of butyllithium (1.6 M, 3.44 mL, 5.5 mmol) was added at −20° C. to a solution of 1-methyl-3-phenyl-1H-indole (1b) (1.08 g, 5.3 mmol) in anhydrous tetrahydrofuran (20 mL) under a nitrogen atmosphere. After 1 hour, a solution of ethyl glyoxylate in toluene (50%, 1.1 mL, 5.5 mmol) was added. The reaction mixture was slowly warmed to room temperature for 2 hours, quenched with water (5 mL) and concentrated in vacuo. The residue was partitioned between dichloromethane (40 mL) and water (15 mL). The organic layer was washed with water (2×15 mL), brine (15 mL), dried over sodium sulfate, filtered and evaporated to dryness. The residue was purified by flash chromatography on silica gel (cyclohexane/ethyl acetate 90/10) to afford the desired alcohol (1c) as a white solid (360 mg, 1.16 mmol, 22%).

$^1$H NMR (400 MHz, CDCl$_3$) δ 1.23 (t, J=7.1 Hz, 3H), 3.37 (d, J=2.4 Hz, 1H), 3.78 (s, 3H), 4.10-4.30 (m, 2H), 5.57 (d, J=2.4 Hz, 1H), 7.14 (t, J=6.9 Hz, 1H), 7.30-7.37 (m, 3H), 7.46 (t, J=7.7 Hz, 2H), 7.55 (d, J=8.3 Hz, 2H), 7.66 (d, J=7.9 Hz, 1H).

MS m/z ([M+H]$^+$) 310, ([M+Na]$^+$) 332.

Step 4: Preparation of ethyl 2-(tert-butoxy)-2-(1-methyl-3-phenyl-1H-indol-2-yl)acetate (1d)

A mixture of ethyl 2-hydroxy-2-(1-methyl-3-phenyl-1H-indol-2-yl)acetate (1c) (300 mg, 0.97 mmol), silver (I) oxide (674 mg, 2.91 mmol) and tert-butylbromide (544 µL, 4.85 mmol) in cyclohexane (10 mL) was vigorously stirred for 2 hours under a nitrogen atmosphere. The reaction mixture was then filtered and concentrated in vacuo. The residue was purified by flash chromatography on silica gel (cyclohexane/ethyl acetate 90/10) to afford the desired ether oxide (1d) as a white solid (35 mg, 0.1 mmol, 10%).

$^1$H NMR (400 MHz, CDCl$_3$) δ 0.97 (s, 9H), 1.29 (t, J=7.1 Hz, 3H), 3.91 (s, 3H), 4.15-4.32 (m, 2H), 5.45 (s, 1H), 7.13 (t, J=7.0 Hz, 1H), 7.30 (t, J=7.0 Hz, 1H), 7.35 (d, J=8.8 Hz, 2H), 7.48 (t, J=7.7 Hz, 2H), 7.58 (d, J=8.3 Hz, 2H), 7.63 (d, J=7.9 Hz, 1H).

MS m/z ([M+1]$^+$) 366, ([M+Na]$^+$) 388.

Step 5: Preparation of intermediate potassium 2-(tert-butoxy)-2-(1-methyl-3-phenyl-1H-indol-2-yl)acetate A solution of ethyl 2-(tert-butoxy)-2-(1-methyl-3-phenyl-1H-indol-2-yl)acetate (1d) (55 mg, 0.15 mmol) and potas-

Step 1: Preparation of intermediate 3-phenyl-1H-indole (1a)

A solution of phenylhydrazine (1 mL, 10.15 mmol) and phenylacetaldehyde (1.32 mL, 10.15 mmol) in acetic acid was refluxed for 6 hours under a nitrogen atmosphere. After cooling to room temperature, the reaction mixture was poured into a saturated aqueous solution of sodium carbonate (100 mL) at 0° C. After extraction with dichloromethane (2×30 mL), the organic layer was dried over sodium sulfate, filtered and evaporated to dryness. The residue was purified by flash chromatography on silica gel (cyclohexane/ethyl acetate 90/10) to afford the desired indole (1a) as a pale oil (940 mg, 4.86 mmol, 48%).

$^1$H NMR (400 MHz, CDCl$_3$) δ 7.19-7.32 (m, 3H), 7.37 (d, J=2.5 Hz, 1H), 7.43-7.48 (m, 3H), 7.68 (d, J=8.3 Hz, 2H), 7.96 (d, J=8.0 Hz, 1H), 8.22 (broad s, 1H).

MS m/z ([M+H]$^+$) 194.

sium hydroxide (8.4 mg, 0.15 mmol) in water (2 mL), in a mixture of tetrahydrofuran (4 mL) and ethanol (1 mL) was refluxed for 2 hours. Water (10 mL) was added to the reaction mixture which was washed with dichloromethane (10 mL). The aqueous layer was lyophilized. The obtained solid was triturated with cyclohexane to afford the desired product (example 1) as a white solid (7.9 mg, 0.021 mmol, 14%).

$^1$H NMR (400 MHz, DMSO-$d_6$) δ 0.81 (s, 9H), 3.86 (s, 3H), 5.08 (s, 1H), 7.00 (t, J=7.4 Hz, 1H), 7.12 (t, J=7.3 Hz, 1H), 7.27 (t, J=7.3 Hz, 1H), 7.37 (d, J=8.1 Hz, 1H), 7.44 (t, J=7.4 Hz, 2H), 7.52 (d, J=7.6 Hz, 1H), 7.88 (d, J=7.4 Hz, 2H).

MS m/z ([M+H]$^+$) 338, ([M+Na]$^+$) 360.

Example 2

Synthesis of potassium 2-(tert-butoxy)-2-(2-phenyl-1-benzothiophen-3-yl)acetate

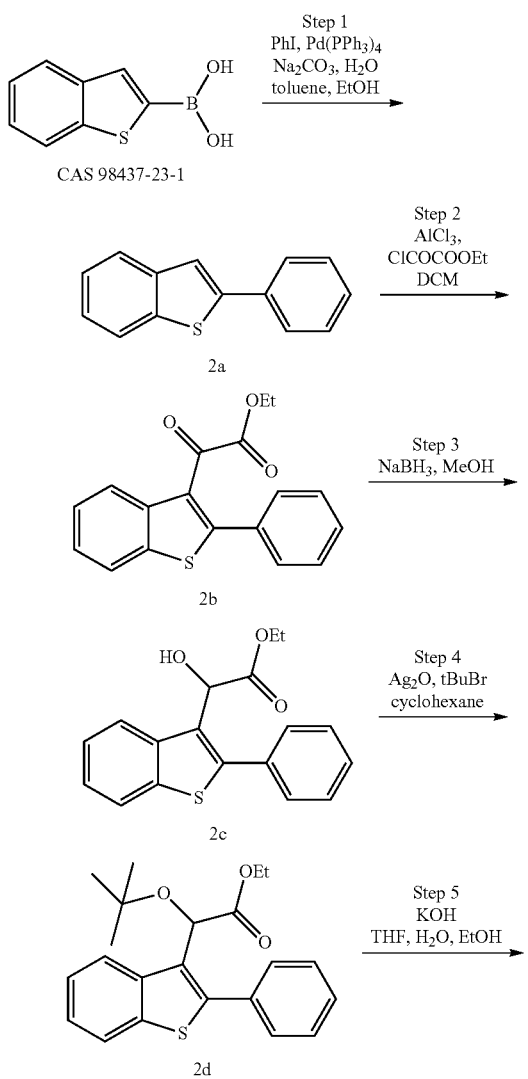

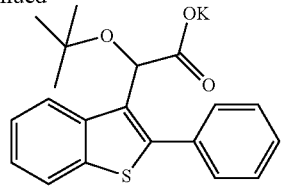

Example 2

Step 1: Preparation of intermediate 2-phenyl-1-benzothiophene (2a)

A solution of benzothiopheneboronic acid (1 g, 5.61 mmol) in ethanol (23 mL) was added to a mixture of iodobenzene (560 µL, 5 mmol), palladium tetrakis(triphenylphosphine) (460 mg, 0.4 mmol) and sodium carbonate (2.38 g, 22.4 mmol) in a mixture of toluene (15 mL) and water (15 mL). The reaction mixture was refluxed for 6 hours and then concentrated in vacuo. The residue was partitioned between ethyl acetate (30 mL) and water (10 mL). The biphasic mixture was acidified with an aqueous solution of hydrochloric acid 1N until pH 2. The aqueous layer was extracted with ethyl acetate (2×20 mL) and the organic layer was washed with water (10 mL), brine (10 mL), dried over sodium sulfate, filtered and evaporated to dryness. The residue was purified by flash chromatography on silica gel (cyclohexane/ethyl acetate 90/10) to afford the desired product (2a) as a yellow oil (640 mg, 3 mmol, 60%).

$^1$H NMR (400 MHz, CDCl$_3$) δ 7.27-7.50 (m, 6H), 7.70-7.85 (m, 4H).

Step 2: Preparation of intermediate ethyl 2-oxo-2-(2-phenyl-1-benzothiophen-3-yl)acetate (2b)

Ethyl chlorooxoacetate (162 µL, 1.45 mmol) was added at 0° C. to a solution of 2-phenyl-1-benzothiophene (2a) (310 mg, 1.46 mmol) and aluminum chloride (III) (389 mg, 2.92 mmol) in dichloromethane (10 mL). After 30 minutes, the reaction mixture was quenched with a saturated aqueous solution of sodium carbonate. The aqueous layer was extracted with ethyl acetate (2×20 mL) and the organic layer was washed with water (20 mL), brine (20 mL), dried over sodium sulfate, filtered and evaporated to dryness. The residue was purified by flash chromatography on silica gel (cyclohexane/ethyl acetate 80/20) to afford the desired product (2b) as a pale oil (370 mg, 1.19 mmol, 70%).

$^1$H NMR (400 MHz, CDCl$_3$) δ 1.05 (t, J=7.1 Hz, 3H), 3.68 (q, J=7.1 Hz, 2H), 7.45-7.60 (m, 7H), 7.86 (d, J=8.0 Hz, 1H), 8.45 (d, J=8.2 Hz, 1H).

MS m/z ([M+H]$^+$) 311.

Step 3: Preparation of intermediate ethyl 2-hydroxy-2-(2-phenyl-1-benzothiophen-3-yl)acetate (2c)

Sodium borohydride (53 mg, 1.40 mmol) was added to a solution of ethyl 2-oxo-2-(2-phenyl-1-benzothiophen-3-yl)acetate (2b) (430 mg, 1.38 mmol) in a mixture of methanol (10 mL) and tetrahydrofuran (5 mL) under a nitrogen atmosphere. The reaction mixture was stirred for 1 hour, quenched with water (2 mL) and concentrated in vacuo. The residue was diluted with dichloromethane (20 mL), washed with water (2×10 mL), brine (10 mL), dried over sodium sulfate, filtered and evaporated to dryness. The residue was purified by flash chromatography on silica gel (dichloromethane/ethanol 99/1) to afford the desired alcohol (2c) as a white solid (190 mg, 0.60 mmol, 44%).

$^1$H NMR (400 MHz, CDCl$_3$) δ 1.16 (t, J=7.1 Hz, 3H), 3.48 (s, 1H), 4.10-4.30 (m, 2H), 5.53 (s, 1H), 7.32-7.36 (m, 2H), 7.40-7.48 (m, 3H), 7.60-7.67 (m, 2H), 7.79-7.87 (m, 2H).

MS m/z ([M+Na]$^+$) 335.

Step 4: Preparation of intermediate ethyl 2-(tert-butoxy)-2-(2-phenyl-1-benzothiophen-3-yl)acetate (2d)

A mixture of ethyl 2-hydroxy-2-(2-phenyl-1-benzothiophen-3-yl)acetate (2c) (190 mg, 0.6 mmol), silver (I) oxide (417 mg, 1.8 mmol) and tertbutylbromide (360 µL, 3.2 mmol) in cyclohexane (5 mL) was vigorously stirred for 2 hours. The reaction mixture was then filtered and concentrated in vacuo. The residue was purified by flash chromatography on silica gel (cyclohexane/ethyl acetate 90/10) to afford the desired ether oxide (2d) as a white solid (30 mg, 0.08 mmol, 13%).

$^1$H NMR (400 MHz, CDCl$_3$) δ 0.99 (s, 9H), 1.23 (t, J=7.1 Hz, 3H), 4.10-4.30 (m, 2H), 5.35 (s, 1H), 7.28-7.35 (m, 2H), 7.40-7.50 (m, 3H), 7.65-7.70 (m, 2H), 7.78 (d, J=6.9 Hz, 1H), 8.29 (d, J=7.4 Hz, 1H).

MS m/z ([M+Na]$^+$) 391.

Step 5: Preparation of potassium 2-(tert-butoxy)-2-(2-phenyl-1-benzothiophen-3-yl)acetate A solution of ethyl 2-(tert-butoxy)-2-(2-phenyl-1-benzothiophen-3-yl)acetate (70 mg, 0.19 mmol) and potassium hydroxide (10.7 mg, 0.19 mmol) in water (3 mL), in a mixture of tetrahydrofuran (3 mL) and ethanol (1 mL) was stirred at room temperature for 20 hours. Water (10 mL) was added to the reaction mixture which was washed with dichloromethane (10 mL). The aqueous layer was lyophilized and the obtained solid was triturated with cyclohexane to afford the desired product (example 2) as a white solid (55 mg, 0.14 mmol, 76%).

$^1$H NMR (400 MHz, DMSO-d$_6$) δ 0.80 (s, 9H), 5.02 (s, 1H), 7.21-7.28 (m, 2H), 7.38-7.44 (m, 1H), 7.49 (t, J=7.6 Hz, 2H), 7.78-7.84 (m, 1H), 8.10 (d, J=7.0 Hz, 2H), 8.47-8.53 (m, 1H).

MS m/z ([M+Na]$^+$) 363.

Example 3

Synthesis of 2-(tert-butoxy)-2-(3-phenyl-1-benzothiophen-2-yl)acetic acid

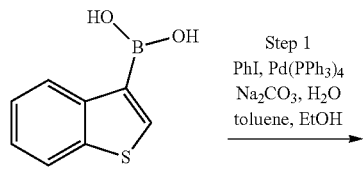

CAS 113893-08-6

Step 1
PhI, Pd(PPh$_3$)$_4$
Na$_2$CO$_3$, H$_2$O
toluene, EtOH

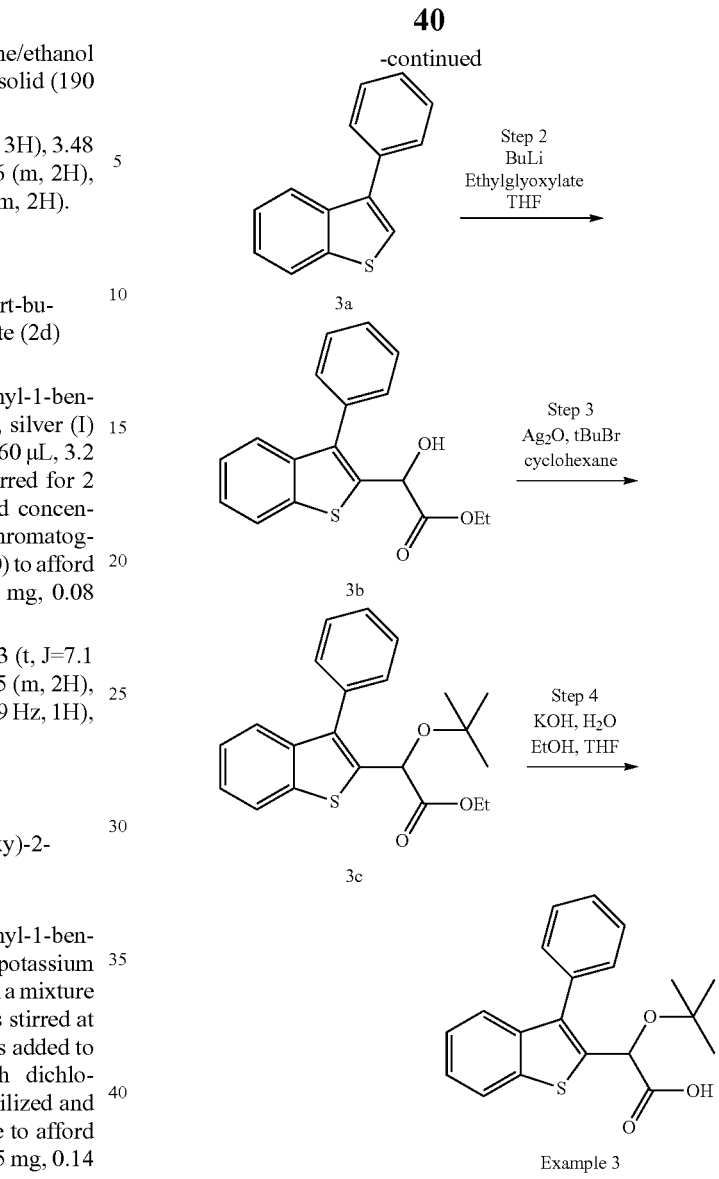

Step 1: Preparation of intermediate 3-phenyl-1-benzothiophene (3a)

A solution of benzothiopheneboronic acid (1 g, 5.61 mmol) in ethanol (23 mL) was added to a mixture of iodobenzene (560 µL, 5 mmol), palladium tetrakis(triphenylphosphine) (460 mg, 0.4 mmol) and sodium carbonate (2.38 g, 22.4 mmol) in a mixture of toluene (15 mL) and water (15 mL). The reaction mixture was refluxed for 6 hours and then concentrated in vacuo. The residue was partitioned between ethyl acetate (30 mL) and water (10 mL). The biphasic mixture was acidified with an aqueous solution of hydrochloric acid 1N until pH 2. The aqueous layer was extracted with ethyl acetate (2×20 mL) and the organic layer was washed with water (10 mL), brine (10 mL), dried over sodium sulfate, filtered and evaporated to dryness. The residue was purified by flash chromatography on silica gel (cyclohexane) to afford the desired product (3a) as a yellow solid (1.18 g, 5.61 mmol, 100%).

$^1$H NMR (400 MHz, CDCl$_3$) δ 7.35-7.45 (m, 4H), 7.49 (t, J=7.6 Hz, 2H), 7.59 (d, J=7.0 Hz, 2H), 7.89-7.95 (m, 2H).

Step 2: Preparation of ethyl 2-hydroxy-2-(3-phenyl-1-benzothiophen-2-yl)acetate (3b)

A solution of butyllithium (1.6 M, 3.75 mL, 6 mmol) was added at −20° C. to a solution of 3-phenyl-1-benzothiophene (3a) (1.18 g, 5.61 mmol) in tetrahydrofuran (20 mL) under a nitrogen atmosphere. After 1 hour, a solution of ethyl glyoxylate in toluene (50%, 1.2 mL, 6 mmol) was added. The reaction mixture was slowly warmed to room temperature for 2 hours, quenched with water (5 mL) and concentrated in vacuo. The residue was partitioned between dichloromethane (40 mL) and water (15 mL). The organic layer was washed with water (2×15 mL), brine (15 mL), dried over sodium sulfate, filtered and evaporated to dryness. The residue was purified by flash chromatography on silica gel (cyclohexane/ethyl acetate 90/10) to afford the desired alcohol (3b) as a white solid (340 mg, 1.09 mmol, 20%).

$^1$H NMR (400 MHz, CDCl$_3$) δ 1.23 (t, J=7.1 Hz, 3H), 3.57 (d, J=5.1 Hz, 1H), 4.15-4.30 (m, 2H), 5.45 (d, J=5.1 Hz, 1H), 7.30-7.35 (m, 2H), 7.38-7.55 (m, 6H), 7.86 (d, J=8.5 Hz, 1H).

MS m/z ([M+Na]$^+$) 335.

Step 3: Preparation of intermediate ethyl 2-(tert-butoxy)-2-(3-phenyl-1-benzothiophen-2-yl)acetate (3c)

A mixture of ethyl 2-hydroxy-2-(3-phenyl-1-benzothiophen-2-yl)acetate (3b) (340 mg, 1.09 mmol), silver (I) oxide (758 mg, 3.27 mmol) and tertbutylbromide (612 μL, 5.45 mmol) in cyclohexane (20 mL) was vigorously stirred for 48 hours under a nitrogen atmosphere. The reaction mixture was then filtered and concentrated in vacuo. The residue was purified by flash chromatography on silica gel (cyclohexane/ethyl acetate 90/10) to afford the desired ether oxide (3c) as a white solid (45 mg, 0.12 mmol, 11%).

$^1$H NMR (400 MHz, CDCl$_3$) δ 1.12 (s, 9H), 1.28 (t, J=7.1 Hz, 3H), 4.15-4.30 (m, 2H), 5.38 (s, 1H), 7.25-7.40 (m, 2H), 7.45-7.60 (m, 6H), 7.90 (d, J=7.9 Hz, 1H).

MS m/z ([M+Na]$^+$) 391.

Step 4: Preparation of 2-(tert-butoxy)-2-(3-phenyl-1-benzothiophen-2-yl)acetic acid A solution of ethyl 2-(tert-butoxy)-2-(3-phenyl-1-benzothiophen-2-yl)acetate (3c) (45 mg, 0.12 mmol) and potassium hydroxide (34 mg, 0.61 mmol) in water (3 mL), in a mixture of tetrahydrofuran (3 mL) and ethanol (1 mL) was refluxed for 5 hours. The reaction mixture was concentrated in vacuo and water (10 mL) was added. The aqueous layer was washed with dichloromethane (10 mL), acidified with a hydrochloric acid solution 1N until pH 2 and extracted with dichloromehane (2×10 mL). The organic layer was dried over sodium sulfate, filtered and evaporated to dryness to afford the desired product (example 3) as a white solid (7.9 mg, 0.023 mmol, 19%).

$^1$H NMR (400 MHz, CDCl$_3$) δ 1.08 (s, 9H), 5.38 (s, 1H), 7.27-7.40 (m, 3H), 7.45-7.60 (m, 5H), 7.90 (d, J=7.1 Hz, 1H).

MS m/z ([M+Na]$^+$) 363.

Example 4

Synthesis of 2-(tert-butoxy)-2-[2-(3,4-dihydro-2H-1-benzopyran-6-yl)-1-benzothiophen-3-yl]acetic acid

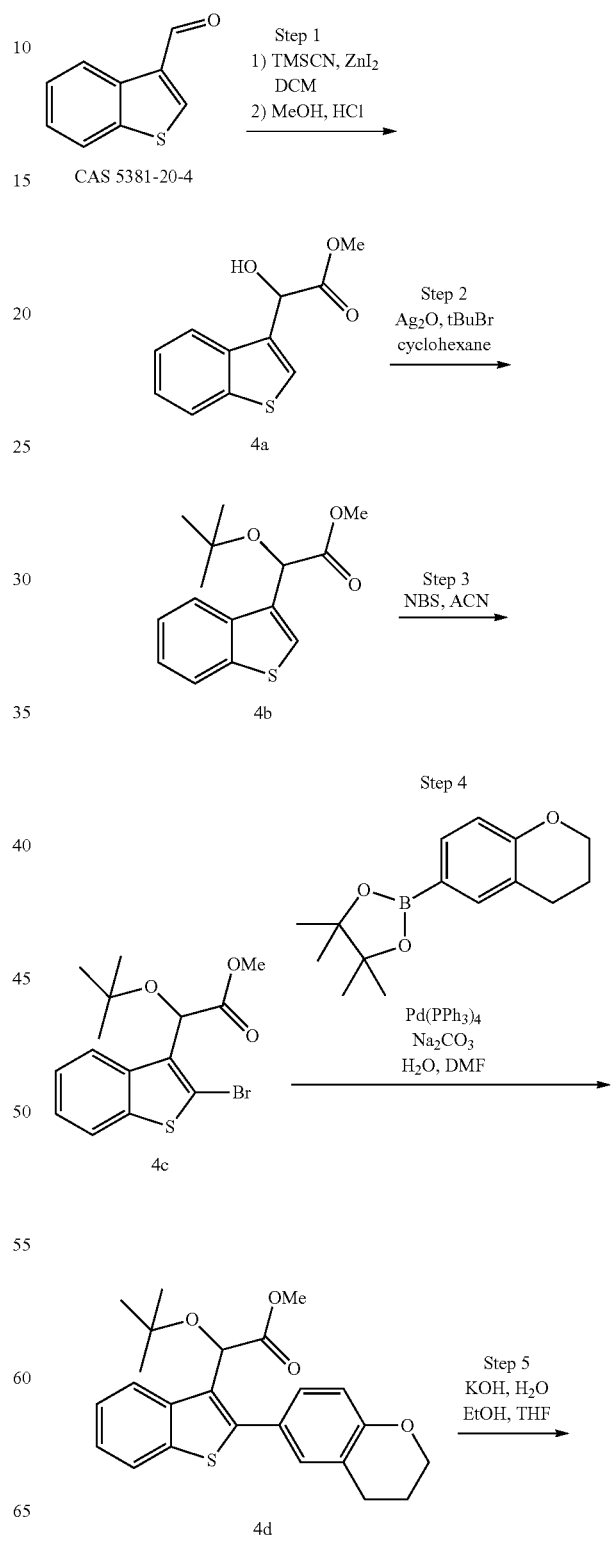

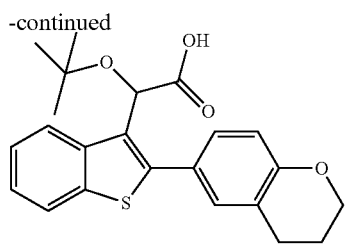

Example 4

Step 1: Preparation of intermediate methyl 2-(1-benzothiophen-3-yl)-2-hydroxyacetate (4a)

Trimethylsilylcyanide (924 μL, 7.39 mmol) was added at 0° C. to a solution of thianaphtene-3-carboxaldehyde (1 g, 6.16 mmol) and zinc iodide (II) (198 mg, 0.62 mmol) in anhydrous dichloromethane (40 mL) under a nitrogen atmosphere. After 2 hours, the reaction mixture was quenched with a saturated aqueous solution of sodium carbonate and extracted with dichloromethane (2×20 mL). The organic layer was washed with brine (10 mL), dried over sodium sulfate, filtered and evaporated to dryness. The residue was dissolved in anhydrous methanol and the solution was cooled at 0° C. Hydrogen chloride was bubbled for 5 minutes. The mixture was then warmed at room temperature for 20 h and concentrated in vacuo. The residue was partitioned between ethyl acetate (10 mL) and a saturated aqueous solution of sodium bicarbonate (10 mL). The aqueous layer was extracted with ethyl acetate (2×10 mL). The organic layer was washed with brine (10 mL), dried over sodium sulfate, filtered and evaporated to dryness. The residue was purified by flash chromatography on silica gel (dichloromethane/ethanol 95/5) to afford the desired alcohol (4a) as a white solid (550 mg, 2.47 mmol, 40%). $^1$H NMR (400 MHz, CDCl$_3$) δ 3.78 (s, 3H), 5.56 (s, 1H), 7.35-7.45 (m, 2H), 7.49 (s, 1H), 7.86-7.92 (m, 2H).

MS m/z ([M−OH]$^+$) 205.

Step 2: Preparation of intermediate methyl 2-(1-benzothiophen-3-yl)-2-(tert-butoxy)acetate (4b)

A mixture of methyl 2-(1-benzothiophen-3-yl)-2-hydroxyacetate (4a) (300 mg, 1.35 mmol), silver (I) oxide (938 mg, 4.05 mmol) and tertbutylbromide (910 μL, 8.1 mmol) in a mixture of cyclohexane (5 mL) and dichloromethane (1 mL) was vigorously stirred for 20 hours under a nitrogen atmosphere. The reaction mixture was then filtered and concentrated in vacuo. The residue was purified by flash chromatography on silica gel (cyclohexane/ethyl acetate 90/10) to afford the desired ether oxide (4b) as a white solid (70 mg, 0.25 mmol, 10%).

$^1$H NMR (400 MHz, CDCl$_3$) δ 1.29 (s, 9H), 3.69 (s, 3H), 5.43 (s, 1H), 7.33-7.42 (m, 2H), 7.56 (s, 1H), 7.85 (d, J=7.5 Hz, 1H), 8.04 (d, J=7.5 Hz, 1H).

MS m/z ([M−H]$^-$) 277.

Step 3: Preparation of intermediate methyl 2-(2-bromo-1-benzothiophen-3-yl)-2-(tert-butoxy)acetate (4c)

N-bromosuccinimide (67 mg, 0.37 mmol) was added at room temperature to a stirred solution of methyl 2-(1-benzothiophen-3-yl)-2-(tert-butoxy)acetate (4b) (70 mg, 0.25 mmol) in acetonitrile (2 mL) under a nitrogen atmosphere. After 20 hours, water (10 mL) was added and the reaction mixture was extracted with dichloromethane (2×10 mL). The organic layer was washed with brine (10 mL), dried over sodium sulfate, filtered and evaporated to dryness. The residue was purified by flash chromatography on silica gel (cyclohexane/ethyl acetate 90/10) to afford the desired product (4c) as a pale oil (40 mg, 0.11 mmol, 45%).

$^1$H NMR (400 MHz, CDCl$_3$) δ 1.24 (s, 9H), 3.66 (s, 3H), 5.51 (s, 1H), 7.30-7.40 (m, 2H), 7.68 (d, J=7.5 Hz, 1H), 8.21 (d, J=7.5 Hz, 1H).

MS m/z ([M+Na]$^+$) 379, 381.

Step 4: Preparation of intermediate methyl 2-(tert-butoxy)-2-[2-(3,4-dihydro-2H-1-benzopyran-6-yl)-1-benzothiophen-3-yl]acetate (4d)

To a solution of methyl 2-(2-bromo-1-benzothiophen-3-yl)-2-(tert-butoxy)acetate (4c) (40 mg, 0.11 mmol) in N,N-dimethylformamide (2 mL) were successively added sodium carbonate (13 mg, 0.12 mmol), water (500 μL), palladium tetrakis(triphenylphosphine) (18.3 mg, 0.016 mmol) and 6-(4,4,5,5-tetramethyl-1,3,2-dioxaborolan-2-yl)chroman (29 mg, 0.11 mmol). The mixture was heated at 100° C. for 2 hours. After cooling to room temperature, water (10 mL) was added. The aqueous layer was extracted with ethyl acetate (2×10 mL). The organic layer was washed with brine (10 mL), dried over sodium sulfate, filtered and evaporated to dryness. The residue was purified by flash chromatography on silica gel (cyclohexane/ethyl acetate 90/10) to afford the desired product (4d) as a white solid (25 mg, 0.061 mmol, 55%).

$^1$H NMR (400 MHz, CDCl$_3$) δ 1.01 (s, 9H), 2.05-2.10 (m, 2H), 2.84-2.88 (m, 2H), 3.73 (s, 3H), 4.24-4.28 (m, 2H), 5.41 (s, 1H), 6.89 (d, J=8.3 Hz, 1H), 7.26-7.40 (m, 4H), 7.76 (d, J=7.5 Hz, 1H), 8.23 (d, J=7.5 Hz, 1H).

MS m/z ([M+Na]$^+$) 433.

Step 5: Preparation of 2-(tert-butoxy)-2-[2-(3,4-dihydro-2H-1-benzopyran-6-yl)-1-benzothiophen-3-yl] acetic acid A solution of methyl 2-(tert-butoxy)-2-[2-(3,4-dihydro-2H-1-benzopyran-6-yl)-1-benzothiophen-3-yl]acetate (4d) (25 mg, 0.061 mmol) and lithium hydroxide (18 mg, 0.75 mmol) in water (3 mL), in a mixture of tetrahydrofuran (3 mL) and methanol (1 mL) was stirred at room temperature for 20 hours. Water (10 mL) was added to the reaction mixture which was washed with dichloromethane (10 mL). The aqueous layer was acidified with a hydrochloric acid solution 1N until pH 2 and extracted with dichloromethane (2×10 mL). The organic layer was washed with brine (10 mL), dried over sodium sulfate, filtered and evaporated to dryness to afford the desired acid (example 4) as a white solid (24 mg, 0.06 mmol, 99%).

$^1$H NMR (400 MHz, CDCl$_3$) δ 1.00 (s, 9H), 2.04-2.08 (m, 2H), 2.84-2.88 (m, 2H), 4.26 (t, J=5.1 Hz, 2H), 5.47 (s, 1H), 6.89 (d, J=8.3 Hz, 1H), 7.28-7.43 (m, 4H), 7.79 (d, J=7.5 Hz, 1H), 7.83 (d, J=7.5 Hz, 1H).

MS m/z ([M−H]$^-$) 395.

Example 5

Synthesis of sodium 2-(tert-butoxy)-2-(1-phenyl-1H-indol-2-yl)acetate

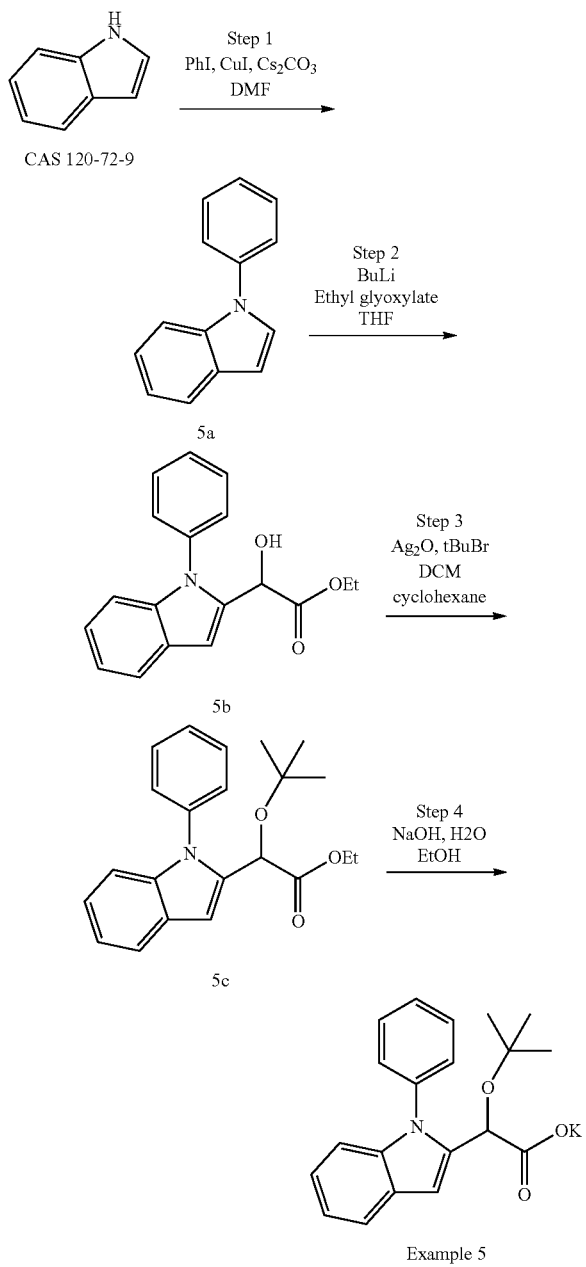

Example 5

Step 1: Preparation of intermediate 1-phenyl-1H-indole (5a)

A mixture of indole (500 mg, 4.27 mmol), copper(I) iodide (122 mg, 0.64 mmol), cesium carbonate (1.9 g, 6 mmol) and phenyliodide (470 µL, 4.2 mmol) in anhydrous N,N-dimethylformamide (10 mL) was refluxed for 24 hours under a nitrogen atmosphere. The reaction mixture was then filtered and concentrated in vacuo. The residue was partitioned between dichloromethane (30 mL) and water (10 mL). The organic layer was washed with water (2×10 mL), brine (10 mL), dried over sodium sulfate, filtered and evaporated to dryness. The residue was purified by flash chromatography on silica gel (cyclohexane/ethyl acetate 95/5) to afford the desired product (5a) as a yellow oil (700 mg, 3.62 mmol, 86%).

$^1$H NMR (400 MHz, CDCl$_3$) δ 6.69 (d, J=4 Hz, 1H), 7.15-7.27 (m, 2H), 7.34-7.39 (m, 2H), 7.51-7.55 (m, 4H), 7.59 (d, J=8.2 Hz, 1H), 7.70 (d, J=7.3 Hz, 1H).

MS m/z ([M+H]$^+$) 194.

Step 2: Preparation of intermediate ethyl 2-hydroxy-2-(1-phenyl-1H-indol-2-yl)acetate (5b)

A solution of butyllithium (1.6 M, 1.19 mL, 1.9 mmol) was added at −78° C. to a solution of 1-phenyl-1H-indole (5a) (350 mg, 1.81 mmol) in tetrahydrofuran (10 mL) under a nitrogen atmosphere. After 45 minutes, a solution of ethyl glyoxylate in toluene (50%, 400 µL, 2 mmol) was added. The reaction mixture was slowly warmed to room temperature for 12 hours, quenched with water (2 mL) and concentrated in vacuo. The residue was partitioned between dichloromethane (30 mL) and water (10 mL). The organic layer was washed with water (2×10 mL), brine (10 mL), dried over sodium sulfate, filtered and evaporated to dryness. The residue was purified by flash chromatography on silica gel (cyclohexane/ethyl acetate 90/10) to afford the desired alcohol (5b) as a white solid (100 mg, 0.33 mmol, 19%).

$^1$H NMR (400 MHz, CDCl$_3$) δ 1.22 (t, J=7.1 Hz, 3H), 3.22 (d, J=6.7 Hz, 2H), 4.10-4.30 (m, 2H), 5.15 (d, J=6.7 Hz, 1H), 6.65 (s, 1H), 7.10-7.20 (m, 3H), 7.45-7.60 (m, 5H), 7.66 (d, J=6.0 Hz, 1H).

MS m/z ([M+H]$^+$) 296, ([M+Na]$^+$) 318.

Step 3: Preparation of intermediate ethyl 2-(tert-butoxy)-2-(1-phenyl-1H-indol-2-yl)acetate (5c)

A mixture of ethyl 2-hydroxy-2-(1-phenyl-1H-indol-2-yl)acetate (5b) (50 mg, 0.17 mmol), silver (I) oxide (130 mg, 0.56 mmol) and tertbutylbromide (114 µL, 1.02 mmol) in cyclohexane (4 mL) and dichloromethane (2 mL) was vigorously stirred for 24 hours. The reaction mixture was then filtered and concentrated in vacuo. The residue was purified by flash chromatography on silica gel (cyclohexane/ethyl acetate 95/5) to afford the desired ether oxide (5c) as a white solid (20 mg, 0.057 mmol, 33%).

$^1$H NMR (400 MHz, CDCl$_3$) δ 1.00 (s, 9H), 1.25 (t, J=7.1 Hz, 3H), 4.11-4.26 (m, 2H), 5.09 (s, 1H), 6.75 (s, 1H), 7.05-7.20 (m, 3H), 7.45-7.65 (m, 6H).

MS m/z ([M+Na]$^+$) 374.

Step 4: Preparation of sodium 2-(tert-butoxy)-2-(1-phenyl-1H-indol-2-yl)acetate A solution of ethyl 2-(tert-butoxy)-2-(1-phenyl-1H-indol-2-yl)acetate (5c) (20 mg, 0.057 mmol) and sodium hydroxide (15 mg, 0.27 mmol) in water (2 mL), in a mixture of tetrahydrofuran (2 mL) and ethanol (1 mL) was stirred at room temperature for 3 hours. The reaction mixture was diluted with water (10 mL) and washed with dichloromethane (10 mL). The aqueous layer was lyophilized to afford the desired product (example 5) as a white solid (15 mg, 0.042 mmol, 75%).

$^1$H NMR (400 MHz, DMSO-d$_6$) δ 0.81 (s, 9H), 4.57 (s, 1H), 6.47 (s, 1H), 7.00-7.05 (m, 3H), 7.45-7.65 (m, 5H).

MS m/z ([M+H]$^+$) 324.

Example 6

Synthesis of 2-(tert-butoxy)-2-[5-(3,4-dihydro-2H-1-benzopyran-6-yl)-2-phenyl-1,3-thiazol-4-yl]acetic acid

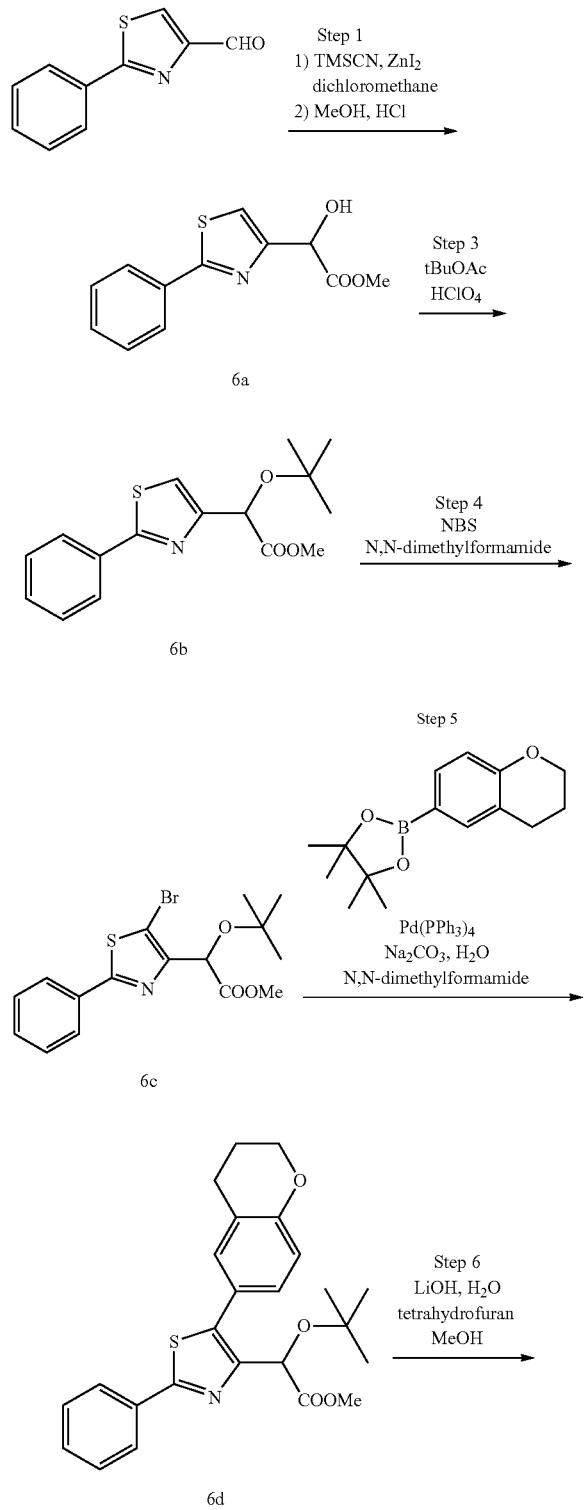

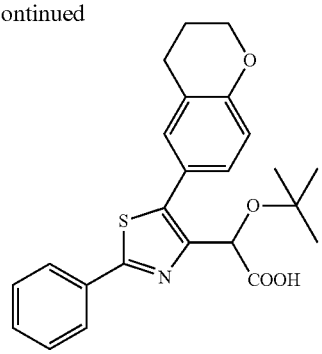

Example 6

Step 1 and Step 2: Preparation of intermediate methyl 2-hydroxy-2-(2-phenyl-1,3-thiazol-4-yl)acetate (6a)

Under a nitrogen atmosphere, trimethylsilylcyanide (824 µL, 6.6 mmol) was added at 0° C. to a solution of 2-phenyl-1,3-thiazole-4-carbaldehyde (1 g, 5.28 mmol) and zinc iodide (II) (166 mg, 0.52 mmol) in dichloromethane (30 mL). After 6 hours, the reaction mixture was quenched with a saturated aqueous solution of sodium bicarbonate and extracted with dichloromethane (2×20 mL). The organic layer was washed with brine (10 mL), dried over sodium sulfate, filtered, and evaporated under reduced pressure. The residue was used for the hydrolysis without further purification. Then, 2-(2-phenyl-1,3-thiazol-4-yl)-2-[(trimethylsilyl)oxy]acetonitrile was dissolved in anhydrous methanol (30 mL) and cooled at 0° C. and hydrogen chloride was bubbled for 2 minutes. The mixture was then warmed at room temperature for 20 h and concentrated under vacuum. A saturated solution of sodium bicarbonate (10 mL) was added to the residue and extracted with dichloromethane (2×15 mL). The organic layer was washed with brine (10 mL), dried over sodium sulfate, filtered, and evaporated under reduced pressure. The residue was purified by flash chromatography on silica gel (cyclohexane/ethyl acetate 70/30) to afford the desired alcohol (6a) as a white yellow oil (950 mg, 3.81 mmol, 72%).

$^1$H NMR (300 MHz, CDCl$_3$) δ 3.83 (s, 3H), 5.38 (s, 1H), 7.33 (s, 1H), 7.40-7.46 (m, 3H), 7.91-7.97 (m, 2H). MS m/z ([M+H]$^+$) 250.

Step 3: Preparation of intermediate methyl 2-(tert-butoxy)-2-(2-phenyl-1,3-thiazol-4-yl)acetate (6b)

Under a nitrogen atmosphere, perchloric acid (70%, 4 mL) was added at −10° C. to a solution of methyl 2-hydroxy-2-(2-phenyl-1,3-thiazol-4-yl)acetate (6a) (800 mg, 3.2 mmol) in terbutyl acetate (25 mL). After 1 hour, the reaction was quenched with a saturated solution of sodium bicarbonate (20 mL) and extracted with dichloromethane (2×20 mL). The organic layer was washed with brine (10 mL), dried over sodium sulfate, filtered and evaporated under reduced pressure. The residue was purified by flash chromatography on silica gel (cyclohexane/ethyl acetate 80/20) to afford the desired product (6b) as a white pale oil (410 mg, 1.34 mmol, 42%).

$^1$H NMR (400 MHz, CDCl$_3$) δ 1.31 (s, 9H), 3.79 (s, 3H), 5.40 (s, 1H), 7.38 (s, 1H), 7.39-7.45 (m, 3H), 7.91-7.97 (m, 2H).

MS m/z ([M+H]$^+$) 306.

Step 4: Preparation of intermediate methyl 2-(5-bromo-2-phenyl-1,3-thiazol-4-yl)-2-(tert-butoxy)acetate (6c)

Under a nitrogen atmosphere, N-bromosuccinimide (108 mg, 0.6 mmol) was added to a solution of methyl 2-(tert-butoxy)-2-(2-phenyl-1,3-thiazol-4-yl)acetate (6b) (30 mg, 0.1 mmol) in N,N-dimethylformamide (2 mL). The reaction mixture was warmed at 70° C. for 3 hours and ethyl acetate (20 mL) was then added. The organic layer was washed with water (2×10 mL), brine (10 mL), dried over sodium sulfate, filtered, and evaporated under reduced pressure. The residue was purified by flash chromatography on silica gel (cyclohexane/ethyl acetate 80/20) to afford the desired product (6c) as a yellow oil (30 mg, 0.078 mmol, 78%).

$^1$H NMR (400 MHz, CDCl$_3$) δ 1.31 (s, 9H), 3.77 (s, 3H), 5.37 (s, 1H), 7.39-7.43 (m, 3H), 7.86-7.91 (m, 2H). MS m/z ([M+H]$^+$) 384/386.

Step 5: Preparation of intermediate methyl 2-(tert-butoxy)-2-[5-(3,4-dihydro-2H-1-benzopyran-6-yl)-2-phenyl-1,3-thiazol-4-yl]acetate (6d)

Under a nitrogen atmosphere, sodium carbonate (8.5 mg, 0.08 mmol), water (500 μL), palladium tetrakis(triphenylphosphine) (13 mg, 0.012 mmol) and 6-(4,4,5,5-tetramethyl-1,3,2-dioxaborolan-2-yl)chroman (21 mg, 0.078 mmol) were added to a solution of methyl 2-(5-bromo-2-phenyl-1,3-thiazol-4-yl)-2-(tert-butoxy)acetate (30 mg, 0.078 mmol) in N,N-dimethylformamide (2 mL). The mixture was heated at 120° C. for 2 hours. The mixture was then cooled at room temperature and water (10 mL) was added. The aqueous layer was extracted with ethyl acetate (2×10 mL). The organic layer was washed with brine (10 mL), dried over sodium sulfate, filtered and evaporated under reduced pressure. The residue was purified by flash chromatography on silica gel (cyclohexane/ethyl acetate 90/10) to afford the desired product (6d) as a white solid (24 mg, 0.055 mmol, 70%).

$^1$H NMR (400 MHz, CDCl$_3$) δ 1.11 (s, 9H), 2.01-2.10 (m, 2H), 2.81-2.88 (m, 2H), 3.74 (s, 3H), 4.22-4.28 (m, 2H), 5.47 (s, 1H), 6.86 (d, J=8.3 Hz, 1H), 7.28-7.35 (m, 2H), 7.39-7.45 (m, 3H), 7.99-8.04 (m, 2H).

MS m/z ([M+H]$^+$) 438.

Step 6: Preparation of 2-(tert-butoxy)-2-[5-(3,4-dihydro-2H-1-benzopyran-6-yl)-2-phenyl-1,3-thiazol-4-yl]acetic acid A solution of methyl 2-(tert-butoxy)-2-[5-(3,4-dihydro-2H-1-benzopyran-6-yl)-2-phenyl-1,3-thiazol-4-yl]acetate (6d) (90 mg, 0.2 mmol) and potassium hydroxide (180 mg, 3.2 mmol) in water (2 mL), tetrahydrofuran (2 mL) and methanol (1 mL) was stirred at room temperature for 1 hour. Water (10 mL) was added to the reaction mixture which was washed with diethyl ether (10 mL). The aqueous layer was acidified to pH 2 with a hydrochloric acid aqueous solution 0.5N and extracted with dichloromethane (2×10 mL). The organic layer was washed with brine (10 mL), dried over Na$_2$SO$_4$, filtered, and evaporated under reduced pressure to afford the desired acid (example 6) as a white solid (66 mg, 0.15 mmol, 78%).

$^1$H NMR (400 MHz, CDCl$_3$) δ 1.27 (s, 9H), 1.95-2.14 (m, 2H), 2.78-2.97 (m, 2H), 4.22-4.28 (m, 2H), 5.29 (s, 1H), 6.87 (d, J=8.3 Hz, 1H), 7.27-7.36 (m, 2H), 7.39-7.46 (m, 3H), 7.89-7.96 (m, 2H).

MS m/z ([M+H]$^+$) 424.

MS m/z ([M−H]$^−$) 422.

Example 7

Synthesis of 2-(tert-butoxy)-2-(3,5-diphenylthiophen-2-yl)acetic acid

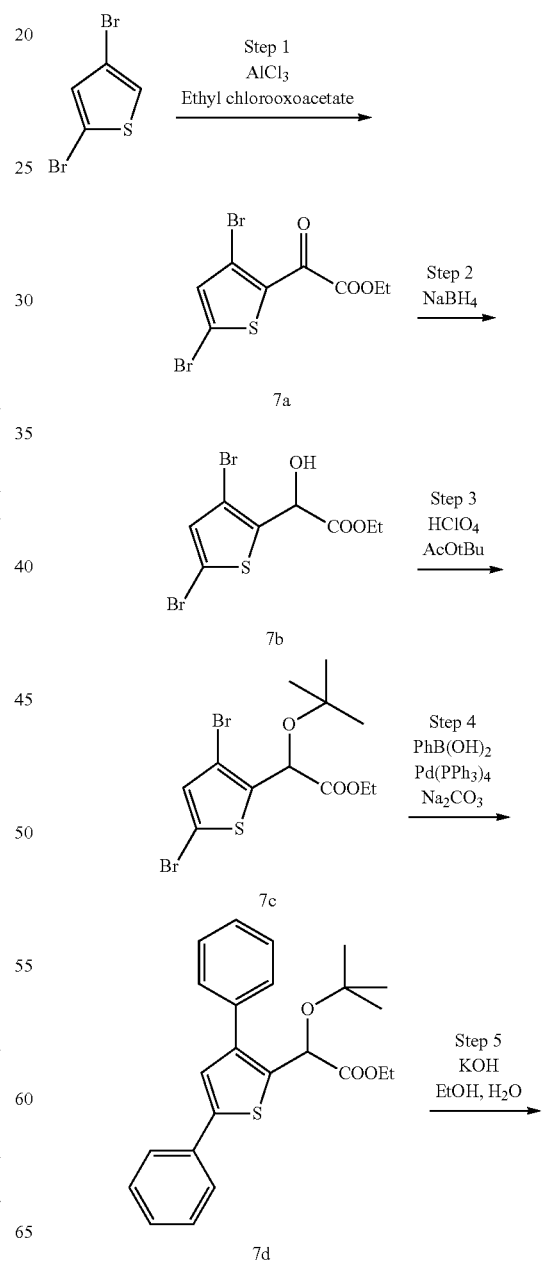

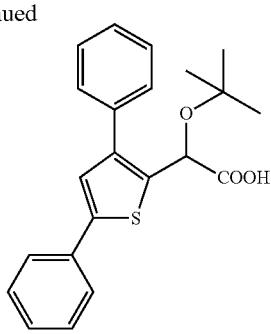

Example 7

Step 1: Preparation of intermediate ethyl 2-(3,5-dibromothiophen-2-yl)-2-oxoacetate (7a)

Aluminium chloride (0.26 g, 1.98 mmol) was added to a solution of 2,4-dibromothiophene (0.30 g, 1.24 mmol) and ethyl chlorooxoacetate (0.19 g, 1.36 mmol) in dichloromethane (10 mL) previously cooled with an ice bath. The reaction mixture was stirred at room temperature for 45 minutes, poured into ice water and extracted with dichloromethane (2×20 mL). The organic layer was dried over sodium sulfate, filtered and concentrated in vacuo to provide ethyl 2-(3,5-dibromothiophen-2-yl)-2-oxoacetate (0.42 g, 1.24 mmol, 100%) as a yellow oil.

$^1$H NMR (300 MHz, CDCl$_3$) δ 1.42 (t, J=7.2 Hz, 3H), 4.42 (q, J=7.2 Hz, 2H), 7.18 (s, 1H).

Step 2: Preparation of intermediate ethyl 2-(3,5-dibromothiophen-2-yl)-2-hydroxyacetate (7b)

Under a nitrogen atmosphere, sodium borohydride (0.14 g, 3.7 mmol) was added portionwise to a solution of ethyl 2-(3,5-dibromothiophen-2-yl)-2-oxoacetate (7a) (0.42 g, 1.24 mmol) in anhydrous tetrahydrofuran (10 mL), previously cooled to −10° C. After 30 minutes stirring, a few drops of 1 M hydrochloric acid were added and the resulting precipitate was filtered. The filtrate was concentrated in vavuo. The residue was dissolved in brine, and extracted with ethyl acetate (2×20 mL). The organic layer was dried over sodium sulfate, filtered, and evaporated to dryness. The residue was purified by flash chromatography on silica gel (cyclohexane/ethyl acetate: 80/20) to provide ethyl 2-(3,5-dibromothiophen-2-yl)-2-hydroxyacetate (0.32 g, 0.93 mmol, 75%).

$^1$H NMR (300 MHz, CDCl$_3$) δ 1.28 (t, J=7.1 Hz, 3H), 4.42 (d, J=4.4 Hz, 1H), 4.21-4.35 (m, 2H), 5.41 (d, J=4.4 Hz, 1H), 6.93 (s, 1H).

Step 3: Preparation of intermediate ethyl 2-(tert-butoxy)-2-(3,5-dibromothiophen-2-yl)acetate (7c)

Ethyl 2-(3,5-dibromothiophen-2-yl)-2-hydroxyacetate (7b) (100 mg, 0.29 mmol) was dissolved in tert-butyl acetate (5.4 mL) at −20° C. and 70% perchloric acid (0.7 mL) was rapidly added. The mixture was stirred at 0° C. for 3 hours then poured in a saturated solution of potassium carbonate. Layers were separated. The aqueous layer was extracted with ethyl acetate (2×20 mL). The organic layers were washed with brine (10 mL), dried over sodium sulfate and concentrated in vacuo. The residue was purified by flash chromatography on silica gel (cyclohexane/ethyl acetate 90/10) to provide ethyl 2-(tert-butoxy)-2-(3,5-dibromothiophen-2-yl)acetate (100 mg, 0.40 mmol, 86%).

$^1$H NMR (300 MHz, CDCl$_3$) δ 1.25 (s, 9H), 1.26 (t, J=7.1 Hz, 3H), 4.14-4.26 (m, 2H), 5.28 (s, 1H), 6.88 (s, 1H).

Step 4: Preparation of ethyl 2-(tert-butoxy)-2-(3,5-diphenylthiophen-2-yl)acetate (7d)

A solution of ethyl 2-(tert-butoxy)-2-(3,5-dibromothiophen-2-yl)acetate (100 mg, 0.25 mmol), phenylboronic acid (36 mg, 0.30 mmol) and sodium carbonate (106 mg, 1.00 mmol) in a mixture of toluene (1.26 mL), ethanol (0.6 mL) and water (0.5 mL) was bubbled with nitrogen for 5 minutes. Palladium tetrakis(triphenylphosphine) (14 mg, 0.01 mmol) was added and the reaction mixture was heated a 95° C. overnight. After cooling to room temperature, water (2 mL) was added. The aqueous layer was extracted with toluene (2×8 mL). The organic layers were washed with brine (5 mL), dried over sodium sulfate and concentrated in vacuo. The residue was purified by flash chromatography on silica gel (cyclohexane/ethyl acetate 80/20) to provide ethyl 2-(tert-butoxy)-2-(3,5-diphenylthiophen-2-yl)acetate (50 mg, 0.13 mmol, 51%).

$^1$H NMR (300 MHz, CDCl$_3$) δ 1.08 (s, 9H), 1.26 (t, J=7.1 Hz, 3H), 4.15-4.28 (m, 2H), 5.36 (s, 1H), 7.22 (s, 1H), 7.27-7.31 (m, 1H), 7.34-7.42 (m, 3H), 7.43-7.53 (m, 4H), 7.59-7.66 (m, 2H).

Step 5: Preparation of 2-(tert-butoxy)-2-(3,5-diphenylthiophen-2-yl)acetic acid A solution of ethyl 2-(tert-butoxy)-2-(3,5-diphenylthiophen-2-yl)acetate (7d) (50 mg, 0.13 mmol) and potassium hydroxide (62 mg, 0.51 mmol) in ethanol (1 mL) and water (3 mL) was refluxed for 60 minutes. The mixture was concentrated in vacuo. Water (10 mL) was added to the residue and the solution was washed with diethyl ether (10 mL). The aqueous layer was acidified with 37% hydrochloric acid until pH 2 and was extracted with ethyl acetate (2×10 mL). The organic layer was dried with sodium sulfate and concentrated in vacuo. The residue was triturated in pentane and evaporated to dryness to provide 2-(tert-butoxy)-2-(3,5-diphenylthiophen-2-yl)acetic acid (example 7) (40 mg, 0.11 mmol, 87%) as a white solid.

$^1$H NMR (300 MHz, CDCl$_3$) δ 1.07 (s, 9H), 5.39 (s, 1H), 7.23 (s, 1H), 7.28-7.34 (m, 1H), 7.35-7.51 (m, 5H), 7.58-7.65 (m, 4H).

Example 8

Synthesis of ethoxy-(1-methyl-2-phenyl-1H-indol-3-yl)-acetic acid

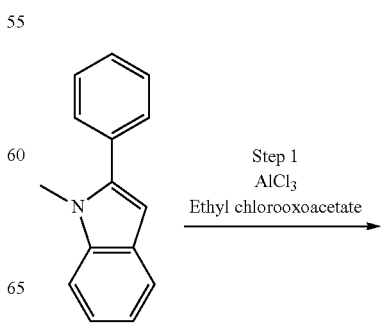

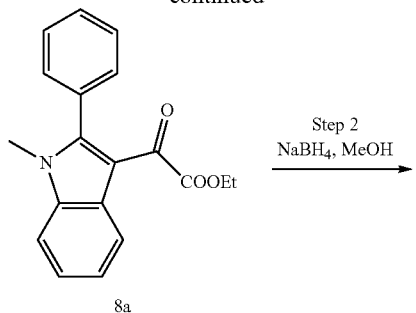

8a

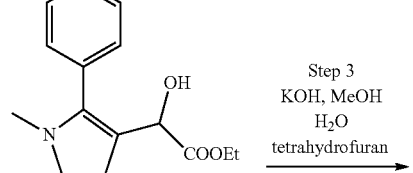

8b

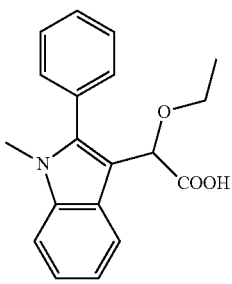

Example 8

Step 1: Preparation of intermediate ethyl (1-methyl-2-phenyl-1H-indol-3-yl)-oxo-acetate (8a)

At 0° C., aluminum (III) chloride (2.5 g, 19 mmol) was added per portion to a solution of 1-methyl-2-phenyl-1H-indole (1 g, 4.8 mmol) and ethyl chlorooxoacetate (900 µL, 8.05 mmol) in dichloromethane (10 mL). The mixture was stirred for 2 hours at 0° C. and then hydrolyzed with a saturated solution of sodium bicarbonate. After removing the aqueous layer, organic layer was washed with water, brine, dried over sodium sulfate, filtered and concentrated under reduced pressure. The residue was purified by flash chromatography on silica gel (cyclohexane/ethyl acetate 90/10) to afford the desired keto-ester (8a) (630 mg, 2.05 mmol, 43%).

$^1$H NMR (300 MHz, CDCl$_3$) δ 1.07 (t, J=7.2 Hz, 3H), 3.56 (q, J=7.2 Hz, 2H), 3.59 (s, 3H), 7.37-7.45 (m, 5H), 7.49-7.54 (m, 3H), 8.44-8.48 (m, 1H).

MS m/z ([M+H]$^+$) 308.

Step 2: Preparation of intermediate ethyl hydroxy-(1-methyl-2-phenyl-1H-indol-3-yl)-acetate (8b)

At 0° C., sodium tetraborohydride (78 mg, 2 mmol) was added to a solution of ethyl (1-methyl-2-phenyl-1H-indol-3-yl)-oxo-acetate (8a) (630 mg, 2.05 mmol) in a mixture of tetrahydrofuran (10 mL) and methanol (15 mL). The mixture was stirred at room temperature for 2 hours and then hydrolyzed with water. Methanol and tetrahydrofuran were removed under reduced pressure and the residue was diluted with dichloromethane. The organic layer was washed with water, brine, dried over sodium sulfate, filtered and concentrated in vacuo. The residue was purified by flash chromatography on silica gel (dichloromethane) to afford the desired alcohol (8b) (440 mg, 1.42 mmol, 69%).

$^1$H NMR (300 MHz, CDCl$_3$) δ 1.18 (t, J=7.2 Hz, 3H), 3.34 (d, J=4.6 Hz, 1H), 3.62 (s, 3H), 4.06-4.14 (m, 1H), 4.20-4.28 (m, 1H), 5.22 (d, J=4.6 Hz, 1H), 7.16 (t, J=7.6 Hz, 1H), 7.27 (t, J=7.6 Hz, 1H), 7.36 (d, J=8.1 Hz, 1H), 7.46-7.53 (m, 5H), 7.67 (d, J=8.1 Hz, 1H).

MS m/z ([M+H]$^+$) 310.

Step 3: Preparation of ethoxy-(1-methyl-2-phenyl-1H-indol-3-yl)-acetic acid

A solution of ethyl hydroxy-(1-methyl-2-phenyl-1H-indol-3-yl)-acetate (8b) (20 mg, 0.055 mmol) and potassium hydroxide (50 mg, 0.89 mmol) in a mixture of water (2 mL), tetrahydrofuran (2 mL) and methanol (0.5 mL) was stirred at 60° C. for 12 hours. Water (10 mL) was added to the reaction mixture which was washed with diethyl ether (10 mL). The aqueous layer was acidified to pH 2 with an aqueous solution of hydrochloric acid 0.5N and extracted with dichloromethane. The organic layer was washed with brine (10 mL), dried over sodium sulfate, filtered, and evaporated under reduced pressure. The residue was purified by preparative TLC (dichloromethane/ethanol) to afford unexpected ethoxy-(1-methyl-2-phenyl-1H-indol-3-yl)-acetic acid (example 8) (5.3 mg, 0.017 mmol, 31%).

$^1$H NMR (300 MHz, CDCl$_3$) δ 0.88 (t, J=7.2 Hz, 3H), 3.25-3.33 (m, 1H), 3.40-3.45 (m, 1H), 3.61 (s, 3H), 5.02 (s, 1H), 7.17 (t, J=7.6 Hz, 1H), 7.28 (t, J=7.6 Hz, 1H), 7.36 (d, J=8.1 Hz, 1H), 7.45-7.55 (m, 5H), 7.73 (d, J=8.1 Hz, 1H).

MS m/z ([M−H]$^−$) 308.

Example 9

Synthesis of 2-(tert-butoxy)-2-[4-(3,4-dihydro-2H-1-benzopyran-6-yl)-2-phenyl-1,3-thiazol-5-yl]acetic acid

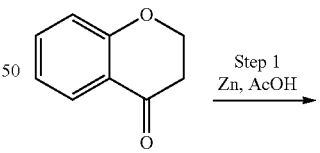

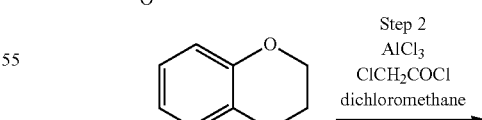

9a

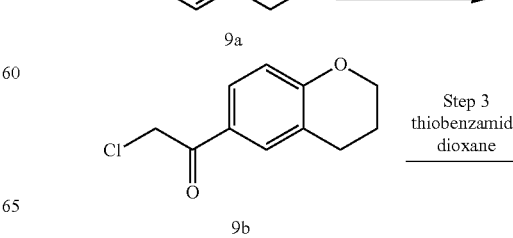

9b

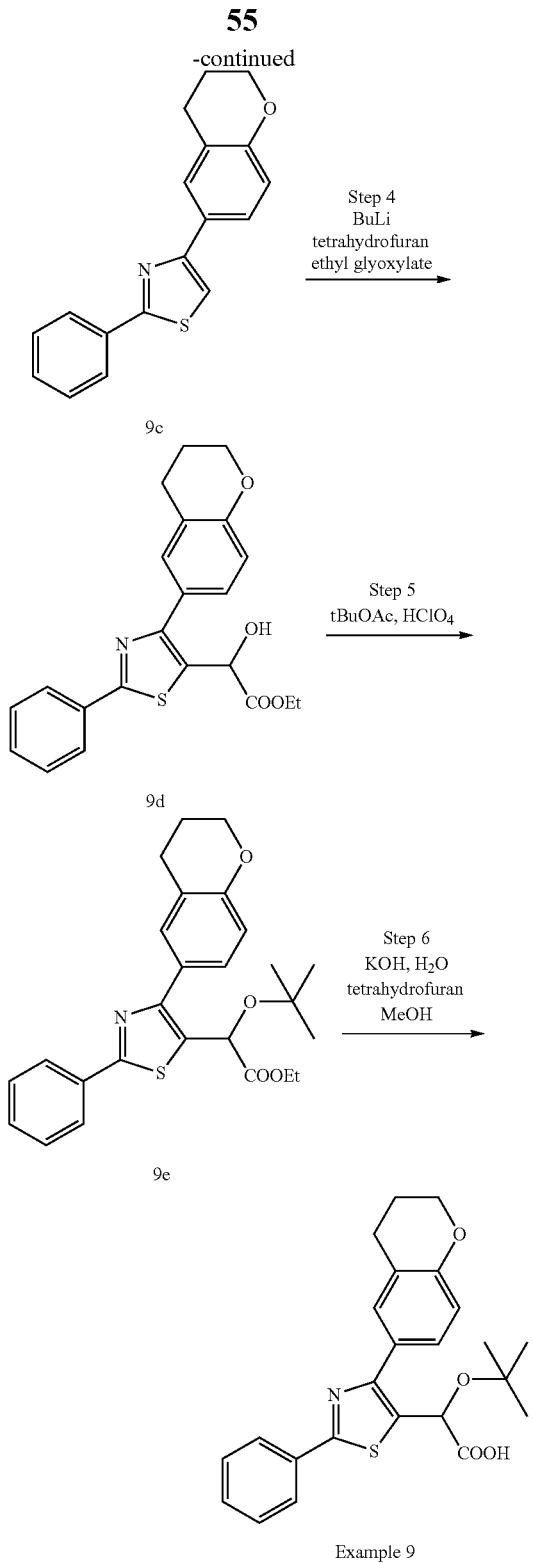

Example 9

Step 1: Preparation of intermediate 3,4-dihydro-2H-1-benzopyran (9a)

A suspension of chromanone (1 g, 6.75 mmol) and zinc powder (3.07 g, 47 mmol) in acetic acid (15 mL) was warmed at 100° C. for 15 hours. Residue of zinc was then removed by filtration on Celite®. The filtrate was concentrated under vacuum by co-evaporation with toluene to give the desired product (9a) without further purification (810 mg, 6.03 mmol, 89%).

$^1$H NMR (300 MHz, CDCl$_3$) δ 1.96-2.07 (m, 2H), 2.80 (t, J=6.5 Hz, 2H), 4.16-4.22 (m, 2H), 6.78-6.86 (m, 2H), 7.03-7.20 (m, 2H).

Step 2: Preparation of intermediate 2-chloro-1-(3,4-dihydro-2H-1-benzopyran-6-yl)ethan-1-one (9b)

Aluminium chloride (III) (1.9 g, 14.25 mmol) was added portion wise at 0° C. to a solution of 3,4-dihydro-2H-1-benzopyran (9a) (450 mg, 3.35 mmol) and 2-chloroacetyl chloride (270 μL, 3.4 mmol) in dichloromethane (10 mL). After 3 hours, the mixture was quenched by a saturated aqueous solution of sodium bicarbonate and extracted with ethyl acetate (3×20 mL). The organic layer was washed with brine, dried over sodium sulfate, filtered and evaporated under reduced pressure. The residue was purified by flash chromatography on silica gel (dichloromethane/cyclohexane 40/60) to afford the desired product (9b) as a white yellow oil (250 mg, 1.19 mmol, 35%).

$^1$H NMR (400 MHz, CDCl$_3$) δ 2.00-2.08 (m, 2H), 2.84 (t, J=6.5 Hz, 2H), 4.23-4.29 (m, 2H), 6.84 (d, J=9 Hz, 1H), 7.68-7.73 (m, 2H).

MS m/z ([M+H]$^+$) 211.

Step 3: Preparation of intermediate 4-(3,4-dihydro-2H-1-benzopyran-6-yl)-2-phenyl-1,3-thiazole (9c)

A solution of 2-chloro-1-(3,4-dihydro-2H-1-benzopyran-6-yl)ethan-1-one (9b) (250 mg, 1.19 mmol) and thiobenzamide (180 mg, 1.3 mmol) in dioxane (10 mL) was refluxed for 15 hours, then the reaction mixture was concentrated. The residue was diluted with dichloromethane (20 mL), washed with water (10 mL), brine (10 mL), dried over sodium sulfate, filtered and evaporated under reduced pressure. The residue was purified by flash chromatography on silica gel (dichloromethane/cyclohexane 60/40) to afford the desired thiazole (9c) as a white solid (330 mg, 1.12 mmol, 94%).

$^1$H NMR (400 MHz, CDCl$_3$) δ 2.00-2.10 (m, 2H), 2.88 (t, J=6.5 Hz, 2H), 4.20-4.26 (m, 2H), 6.84 (d, J=8.5 Hz, 1H), 7.31 (s, 1H), 7.40-7.44 (m, 3H), 7.66 (dd, J=2.2 and 8.5 Hz, 1H), 7.74 (d, J=2.2 Hz, 1H), 8.00-8.07 (m, 2H).

MS m/z ([M+H]$^+$) 294.

Step 4: Preparation of intermediate ethyl 2-[4-(3,4-dihydro-2H-1-benzopyran-6-yl)-2-phenyl-1,3-thiazol-5-yl]-2-hydroxyacetate (9d)

Butyl lithium (1.6M, 930 μL, 1.5 mmol) was added at −78° C. to a solution of 4-(3,4-dihydro-2H-1-benzopyran-6-yl)-2-phenyl-1,3-thiazole (9c) (330 mg, 1.12 mmol) in anhydrous tetrahydrofuran (10 mL). After 20 minutes, ethyl glyoxylate 50% in toluene (400 μL, 2 mmol) was added at −78° C. and the mixture was stirred for 2 hours, hydrolyzed with water and concentrated in vacuo. The residue was diluted with ethyl acetate (20 mL) and the organic layer was washed with water (10 mL), brine (10 mL), dried over sodium sulfate, filtered and evaporated under reduced pressure. The residue was purified by flash chromatography on silica gel (cyclohexane/ethyl acetate 80/20) to afford the desired alcohol (9d) as a white solid (130 mg, 0.33 mmol, 29%).

$^1$H NMR (400 MHz, CDCl$_3$) δ 1.27 (t, J=7.1 Hz, 3H), 2.00-2.10 (m, 2H), 2.87 (t, J=6.5 Hz, 2H), 3.56 (s, 1H), 4.21-4.35 (m, 4H), 5.53 (s, 1H), 6.87 (d, J=8.5 Hz, 1H), 7.42-7.44 (m, 3H), 7.50-7.52 (m, 2H), 7.96-7.98 (m, 2H).

MS m/z ([M+H]$^+$) 396.

Step 5: Preparation of intermediate ethyl 2-(tert-butoxy)-2-[4-(3,4-dihydro-2H-1-benzopyran-6-yl)-2-phenyl-1,3-thiazol-5-yl]acetate (9e)

Using the procedure described in example 6, step 3, the intermediate ethyl 2-[4-(3,4-dihydro-2H-1-benzopyran-6-yl)-2-phenyl-1,3-thiazol-5-yl]-2-hydroxyacetate (9d) (130 mg, 0.33 mmol) was converted, after purification by flash chromatography on silica gel (cyclohexane/ethyl acetate 90/10), to ethyl 2-(tert-butoxy)-2-[4-(3,4-dihydro-2H-1-benzopyran-6-yl)-2-phenyl-1,3-thiazol-5-yl]acetate (9e) (25 mg, 0.055 mmol, 17%) as a white solid.

$^1$H NMR (400 MHz, CDCl$_3$) δ 1.11 (s, 9H), 1.29 (t, J=7.1 Hz, 3H), 2.03-2.08 (m, 2H), 2.79-2.94 (m, 2H), 4.20-4.30 (m, 4H), 5.42 (s, 1H), 6.89 (d, J=8.5 Hz, 1H), 7.40-7.47 (m, 5H), 7.96-7.98 (m, 2H).

MS m/z ([M+H]$^+$) 452.

Step 6: Preparation of 2-(tert-butoxy)-2-[4-(3,4-dihydro-2H-1-benzopyran-6-yl)-2-phenyl-1,3-thiazol-5-yl]acetic acid A solution of ethyl 2-(tert-butoxy)-2-[4-(3,4-dihydro-2H-1-benzopyran-6-yl)-2-phenyl-1,3-thiazol-5-yl]acetate (9e) (25 mg, 0.055 mmol) and potassium hydroxide (50 mg, 0.89 mmol) in a mixture of water (2 mL), tetrahydrofuran (2 mL) and methanol (300 μL) was stirred at 60° C. for 1 hour and then concentrated in vacuo. Water (10 mL) was added and the aqueous layer was acidified to pH 2 with a hydrochloric acid aqueous solution 0.1N. After extraction of the aqueous layer with dichloromethane (2×10 mL), the organic layer was washed with brine (10 mL), dried over sodium sulfate, filtered and evaporated under reduced pressure to afford the desired acid (example 9) as a white solid (22 mg, 0.052 mmol, 94%).

$^1$H NMR (300 MHz, CDCl$_3$) δ 1.10 (s, 9H), 2.00-2.09 (m, 2H), 2.80-2.93 (m, 2H), 4.21-4.27 (m, 2H), 5.48 (s, 1H), 6.89 (d, J=8.5 Hz, 1H), 7.40-7.43 (m, 3H), 7.54-7.59 (m, 3H), 7.96-7.98 (m, 2H).

MS m/z ([M+H]$^+$) 424.
MS m/z ([M−H]$^−$) 422.

Example 10

Synthesis of 2-(tert-butoxy)-2-[3-(3,4-dihydro-2H-1-benzopyran-6-yl)-5-phenylthiophen-2-yl]acetic acid

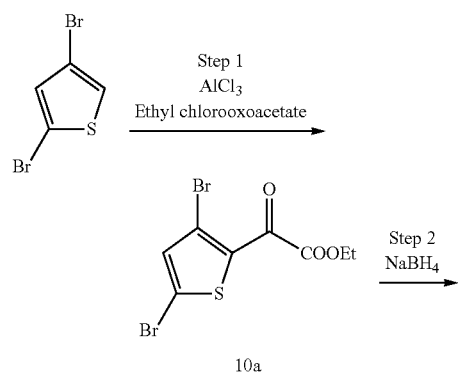

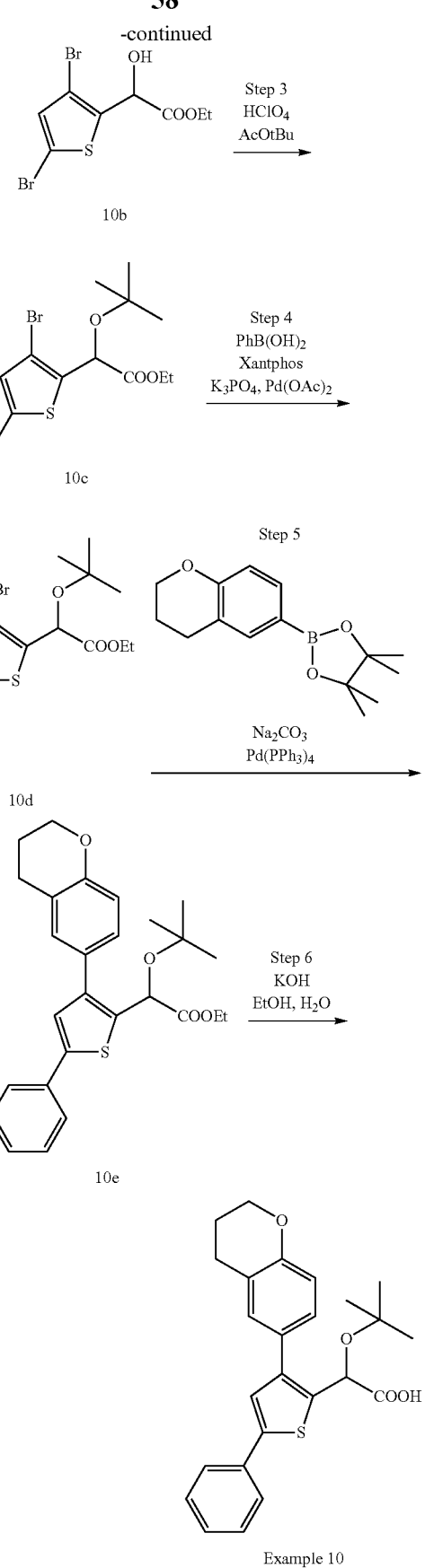

Example 10

Step 1: Preparation of intermediate ethyl 2-(3,5-dibromothiophen-2-yl)-2-oxoacetate (10a)

Aluminium chloride (0.26 g, 1.98 mmol) was added to a solution of 2,4-dibromothiophene (0.30 g, 1.24 mmol) and ethyl chlorooxoacetate (0.19 g, 1.36 mmol) in dichloromethane (10 mL) previously cooled with an ice bath. The reaction mixture was stirred at room temperature 45 minutes, poured into ice water and extracted with dichloromethane (2×20 mL). The organic layer was dried over sodium sulfate, filtered and concentrated in vacuo to provide the desired keto-ester (10a) (0.42 g, 1.24 mmol, 100%) as a yellow oil.

$^1$H NMR (300 MHz, CDCl$_3$) δ 1.42 (t, J=7.2 Hz, 3H), 4.42 (q, J=7.2 Hz, 2H), 7.18 (s, 1H).

Step 2: Preparation of intermediate ethyl 2-(3,5-dibromothiophen-2-yl)-2-hydroxyacetate (10b)

Under a nitrogen atmosphere, sodium borohydride (0.14 g, 3.7 mmol) was added portionwise to a solution of ethyl 2-(3,5-dibromothiophen-2-yl)-2-oxoacetate (10a) (0.42 g, 1.24 mmol) in anhydrous tetrahydrofuran (10 mL), previously cooled to −10° C. After 30 minutes stirring, a few drops of 1 M hydrochloric acid were added and the resulting precipitate was filtered. The filtrate was concentrated in vavuo. The residue was dissolved in brine, and extracted with ethyl acetate (2×20 mL). The organic layer was dried over sodium sulfate, filtered, and evaporated to dryness. The residue was purified by flash chromatography on silica gel (cyclohexane/ethyl acetate 80/20) to provide the desired alcohol (10b) (0.32 g, 0.93 mmol, 75%).

$^1$H NMR (300 MHz, CDCl$_3$) δ 1.28 (t, J=7.1 Hz, 3H), 4.42 (d, J=4.5 Hz, 1H), 4.21-4.35 (m, 2H), 5.41 (d, J=4.4 Hz, 1H) 6.93 (s, 1H).

Step 3: Preparation of intermediate ethyl 2-(tert-butoxy)-2-(3,5-dibromothiophen-2-yl)acetate (10c)

Ethyl 2-(3,5-dibromothiophen-2-yl)-2-hydroxyacetate (10b) (160 mg, 0.47 mmol) was dissolved in tert-butyl acetate (8.7 mL) at −20° C. and 70% perchloric acid (1.1 mL) was rapidly added. The mixture was stirred at 0° C. for 3 hours then poured in a saturated solution of potassium carbonate. Layers were separated. The aqueous layer was extracted with ethyl acetate (2×20 mL). The organic layers were washed with brine (10 mL), dried over sodium sulfate and concentrated in vacuo. The residue was purified by flash chromatography on silica gel (cyclohexane/ethyl acetate 90/10) to provide the desired product (10c) (160 mg, 0.40 mmol, 86%).

$^1$H NMR (300 MHz, CDCl$_3$) δ 1.25 (s, 9H), 1.26 (t, J=7.1 Hz, 3H), 4.14-4.26 (m, 2H), 5.28 (s, 1H), 6.88 (s, 1H).

Step 4: Preparation of intermediate ethyl 2-(3-bromo-5-phenylthiophen-2-yl)-2-(tert-butoxy)acetate (10d)

To a solution of ethyl 2-(tert-butoxy)-2-(3,5-dibromothiophen-2-yl)acetate (10c) (70 mg, 0.17 mmol) in tetrahydrofuran (1 mL) were added tripotassium phosphate (111 mg, 0.52 mmol), phenylboronic acid (23 mg, 0.19 mmol) and a solution of palladium acetate (1.2 mg, 5.2 μmol) and xantphos (3.0 mg, 5.2 μmol) in tetrahydrofuran (1 mL) previously stirred for 5 minutes. The reaction mixture was heated at 60° C. for 3 hours. The mixture was then filtered and the precipitate was rinsed with dichloromethane (5 mL). The filtrate was concentrated in vacuo. The residue was purified by flash chromatography (cyclohexane/ethyl acetate 80/20) to provide the desired product (10d) (45 mg, 0.11 mmol, 65%).

$^1$H NMR (300 MHz, CDCl$_3$) δ 1.27 (t, J=7.1 Hz, 3H), 1.29 (s, 9H), 4.16-4.28 (m, 2H), 5.37 (s, 1H), 7.12 (s, 1H), 7.30-7.41 (m, 3H), 7.52-7.57 (m, 2H).

Step 5: Preparation of intermediate ethyl 2-(tert-butoxy)-2-[3-(3,4-dihydro-2H-1-benzopyran-6-yl)-5-phenylthiophen-2-yl]acetate (10e)

A solution of ethyl 2-(3-bromo-5-phenylthiophen-2-yl)-2-(tert-butoxy)acetate (10d) (86 mg, 0.22 mmol), 6-(4,4,5,5-tetramethyl-1,3,2-dioxaborolan-2-yl)chroman (101 mg, 0.39 mmol) and sodium carbonate (92 mg, 0.87 mmol) in a mixture of toluene (1.26 mL), ethanol (0.6 mL) and water (0.5 mL) was bubbled with nitrogen for 5 minutes. Palladium tetrakis(triphenylphosphine) (12 mg, 0.01 mmol) was added and the reaction mixture was heated at 95° C. overnight. After cooling to room temperature, water (2 mL) was added. The aqueous layer was extracted with toluene (2×8 mL). The organic layers were washed with brine (5 mL), dried over sodium sulfate and concentrated in vacuo. The residue was purified by flash chromatography on silica gel (cyclohexane/ethyl acetate 80/20) to provide the desired product (10e) (80 mg, 0.18 mmol, 82%).

$^1$H NMR (300 MHz, CDCl$_3$) δ 1.11 (s, 9H), 1.27 (t, J=7.1 Hz, 3H), 2.01-2.11 (m, 2H), 2.80-2.89 (m, 2H), 4.17-4.28 (m, 4H), 5.34 (s, 1H), 7.14-7.22 (m, 3H), 7.23-7.30 (m, 2H), 7.32-7.40 (m, 2H), 7.58-7.63 (m, 2H).

Step 6: Preparation of 2-(tert-butoxy)-2-[3-(3,4-dihydro-2H-1-benzopyran-6-yl)-5-phenylthiophen-2-yl] acetic acid A solution of ethyl 2-(tert-butoxy)-2-[3-(3,4-dihydro-2H-1-benzopyran-6-yl)-5-phenylthiophen-2-yl]acetate (10e) (80 mg, 0.18 mmol) and potassium hydroxide (87 mg, 0.71 mmol) in ethanol (2 mL) and water (6 mL) was refluxed for 60 minutes. The mixture was concentrated in vacuo. Water (10 mL) was added to the residue and the solution was washed with diethyl ether (10 mL). The aqueous layer was acidified with 37% hydrochloric acid until pH 2 and was extracted with ethyl acetate (2×10 mL). The organic layer was dried with sodium sulfate and concentrated in vacuo. The residue was purified by preparative TLC (dichloromethane/methanol 95/5) to provide the desired acid (example 10) (27 mg, 0.06 mmol, 36%) as a white solid.

$^1$H NMR (300 MHz, CDCl$_3$) δ 1.10 (s, 9H), 2.01-2.10 (m, 2H), 2.81-2.89 (m, 2H), 4.24 (t, J=5.2 Hz, 2H), 5.39 (s, 1H), 6.86 (d, J=8.3 Hz, 1H), 7.18 (s, 1H), 7.28-7.41 (m, 5H), 7.57-7.62 (m, 2H).

Example 11

Synthesis of 2-(tert-butoxy)-2-[2-(3,4-dihydro-2H-1-benzopyran-6-yl)-5-phenylthiophen-3-yl]acetic acid

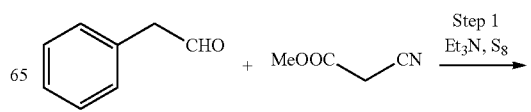

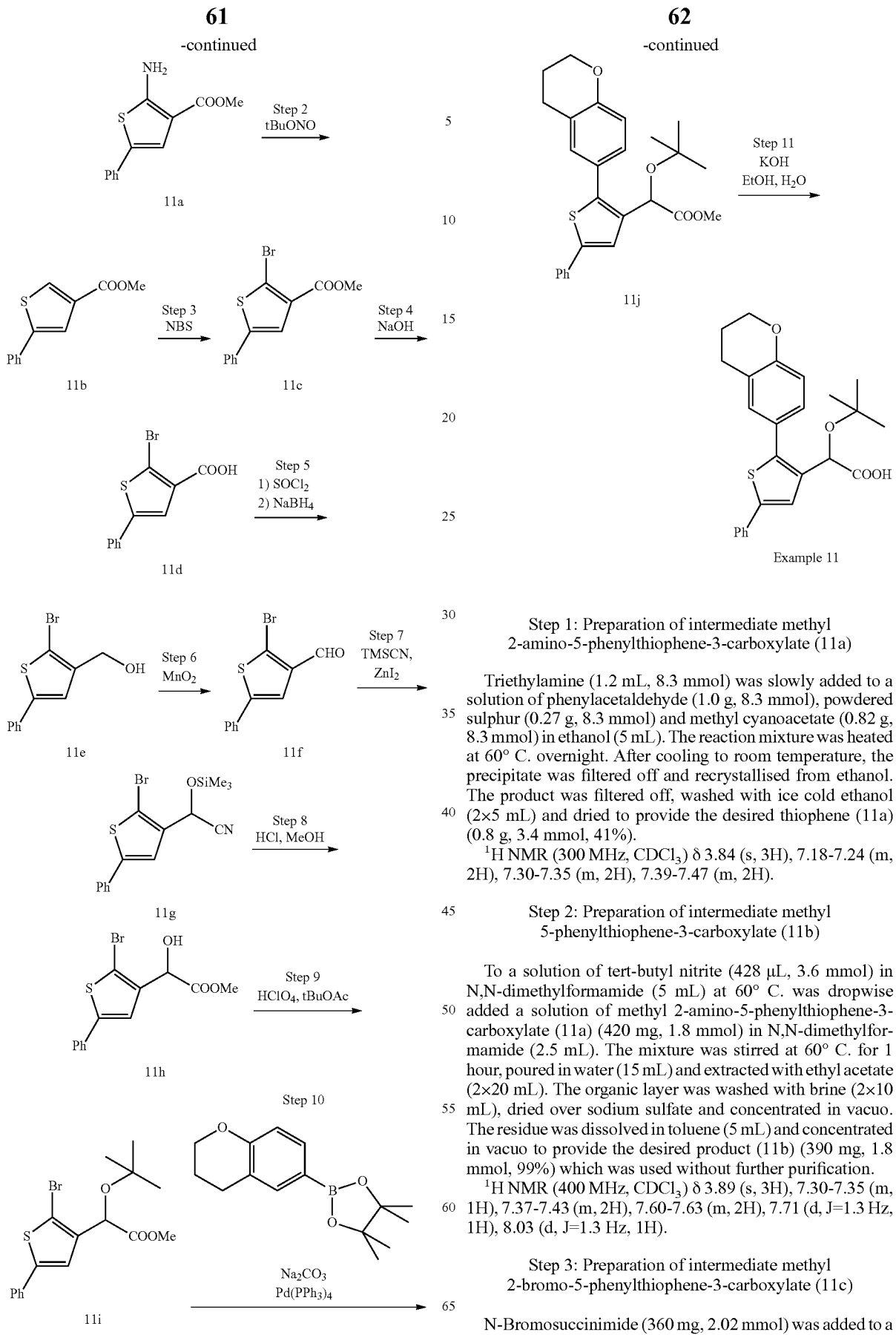

Step 1: Preparation of intermediate methyl 2-amino-5-phenylthiophene-3-carboxylate (11a)

Triethylamine (1.2 mL, 8.3 mmol) was slowly added to a solution of phenylacetaldehyde (1.0 g, 8.3 mmol), powdered sulphur (0.27 g, 8.3 mmol) and methyl cyanoacetate (0.82 g, 8.3 mmol) in ethanol (5 mL). The reaction mixture was heated at 60° C. overnight. After cooling to room temperature, the precipitate was filtered off and recrystallised from ethanol. The product was filtered off, washed with ice cold ethanol (2×5 mL) and dried to provide the desired thiophene (11a) (0.8 g, 3.4 mmol, 41%).

$^1$H NMR (300 MHz, CDCl$_3$) δ 3.84 (s, 3H), 7.18-7.24 (m, 2H), 7.30-7.35 (m, 2H), 7.39-7.47 (m, 2H).

Step 2: Preparation of intermediate methyl 5-phenylthiophene-3-carboxylate (11b)

To a solution of tert-butyl nitrite (428 µL, 3.6 mmol) in N,N-dimethylformamide (5 mL) at 60° C. was dropwise added a solution of methyl 2-amino-5-phenylthiophene-3-carboxylate (11a) (420 mg, 1.8 mmol) in N,N-dimethylformamide (2.5 mL). The mixture was stirred at 60° C. for 1 hour, poured in water (15 mL) and extracted with ethyl acetate (2×20 mL). The organic layer was washed with brine (2×10 mL), dried over sodium sulfate and concentrated in vacuo. The residue was dissolved in toluene (5 mL) and concentrated in vacuo to provide the desired product (11b) (390 mg, 1.8 mmol, 99%) which was used without further purification.

$^1$H NMR (400 MHz, CDCl$_3$) δ 3.89 (s, 3H), 7.30-7.35 (m, 1H), 7.37-7.43 (m, 2H), 7.60-7.63 (m, 2H), 7.71 (d, J=1.3 Hz, 1H), 8.03 (d, J=1.3 Hz, 1H).

Step 3: Preparation of intermediate methyl 2-bromo-5-phenylthiophene-3-carboxylate (11c)

N-Bromosuccinimide (360 mg, 2.02 mmol) was added to a solution of methyl 5-phenylthiophene-3-carboxylate (11b)

(440 mg, 2.02 mmol) in a mixture of N,N-dimethylformamide (4 mL) and tetrahydrofuran (4 mL). The reaction mixture was stirred at room temperature for 1 hour. N-Bromosuccinimide (72 mg, 0.40 mmol) was added and the stirring was maintained for 1 hour. The mixture was poured in water (10 mL) and extracted with dichloromethane (2×15 mL). The organic layer was dried over sodium sulfate, filtered, and concentrated in vacuo. The residue was purified by flash chromatography on silica gel (cyclohexane/ethyl acetate 90/10) to provide the desired product (11c) (390 mg, 1.3 mmol, 65%).

$^1$H NMR (400 MHz, CDCl$_3$) δ 3.90 (s, 3H), 7.31-7.36 (m, 1H), 7.37-7.42 (m, 2H), 7.51-7.54 (m, 2H), 7.55 (s, 1H).

Step 4: Preparation of intermediate 2-bromo-5-phenylthiophene-3-carboxylic acid (11d)

A solution of methyl 2-bromo-5-phenylthiophene-3-carboxylate (11c) (290 mg, 0.97 mmol) and sodium hydroxide (156 mg, 3.90 mmol) in a mixture of ethanol (6 mL) and water (2 mL) was refluxed for 30 minutes. The mixture was concentrated in vacuo. The remained aqueous layer was washed with diethyl ether (5 mL), acidified with 1N hydrochloric acid until pH 3 and was extracted with dichloromethane (2×10 mL). The organic layer was dried over sodium sulfate and concentrated in vacuo to provide the desired acid (11d) (260 mg, 0.92 mmol, 95%), which was used without further purification.

MS m/z ([M−H]$^-$) 283/281.

Step 5: Preparation of intermediate (2-bromo-5-phenylthiophen-3-yl)methanol (11e)

Under a nitrogen atmosphere, a suspension of 2-bromo-5-phenylthiophene-3-carboxylic acid (11d) (260 mg, 0.92 mmol) in thionyl chloride (2 mL) was refluxed for 30 minutes. The reaction mixture was concentrated in vacuo and co-evaporated with toluene to provide an oil which was slowly added to a solution of sodium borohydride (81 mg, 0.92 mmol) in anhydrous dimethoxyethane (8 mL) under a nitrogen atmosphere at 10° C. After stirring at room temperature for 30 minutes, the reaction mixture was concentrated in vacuo. Water (8 mL) was added to the residue, followed by acetic acid (1.5 mL) to ensure sodium borohydride decomposition. The mixture was basified with 28% ammonium hydroxide until pH 8 and extracted with ethyl dichloromethane (2×10 mL). The organic layer was dried over sodium sulfate, filtered and evaporated to dryness to provide the desired alcohol (11e) (220 mg, 0.82 mmol, 89%) as a pink oil, which was used without further purification.

$^1$H NMR (300 MHz, CDCl$_3$) δ 4.64 (s, 2H), 7.23 (s, 1H), 7.29-7.41 (m, 3H), 7.49-7.54 (m, 2H).

Step 6: Preparation of intermediate 2-bromo-5-phenylthiophene-3-carbaldehyde (11f)

A solution of (2-bromo-5-phenylthiophen-3-yl)methanol (11e) (220 mg, 0.83 mmol) and manganese dioxide (720 mg, 8.3 mmol) in dichloromethane (3 mL) was stirred at room temperature for 160 minutes. The reaction mixture was filtered over Celite® and the filtrate was evaporated to dryness to provide the desired aldehyde (11f) (180 mg, 0.67 mmol, 81%), which was used without further purification.

$^1$H NMR (300 MHz, CDCl$_3$) δ 7.33-7.45 (m, 3H), 7.50-7.56 (m, 3H), 9.93 (s, 1H).

Step 7: Preparation of intermediate 2-(2-bromo-5-phenylthiophen-3-yl)-2-[(trimethylsilyl)oxy]acetonitrile (11g)

Under a nitrogen atmosphere, zinc iodide (21 mg, 0.07 mmol) and trimethylsilylcyanide (790 µL, 0.81 mmol) were successively added to a solution of 2-bromo-5-phenylthiophene-3-carbaldehyde (11f) (180 mg, 0.67 mmol) in anhydrous dichloromethane (5 mL) previously cooled at 0° C. The mixture was stirred at room temperature for 75 minutes. A saturated solution of sodium bicarbonate (5 mL) was added and the organic layers were dried over sodium sulfate and evaporated to dryness to provide the desired product (11g) (230 mg, 0.63 mmol, 93%), which was used without further purification.

$^1$H NMR (300 MHz, CDCl$_3$) δ 0.25 (s, 9H), 5.52 (s, 1H), 7.32-7.43 (m, 4H), 7.51-7.55 (m, 2H).

Step 8: Preparation of intermediate methyl 2-(2-bromo-5-phenylthiophen-3-yl)-2-hydroxyacetate (11h)

Anhydrous methanol (10 mL) was cooled at 0° C. and bubbled for 5 minutes with hydrogen chloride. 2-(2-bromo-5-phenylthiophen-3-yl)-2-[(trimethylsilyl)oxy]acetonitrile (11g) (230 mg, 0.63 mmol) was added. The mixture was then warmed at room temperature for 5 minutes and concentrated in vacuo. A saturated solution of NaHCO$_3$ (10 mL) was added to the residue and extracted with ethyl acetate (2×10 mL). The organic layer was dried over sodium sulfate and evaporated to dryness to provide the desired ester (11h) (160 mg, 0.49 mmol, 78%) which was used without further purification.

$^1$H NMR (300 MHz, CDCl$_3$) δ 3.77 (s, 3H), 5.22 (s, 1H), 7.02 (s, 1H), 7.30-7.40 (m, 3H), 7.47-7.52 (m, 2H).

Step 9: Preparation of intermediate methyl 2-(2-bromo-5-phenylthiophen-3-yl)-2-(tert-butoxy)acetate (11i)

Methyl 2-(2-bromo-5-phenylthiophen-3-yl)-2-hydroxyacetate (11h) (75 mg, 0.23 mmol) was dissolved in tert-butyl acetate (8.6 mL) at 0° C. and 70% perchloric acid (1.1 mL) was rapidly added. The mixture was stirred at 0° C. for 30 minutes then poured in a saturated solution of potassium carbonate. Layers were separated. The aqueous layer was extracted with ethyl acetate (2×15 mL). The organic layers were washed with brine (8 mL), dried over sodium sulfate and concentrated in vacuo to provide the desired product (11i) (77 mg, 0.20 mmol, 87%) which was used without further purification.

$^1$H NMR (300 MHz, CDCl$_3$) δ 1.26 (s, 9H), 3.73 (s, 3H), 5.17 (s, 1H), 7.27-7.40 (m, 4H), 7.48-7.54 (m, 2H).

Step 10: Preparation of intermediate methyl 2-(tert-butoxy)-2-[2-(3,4-dihydro-2H-1-benzopyran-6-yl)-5-phenylthiophen-3-yl]acetate (11j)

A solution of methyl 2-(2-bromo-5-phenylthiophen-3-yl)-2-(tert-butoxy)acetate (11i) (77 mg, 0.20 mmol), 6-(4,4,5,5-tetramethyl-1,3,2-dioxaborolan-2-yl)chroman (94 mg, 0.36 mmol) and sodium carbonate (85 mg, 0.80 mmol) in a mixture of toluene (1.26 mL), ethanol (0.6 mL) and water (0.5 mL) was bubbled with nitrogen for 5 minutes. Palladium tetrakis(triphenylphosphine) (12 mg, 0.01 mmol) was added and the reaction mixture was heated a 95° C. for 4 h. After cooling to room temperature, water (2 mL) was added. The aqueous layer was extracted with toluene (2×8 mL). The organic layers were washed with brine (5 mL), dried over sodium sulfate and concentrated in vacuo. The residue was purified by flash chromatography on silica gel (cyclohexane/ethyl acetate 85/15) to provide the desired product (11j) (60 mg, 0.14 mmol, 68%).

$^1$H NMR (300 MHz, CDCl$_3$) δ 1.06 (s, 9H), 2.02-2.10 (m 2H), 2.82-2.89 (m 2H), 3.77 (s, 3H), 4.23-4.26 (m, 2H), 5.16 (s, 1H), 6.87 (d, J=8.4 Hz, 1H), 7.23-7.38 (m, 5H), 7.46 (s, 1H), 7.58-7.63 (m, 2H).

Step 11: Preparation of 2-(tert-butoxy)-2-[2-(3,4-dihydro-2H-1-benzopyran-6-yl)-5-phenylthiophen-3-yl]acetic acid A solution of methyl 2-(tert-butoxy)-2-[2-(3,4-dihydro-2H-1-benzopyran-6-yl)-5-phenylthiophen-3-yl]acetate (11j) (57 mg, 0.13 mmol) and potassium hydroxide (64 mg, 0.52 mmol) in a mixture of ethanol (2 mL) and water (6 mL) was refluxed for 4 hours. The mixture was concentrated in vacuo. Water (5 mL) was added and the aqueous layer was washed with diethyl ether (5 mL), then extracted with dichloromethane (5 mL). The organic layer was washed with 1N hydrochloric acid (5 mL), dried over sodium sulfate and evaporated to dryness to provide the desired acid (45 mg, 0.11 mmol, 81%) as a white solid.

$^1$H NMR (400 MHz, CDCl$_3$) δ 1.06 (s, 9H), 2.02-2.08 (m 2H), 2.83-2.88 (m 2H), 4.23-4.26 (m, 2H), 5.17 (s, 1H), 6.87 (d, J=8.4 Hz, 1H), 7.26-7.30 (m, 2H), 7.35-7.42 (m, 4H), 7.57-7.61 (m, 2H).

MS m/z ([M−H]$^-$) 421.

Example 12

Synthesis of 2-[2-(3,4-dihydro-2H-1-benzopyran-6-yl)-1-methyl-1H-indol-3-yl]pentanoic acid

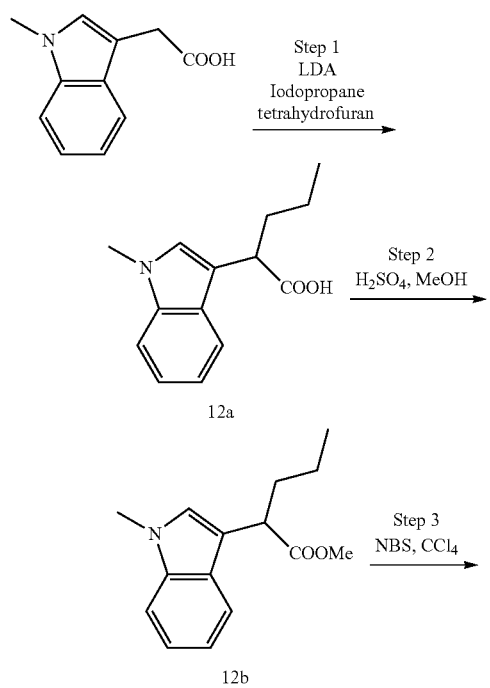

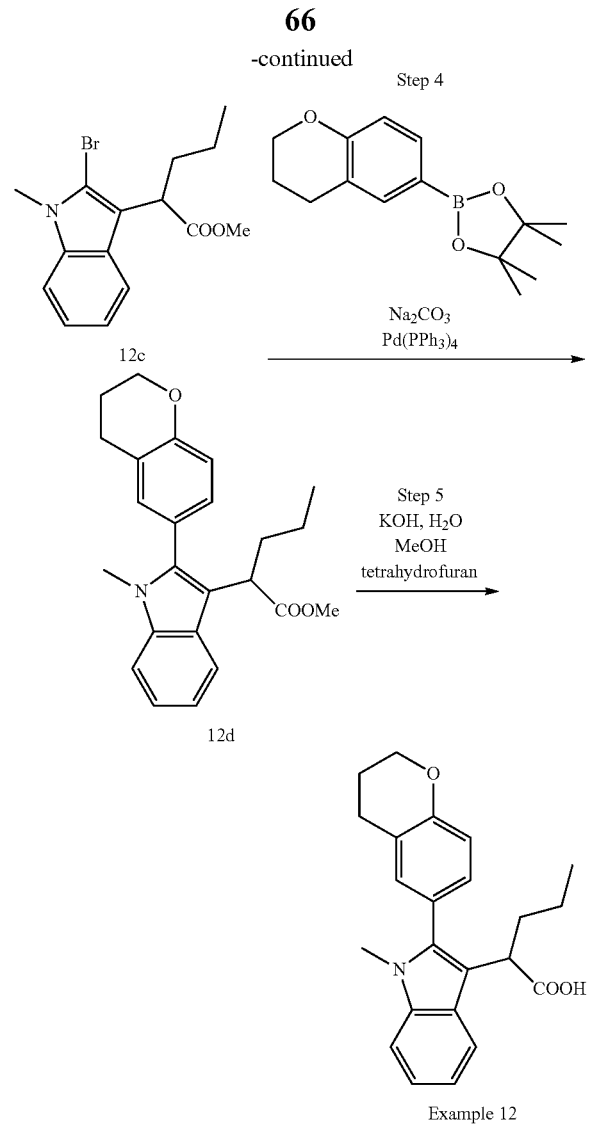

Example 12

Step 1: Preparation of intermediate 2-(1-methyl-1H-indol-3-yl)pentanoic acid (12a)

Under a nitrogen atmosphere, butyl lithium (1.6M, 10 mL, 16 mmol) was added at −78° C. to a solution of diisopropylamine (2.22 mL, 15.84 mmol) in anhydrous tetrahydrofurane. After 25 minutes, a solution of 1-methyl-3-indoleacetic acid (1 g, 5.28 mmol) in tetrahydrofurane (20 mL) was slowly added at −78° C., followed by the addition of propyliodide (1 mL, 10 mmol) after 45 minutes. The mixture was then warmed to room temperature and stirred for 2 hours. The mixture was quenched with water (2 mL) and concentrated in vacuo. The residue was diluted with water (20 mL) and washed with diethyl ether (20 mL). The organic layer was acidified with hydrochloric acid aqueous solution 1N to pH 3 and extracted with dichloromethane (3×10 mL). The organic layer was washed with brine, dried over sodium sulfate, filtered and evaporated under reduced pressure to afford the desired acid (12a) as a brown solid without further purification (1.22 g, 5.28 mmol, 100%).

MS m/z ([M+H]$^+$) 232.

MS m/z ([M−H]$^-$) 230.

Step 2: Preparation of intermediate methyl 2-(1-methyl-1H-indol-3-yl)pentanoate (12b)

A mixture of 2-(1-methyl-1H-indol-3-yl)pentanoic acid (12a) (1.22 g, 5.28 mmol) and concentrated sulfuric acid (1 mL) in methanol (40 mL) was refluxed for 3 hours. After concentration, the mixture was quenched with a saturated aqueous solution of sodium carbonate and the aqueous layer was extracted with dichloromethane (2×20 mL). The organic layer was dried over sodium sulfate, filtered and evaporated under reduced pressure. The residue was purified by flash chromatography on silica gel (cyclohexane/ethyl acetate 93/7) to afford the desired ester (12b) as a white solid (910 mg, 3.71 mmol, 70%).

$^1$H NMR (400 MHz, CDCl$_3$) δ 0.94 (t, J=7.3 Hz, 3H), 1.31-1.42 (m, 2H), 1.83-1.94 (m, 1H), 2.04-2.17 (m, 1H), 3.66 (s, 3H), 3.76 (s, 3H), 3.89 (t, J=7.6 Hz, 1H), 7.02 (s, 1H), 7.12 (t, J=7.4 Hz, 1H), 7.21 (t, J=7.4 Hz, 1H), 7.30 (d, J=8.0 Hz, 1H), 7.68 (d, J=8.0 Hz, 1H).

MS m/z ([M+H]$^+$) 246.

Step 3: Preparation of intermediate methyl 2-(2-bromo-1-methyl-1H-indol-3-yl)pentanoate (12c)

A solution of methyl 2-(1-methyl-1H-indol-3-yl)pentanoate (12b) (860 mg, 3.44 mmol) and N-bromosuccinimide (623 mg, 3.5 mmol) in tetrachloromethane (20 mL) was stirred at room temperature for 5 hours. The mixture was then filtered and the filtrate was washed with water (10 mL), brine (10 mL), dried over sodium sulfate, filtered and evaporated under reduced pressure to afford the desired product (12c) as a brown oil without further purification (1.13 g, 3.44 mmol, 100%).

$^1$H NMR (300 MHz, CDCl$_3$) δ 0.90 (t, J=7.3 Hz, 3H), 1.16-1.38 (m, 2H), 1.91-2.06 (m, 1H), 2.11-2.26 (m, 1H), 3.64 (s, 3H), 3.76 (s, 3H), 3.94 (dd, J=6.5 Hz, J=9.0 Hz, 1H), 7.08 (t, J=7.4 Hz, 1H), 7.21 (t, J=7.4 Hz, 1H), 7.28 (d, J=8.2 Hz, 1H), 7.69 (d, J=8.2 Hz, 1H).

MS m/z ([M+H]$^+$) 324/326.

Step 4: Preparation of intermediate methyl 2-[2-(3,4-dihydro-2H-1-benzopyran-6-yl)-1-methyl-1H-indol-3-yl]pentanoate (12d)

Under a nitrogen atmosphere, sodium carbonate (370 mg, 3.5 mmol), water (20 mL), palladium tetrakis(triphenylphosphine) (620 mg, 0.54 mmol) and 6-(4,4,5,5-tetramethyl-1,3,2-dioxaborolan-2-yl)chroman (904 mg, 3.48 mmol) were added to a solution of methyl 2-(2-bromo-1-methyl-1H-indol-3-yl)pentanoate (1.13 g, 3.4 mmol) in N,N-dimethylformamide (80 mL). The mixture was heated at 110° C. for 2 hours, concentrated in vacuo and water (40 mL) was added. The aqueous layer was extracted with ethyl acetate (2×20 mL). The organic layer was washed with brine (20 mL), dried over sodium sulfate, filtered and evaporated under reduced pressure. The residue was purified by flash chromatography on silica gel (cyclohexane/ethyl acetate 95/5) to afford the desired product (12d) as a white solid (1.1 g, 2.91 mmol, 86%).

$^1$H NMR (400 MHz, CDCl$_3$) δ 0.74 (t, J=7.3 Hz, 3H), 1.04-1.18 (m, 2H), 1.87-1.99 (m, 1H), 2.03-2.15 (m, 3H), 2.82-2.90 (m, 2H), 3.55 (s, 3H), 3.63 (s, 3H), 3.71 (dd, J=6.8 Hz, J=8.7 Hz, 1H), 4.25-4.31 (m, 2H), 6.90 (d, J=8.3 Hz, 1H), 7.05-7.15 (m, 3H), 7.21 (t, J=7.0 Hz, 1H), 7.31 (d, J=8.1 Hz, 1H), 7.81 (d, J=8.1 Hz, 1H).

MS m/z ([M+H]$^+$) 378.

Step 5: Preparation of 2-[2-(3,4-dihydro-2H-1-benzopyran-6-yl)-1-methyl-1H-indol-3-yl]pentanoic acid A solution of methyl 2-[2-(3,4-dihydro-2H-1-benzopyran-6-yl)-1-methyl-1H-indol-3-yl]pentanoate (12d) (1.1 g, 2.91 mmol) and potassium hydroxide (820 mg, 14.55 mmol) in a mixture of water (4 mL), tetrahydrofuran (1 mL) and methanol (4 mL) was stirred at 80° C. for 5 hours and then concentrated in vacuo. Water (20 mL) was added and the aqueous layer was acidified to pH 2 with a hydrochloric acid aqueous solution 1N. After extraction of the aqueous layer with ethyl acetate (2×20 mL), the organic layer was washed with brine (20 mL), dried over sodium sulfate, filtered and evaporated under reduced pressure to afford the desired acid (example 12) as a white solid (800 mg, 2.2 mmol, 76%).

$^1$H NMR (400 MHz, CDCl$_3$) δ 0.73 (t, J=7.3 Hz, 3H), 1.05-1.18 (m, 2H), 1.89-2.01 (m, 1H), 2.02-2.13 (m, 3H), 2.77-2.92 (m, 2H), 3.55 (s, 3H), 3.71 (dd, J=6.8 and 8.7 Hz, 1H), 4.23-4.29 (m, 2H), 6.90 (d, J=8.3 Hz, 1H), 7.05-7.15 (m, 3H), 7.21 (t, J=7.0 Hz, 1H), 7.31 (d, J=8.1 Hz, 1H), 7.78 (d, J=8.1 Hz, 1H).

MS m/z ([M+H]$^+$) 364.

MS m/z ([M−H]$^−$) 362.

Example 13

Synthesis of 2-(tert-butoxy)-2-[4-(3,4-dihydro-2H-1-benzopyran-6-yl)-2-methyl-1,3-thiazol-5-yl]acetic acid

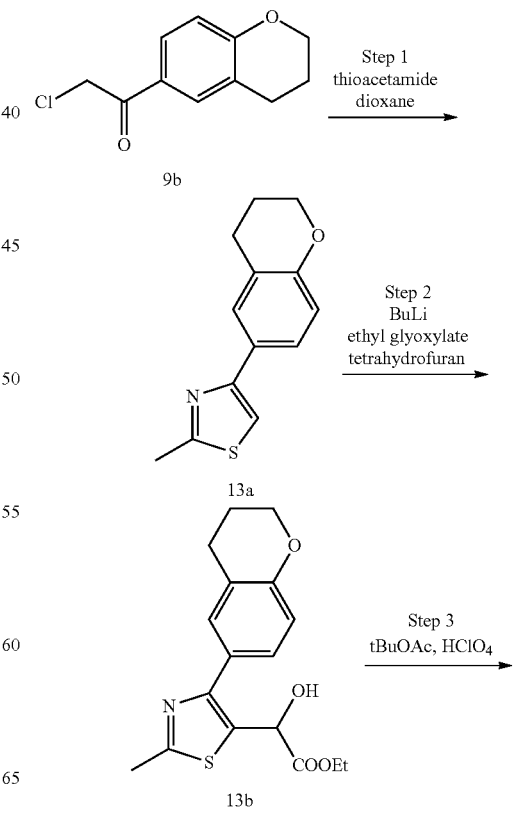

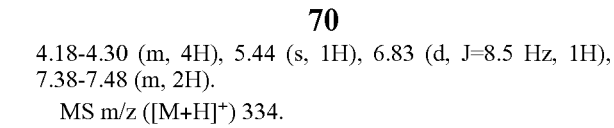

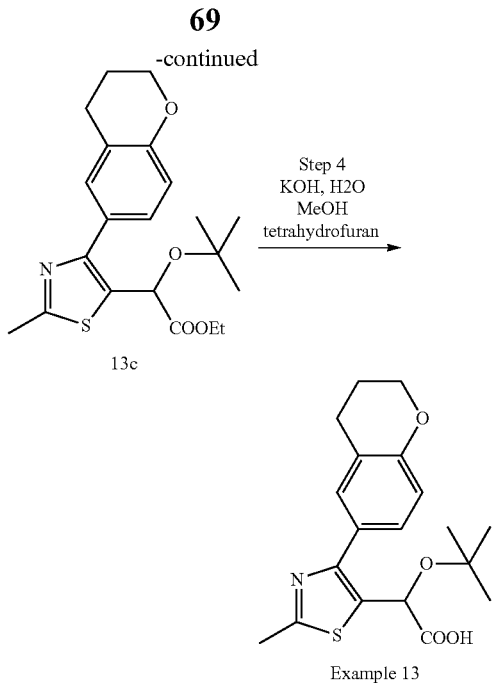

Example 13

Step 1: Preparation of intermediate 4-(3,4-dihydro-2H-1-benzopyran-6-yl)-2-methyl-1,3-thiazole (13a)

A solution of 2-chloro-1-(3,4-dihydro-2H-1-benzopyran-6-yl)ethan-1-one (9b) (270 mg, 1.28 mmol) and thioacetamide (106 mg, 1.41 mmol) in dioxane (10 mL) was refluxed for 20 hours, then the reaction mixture was concentrated in vacuo. The residue was diluted with dichloromethane (20 mL), washed with water (10 mL), brine (10 mL), dried over sodium sulfate, filtered and evaporated under reduced pressure. The residue was purified by flash chromatography on silica gel (cyclohexane/ethyl acetate 80/20) to afford the desired thiazole (13a) as a yellow oil (260 mg, 1.12 mmol, 88%).

$^1$H NMR (400 MHz, CDCl$_3$) δ 1.99-2.07 (m, 2H), 2.76 (s, 3H), 2.85 (t, J=6.5 Hz, 2H), 4.18-4.24 (m, 2H), 6.82 (d, J=8.5 Hz, 1H), 7.14 (s, 1H), 7.55 (dd, J=2.2 Hz, J=8.5 Hz, 1H), 7.71 (d, J=2.2 Hz, 1H).

MS m/z ([M+H]$^+$) 232.

Step 2: Preparation of intermediate ethyl 2-[4-(3,4-dihydro-2H-1-benzopyran-6-yl)-2-methyl-1,3-thiazol-5-yl]-2-hydroxyacetate (13b)

Under a nitrogen atmosphere, butyl lithium (1.6M, 840 μL, 1.34 mmol) was added at −78° C. to a solution of 4-(3,4-dihydro-2H-1-benzopyran-6-yl)-2-methyl-1,3-thiazole (13a) (260 mg, 1.12 mmol) in anhydrous tetrahydrofuran (5 mL). After 30 minutes, ethyl glyoxylate 50% in toluene (500 μL, 2.5 mmol) was added at −78° C. and the mixture was stirred for 2 hours, hydrolyzed with water and concentrated in vacuo. The residue was diluted with ethyl acetate (20 mL) and the organic layer was washed with water (10 mL), brine (10 mL), dried over sodium sulfate, filtered and evaporated under reduced pressure. The residue was purified by flash chromatography on silica gel (cyclohexane/ethyl acetate 80/20) to afford the desired alcohol (13b) as a white solid (90 mg, 0.27 mmol, 24%).

$^1$H NMR (400 MHz, CDCl$_3$) δ 1.24 (t, J=7.1 Hz, 3H), 1.84-1.93 (m, 2H), 2.70 (s, 3H), 2.81 (t, J=6.5 Hz, 2H), 4.18-4.30 (m, 4H), 5.44 (s, 1H), 6.83 (d, J=8.5 Hz, 1H), 7.38-7.48 (m, 2H).

MS m/z ([M+H]$^+$) 334.

Step 3: Preparation of intermediate ethyl 2-(tert-butoxy)-2-[4-(3,4-dihydro-2H-1-benzopyran-6-yl)-2-methyl-1,3-thiazol-5-yl]acetate (13c)

Under a nitrogen atmosphere, perchloric acid (70%, 700 μL) was added at −10° C. to a solution of ethyl 2-[4-(3,4-dihydro-2H-1-benzopyran-6-yl)-2-methyl-1,3-thiazol-5-yl]-2-hydroxyacetate (13b) (90 mg, 0.27 mmol) in terbutyl acetate (5 mL). After 1 hour, the reaction was quenched with a saturated aqueous solution of sodium bicarbonate (10 mL) and extracted with ethyl acetate (2×10 mL). The organic layer was washed with brine (10 mL), dried over sodium sulfate, filtered and evaporated under reduced pressure. The residue was purified by flash chromatography on silica gel (cyclohexane/ethyl acetate 70/30) to afford the desired product (13c) as a white solid (50 mg, 0.13 mmol, 48%).

$^1$H NMR (400 MHz, CDCl$_3$) δ 1.08 (s, 9H), 1.28 (t, J=7.1 Hz, 3H), 1.98-2.09 (m, 2H), 2.69 (s, 3H), 2.79-2.90 (m, 2H), 4.17-4.29 (m, 4H), 5.35 (s, 1H), 6.84 (d, J=8.5 Hz, 1H), 7.35-7.45 (m, 2H).

MS m/z ([M+H]$^+$) 390.

Step 4: Preparation of 2-(tert-butoxy)-2-[4-(3,4-dihydro-2H-1-benzopyran-6-yl)-2-methyl-1,3-thiazol-5-yl]acetic acid A solution of ethyl 2-(tert-butoxy)-2-[4-(3,4-dihydro-2H-1-benzopyran-6-yl)-2-methyl-1,3-thiazol-5-yl]acetate (13c) (50 mg, 0.13 mmol) and potassium hydroxide (55 mg, 0.97 mmol) in water (2 mL) and methanol (2 mL) was stirred at 80° C. for 1 hour and then concentrated. Water (10 mL) was added and the aqueous layer was washed with diethyl ether (10 mL), acidified to pH 2 with a hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 13) as a white solid (45 mg, 0.12 mmol, 96%).

$^1$H NMR (400 MHz, CDCl$_3$) δ 1.07 (s, 9H), 1.98-2.07 (m, 2H), 2.71 (s, 3H), 2.76-2.90 (m, 2H), 4.18-4.27 (m, 2H), 5.41 (s, 1H), 6.85 (d, J=8.4 Hz, 1H), 7.44 (d, J=2.1 Hz, 1H), 7.49 (dd, J=2.1, J=8.4 Hz, 1H).

MS m/z ([M+H]$^+$) 362.

MS m/z ([M−H]$^-$) 360.

Example 14

Synthesis of 2-(tert-butoxy)-2-[3-(3,4-dihydro-2H-1-benzopyran-6-yl)thieno[2,3-b]pyridin-2-yl]acetic acid

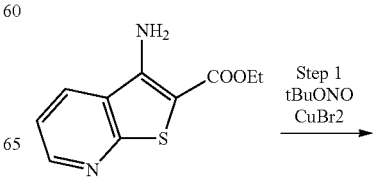

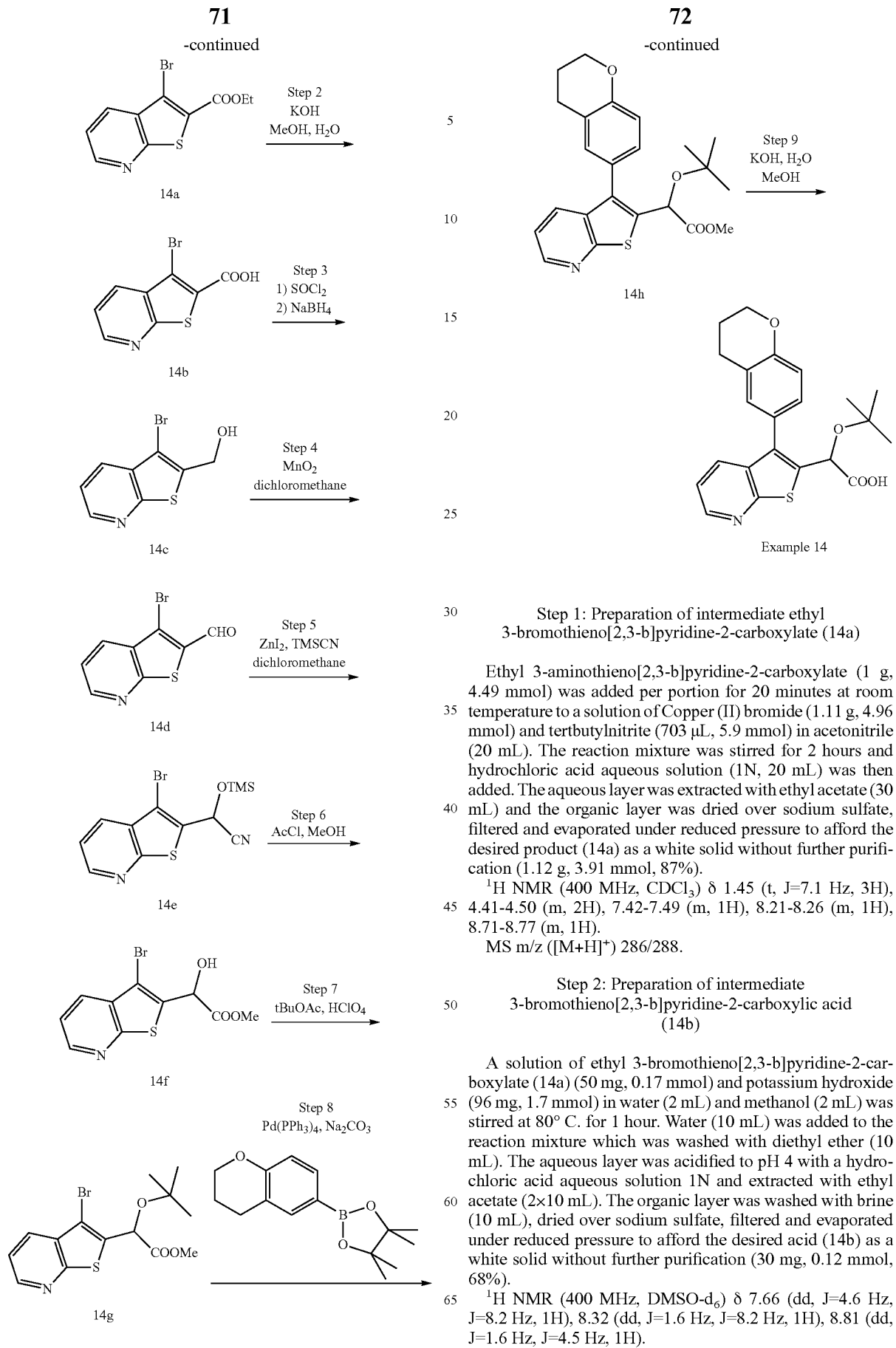

Step 1: Preparation of intermediate ethyl 3-bromothieno[2,3-b]pyridine-2-carboxylate (14a)

Ethyl 3-aminothieno[2,3-b]pyridine-2-carboxylate (1 g, 4.49 mmol) was added per portion for 20 minutes at room temperature to a solution of Copper (II) bromide (1.11 g, 4.96 mmol) and tertbutylnitrite (703 µL, 5.9 mmol) in acetonitrile (20 mL). The reaction mixture was stirred for 2 hours and hydrochloric acid aqueous solution (1N, 20 mL) was then added. The aqueous layer was extracted with ethyl acetate (30 mL) and the organic layer was dried over sodium sulfate, filtered and evaporated under reduced pressure to afford the desired product (14a) as a white solid without further purification (1.12 g, 3.91 mmol, 87%).

$^1$H NMR (400 MHz, CDCl$_3$) δ 1.45 (t, J=7.1 Hz, 3H), 4.41-4.50 (m, 2H), 7.42-7.49 (m, 1H), 8.21-8.26 (m, 1H), 8.71-8.77 (m, 1H).

MS m/z ([M+H]$^+$) 286/288.

Step 2: Preparation of intermediate 3-bromothieno[2,3-b]pyridine-2-carboxylic acid (14b)

A solution of ethyl 3-bromothieno[2,3-b]pyridine-2-carboxylate (14a) (50 mg, 0.17 mmol) and potassium hydroxide (96 mg, 1.7 mmol) in water (2 mL) and methanol (2 mL) was stirred at 80° C. for 1 hour. Water (10 mL) was added to the reaction mixture which was washed with diethyl ether (10 mL). The aqueous layer was acidified to pH 4 with a hydrochloric acid aqueous solution 1N and extracted with ethyl acetate (2×10 mL). The organic layer was washed with brine (10 mL), dried over sodium sulfate, filtered and evaporated under reduced pressure to afford the desired acid (14b) as a white solid without further purification (30 mg, 0.12 mmol, 68%).

$^1$H NMR (400 MHz, DMSO-d$_6$) δ 7.66 (dd, J=4.6 Hz, J=8.2 Hz, 1H), 8.32 (dd, J=1.6 Hz, J=8.2 Hz, 1H), 8.81 (dd, J=1.6 Hz, J=4.5 Hz, 1H).

MS m/z ([M+H]$^+$) 260/258.

Step 3: Preparation of intermediate {3-bromothieno[2,3-b]pyridin-2-yl}methanol (14c)

A solution of 3-bromothieno[2,3-b]pyridine-2-carboxylic acid (14b) (30 mg, 0.12 mmol) in thionyl chloride (2 mL) was refluxed for 1 hour. All volatiles were removed by co-evaporation with toluene. The residue was diluted in dimethoxyethane (2 mL) and sodium tetraborohydride (5 mg, 0.13 mmol) was added to the solution at room temperature. The reaction mixture was stirred for 1 hour, then quenched with water (10 mL) and extracted with ethyl acetate (2×10 mL). The organic layer was washed with brine (10 mL), dried over sodium sulfate, filtered and evaporated under reduced pressure to afford the desired alcohol (14c) as a white solid without further purification (20 mg, 0.081 mmol, 68%).

$^1$H NMR (400 MHz, CDCl$_3$) δ 5.01 (s, 2H), 7.41 (dd, J=4.7 Hz, J=8.1 Hz, 1H), 8.03 (dd, J=1.6 Hz, J=8.1 Hz, 1H), 8.60 (dd, J=1.6 Hz, J=4.7 Hz, 1H).

MS m/z ([M+H]$^+$) 244/246.

Step 4: Preparation of intermediate 3-bromothieno[2,3-b]pyridine-2-carbaldehyde (14d)

A mixture of {3-bromothieno[2,3-b]pyridin-2-yl}methanol (14c) (394 mg, 1.61 mmol) and manganese (II) oxide (1.4 g, 16.1 mmol) in dichloromethane (10 mL) was stirred for 20 hours, filtrated and evaporated to dryness to give the desired aldehyde (14d) without further purification (270 mg, 1.12 mmol, 70%).

$^1$H NMR (400 MHz, CDCl$_3$) δ 7.50 (dd, J=4.7 Hz, J=8.1 Hz, 1H), 8.28 (dd, J=1.6 Hz, J=8.1 Hz, 1H), 8.77 (dd, J=1.6 Hz, J=4.7 Hz, 1H), 10.30 (s, 1H). MS m/z ([M+H]$^+$) 242/244.

Step 5: Preparation of intermediate 2-{3-bromothieno[2,3-b]pyridin-2-yl}-2-[(trimethylsilyl)oxy]acetonitrile (14e)

Under a nitrogen atmosphere, trimethylsilylcyanide (163 µL, 1.3 mmol) was added at room temperature to a solution of 3-bromothieno[2,3-b]pyridine-2-carbaldehyde (14d) (270 mg, 1.12 mmol) and zinc iodide (II) (38 mg, 0.12 mmol) in dichloromethane (10 mL). After 16 hours, the reaction mixture was quenched with a saturated aqueous solution of sodium carbonate and extracted with dichloromethane (2×20 mL). The organic layer was washed with brine (10 mL), dried over sodium sulfate, filtered and evaporated under reduced pressure to give the desired product (14e) without further purification (290 mg, 0.85 mmol, 76%).

$^1$H NMR (400 MHz, CDCl$_3$) δ 0.29 (s, 9H), 5.93 (s, 1H), 7.46 (dd, J=4.7 Hz, J=8.1 Hz, 1H), 8.09 (dd, J=1.6 Hz, J=8.1 Hz, 1H), 8.67 (dd, J=1.6 Hz, J=4.7 Hz, 1H).

Step 6: Preparation of intermediate methyl 2-{3-bromothieno[2,3-b]pyridin-2-yl}-2-hydroxyacetate (14f)

Acetyl chloride (725 µL, 10.2 mmol) was dropped at 0° C. in methanol (10 mL). After 30 minutes, a solution of 2-{3-bromothieno[2,3-b]pyridin-2-yl}-2-[(trimethylsilyl)oxy]acetonitrile (14e) (290 mg, 0.85 mmol) in methanol (5 mL) was added at 0° C. to the reaction. The mixture was then warmed at room temperature for 20 hours and concentrated in vacuo. A saturated aqueous solution of sodium bicarbonate (20 mL) was added to the residue and extracted with dichloromethane (2×20 mL). The organic layer was washed with brine (10 mL), dried over sodium sulfate, filtered and evaporated under reduced pressure. The residue was purified by flash chromatography on silica gel (dichloromethane/ethyl acetate 90/10) to afford the desired hydroxyl-ester (14f) as a white solid (180 mg, 0.6 mmol, 70%).

$^1$H NMR (400 MHz, CDCl$_3$) δ 3.83 (s, 3H), 5.73 (s, 1H), 7.42 (dd, J=4.7 Hz, J=8.1 Hz, 1H), 8.06 (dd, J=1.6 Hz, J=8.1 Hz, 1H), 8.61 (dd, J=1.6 Hz, J=4.7 Hz, 1H).

MS m/z ([M+H]$^+$) 302/304.

Step 7: Preparation of intermediate methyl 2-{3-bromothieno[2,3-b]pyridin-2-yl}-2-(tert-butoxy)acetate (14g)

Under a nitrogen atmosphere, perchloric acid (70%, 750 µL) was added at −10° C. to a solution of methyl 2-{3-bromothieno[2,3-b]pyridin-2-yl}-2-hydroxyacetate (14f) (180 mg, 0.6 mmol) in tertbutyl acetate (5 mL). After 1 hour, the reaction was quenched with a saturated aqueous solution of sodium bicarbonate and extracted with dichloromethane (2×10 mL). The organic layer was washed with brine (10 mL), dried over sodium sulfate, filtered and evaporated under reduced pressure. The residue was purified by flash chromatography on silica gel (dichloromethane/ethyl acetate 90/10) to afford the desired product (14g) as a white solid (55 mg, 0.15 mmol, 26%).

$^1$H NMR (400 MHz, CDCl$_3$) δ 1.29 (s, 9H), 3.76 (s, 3H), 5.58 (s, 1H), 7.37 (dd, J=4.7 Hz, J=8.1 Hz, 1H), 8.02 (dd, J=1.6 Hz, J=8.1 Hz, 1H), 8.58 (dd, J=1.6 Hz, J=4.7 Hz, 1H).

MS m/z ([M+H]$^+$) 358/360.

Step 8: Preparation of intermediate methyl 2-(tert-butoxy)-2-[3-(3,4-dihydro-2H-1-benzopyran-6-yl)thieno[2,3-b]pyridin-2-yl]acetate (14h)

Under a nitrogen atmosphere, sodium carbonate (16 mg, 0.15 mmol), water (1 mL), palladium tetrakis(triphenylphosphine) (27 mg, 0.02 mmol) and 6-(4,4,5,5-tetramethyl-1,3,2-dioxaborolan-2-yl)chroman (40 mg, 0.15 mmol) were added to a solution of methyl 2-{3-bromothieno[2,3-b]pyridin-2-yl}-2-(tert-butoxy)acetate (14g) (55 mg, 0.15 mmol) in N,N-dimethylformamide (4 mL). The mixture was heated at 110° C. for 1 hour. The mixture was then cooled at room temperature, concentrated and water (20 mL) was added. The aqueous layer was extracted with ethyl acetate (2×20 mL). The organic layer was washed with brine (20 mL), dried over sodium sulfate, filtered and evaporated under reduced pressure. The residue was purified by flash chromatography on silica gel (dichloromethane/ethyl acetate 90/10) to afford the desired product (14h) as a white solid (30 mg, 0.07 mmol, 49%).

$^1$H NMR (400 MHz, CDCl$_3$) δ 1.11 (s, 9H), 2.04-2.13 (m, 2H), 2.78-2.93 (m, 2H), 3.74 (s, 3H), 4.25-4.31 (m, 2H), 5.39 (s, 1H), 6.93 (d, J=8.3 Hz, 1H), 7.10-7.15 (m, 2H), 7.23 (dd, J=4.7 Hz, J=8.1 Hz, 1H), 7.78 (dd, J=1.6 Hz, J=8.1 Hz, 1H), 8.54 (dd, J=1.6 Hz, J=4.7 Hz, 1H).

MS m/z ([M+H]$^+$) 412.

Step 9: Preparation of 2-(tert-butoxy)-2-[3-(3,4-dihydro-2H-1-benzopyran-6-yl)thieno[2,3-b]pyridin-2-yl]acetic acid A solution of methyl 2-(tert-butoxy)-2-[3-(3,4-dihydro-2H-1-benzopyran-6-yl)thieno[2,3-b]pyridin-2-yl]acetate (14h) (30 mg, 0.07 mmol) and potassium hydroxide (59 mg, 1.05 mmol) in a mixture of water (2 mL) and methanol (3 mL) was stirred at 60° C. for 1 hour. Water (10 mL) was added to the reaction mixture which was washed with diethyl ether (10 mL). The aqueous layer was acidified to pH 2 with hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 14) as a white solid without further purification (22 mg, 0.06 mmol, 86%).

$^{1}$H NMR (400 MHz, CDCl$_{3}$) δ 1.12 (s, 9H), 2.03-2.12 (m, 2H), 2.79-2.95 (m, 2H), 4.24-4.30 (m, 2H), 5.41 (s, 1H), 6.93 (d, J=8.3 Hz, 1H), 7.25-7.27 (m, 3H), 7.84 (dd, J=1.6 Hz, J=8.1 Hz, 1H), 8.57 (dd, J=1.6 Hz, J=4.7 Hz, 1H).

MS m/z ([M+H]$^{+}$) 398.
MS m/z ([M−H]$^{−}$) 396.

Example 15

Synthesis of 2-(tert-butoxy)-2-[5-(3,4-dihydro-2H-1-benzopyran-6-yl)-2-methyl-1,3-thiazol-4-yl]acetic acid

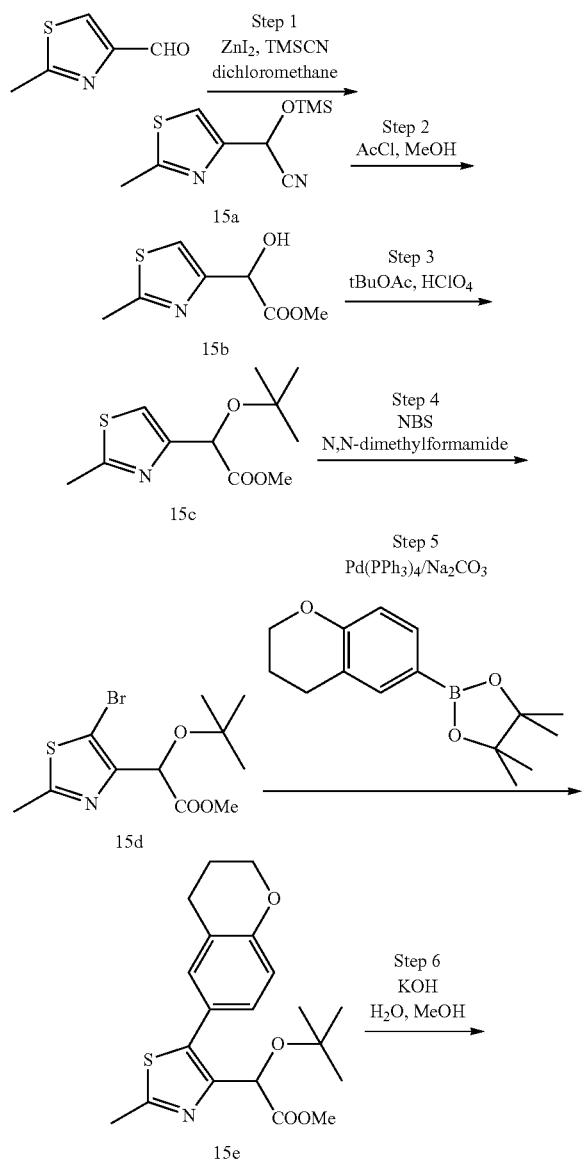

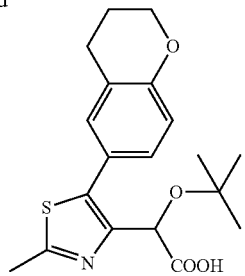

Example 15

Step 1: Preparation of intermediate 2-(2-methyl-1,3-thiazol-4-yl)-2-[(trimethylsilyl)oxy]acetonitrile (15a)

Under a nitrogen atmosphere, trimethylsilylcyanide (1025 µL, 8.2 mmol) was added at 0° C. to a solution of 2-methyl-1,3-thiazole-4-carbaldehyde (500 mg, 3.93 mmol) and zinc iodide (II) (127 mg, 0.4 mmol) in dichloromethane (20 mL). After 16 hours, the reaction mixture was quenched with a saturated aqueous solution of sodium carbonate and extracted with dichloromethane (2×20 mL). The organic layer was washed with brine (10 mL), dried over sodium sulfate, filtered, and evaporated under reduced pressure to afford the desired product without further purification.

Step 2: Preparation of intermediate methyl 2-hydroxy-2-(2-methyl-1,3-thiazol-4-yl)acetate (15b)

Acetyl chloride 725 µL, 10.2 mmol) was dropped at 0° C. in methanol (10 mL). After 30 minutes, a solution of 2-(2-methyl-1,3-thiazol-4-yl)-2-[(trimethylsilyl)oxy]acetonitrile (15a) (3.93 mmol) in methanol (30 mL) was added at 0° C. to the reaction. The mixture was then warmed at room temperature for 20 hours and concentrated under vacuum. A saturated aqueous solution of sodium bicarbonate (20 mL) was added to the residue and extracted with dichloromethane (2×20 mL). The organic layer was washed with brine (10 mL), dried over sodium sulfate, filtered and evaporated under reduced pressure. The residue was purified by flash chromatography on silica gel (dichloromethane/ethyl acetate 80/20) to afford the desired hydroxyl-ester (15b) as a yellow oil (560 mg, 2.99 mmol, 90%).

$^{1}$H NMR (400 MHz, CDCl$_{3}$) δ 2.70 (s, 3H), 3.68 (d, J=6.1 Hz, 1H), 3.80 (s, 3H), 5.29 (d, J=6.1 Hz, 1H), 7.17 (s, 1H).
MS m/z ([M+H]$^{+}$) 188.

Step 3: Preparation of intermediate methyl 2-(tert-butoxy)-2-(2-methyl-1,3-thiazol-4-yl)acetate (15c)

Under a nitrogen atmosphere, perchloric acid (70%, 3.75 mL) was added at −10° C. to a solution of methyl 2-hydroxy-2-(2-methyl-1,3-thiazol-4-yl)acetate (15b) (590 mg, 3.15 mmol) in tertbutyl acetate (25 mL). After 1 hour, the reaction was quenched with a saturated aqueous solution of sodium carbonate and extracted with dichloromethane (2×20 mL). The organic layer was washed with brine (10 mL), dried over sodium sulfate, filtered and evaporated under reduced pressure. The residue was purified by flash chromatography on silica gel (dichloromethane/ethyl acetate 75/25) to afford the desired product (15c) as a white solid (160 mg, 0.66 mmol, 21%).

$^{1}$H NMR (400 MHz, CDCl$_{3}$) δ 1.27 (s, 9H), 2.77 (s, 3H), 3.76 (s, 3H), 5.28 (s, 1H), 7.21 (s, 1H).
MS m/z ([M+Na]$^{+}$) 266.

Step 4: Preparation of intermediate methyl 2-(5-bromo-2-methyl-1,3-thiazol-4-yl)-2-(tert-butoxy)acetate (15d)

Under a nitrogen atmosphere, N-bromosuccinimide (39 mg, 0.22 mmol) was added to a solution of methyl 2-(tert-butoxy)-2-(2-methyl-1,3-thiazol-4-yl)acetate (15c) (50 mg, 0.21 mmol) in N,N-dimethylformamide (4 mL). The reaction mixture was warmed at 70° C. for 30 minutes then concentrated in vacuo. The residue was diluted with ethyl acetate (40 mL) and washed with water (2×20 mL), brine (20 mL), dried over sodium sulfate, filtered and evaporated under reduced pressure to give the desired product as a yellow oil without further purification (70 mg, 0.21 mmol, 100%).

$^1$H NMR (400 MHz, CDCl$_3$) δ 1.27 (s, 9H), 2.64 (s, 3H), 3.75 (s, 3H), 5.28 (s, 1H).

MS m/z ([M+H]$^+$) 322/324.

Step 5: Preparation of intermediate methyl 2-(tert-butoxy)-2-[5-(3,4-dihydro-2H-1-benzopyran-6-yl)-2-methyl-1,3-thiazol-4-yl]acetate (15e)

Under a nitrogen atmosphere, sodium carbonate (22 mg, 0.21 mmol), water (1 mL), palladium tetrakis(triphenylphosphine) (32 mg, 0.03 mmol) and 6-(4,4,5,5-tetramethyl-1,3,2-dioxaborolan-2-yl)chroman (55 mg, 0.21 mmol) were added to a solution of methyl 2-(5-bromo-2-methyl-1,3-thiazol-4-yl)-2-(tert-butoxy)acetate (15d) (70 mg, 0.21 mmol) in N,N-dimethylformamide (4 mL). The mixture was heated at 110° C. for 1 hour. The mixture was then cooled at room temperature, concentrated and water (20 mL) was added. The aqueous layer was extracted with ethyl acetate (2×20 mL). The organic layer was washed with brine (20 mL), dried over sodium sulfate, filtered and evaporated under reduced pressure. The residue was purified by flash chromatography on silica gel (dichloromethane/ethyl acetate 90/10) to afford the desired product as a white solid (48 mg, 0.13 mmol, 61%).

$^1$H NMR (400 MHz, CDCl$_3$) δ 1.06 (s, 9H), 1.99-2.09 (m, 2H), 2.67 (s, 3H), 2.78-2.86 (m, 2H), 3.76 (s, 3H), 4.20-4.26 (m, 2H), 5.21 (s, 1H), 6.82 (d, J=8.3 Hz, 1H), 7.19-7.25 (m, 2H).

MS m/z ([M+H]$^+$) 376.

Step 6: Preparation of 2-(tert-butoxy)-2-[5-(3,4-dihydro-2H-1-benzopyran-6-yl)-2-methyl-1,3-thiazol-4-yl]acetic acid A solution of methyl 2-(tert-butoxy)-2-[5-(3,4-dihydro-2H-1-benzopyran-6-yl)-2-methyl-1,3-thiazol-4-yl]acetate (15d) (56 mg, 0.15 mmol) and potassium hydroxide (110 mg, 1.95 mmol) in a mixture of water (2 mL) and methanol (3 mL) was stirred at 60° C. for 1 hour. Water (10 mL) was added to the reaction mixture which was washed with diethyl ether (10 mL). The aqueous layer was acidified to pH 2 with a hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 15) as a white solid without further purification (52 mg, 0.14 mmol, 93%).

$^1$H NMR (400 MHz, CDCl$_3$) δ 1.06 (s, 9H), 1.99-2.08 (m, 2H), 2.68 (s, 3H), 2.83 (t, J=6.0 Hz, 2H), 4.20-4.26 (m, 2H), 5.19 (s, 1H), 6.85 (d, J=8.3 Hz, 1H), 7.22-7.28 (m, 2H).

MS m/z ([M+H]$^+$) 362.
MS m/z ([M−H]$^−$) 360.

Example 16

Synthesis of 2-(tert-butoxy)-2-[1-(3,4-dihydro-2H-1-benzopyran-6-yl)thieno[3,2-f]quinolin-2-yl]acetic acid

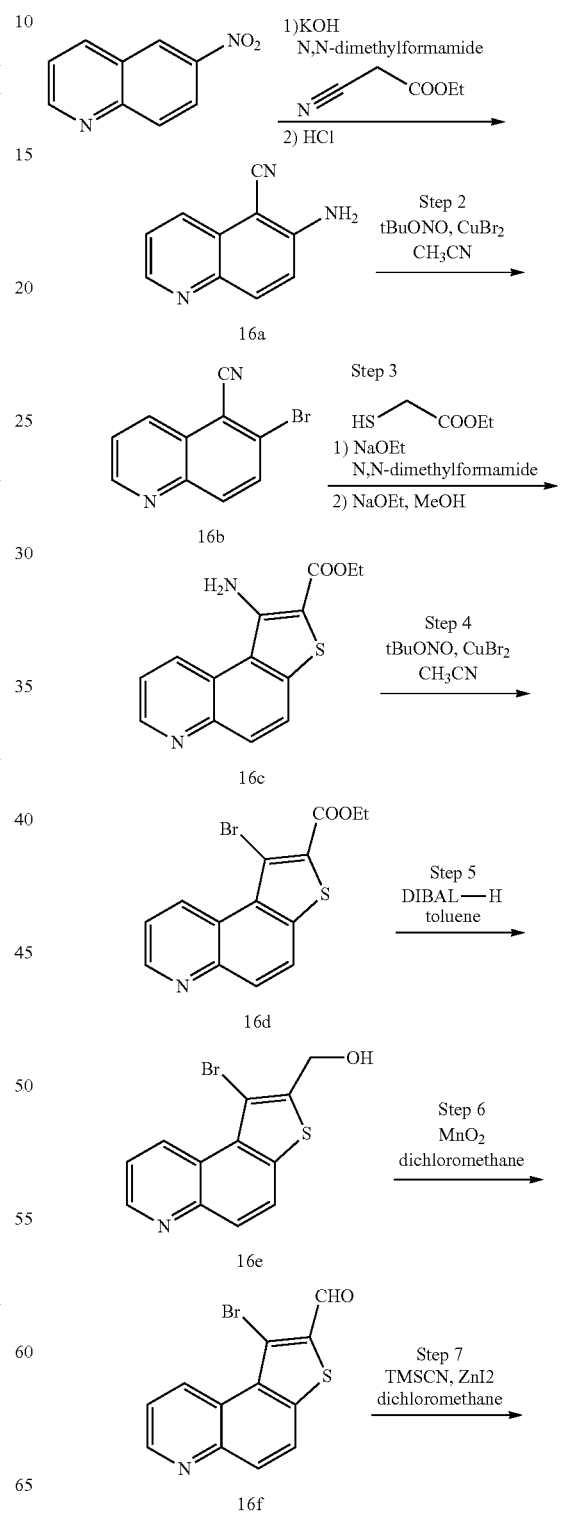

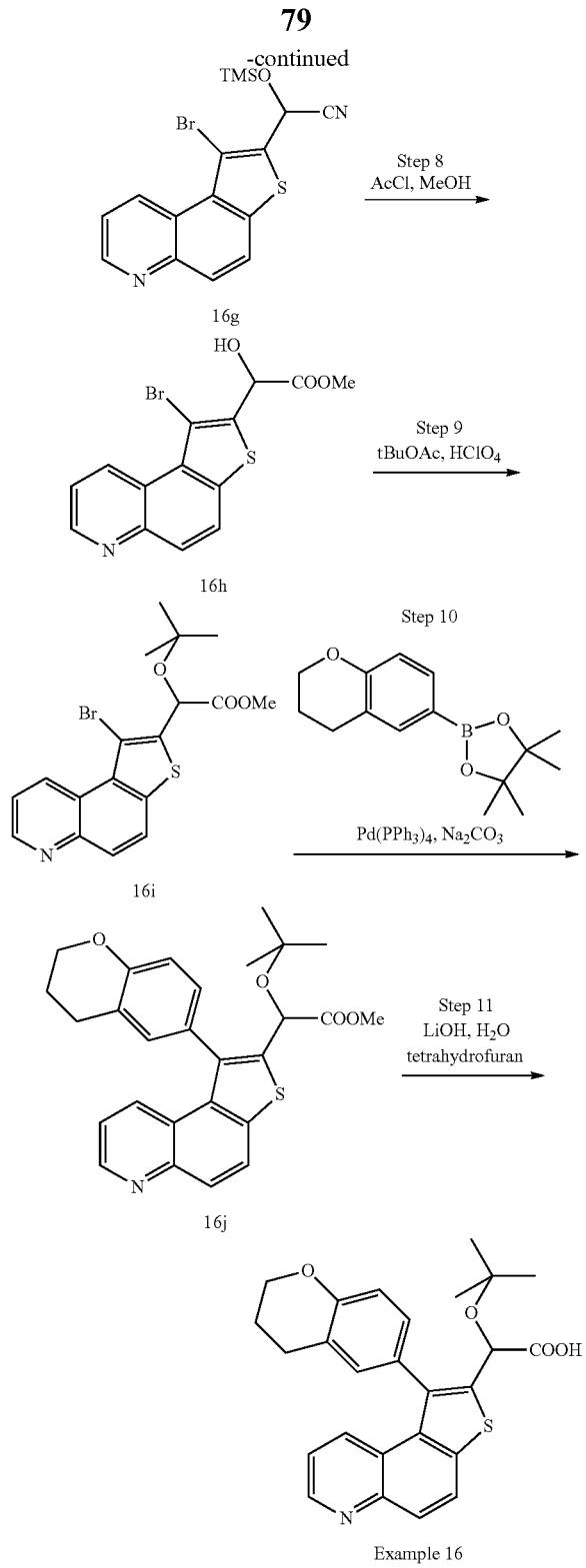

perature for 22 hours. Then the solvent was removed in vacuo and the residue was hydrolyzed with chlorohydric acid (10%) at reflux for 3 hours. The mixture was basified with sodium hydroxide (10%) and extracted three times with chloroform. The organic layer was washed with brine, dried over sodium sulfate, filtered, and evaporated under reduced pressure. The residue was purified by flash chromatography on silica gel (dichloromethane/methanol 95/5) to give the desired product (16a) (3.4 g, 20.1 mmol, 70%).

$^1$H NMR (400 MHz, CDCl$_3$) δ 4.92 (m, NH$_2$), 7.14 (d, J=9.2 Hz, 1H), 7.46 (dd, J=4.3 Hz, 8.4 Hz, 1H), 8.04 (d, J=9.2 Hz, 1H), 8.20-8.24 (m, 1H), 8.72 (dd, J=1.6 Hz, 4.3 Hz, 1H).

MS m/z ([M+H]$^+$) 170.

Step 2: Preparation of intermediate 6-bromoquinoline-5-carbonitrile (16b)

Under argon, Copper Bromide (II) (1.58 g, 7.09 mmol) was added to a solution of 6-aminoquinoline-5-carbonitrile (16a) (1g, 5.91 mmol) in acetonitrile (25 mL). After 10 minutes at room temperature, tert-butyl nitrite (920 82 L, 7.68 mmol) was added to a mixture and it was heated at 60° C. for 8 hours. The mixture was stirred at room temperature for 10 hours more. Hydrochloric acid solution (1N) was added to the mixture which was stirred for 4 hours and extracted three times with ethyl acetate. The organic layer was washed with a hydrochloric acid solution (1N), brine, dried over sodium sulfate and evaporated under reduced pressure to give the desired product (16b) as a beige solid (1.34 g, 5.75 mmol, 98%).

$^1$H NMR (400 MHz, CDCl$_3$) δ 7.65 (dd, J=4.2 Hz, 8.5 Hz, 1H), 7.94 (d, J=9.1 Hz, 1H), 8.21 (d, J=9.1 Hz, 1H), 8.49-8.55 (m, 1H), 9.02-9.07 (m, 1H).

MS m/z ([M+H]$^+$) 233/235.

Step 3: Preparation of intermediate ethyl 1-aminothieno[3,2-f]quinoline-2-carboxylate (16c)

A solution of 6-bromoquinoline-5-carbonitrile (16b) (300 mg, 1.29 mmol), ethyl mercaptoacetate (212 µL, 1.93 mmol) and sodium ethoxide (122.6 mg, 1.80 mmol) in dimethylformamide (10 mL) was stirred at room temperature for 15 hours. A saturated aqueous solution of sodium bicarbonate was added to the mixture. It was extracted twice with ethyl acetate. The organic layer was washed with brine, dried over sodium sulfate, filtered and concentrated in vacuo. The intermediate ethyl 2-[(5-cyanoquinolin-6-yl)sulfanyl]acetate obtained was reacted with sodium ethoxide (122.6 mg, 1.80 mmol) in dimethylformamide (8 mL) by stirring at 90° C. for 3 hours. The reaction was cooled to room temperature and water was added (10 mL). The resulting precipitate was filtered and washed with water twice and dried under vacuum with phosphorus pentoxide to afford the desired product (16c) as a solid (299 mg, 1.10 mmol, 85%).

$^1$H NMR (400 MHz, CDCl$_3$) δ 1.43 (t, J=7.1 Hz, 3H), 4.41 (q, J=7.1 Hz, 2H), 7.56 (dd, J=4.3 and 8.3 Hz, 1H), 7.95 (d, J=9.0 Hz, 1H), 8.09 (d, J=9.0 Hz, 1H), 8.90 (d, J=8.6 Hz, 1H), 8.93-8.98 (m, 1H).

MS m/z ([M+H]$^+$) 273.

Step 4: Preparation of intermediate ethyl 1-bromothieno[3,2-f]quinoline-2-carboxylate (16d)

Under argon, Copper Bromide (II) (292 mg, 1.31 mmol) was added to a solution of ethyl 1-aminothieno[3,2-f]quinoline-2-carboxylate (16c) (297 mg, 1.09 mmol) in acetonitrile (9.5 mL). After 10 minutes at room temperature, tert-butyl Step 1: Preparation of intermediate 6-aminoquinoline-5-carbonitrile (16a)

Nitroquinoline (5 g, 28.71 mmol) was added to a stirred solution of ethyl cyanoacetate (9.74 g, 86.13 mmol) and potassium hydroxide (4.83 g, 86.13 mmol) in N,N-dimethylformamide (87 mL). The mixture was stirred at room temnitrite (169 µL, 1.42 mmol) was added to the mixture which was heated at 60° C. for 5 hours. The reaction was cooled to room temperature and hydrochloric acid solution (1N) was added to the mixture which was stirred for 30 minutes and extracted twice with dichloromethane. The organic layer was washed with a hydrochloric acid solution (1N), brine, dried with sodium sulfate and evaporated under reduced pressure to give the desired product (16d) as a beige solid (324.3 mg, 0.96 mmol, 88.5%).

$^1$H NMR (400 MHz, CDCl$_3$) δ 1.47 (t, J=7.1 Hz, 3H), 4.49 (q, J=7.1 Hz, 2H), 7.72-7.81 (m, 1H), 8.17 (d, J=9.0 Hz, 1H), 8.41-8.51 (m, 1H), 9.00-9.06 (m, 1H), 10.42-10.51 (m, 1H).

MS m/z ([M+H]$^+$) 336/338.

Step 5: Preparation of intermediate {1-bromothieno[3,2-f]quinolin-2-yl}methanol (16e)

Under nitrogen atmosphere at −10° C., a solution of diisobutylaluminium hydride 1M in toluene (2.34 mL, 2.34 mmol) was added slowly to a solution of ethyl 1-bromothieno[3,2-f]quinoline-2-carboxylate (16d) in toluene (17 mL). Then the mixture was stirred at room temperature for 20 minutes more. The mixture was cooled in an ice bath and a solution of sulfuric acid 5% (5 mL) was added. The mixture was basified with saturated aqueous sodium hydrogencarbonate and extracted twice with ethyl acetate. The organic layer was washed with brine, dried with sodium sulfate and evaporated under reduced pressure to give the desired alcohol (16e) as a yellow powder (200 mg, 0.68 mmol, 87%).

$^1$H NMR (400 MHz, CDCl$_3$) δ 5.08 (s, 2H), 7.57 (dd, J=4.3 Hz, 8.6 Hz, 1H), 8.05 (s, 2H), 8.95-8.99 (m, 1H), 9.97 (dd, J=1.5 Hz, 8.6 Hz, 1H).

MS m/z ([M+H]$^+$) 294/296.

Step 6: Preparation of intermediate 1-bromothieno[3,2-f]quinoline-2-carbaldehyde (16f)

Under nitrogen atmosphere, manganese dioxide (318 mg, 3.65 mmol) was added to a solution of {1-bromothieno[3,2-f]quinolin-2-yl}methanol (16e) (215 mg, 0.731 mmol) in dichloromethane (31 mL) at room temperature. The mixture was vigorously stirred for 7 hours, then it was filtered and concentrated to give the desired aldehyde (16f) as a yellow solid (170 mg, 0.58 mmol, 58%)

$^1$H NMR (400 MHz, CDCl$_3$) δ 7.63 (dd, J=4.2 Hz, 8.6 Hz, 1H), 8.03-8.11 (m, 1H), 8.17-8.22 (m, 1H), 9.00-9.05 (m, 1H), 9.95-10.01 (m, 1H), 10.37 (s, 1H).

MS m/z ([M+H]$^+$) 292/294.

Step 7: Preparation of intermediate 2-{1-bromothieno[3,2-f]quinolin-2-yl}-2-[(trimethylsilyl)oxy]acetonitrile (16g)

Under a nitrogen atmosphere, trimethylsilylcyanide (87 µL, 0.70 mmol) was added at 0° C. to a solution of 1-bromothieno[3,2-f]quinoline-2-carbaldehyde (16f) (170 mg, 0.58 mmol) and zinc iodide (II) (18.5 mg, 0.06 mmol) in dichloromethane (14 mL). After 6 hours and 18 hours, trimethylsilylcyanide (87.3 µL, 0.70 mmol) and zinc iodide (II) (18.5 mg, 0.06 mmol) was added successively to the mixture at 0° C. It was stirred for 24 hours more. The reaction mixture was quenched with a saturated aqueous solution of sodium carbonate and extracted twice with dichloromethane. The organic layer was washed with brine, dried over Na$_2$SO$_4$, filtered, and evaporated under reduced pressure to provide the product (16g) (215 mg, 0.55 mmol, 94%) which was used without further purification.

$^1$H NMR (400 MHz, CDCl$_3$) δ 0.32 (s, 9H), 6.01 (s, 1H), 7.59 (dd, J=4.3 Hz, 8.7 Hz, 1H), 8.03-8.13 (m, 2H), 8.99 (dd, J=1.5 Hz, 4.2 Hz, 1H), 9.88-9.93 (m, 1H).

MS m/z ([M+H]$^+$) 392/394.

Step 8: Preparation of intermediate methyl 2-{1-bromothieno[3,2-f]quinolin-2-yl}-2-hydroxy acetate (16h)

Under nitrogen atmosphere, at −10° C., acetyl chloride (778 µL, 10.94 mmol) was added in anhydrous methanol (1.2 mL). The mixture was stirred for 30 minutes. A solution of 2-{1-bromothieno[3,2-f]quinolin-2-yl}-2-[(trimethylsily)oxy]acetonitrile (16g) in a mixture of methanol (2 mL) and dichloromethane (0.5 mL) was added to the mixture at −5° C. which was stirred at 0° C. for 5 hours. The mixture was then warmed to room temperature for 24 hours more. The reaction mixture was quenched with a saturated aqueous solution of sodium carbonate and extracted twice with dichloromethane. The organic layer was washed with brine, dried over sodium sulfate, filtered, and evaporated under reduced pressure to provide the desired hydroxyl-ester (16h) (152 mg, 0.43 mmol, 79%) as a beige powder.

$^1$H NMR (400 MHz, CDCl$_3$) δ 3.84 (s, 3H), 5.84-5.88 (m, 1H), 7.57 (dd, J=4.3 Hz, 8.7 Hz, 1H), 8.00-8.09 (m, 2H), 8.95-8.99 (m, 1H), 9.98-10.03 (m, 1H).

MS m/z ([M+H]$^+$) 352/354.

Step 9: Preparation of intermediate methyl 2-{1-bromothieno[3,2-f]quinolin-2-yl}-2-(tert-butoxy)acetate (16i)

To a suspension of methyl 2-{1-bromothieno[3,2-f]quinolin-2-yl}-2-hydroxyacetate (16h) (152 mg, 0.43 mmol) in tert-butylacetate (2.3 mL) at −10° C. was added perchloric acid (69.4 µL). The mixture was stirred at −5° C. for 5 hours and then warmed at room temperature for 1 hour more. The mixture was then basified with a saturated aqueous solution of sodium bicarbonate until pH 8. The aqueous layer was extracted with ethyl acetate. The organic layer was washed with brine, dried over sodium sulfate, filtered and concentrated in vacuo. The residue was purified by 2 preparative TLC (cyclohexane/ethyl acetate 60/40) to afford the desired product (16i) (55 mg, 0.13 mmol, 31%) as beige powder.

$^1$H NMR (400 MHz, CDCl$_3$) δ 1.32 (s, 9H), 3.76 (s, 3H), 5.70 (s, 1H), 7.55 (dd, J=4.3 Hz, 8.7 Hz, 1H), 8.04 (s, 2H), 8.94-8.98 (m, 1H), 9.96 (dd, J=1.4 Hz, 8.6 Hz, 1H).

MS m/z ([M+H]$^+$) 408/410.

Step 10: Preparation of intermediate methyl 2-(tert-butoxy)-2-[1-(3,4-dihydro-2H-1-benzopyran-6-yl)thieno[3,2-f]quinolin-2-yl]acetate (16j)

Under argon atmosphere, sodium carbonate (15.7 mg, 0.15 mmol), water (0.8 mL), and methyl 2-{1-bromothieno[3,2-f]quinolin-2-yl}-2-(tert-butoxy)acetate (16i) (55 mg, 0.14 mmol) were added to a solution of 6-(4,4,5,5-tetramethyl-1,3,2-dioxaborolan-2-yl)chroman (38.5 mg, 0.15 mmol) in N,N-dimethylformamide (3 mL). The solution was degassed under argon and palladium tetrakis(triphenylphosphine) (47 mg, 0.04 mmol) was added. The mixture was heated at 100° C. for 4 hours. The mixture was then cooled at room temperature, water was added and the aqueous layer was extracted with ethyl acetate. The organic layer was washed with brine, dried over sodium sulfate, filtered, and evaporated under reduced pressure. The residue was purified by preparative TLC (cyclohexane/ethyl acetate 70/30) to afford the desired product (16j) (19 mg, 0.04 mmol, 31%).

$^1$H NMR (400 MHz, CDCl$_3$) δ 1.14-1.15 (m, 9H), 2.05-2.18 (m, 2H), 2.79-2.90 (m, 2H), 3.69-3.72 (m, 3H), 4.29-4.37 (m, 2H), 5.19-5.21 (m, 1H), 6.94-7.08 (m, 2H), 7.12-7.17 (m, 2H), 7.85 (d, J=9.1 Hz, 1H), 7.99 (d, J=9.1 Hz, 1H), 8.08 (d, J=9.0 Hz, 1H), 8.80 (dd, J=1.6 Hz, 4.3 Hz, 1H).

MS m/z ([M+H]$^+$) 462.

Step 11: Preparation of intermediate 2-(tert-butoxy)-2-[1-(3,4-dihydro-2H-1-benzopyran-6-yl)thieno[3,2-f]quinolin-2-yl]acetic acid Lithium hydroxide (2.9 mg, 0.12 mmol) was added to a solution of methyl 2-(tert-butoxy)-2-[1-(3,4-dihydro-2H-1-benzopyran-6-yl)thieno[3,2-f]quinolin-2-yl]acetate (16j) 19 mg, 0.04 mmol) dissolved in tetrahydrofuran/water (0.5 mL/0.41 mL). The reaction was warmed to 70° C. for 2 hours and then concentrated. Residue was diluted with water and washed with dichloromethane. The aqueous layer was acidified with an aqueous solution of chlorohydric acid 1N and extracted with dichloromethane three times. The organic layer was washed with brine, dried over sodium sulfate, filtered and evaporated under reduced pressure to afford the desired acid (example 16) (7.8 mg, 0.02 mmol, 42%).

$^1$H NMR (400 MHz, CDCl$_3$) δ 1.16-1.18 (m, 9H), 2.05-2.17 (m, 2H), 2.87-2.95 (m, 2H), 4.29-4.36 (m, 2H), 5.20-5.23 (m, 1H), 6.92-7.18 (m, 4H), 7.44-7.50 (m, 1H), 7.84-7.90 (m, 1H), 7.99-8.09 (m, 1H), 8.80-8.85 (m, 1H).

MS m/z ([M+H]$^+$) 448.

Example 17

Synthesis of 2-(tert-butoxy)-2-[4-(3,4-dihydro-2H-1-benzopyran-6-yl)-2,5-dimethylthiophen-3-yl]acetic acid

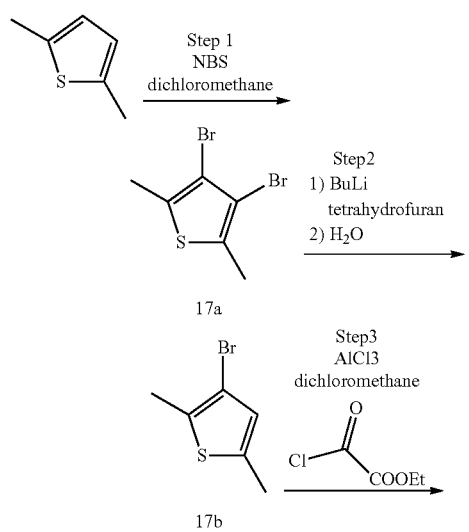

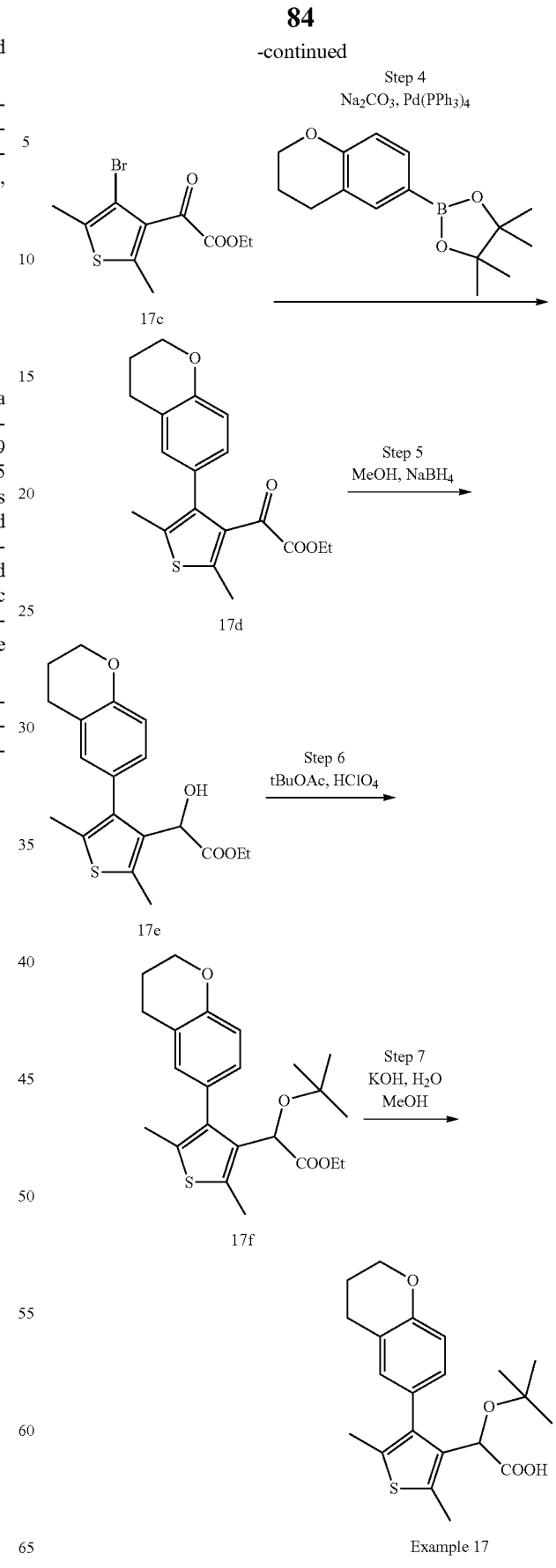

Step 1: Preparation of intermediate 3,4-dibromo-2,5-dimethyl-thiophene (17a)

To a solution of 2,5-dimethylthiophene (1 g, 8.91 mmol) in chloroform (50 mL) was added per portion N-bromosuccinimide (4.7 g, 26.7 mmol) at room temperature. After 20 hours, the reaction mixture was concentrated in vacuo. The residue was diluted with diethyl ether and the precipitate was filtered off. The filtrate was concentrated in vacuo and purified by flash chromatography on silica gel (cyclohexane) to afford the desired thiophene (17a) as a yellow solid (1.6 g, 5.93 mmol, 67%).

$^1$H NMR (300 MHz, CDCl$_3$) δ 2.40 (s, 6H).

Step 2: Preparation of intermediate 3-bromo-2,5-dimethyl-thiophene (17b)

Under nitrogen atmosphere, a solution of butyl lithium (1.6M in hexanes, 3.75 mL, 6 mmol) was slowly added at −78° C. to a solution of 3,4-dibromo-2,5-dimethyl-thiophene (17a) (1.6 g, 5.93 mmol) in anhydrous tetrahydrofurane (30 mL). After 1 hour, the reaction mixture was quenched with water (5 mL) and concentrated in vacuo. The residue was diluted with ethyl acetate (30 mL). The organic layer was washed with water (20 mL), brine (20 mL), dried over sodium sulfate, filtered and evaporated under reduced pressure to afford the desired product (17b) as a yellow solid (1.05 g, 5.49 mmol, 93%) without further purification.

$^1$H NMR (300 MHz, CDCl$_3$) δ 2.33 (s, 3H), 2.40 (s, 3H), 6.55 (s, 1H).

Step 3: Preparation of intermediate ethyl (4-bromo-2,5-dimethyl-thiophen-3-yl)-oxo-acetate (17c)

Under a nitrogen atmosphere, aluminium chloride (1.46 g, 11 mmol) was added per portions at 0° C. to a solution of 3-bromo-2,5-dimethylthiophene (17b) (1.05 g, 5.49 mmol) and ethyl chlorooxoacetate (614 µL, 5.5 mmol) in dichloromethane (12 mL). After 2 hours of vigorous stirring, the reaction mixture was slowly hydrolyzed at 0° C. with water. The organic layer was separated, washed with hydrochloric acid aqueous solution 1N, brine, dried over sodium sulfate, filtered and evaporated under reduced pressure. The residue was purified by flash chromatography on silica gel (cyclohexane/ethyl acetate 95/5)) to afford the desired keto-ester (17c) as a orange solid (630 mg, 2.16 mmol, 39%).

$^1$H NMR (300 MHz, CDCl$_3$) δ 1.40 (t, J=7 Hz, 3H), 2.35 (s, 3H), 2.60 (s, 3H), 4.40 (q, J=7 Hz, 2H).

MS m/z ([M+H]$^+$) 291/293.

Step 4: Preparation of intermediate ethyl 2-[4-(3,4-dihydro-2H-1-benzopyran-6-yl)-2,5-dimethyl thiophen-3-yl]-2-oxoacetate (17d)

Under a nitrogen atmosphere, sodium carbonate (78 mg, 0.7 mmol), palladium tetrakis(triphenylphosphine) (81 mg, 0.07 mmol) and 6-(4,4,5,5-tetramethyl-1,3,2-dioxaborolan-2-yl)chroman (182 mg, 0.7 mmol) were added to a solution of ethyl (4-bromo-2,5-dimethyl-thiophen-3-yl)-oxo-acetate (17c) (200 mg, 0.69 mmol) in a mixture of water (3.5 mL) and N,N-dimethylformamide (11 mL). The mixture was heated at 110° C. for 1 hour. The mixture was then cooled at room temperature, concentrated in vacuo and water (30 mL) was added. The aqueous layer was extracted with ethyl acetate (2×30 mL). The organic layer was washed with brine (30 mL), dried over sodium sulfate, filtered and evaporated under reduced pressure. The residue was purified by flash chromatography on silica gel (cyclohexane/ethyl acetate 80/20) to afford the desired product (17d) as a white solid (90 mg, 0.26 mmol, 38%).

$^1$H NMR (300 MHz, CDCl$_3$) δ 1.08 (t, J=7.1 Hz, 3H), 1.96-2.07 (m, 2H), 2.26 (s, 3H), 2.64 (s, 3H), 2.77 (t, J=6.4 Hz, 2H), 3.70 (q, J=7.1 Hz, 2H), 4.16-4.21 (m, 2H), 6.76-6.83 (m, 2H), 6.93 (dd, J=2.2 Hz, 8.3 Hz, 1H).

MS m/z ([M+H]$^+$) 345.

Step 5: Preparation of intermediate ethyl 2-[4-(3,4-dihydro-2H-1-benzopyran-6-yl)-2,5-dimethyl thiophen-3-yl]-2-hydroxyacetate (17e)

At 0° C., sodium tetraborohydride (10 mg, 0.26 mmol) was added to a solution of ethyl 2-[4-(3,4-dihydro-2H-1-benzopyran-6-yl)-2,5-dimethyl thiophen-3-yl]-2-oxoacetate (17d) (90 mg, 0.26 mmol) in methanol (5 mL). After 1 hour, water (5 mL) was added, the reaction mixture was concentrated in vacuo and the residue was diluted with ethyl acetate (10 mL). The organic layer was washed with water (10 mL), brine (10 mL), dried over sodium sulfate, filtered and evaporated under reduced pressure to afford the desired alcohol (17e) as a white solid without further purification (88 mg, 0.25 mmol, 98%).

$^1$H NMR (300 MHz, CDCl$_3$) δ 1.21 (t, J=7.1 Hz, 3H), 2.20 (s, 3H), 2.39 (s, 3H), 2.79 (t, J=6.4 Hz, 2H), 4.04-4.29 (m, 4H), 4.98 (s, 1H), 6.79 (d, J=8.3 Hz, 1H), 6.89-6.98 (m, 2H).

MS m/z ([M+Na]$^+$) 369.

Step 6: Preparation of intermediate ethyl 2-[4-(3,4-dihydro-2H-1-benzopyran-6-yl)-2,5-dimethyl thiophen-3-yl]-tert-butoxy-acetate (17f)

Under a nitrogen atmosphere, perchloric acid (70%, 1.5 mL) was added at −10° C. to a solution of ethyl 2-[4-(3,4-dihydro-2H-1-benzopyran-6-yl)-2,5-dimethyl thiophen-3-yl]-2-hydroxyacetate (17e) (88 mg, 0.25 mmol) in tert-butyl acetate (10 mL). After 1 hour, the reaction was quenched with a saturated aqueous solution of sodium carbonate and extracted with dichloromethane (2×30 mL). The organic layer was washed with brine (20 mL), dried over sodium sulfate, filtered and evaporated under reduced pressure. The residue was purified by flash chromatography on silica gel (dichloromethane)) to afford the desired product (17f) as a white solid (43 mg, 0.11 mmol, 43%).

$^1$H NMR (400 MHz, CDCl$_3$) δ 1.00 (s, 9H), 1.23 (t, J=7.1 Hz, 3H), 2.01-2.09 (m, 2H), 2.04 (s, 3H), 2.50 (s, 3H), 2.73-2.87 (m, 2H), 4.05-4.19 (m, 2H), 4.20-4.26 (m, 2H), 4.78 (s, 1H), 6.81 (d, J=8.3 Hz, 1H), 6.92-7.01 (m, 2H).

MS m/z ([M+Na]$^+$) 425.

Step 7: Preparation of 2-(tert-butoxy)-2-[4-(3,4-dihydro-2H-1-benzopyran-6-yl)-2,5-dimethylthiophen-3-yl]acetic acid A solution of ethyl 2-[4-(3,4-dihydro-2H-1-benzopyran-6-yl)-2,5-dimethyl thiophen-3-yl]-tert-butoxy-acetate (17f) (17 mg, 0.04 mmol) and potassium hydroxide (28 mg, 0.5 mmol) in a mixture of water (1 mL) and methanol (1 mL) was stirred at 70° C. for 1 hour. Methanol was then evaporated and water (10 mL) was added to the reaction mixture which was washed with diethyl ether (10 mL). The aqueous layer was acidified to pH 2 with a hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 17) as a white solid without further purification (13 mg, 0.03 mmol, 85%).

$^1$H NMR (400 MHz, CDCl$_3$) δ 1.02 (s, 9H), 1.99-2.07 (m, 2H), 2.20 (s, 3H), 2.42 (s, 3H), 2.80 (t, J=6.4 Hz, 2H), 4.19-4.25 (m, 2H), 4.92 (s, 1H), 6.81 (d, J=8.3 Hz, 1H), 6.92-7.12 (m, 2H).

MS m/z ([M−H]$^−$) 373.

Example 18

Synthesis of (tert-butoxy)[4-(3,4-dihydro-2H-1-benzopyran-6-yl)-2,5-dimethyl-1,1-dioxo-1λ$^6$-thiophen-3-yl]acetic acid

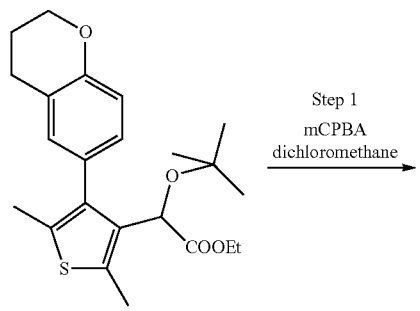

Step 1
mCPBA
dichloromethane

17f

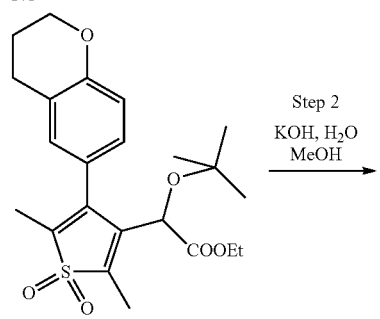

Step 2
KOH, H$_2$O
MeOH

18a

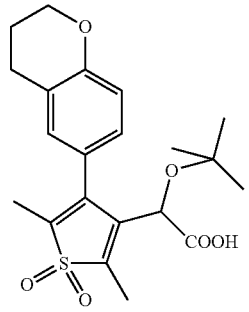

Example 18

Step 1: Preparation of intermediate ethyl 2-(tert-butoxy)-2-[4-(3,4-dihydro-2H-1-benzopyran-6-yl)-2,5-dimethyl-1,1-dioxo-1λ$^6$-thiophen-3-yl]acetate (18a)

Under a nitrogen atmosphere, 3-chloroperbenzoic acid (77%, 40 mg) was added at room temperature to a solution of ethyl 2-(tert-butoxy)-2-[4-(3,4-dihydro-2H-1-benzopyran-6-yl)-2,5-dimethylthiophen-3-yl]acetate (17f) (26 mg, 0.06 mmol) in dichloromethane (5 mL). After 1 hour, the reaction was quenched with a saturated aqueous solution of sodium carbonate (10 mL) and extracted with dichloromethane (2×10 mL). The organic layer was washed with brine (20 mL), dried over sodium sulfate, filtered and evaporated under reduced pressure. The residue was purified by flash chromatography on silica gel (cyclohexane/ethyl acetate 80/20) to afford the desired product (18a) as a white solid (17 mg, 0.04 mmol, 65%).

$^1$H NMR (400 MHz, CDCl$_3$) δ 1.05 (s, 9H), 1.23 (t, J=7.1 Hz, 3H), 1.95 (s, 3H), 1.99-2.09 (m, 2H), 2.26 (s, 3H), 2.79 (t, J=6.4 Hz, 2H), 4.13 (q, J=7.1 Hz, 2H), 4.21-4.27 (m, 2H), 4.64 (s, 1H), 6.83 (d, J=8.3 Hz, 1H), 6.89-6.97 (m, 2H).

MS m/z ([M+Na]$^+$) 457.

Step 2: Preparation of (tert-butoxy)[4-(3,4-dihydro-2H-1-benzopyran-6-yl)-2,5-dimethyl-1,1-dioxo-1λ$^6$-thiophen-3-yl]acetic acid A solution of ethyl 2-(tert-butoxy)-2-[4-(3,4-dihydro-2H-1-benzopyran-6-yl)-2,5-dimethyl-1,1-dioxo-1λ$^6$-thiophen-3-yl]acetate (18a) (17 mg, 0.04 mmol) and potassium hydroxide (22 mg, 0.4 mmol) in a mixture of water (1 mL) and methanol (2 mL) was stirred at 70° C. for 1 hour. Methanol was then evaporated and water (10 mL) was added to the reaction mixture which was washed with diethyl ether (10 mL). The aqueous layer was acidified to pH 2 with a hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 18) as a white solid without further purification (15 mg, 0.04 mmol, 100%).

$^1$H NMR (400 MHz, CDCl$_3$) δ 1.11 (s, 9H), 1.98 (s, 3H), 2.00-2.08 (m, 2H), 2.21 (s, 3H), 2.80 (t, J=6.4 Hz, 2H), 4.20-4.26 (m, 2H), 4.78 (s, 1H), 6.84 (d, J=8.3 Hz, 1H), 6.97-7.06 (m, 2H).

MS m/z ([M+Na]$^+$) 429.

Example 19

Synthesis of 2-(tert-butoxy)-2-[2-(3,4-dihydro-2H-1-benzopyran-6-yl)imidazo[1,2-a]pyridine-3-yl]acetic acid

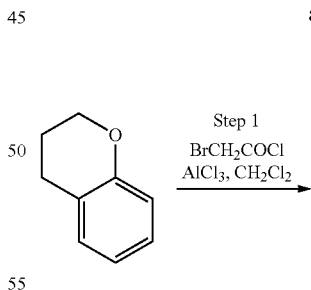

Step 1
BrCH$_2$COCl
AlCl$_3$, CH$_2$Cl$_2$

9a

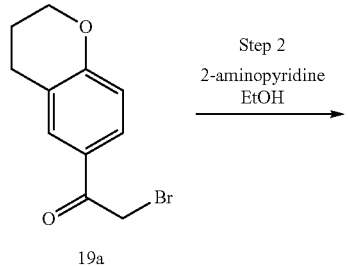

Step 2
2-aminopyridine
EtOH

19a

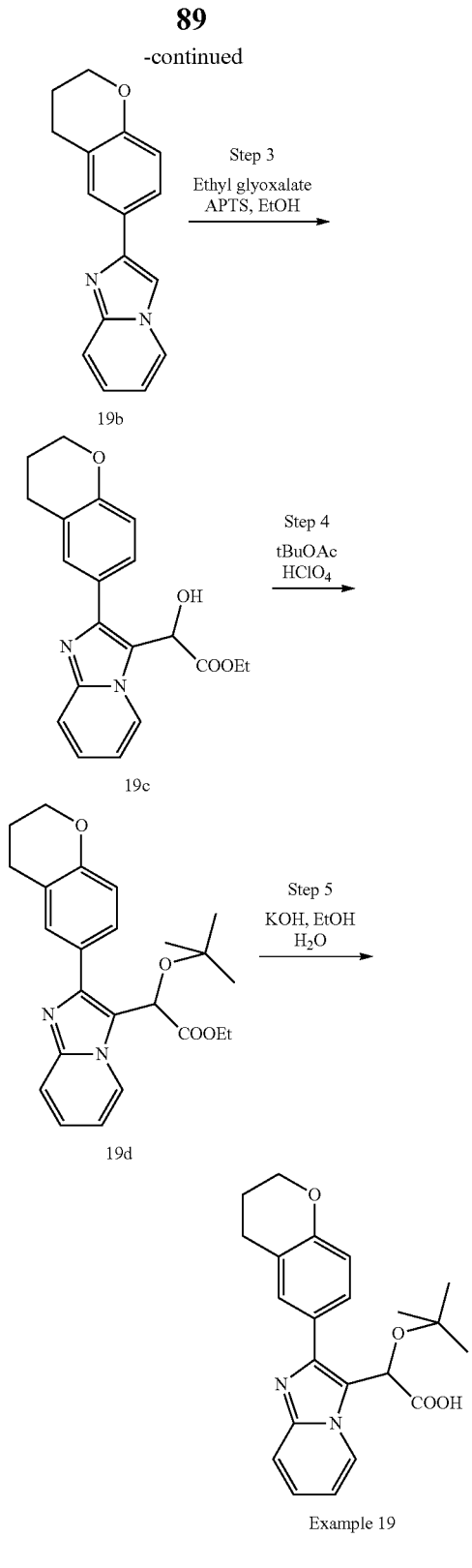

Example 19

Step 1: Preparation of intermediate 2-bromo-1-(3,4-dihydro-2H-1-benzopyran-6-yl)ethan-1-one (19a)

To a solution of 3,4-dihydro-2H-1-benzopyran (9a) (0.70 g, 5.22 mmol) in anhydrous dichloromethane (10 mL) under nitrogen atmosphere were added at 0° C. aluminium trichloride (2.09 g, 15.6 mmol) and bromoacetyl chloride (0.73 mL, 8.76 mmol). The mixture was stirred at 0° C. for 30 minutes and poured in ice (50 mL). The aqueous layer was extracted with ethyl acetate (2×20 mL). The organic layers were successively washed with a saturated solution of sodium hydrogenocarbonate, brine, dried over sodium sulfate and concentrated in vacuo. The residue was purified by flash chromatography on silica gel (cyclohexane/ethyl acetate: 80/20) to provide a 80/20 mixture of 2-bromo-1-(3,4-dihydro-2H-1-benzopyran-6-yl)etha-1-none (19a) and 2-bromo-1-(3,4-dihydro-2H-1-benzopyran-8-yl)ethan-1-one (0.45 g, 1.76 mmol, 34%) as yellow oil.

$^1$H NMR (300 MHz, CDCl$_3$) δ 1.99-2.11 (m, 2H), 2.81-2.85 (m, 2H), 4.24-4.27 (m, 2H), 4.37 (s, 2H), 6.84 (d, J=9.3 Hz, 1H), 7.72-7.74 (m, 2H).

MS m/z ([M+H]$^+$) 255, 257.

Step 2: Preparation of intermediate 2-(3,4-dihydro-2H-1-benzopyran-6-yl)-imidazo[1,2-a]pyridine (19b)

A solution of the 80/20 mixture of 2-bromo-1-(3,4-dihydro-2H-1-benzopyran-6-yl)ethan-1-one (19a) and 2-bromo-1-(3,4-dihydro-2H-1-benzopyran-8-yl)ethan-1-one (450 mg, 1.76 mmol) and 2-aminopyridine (166 mg, 1.76 mmol) in ethanol (10 mL) was heated at 60° C. overnight. The mixture was concentrated in vacuo. A 1M solution of sodium hydroxide (10 mL) and ethyl acetate (10 mL) were added. The aqueous layer was extracted with ethyl acetate (10 mL). The organic layer was dried over sodium sulfate and concentrated in vacuo. The residue was purified by flash chromatography on silica gel (cyclohexane/ethyl acetate 40/60) to provide the desired imidazo-pyridine (19b) (228 mg, 0.91 mmol, 64%) as a beige solid.

$^1$H NMR (300 MHz, CDCl$_3$) δ 2.00-2.07 (m, 2H), 2.86 (t, J=6.6 Hz, 2H), 4.20-4.23 (m, 2H), 6.75 (dt, J=1.0 Hz, 6.7 Hz, 1H), 6.84 (d, J=8.4 Hz, 1H), 7.12-7.17 (m, 1H), 7.58-7.63 (m, 2H), 7.73-7.75 (m, 2H), 8.09 (d, J=6.7 Hz, 1H).

MS m/z ([M+H]$^+$) 251.

Step 3: Preparation of intermediate ethyl 2-[2-(3,4-dihydro-2H-1-benzopyran-6-yl)imidazo[1,2-a]pyridin-3-yl]-2-hydroxyacetate (19c)

A mixture of 2-(3,4-dihydro-2H-1-benzopyran-6-yl)-imidazo[1,2-a]pyridine (19b) (50 mg, 0.2 mmol), ethyl glyoxylate 50% in toluene (0.20 mL, 1.0 mmol) and p-toluenesulfonic acid (6 mg, 0.03 mmol) in ethanol (1 mL) was heated at 80° C. for 1 hour. Ethyl glyoxylate 50% in toluene (0.10 mL, 0.5 mmol) was added and the heating was maintained for one supplementary hour. The mixture was concentrated in vacuo. The residue was dissolved in ethyl acetate (10 mL), washed with a saturated solution of sodium hydrogencarbonate (5 mL), dried over sodium sulfate and concentrated in vacuo. The residue was purified by flash chromatography on silica gel (cyclohexane/ethyl acetate 40/60) to provide the desired hydroxyl-ester (19c) (56 mg, 0.159 mmol, 80%) as a white solid.

$^1$H NMR (300 MHz, CDCl$_3$) δ 1.14 (t, J=7.1 Hz, 3H), 1.95-2.02 (m, 2H), 2.76 (t, J=6.4 Hz, 2H), 4.05-4.27 (m, 4H), 5.73 (s, 1H), 6.72-6.78 (m, 2H), 7.13-7.19 (m, 1H), 7.34-7.40 (m, 2H), 7.53 (d, J=9.0 Hz, 1H), 8.25 (d, J=6.9 Hz, 1H).

MS m/z ([M+H]$^+$) 353.

Step 4: Preparation of intermediate ethyl 2-(tert-butoxy)-2-[2-(3,4-dihydro-2H-1-benzopyran-6-yl)imidazo[1,2-a]pyridin-3-yl]acetate (19d)

To a solution of ethyl 2-[2-(3,4-dihydro-2H-1-benzopyran-6-yl)imidazo[1,2-a]pyridin-3-yl]-2-hydroxyacetate (53 mg, 0.15 mmol) in tert-butyl acetate (4.6 mL) at −20° C. was added perchloric acid (0.6 mL). The mixture was stirred at 0° C. for 2 hours before being poured into a saturated aqueous solution of sodium bicarbonate (10 mL). The layers were separated and the aqueous layer was extracted with ethyl acetate (2×10 mL). The organic layers were dried over sodium sulfate and concentrated in vacuo. The residue was purified by flash chromatography on silica gel (cyclohexane/ethyl acetate 60/40) to provide the desired product (19d) (38 mg, 0.093 mmol, 57%) as a colorless oil.

$^1$H NMR (300 MHz, CDCl$_3$) δ 1.03 (s, 9H), 1.26 (t, J=7.1 Hz, 3H), 2.01-2.09 (m, 2H), 2.80-2.94 (m, 2H), 4.13-4.29 (m, 4H), 5.67 (s, 1H), 6.77 (dt, J=1.1 Hz, 6.8 Hz, 1H), 6.88 (d, J=8.7 Hz, 1H), 7.16-7.22 (m, 1H), 7.53-7.60 (m, 3H), 8.77 (d, J=6.9 Hz, 1H).

MS m/z ([M+H]$^+$) 409.

Step 5: Preparation of 2-(tert-butoxy)-2-[2-(3,4-dihydro-2H-1-benzopyran-6-yl)imidazo[1,2-a]pyridin-3-yl]acetic acid A mixture of ethyl 2-(tert-butoxy)-2-[2-(3,4-dihydro-2H-1-benzopyran-6-yl)imidazo[1,2-a]pyridin-3-yl]acetate (19d) (38 mg, 0.093 mmol) and potassium hydroxide (21 mg, 0.37 mmol) in a mixture of ethanol (3 mL) and water (1 mL) was refluxed for 1 hour. The mixture was concentrated in vacuo. Water (1 mL) was added to the residue and the aqueous layer was extracted with ethyl acetate (5 mL). The aqueous layer was acidified with 1M hydrochloric acid until pH 3 and extracted with ethyl acetate (5 mL). The organic layer was concentrated in vacuo. Ethanol (5 mL) was added the solid was filtered to provide the desired acid (example 19) (19 mg, 0.050 mmol, 54%) as a white solid.

$^1$H NMR (400 MHz, DMSO-d$_6$) δ 0.99 (s, 9H), 1.95-1.99 (m, 2H), 2.82-2.83 (m, 2H), 4.19 (t, J=5.2 Hz, 2H), 5.62 (s, 1H), 6.87 (d, J=8.1 Hz, 1H), 6.96 (t, J=7.7 Hz, 1H), 7.27-7.31 (m, 1H), 7.54-7.59 (m, 3H), 8.64 (d, J=6.9 Hz, 1H).

MS m/z ([M+H]$^+$) 381.
MS m/z ([M−H]$^−$) 379.

Example 20

Synthesis of 2-(tert-butoxy)-2-[2-(3,4-dihydro-2H-1-benzopyran-6-yl)-1-benzofuran-3-yl]acetic acid

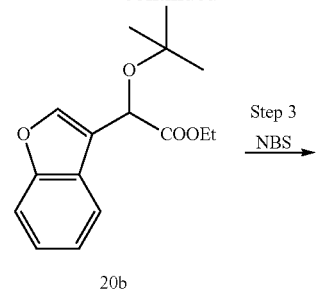

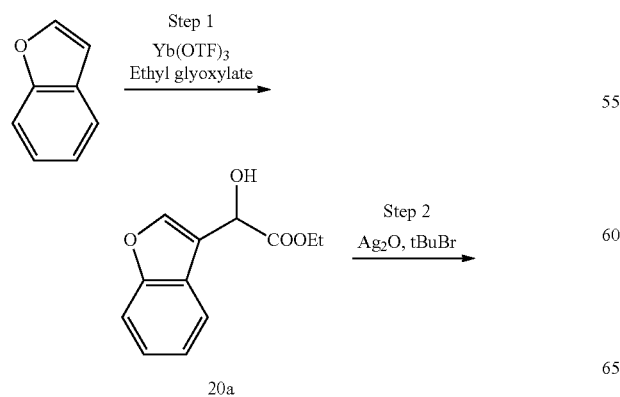

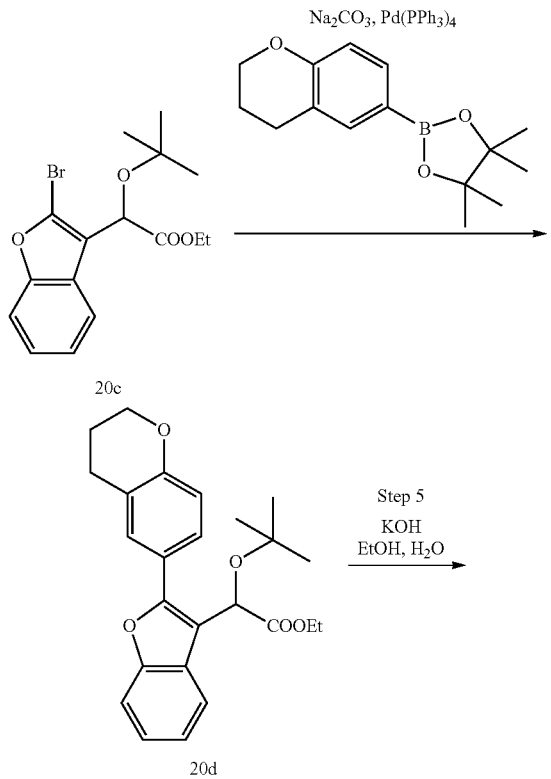

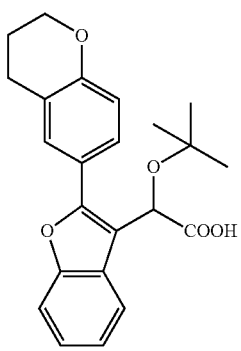

Example 20

Step 1: Preparation of intermediate ethyl 2-(1-benzofuran-3-yl)-2-hydroxyacetate (20a)

Ethyl glyoxylate 50% in toluene (3.72 mL, 18.6 mmol) was added to a solution of benzofuran (2.0 g, 16.9 mmol) and ethyl ytterbium (III) triflate (0.53 g, 0.8 mmol) in dichloromethane (15 mL). The reaction mixture was stirred at room temperature for 48 hours with two additions of an equivalent of ethyl glyoxylate 50% in toluene each day. The reaction mixture was concentrated in vacuo. The residue was purified by flash chromatography (cyclohexane/ethyl acetate 95/05 to 80/20) to provide the desired hydroxyl-ester (20a) (1.15 g, 5.2 mmol, 31%).

$^1$H NMR (300 MHz, CDCl$_3$) δ 1.28 (t, J=7.1 Hz, 3H), 3.52 (d, J=6.4 Hz, 1H), 4.23-4.38 (m, 2H), 5.31 (d, J=6.4 Hz, 1H), 6.77 (s, 1H), 7.20-7.33 (m, 2H), 7.46-7.50 (m, 1H), 7.55-7.58 (m, 1H).

Step 2: Preparation of intermediate ethyl 2-(1-benzofuran-3-yl)-2-(tert-butoxy)acetate (20b)

Silver oxide (1.58 g, 6.8 mmol) and tert-butyl bromide (1.53 mL, 13.6 mmol) were successively added to a solution of ethyl 2-(1-benzofuran-3-yl)-2-hydroxyacetate (0.50 g, 2.3 mmol) in a mixture of cyclohexane (10 mL) and dichloromethane (5 mL).

The reaction mixture was stirred at room temperature for 24 hours, and then, filtered over Celite®. The filtrate was concentrated in vacuo. The residue was purified by flash chromatography on silica gel (cyclohexane/ethyl acetate 90/10) to provide the desired product (20b) (0.36 g, 1.3 mmol, 57%).

$^1$H NMR (300 MHz, CDCl$_3$) δ 1.28 (t, J=7.1 Hz, 3H), 1.31 (s, 9H), 4.26 (q, J=7.1 Hz, 2H), 5.23 (s, 1H), 6.74 (s, 1H), 7.18-7.30 (m, 2H), 7.46-7.49 (m, 1H), 7.52-7.56 (M, 1H).

Step 3: Preparation of intermediate ethyl 2-(2-bromo-1-benzofuran-3-yl)-2-(tert-butoxy)acetate (20c)

N-Bromosuccinimide (265 mg, 1.48 mmol) and 1,1'-Azobis(cyanocyclohexane) (20 mg, 0.06 mmol) were added to a solution of ethyl 2-(1-benzofuran-3-yl)-2-(tert-butoxy)acetate (20b) (340 mg, 1.23 mmol) in chloroform (5 mL). The reaction mixture was refluxed for 5 hours. Water (5 mL) was added and the mixture was extracted with ethyl acetate (2×10 mL). The organic layer was dried over sodium sulfate and evaporated to dryness. The residue was purified by flash chromatography on silica gel (cyclohexane/ethyl acetate: 95/05) to provide ethyl 2-(2-bromo-1-benzofuran-3-yl)-2-(tert-butoxy)acetate (20c) (200 mg, 0.56 mmol, 46%).

$^1$H NMR (300 MHz, CDCl$_3$) δ 1.24 (t, J=7.1 Hz, 3H), 1.30 (s, 9H), 4.20-4.27 (m, 2H), 5.38 (s, 1H), 7.30-7.38 (m, 2H), 7.46-7.55 (m, 2H).

Step 4: Preparation of intermediate ethyl 2-(tert-butoxy)-2-[2-(3,4-dihydro-2H-1-benzopyran-6-yl)-1-benzofuran-3-yl]acetate (20d)

A mixture of ethyl 2-(2-bromo-1-benzofuran-3-yl)-2-(tert-butoxy)acetate (20c) (100 mg, 0.28 mmol), sodium carbonate (120 mg, 1.13 mmol), 6-(4,4,5,5-tetramethyl-1,3,2-dioxaborolan-2-yl)chroman (132 mg, 0.51 mmol) and palladium tetrakis(triphenylphosphine) (16 mg, 0.01 mmol) in toluene (1.26 mL), water (0.50 mL) and ethanol (0.60 mL) was heated at 95° C. for 24 hours. After cooling to room temperature, the mixture was poured into water (2 mL). The aqueous layer was extracted with toluene (2×5 mL). The organic layer was washed with brine (10 mL), dried over sodium sulfate and concentrated in vacuo. The residue was purified by preparative TLC (cyclohexane/ethyl acetate 80/20) to provide the desired product (20d) (61 mg, 0.15 mmol, 53%).

$^1$H NMR (300 MHz, CDCl$_3$) δ 1.11 (s, 9H), 1.27 (t, J=7.1 Hz, 3H), 2.05-2.11 (m, 2H), 2.84-2.91 (m, 2H), 4.20-4.28 (m, 4H), 5.32 (s, 1H), 6.93 (d, J=8.2 Hz, 1H), 7.21-7.35 (m, 4H), 7.52-7.59 (s, 2H).

Step 5: Preparation of 2-(tert-butoxy)-2-[2-(3,4-dihydro-2H-1-benzopyran-6-yl)-1-benzofuran-3-yl]acetic acid A solution of ethyl 2-(tert-butoxy)-2-[2-(3,4-dihydro-2H-1-benzopyran-6-yl)-1-benzofuran-3-yl]acetate (20d) (60 mg, 0.15 mmol) and potassium hydroxide (72 mg, 0.59 mmol) in a mixture of ethanol (2 mL) and water (6 mL) was refluxed for 4 hours. The mixture was concentrated in vacuo. Water (5 mL) was added to the residue and the solution was washed with diethyl ether (10 mL). The aqueous layer was acidified with concentrated hydrochloric acid until pH 2 and was extracted with ethyl acetate (2×10 mL). The organic layer was dried with sodium sulfate and evaporated to dryness. The residue was purified by preparative TLC (dichloromethane/methanol 90/10) to provide the desired acid (example 20) (16 mg, 0.042 mmol, 29%).

$^1$H NMR (300 MHz, CD$_3$OD) δ 1.03 (s, 9H), 1.95-2.09 (m, 2H), 2.80-2.93 (m, 2H), 4.21 (t, J=5.6 Hz, 2H), 6.87 (s, 1H), 7.19-7.30 (m, 3H), 7.36-7.44 (m, 3H), 7.53 (d, J=7.3 Hz, 1H).

MS m/z ([M−H]$^−$) 379.

Example 21

Synthesis of 2-(tert-butoxy)-2-[3-(3,4-dihydro-2H-1-benzopyran-6-yl)-1-benzothiophen-2-yl]acetic acid

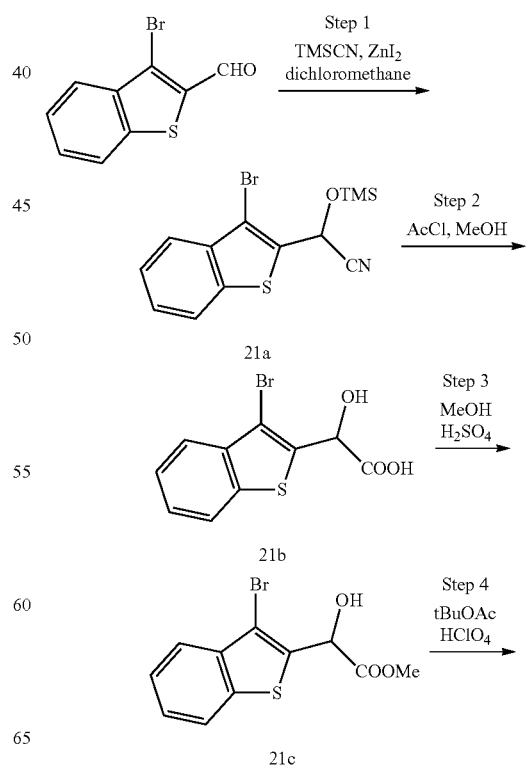

-continued

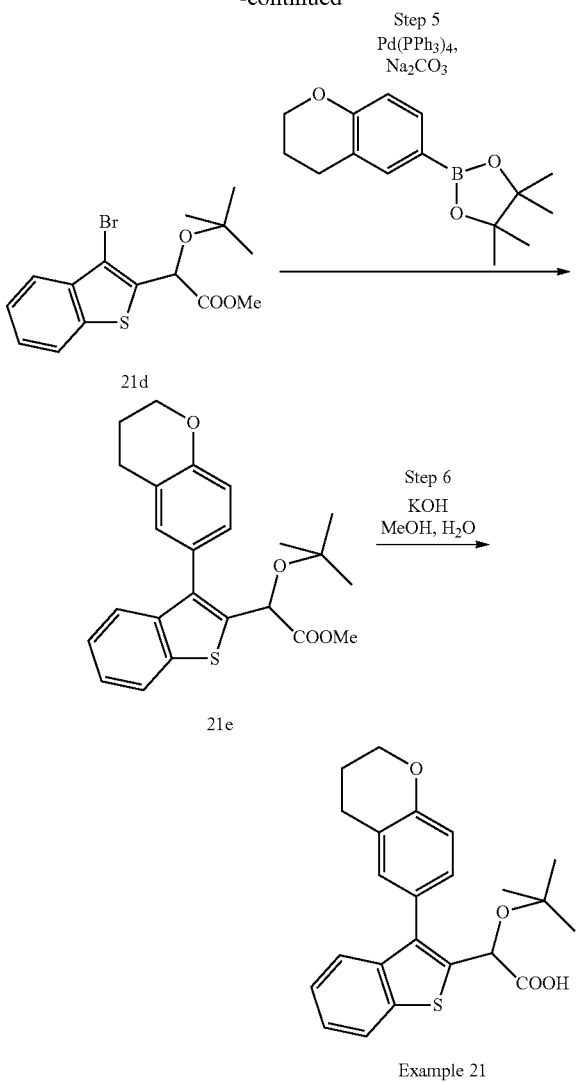

Example 21

Step 1: Preparation of intermediate (3-bromo-benzo[b]thiophen-2-yl)-trimethylsilanyloxy-acetonitrile (21a)

At room temperature, trimethylsilylcyanide (312 µL, 2.5 mmol) was added to a solution of 3-bromo-benzothiophene-2-carboxaldehyde (500 mg, 2.07 mmol) and zinc iodide (64 mg, 0.2 mmol) in dichloromethane (20 mL). After 4 hours, the reaction was completed and the mixture was diluted with dichloromethane (20 mL). The organic layer was washed with a saturated aqueous solution of sodium bicarbonate (20 mL), with water (2×20 mL), brine (20 mL), dried over sodium sulfate, filtered and evaporated to afford the desired product (21a) without further purification (700 mg, 2.07 mmol, 100%).

$^1$H NMR (300 MHz, CDCl$_3$) δ 0.28 (s, 9H), 5.96 (s, 1H), 7.42-7.52 (m, 2H), 7.80-7.87 (m, 2H).

Step 2: Preparation of intermediate (3-bromo-benzo[b]thiophen-2-yl)-hydroxy-acetic acid (21b)

Acetyl chloride (3 mL, 42 mmol) was dropped at 0° C. in methanol (20 mL). After 30 minutes, a solution of (3-bromo-benzo[b]thiophen-2-yl)-trimethylsilanyloxy-acetonitrile (21a) (700 mg, 2.07 mmol) in methanol (10 mL) was added at 0° C. to the reaction.

The mixture was warmed at room temperature for 20 hours and then concentrated under vacuum. The residue was diluted with ethyl acetate (30 mL). The organic layer was washed with a solution of sodium hydroxide 1M for 2 hours and was then acidified to pH 2 with a solution of hydrochloric acid 1N. The organic layer was washed with brine (20 mL), dried over sodium sulfate, filtered and evaporated under reduced pressure to afford the desired acid (21b) as a yellow solid (590 mg, 2.05 mmol, 99%) without further purification.

$^1$H NMR (400 MHz, CDCl$_3$) δ 5.82 (s, 1H), 7.40-7.47 (m, 2H), 7.79-7.85 (m, 2H).

MS m/z ([M−H]$^-$) 285/287.

Step 3: Preparation of intermediate methyl (3-bromo-benzo[b]thiophen-2-yl)-hydroxy-acetate (21c)

A solution of (3-bromo-benzo[b]thiophen-2-yl)-hydroxy-acetic acid (21b) (590 mg, 2.05 mmol) and sulfuric acid (500 µL) in methanol (10 mL) was refluxed for 1 hour. The reaction mixture was then concentrated in vacuo and the residue was diluted with ethyl acetate (20 mL). The organic layer was washed with water (2×20 mL), a saturated solution of sodium bicarbonate (20 mL), brine (20 mL), dried over sodium sulfate, filtered and evaporated under reduced pressure to afford the desired ester (21c) as a orange solid (560 mg, 1.86 mmol, 91%) without further purification.

$^1$H NMR (400 MHz, CDCl$_3$) δ 3.81 (s, 3H), 5.74 (s, 1H), 7.38-7.49 (m, 2H), 7.80-7.84 (m, 2H).

MS m/z ([M+H]$^+$) 283/285.

Step 4: Preparation of intermediate methyl (3-bromo-benzo[b]thiophen-2-yl)-tert-butoxy-acetate (21d)

Under a nitrogen atmosphere, perchloric acid (70%, 1.9 mL) was added at −10° C. to a solution of methyl (3-bromo-benzo[b]thiophen-2-yl)-hydroxy-acetate (21c) (560 mg, 1.86 mmol) in tertbutyl acetate (15 mL). After 1 hour, the reaction was quenched with a saturated solution of sodium carbonate and extracted with dichloromethane (2×30 mL). The organic layer was washed with brine (20 mL), dried over sodium sulfate, filtered and evaporated under reduced pressure. The residue was purified by flash chromatography on silica gel (cyclohexane/ethyl acetate 95/5) to afford the desired product (21d) as a yellow oil (500 mg, 1.40 mmol, 75%).

$^1$H NMR (400 MHz, CDCl$_3$) δ 1.29 (s, 9H), 3.74 (s, 3H), 5.61 (s, 1H), 7.36-7.46 (m, 2H), 7.79-7.81 (m, 2H).

Step 5: Preparation of intermediate methyl 2-(tert-butoxy)-2-[3-(3,4-dihydro-2H-1-benzopyran-6-yl)-1-benzothiophen-2-yl]acetate (21e)

Under a nitrogen atmosphere, sodium carbonate (33 mg, 0.3 mmol), palladium tetrakis(triphenylphosphine) (35 mg, 0.03 mmol) and 6-(4,4,5,5-tetramethyl-1,3,2-dioxaborolan-2-yl)chroman (78 mg, 0.3 mmol) were added to a solution of methyl (3-bromo-benzo[b]thiophen-2-yl)-tert-butoxy-acetate (21d) (100 mg, 0.28 mmol) in a mixture of water (1 mL) and N,N-dimethylformamide (3 mL). The mixture was heated at 110° C. for 1 hour. The mixture was then cooled at room temperature, concentrated and water (30 mL) was added. The aqueous layer was extracted with ethyl acetate (2×30 mL). The organic layer was washed with brine (30 mL), dried over sodium sulfate, filtered and evaporated under reduced pressure. The residue was purified by flash chromatography on silica gel (cyclohexane/ethyl acetate 90/10) to afford the desired product as a white solid (60 mg, 0.15 mmol, 54%).

$^1$H NMR (400 MHz, CDCl$_3$) δ 1.10 (s, 9H), 2.05-2.13 (m, 2H), 2.78-2.93 (m, 2H), 3.73 (s, 3H), 4.25-4.30 (m, 2H), 5.37 (s, 1H), 6.92 (d, J=8.3 Hz, 1H), 7.10-7.16 (m, 2H), 7.26-7.35 (m, 2H), 7.51 (d, J=7.2 Hz, 1H), 7.84 (d, J=7.2 Hz, 1H).

Step 6: Preparation of 2-(tert-butoxy)-2-[3-(3,4-dihydro-2H-1-benzopyran-6-yl)-1-benzothiophen-2-yl]acetic acid A solution of methyl 2-(tert-butoxy)-2-[3-(3,4-dihydro-2H-1-benzopyran-6-yl)-1-benzothiophen-2-yl]acetate (20 mg, 0.05 mmol) and potassium hydroxide (28 mg, 0.5 mmol) in a mixture of water (1 mL) and methanol (2 mL) was stirred at 70° C. for 1 hour. Methanol was then evaporated and water (10 mL) was added to the reaction mixture which was washed with diethyl ether (10 mL). The aqueous layer was acidified to pH 2 with a hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 21) as a white solid without further purification (15 mg, 0.04 mmol, 75%)

$^1$H NMR (400 MHz, CDCl$_3$) δ 1.11 (s, 9H), 2.03-2.12 (m, 2H), 2.78-2.94 (m, 2H), 4.24-4.30 (m, 2H), 5.39 (s, 1H), 6.93 (d, J=8.3 Hz, 1H), 7.20-7.40 (m, 4H), 7.55 (d, J=7.2 Hz, 1H), 7.83 (d, J=7.2 Hz, 1H).

MS m/z ([M−H]$^-$) 395.

Example 22

Synthesis of 2-(tert-butoxy)-2-[3-(3,4-dihydro-2H-1-benzopyran-6-yl)-1,1-dioxo-1λ$^6$-benzothiophen-2-yl]acetic acid

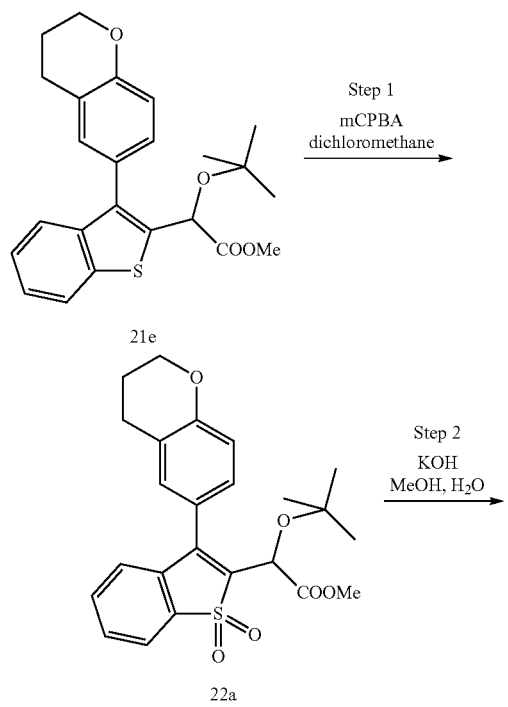

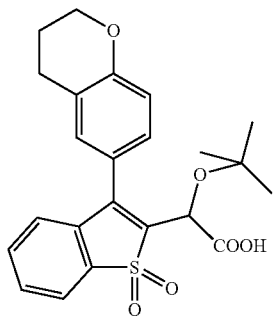

Example 22

Step 1: Preparation of intermediate methyl 2-(tert-butoxy)-2-[3-(3,4-dihydro-2H-1-benzopyran-6-yl)-1,1-dioxo-1λ$^6$-benzothiophen-2-yl]acetate (22a)

Under a nitrogen atmosphere, 3-chloroperbenzoic acid (77%, 52 mg) was added at room temperature to a solution of methyl 2-(tert-butoxy)-2-[3-(3,4-dihydro-2H-1-benzopyran-6-yl)-1-benzothiophen-2-yl]acetate (21e) (40 mg, 0.1 mmol) in dichloromethane (5 mL). After 1 hour, the reaction was quenched with a saturated solution of sodium carbonate (10 mL) and extracted with dichloromethane (2×10 mL). The organic layer was washed with brine (20 mL), dried over sodium sulfate, filtered and evaporated under reduced pressure. The residue was purified by flash chromatography on silica gel (dichloromethane/ethyl acetate 97/3) to afford the desired sulfone (22a) as a white solid (39 mg, 0.09 mmol, 90%).

$^1$H NMR (400 MHz, CDCl$_3$) δ1.19 (s, 9H), 2.03-2.10 (m, 2H), 2.77-2.92 (m, 2H), 3.64 (s, 3H), 4.24-4.30 (m, 2H), 5.11 (s, 1H), 6.91 (d, J=8.3 Hz, 1H), 7.17-7.26 (m, 3H), 7.48-7.52 (m, 2H), 7.76 (m, 1H).

Step 2: Preparation of 2-(tert-butoxy)-2-[3-(3,4-dihydro-2H-1-benzopyran-6-yl)-1,1-dioxo-1λ$^6$-benzothiophen-2-yl]acetic acid A solution of methyl 2-(tert-butoxy)-2-[3-(3,4-dihydro-2H-1-benzopyran-6-yl)-1,1-dioxo-1λ$^6$-benzothiophen-2-yl]acetate (22a) (39 mg, 0.09 mmol) and potassium hydroxide (50 mg, 0.9 mmol) in a mixture of water (2 mL) and methanol (3 mL) was stirred at 50° C. for 1 hour. Methanol was then evaporated and water (10 mL) was added to the reaction mixture which was washed with diethyl ether (10 mL). The aqueous layer was acidified to pH 2 with a hydrochloric acid aqueous solution 1N and extracted with dichloromethane (2×10 mL). The organic layer was washed with brine (10 mL), dried over sodium sulfate, filtered and evaporated under reduced pressure to afford the desired acid (example 22) as a white solid without further purification (31 mg, 0.07 mmol, 82%).

$^1$H NMR (400 MHz, CDCl$_3$) δ 1.23 (s, 9H), 2.03-2.12 (m, 2H), 2.78-2.94 (m, 2H), 4.24-4.31 (m, 2H), 5.08 (s, 1H), 6.95 (d, J=8.3 Hz, 1H), 7.23-7.40 (m, 3H), 7.48-7.51 (m, 2H), 7.72-7.78 (m, 1H).

MS m/z ([M−COOH]$^-$) 383.

Example 23

Synthesis of 2-(tert-butoxy)-2-[3-(3,4-dihydro-2H-1-benzopyran-6-yl)-4-methyl-1-benzothiophen-2-yl] acetic acid

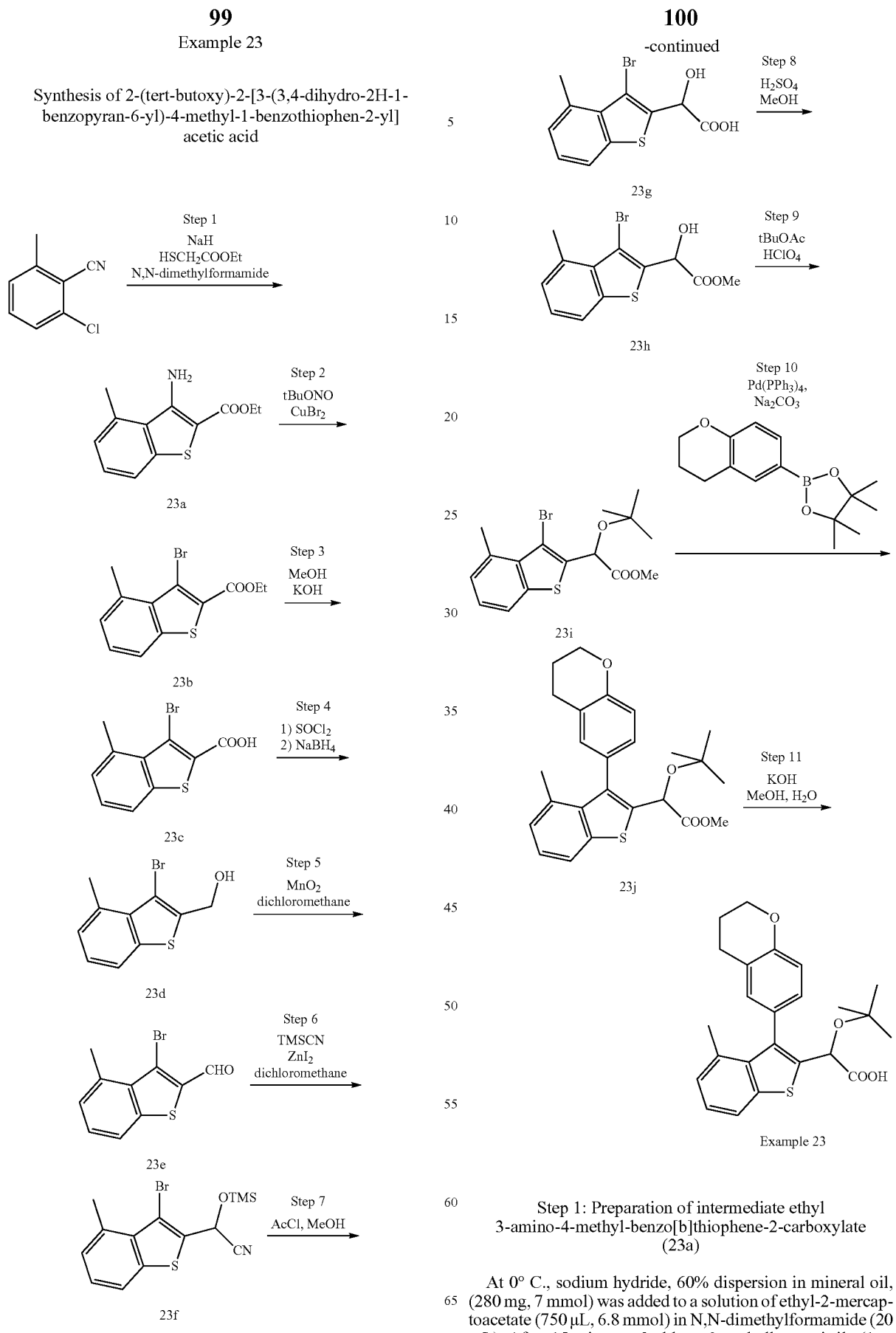

Step 1: Preparation of intermediate ethyl 3-amino-4-methyl-benzo[b]thiophene-2-carboxylate (23a)

At 0° C., sodium hydride, 60% dispersion in mineral oil, (280 mg, 7 mmol) was added to a solution of ethyl-2-mercaptoacetate (750 µL, 6.8 mmol) in N,N-dimethylformamide (20 mL). After 15 minutes, 2-chloro-6-methylbenzonitrile (1 g, 6.60 mmol) was also added to the mixture which was stirred at room temperature for 2 hours more. The mixture was then concentrated and the residue was diluted with ethyl acetate. The organic layer was washed with water (30 mL), brine (30 mL), dried over sodium sulfate, filtered and evaporated. The crude product was purified by flash chromatography on silica gel (cyclohexane/dichloromethane 50/50) to afford the desired benzothiophene (23a) as a white solid (800 mg, 3.40 mmol, 52%).

$^1$H NMR (400 MHz, CDCl$_3$) δ 1.39 (t, J=7.1 Hz, 3H), 2.82 (s, 3H), 4.34 (q, J=7.1 Hz, 2H), 7.03 (d, J=7.2 Hz, 1H), 7.28 (dd, J=7.2 Hz, 8.1 Hz, 1H), 7.53 (d, J=8.1 Hz, 1H).

MS m/z ([M+H]$^+$) 236.

Step 2: Preparation of intermediate ethyl 3-bromo-4-methyl-benzo[b]thiophene-2-carboxylate (23b)

At room temperature, a solution of ethyl 3-amino-4-methyl-benzo[b]thiophene-2-carboxylate (23a) (800 mg, 3.40 mmol) in acetonitrile (5 mL) was added to a solution of copper (II) bromide (840 mg, 3.74 mmol) and tert-butylnitrite (530 μL, 4.45 mmol) in acetonitrile (20 mL). After 2 hours, the mixture was hydrolyzed with hydrochloric acid solution 1N (5 mL) and diluted with water (20 mL) and ethyl acetate (30 mL). The organic layer was washed with brine (30 mL), dried over sodium sulfate, filtered and evaporated. The crude product was purified by flash chromatography on silica gel (cyclohexane/ethyl acetate 95/5) to afford the desired product (23b) as a white solid (640 mg, 2.14 mmol, 63%).

$^1$H NMR (400 MHz, CDCl$_3$) δ 1.42 (t, J=7.1 Hz, 3H), 3.02 (s, 3H), 4.42 (q, J=7.1 Hz, 2H), 7.19 (d, J=7.2 Hz, 1H), 7.34 (dd, J=7.2 Hz, 8.1 Hz, 1H), 7.68 (d, J=8.1 Hz, 1H).

MS m/z ([M+H]$^+$) 299/301.

Step 3: Preparation of intermediate 3-bromo-4-methyl-benzo[b]thiophene-2-carboxylic acid (23c)

A solution of ethyl 3-bromo-4-methyl-benzo[b]thiophene-2-carboxylate (23b) (640 mg, 2.14 mmol) and potassium hydroxide (1.17 g, 21 mmol) in a mixture of methanol (10 mL) and water (5 mL) was warmed at 70° C. After 1 hour, methanol was evaporated and water (10 mL) was added to the reaction mixture which was washed with diethyl ether (10 mL). The aqueous layer was acidified to pH 2 with a hydrochloric acid solution 1N and extracted with ethyl acetate (2×10 mL). The organic layer was washed with brine (10 mL), dried over sodium sulfate, filtered and evaporated under reduced pressure to afford the desired acid (23c) as a white solid without further purification (420 mg, 1.55 mmol, 72%).

$^1$H NMR (400 MHz, CDCl$_3$) δ 3.03 (s, 3H), 7.21 (d, J=7.2 Hz, 1H), 7.38 (dd, J=7.2 Hz, 8.1 Hz, 1H), 7.72 (d, J=8.1 Hz, 1H).

MS m/z ([M+H]$^+$) 271/273.

Step 4: Preparation of intermediate (3-bromo-4-methyl-benzo[b]thiophen-2-yl)-methanol (23d)

A solution of 3-bromo-4-methyl-benzo[b]thiophene-2-carboxylic acid (23c) (420 mg, 1.55 mmol) in thionyl chloride (10 mL) was refluxed for 1 hour. Thionyl chloride was then evaporated under reduced pressure and the residue was diluted with dimethoxyethane (20 mL). Sodium tetraborohydride (70 mg, 1.85 mmol) was then added to the solution. After 1 hour, the mixture was hydrolyzed with water (5 mL) and diluted with ethyl acetate (20 mL). The organic layer was washed with brine (10 mL), dried over sodium sulfate, filtered and evaporated to dryness to afford the desired alcohol (23d) as a white solid without further purification (400 mg, 1.55 mmol, 100%).

$^1$H NMR (400 MHz, CDCl$_3$) δ 2.94 (s, 3H), 4.94 (s, 2H), 7.13 (d, J=7.2 Hz, 1H), 7.22 (dd, J=7.2 Hz, 8.1 Hz, 1H), 7.67 (d, J=8.1 Hz, 1H).

Step 5: Preparation of intermediate 3-bromo-4-methyl-benzo[b]thiophene-2-carbaldehyde (23e)

At room temperature, a solution of (3-bromo-4-methyl-benzo[b]thiophen-2-yl)-methanol (23d) (400 mg, 1.55 mmol) and manganese dioxide (652 mg, 7.5 mmol) in dichloromethane (20 mL) was stirred for 2 hours. The mixture was then filtered and evaporated under reduced pressure to afford the desired aldehyde (23e) as a white solid without further purification (310 mg, 1.21 mmol, 78%).

$^1$H NMR (400 MHz, CDCl$_3$) δ 3.01 (s, 3H), 7.22 (d, J=7.2 Hz, 1H), 7.39 (dd, J=7.2 Hz, 8.1 Hz, 1H), 7.73 (d, J=8.1 Hz, 1H), 10.30 (s, 1H).

MS m/z ([M+H]$^+$) 255/257.

Step 6: Preparation of intermediate (3-bromo-4-methyl-benzo[b]thiophen-2-yl)-trimethylsilanyloxy-acetonitrile (23f)

At room temperature, trimethylsilylcyanide (169 μL, 1.35 mmol) was added to a solution of 3-bromo-4-methyl-benzo[b]thiophene-2-carbaldehyde (23e) (310 mg, 1.21 mmol) and zinc iodide (32 mg, 0.1 mmol) in dichloromethane (10 mL). After 4 hours, the reaction was completed and the mixture was diluted with dichloromethane (10 mL). The organic layer was washed with a saturated aqueous solution of sodium carbonate (20 mL), with water (2×20 mL), brine (20 mL), dried over sodium sulfate, filtered and evaporated to dryness to afford the desired product (23f) without further purification (428 mg, 1.21 mmol, 100%).

$^1$H NMR (400 MHz, CDCl$_3$) δ 0.28 (s, 9H), 2.94 (s, 3H), 5.93 (s, 1H), 7.17 (d, J=7.2 Hz, 1H), 7.26 (dd, J=7.2 Hz, 8.1 Hz, 1H), 7.69 (d, J=8.1 Hz, 1H).

Step 7: Preparation of intermediate (3-bromo-4-methyl-benzo[b]thiophen-2-yl)-hydroxy-acetic acid (23g)

Acetyl chloride (2.6 mL, 36.3 mmol) was dropped at 0° C. in methanol (20 mL). After minutes, a solution of (3-bromo-4-methyl-benzo[b]thiophen-2-yl)-trimethylsilanyloxy-acetonitrile (428 mg, 1.21 mmol) in methanol (5 mL) was added at 0° C. to the reaction. The mixture was warmed at room temperature for 2 hours and then concentrated under vacuum. The residue was diluted with ethyl acetate (30 mL). The organic layer was washed with an aqueous solution of sodium hydroxyde 1M for 2 hours and was then acidified to pH 2 with an hydrochloric acid solution 1N. The organic layer was washed with brine (20 mL), dried over sodium sulfate, filtered, and evaporated under reduced pressure to afford the desired acid (23g) as a white solid (270 mg, 0.9 mmol, 74%) without further purification.

$^1$H NMR (400 MHz, CDCl$_3$) δ 2.95 (s, 3H), 5.85 (s, 1H), 7.15 (d, J=7.2 Hz, 1H), 7.26 (dd, J=7.2 Hz, 8.1 Hz, 1H), 7.65 (d, J=8.1 Hz, 1H).

MS m/z ([M−H]$^−$) 299/301.

Step 8: Preparation of intermediate methyl (3-bromo-4-methyl-benzo[b]thiophen-2-yl)-hydroxy-acetate (23h)

A solution of (3-bromo-4-methyl-benzo[b]thiophen-2-yl)-hydroxy-acetic acid (23g) (270 mg, 0.9 mmol) and sulfuric acid (500 μL) in methanol (5 mL) was refluxed for 1 hour. The reaction mixture was then concentrated and the residue was diluted with ethyl acetate (20 mL). The organic layer was washed with water (2×20 mL), a saturated aqueous solution of sodium bicarbonate (20 mL), brine (20 mL), dried over sodium sulfate, filtered and evaporated under reduced pressure to afford the desired product (23h) as a orange solid (250 mg, 0.79 mmol, 88%) without further purification.

$^1$H NMR (400 MHz, CDCl$_3$) δ 2.96 (s, 3H), 3.82 (s, 3H), 5.77 (s, 1H), 7.15 (d, J=7.2 Hz, 1H), 7.24 (dd, J=7.2 Hz, 8.1 Hz, 1H), 7.66 (d, J=8.1 Hz, 1H).

MS m/z ([M−OH]$^+$) 297/299.

Step 9: Preparation of intermediate methyl (3-bromo-4-methyl-benzo[b]thiophen-2-yl)-tert-butoxy-acetate (23i)

Under a nitrogen atmosphere, perchloric acid (70%, 1.33 mL) was added at −10° C. to a solution of methyl (3-bromo-4-methyl-benzo[b]thiophen-2-yl)-hydroxy-acetate (23h) (250 mg, 0.79 mmol) in tert-butyl acetate (10 mL). After 1 hour, the reaction was quenched with a saturated aqueous solution of sodium bicarbonate and extracted with dichloromethane (2×30 mL). The organic layer was washed with brine (20 mL), dried over sodium sulfate, filtered and evaporated under reduced pressure. The residue was purified by flash chromatography on silica gel (cyclohexane/ethyl acetate 90/10) to afford the desired product (23i) as a white solid (220 mg, 0.59 mmol, 75%).

$^1$H NMR (400 MHz, CDCl$_3$) δ 1.29 (s, 9H), 2.94 (s, 3H), 3.74 (s, 3H), 5.62 (s, 1H), 7.12 (d, J=7.2 Hz, 1H), 7.24 (dd, J=7.2 Hz, 8.1 Hz, 1H), 7.66 (d, J=8.1 Hz, 1H).

Step 10: Preparation of intermediate methyl 2-(tert-butoxy)-2-[3-(3,4-dihydro-2H-1-benzopyran-6-yl)-4-methyl-1-benzothiophen-2-yl]acetate (23j)

Under a nitrogen atmosphere, sodium carbonate (33 mg, 0.3 mmol), palladium tetrakis(triphenylphosphine) (35 mg, 0.03 mmol) and 6-(4,4,5,5-tetramethyl-1,3,2-dioxaborolan-2-yl)chroman (78 mg, 0.3 mmol) were added to a solution of methyl (3-bromo-4-methyl-benzo[b]thiophen-2-yl)-tert-butoxy-acetate (23i) (100 mg, 0.28 mmol) in a mixture of water (1 mL) and N,N(-dimethylformamide (3 mL). The mixture was heated at 100° C. for 1 hour. The mixture was then cooled at room temperature, concentrated in vacuo and water (30 mL) was added. The aqueous layer was extracted with ethyl acetate (2×30 mL). The organic layer was washed with brine (30 mL), dried over sodium sulfate, filtered and evaporated under reduced pressure. The residue was purified by flash chromatography on silica gel (cyclohexane/ethyl acetate 90/10) to afford the desired product (23j) as a white solid (65 mg, 0.15 mmol, 57%).

$^1$H NMR (400 MHz, CDCl$_3$) δ 1.11 (s, 9H), 1.99 (s, 3H), 2.04-2.12 (m, 2H), 2.75-2.87 (m, 2H), 3.67 and 3.69 (2s, 3H), 4.23-4.31 (m, 2H), 5.12 and 5.13 (2s, 1H), 6.74-6.80 (m, 1H), 6.89-7.02 (m, 3H), 7.12 (t, J=7.2 Hz, 1H), 7.69 (d, J=7.2 Hz, 1H).

MS m/z ([M+Na]$^+$) 447.

Step 11: Preparation of 2-(tert-butoxy)-2-[3-(3,4-dihydro-2H-1-benzopyran-6-yl)-4-methyl-1-benzothiophen-2-yl]acetic acid A solution of methyl 2-(tert-butoxy)-2-[3-(3,4-dihydro-2H-1-benzopyran-6-yl)-4-methyl-1-benzothiophen-2-yl]acetate (23j) (17 mg, 0.04 mmol) and potassium hydroxide (28 mg, 0.5 mmol) in a mixture of water (1 mL) and methanol (2 mL) was stirred at 70° C. for 1 hour. Methanol was then evaporated and water (10 mL) was added to the reaction mixture which was washed with diethyl ether (10 mL). The aqueous layer was acidified to pH 2 with an hydrochloric acid solution 1N and extracted with ethyl acetate (2×10 mL). The organic layer was washed with brine (10 mL), dried over sodium sulfate, filtered and evaporated under reduced pressure to afford the desired acid (example 23) as a white solid without further purification (13 mg, 0.03 mmol, 82%).

$^1$H NMR (400 MHz, CDCl$_3$) δ 1.14 (s, 9H), 2.00 (s, 3H), 2.03-2.11 (m, 2H), 2.75-2.88 (m, 2H), 4.23-4.29 (m, 2H), 5.13 and 5.15 (2s, 1H), 6.1-7.04 (m, 3H), 7.21 (t, J=7.2 Hz, 1H), 7.31-7.38 (m, 1H), 7.68 (d, J=7.2 Hz, 1H).

MS m/z ([M−H]$^−$) 409.

Example 24

Synthesis of 2-(tert-butoxy)-2-[3-(3,4-dihydro-2H-1-benzopyran-6-yl)-4-methyl-1,1-dioxo-1λ$^6$-benzothiophen-2-yl]acetic acid

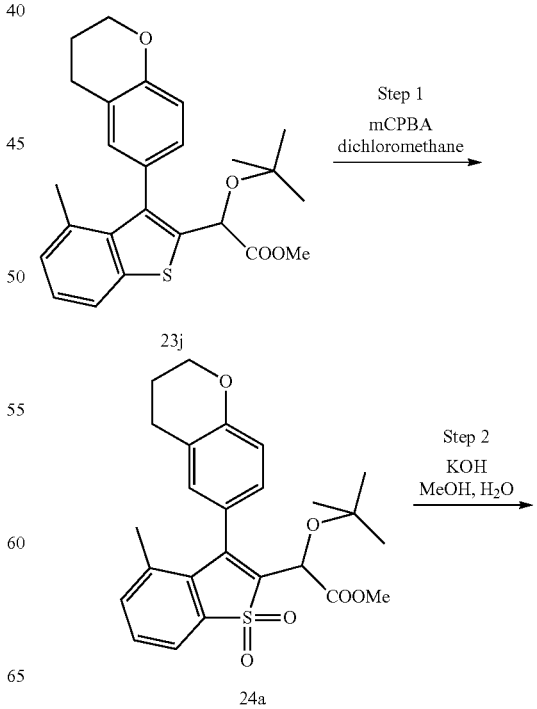

-continued

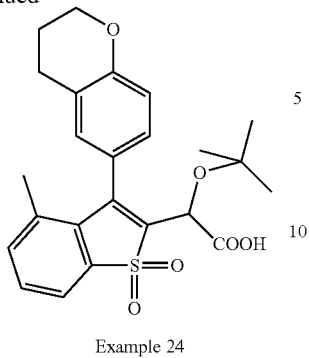

Example 24

Step 1: Preparation of intermediate methyl 2-(tert-butoxy)-2-[3-(3,4-dihydro-2H-1-benzopyran-6-yl)-4-methyl-1,1-dioxo-1$\lambda^6$-benzothiophen-2-yl]acetate (24a)

Using the procedure described in example 18, step 7, the intermediate methyl 2-(tert-butoxy)-2-[3-(3,4-dihydro-2H-1-benzopyran-6-yl)-4-methyl-1-benzothiophen-2-yl]acetate (23j) (55 mg, 0.13 mmol) is converted, without purification, to methyl 2-(tert-butoxy)-2-[3-(3,4-dihydro-2H-1-benzopyran-6-yl)-4-methyl-1,1-dioxo-1$\lambda^6$-benzothiophen-2-yl]acetate (24a) (55 mg, 0.12 mmol, 92%) as a white oil $^1$H NMR (400 MHz, CDCl$_3$) δ 1.18 and 1.20 (2s, 9H), 1.79 and 1.80 (2s, 3H), 2.04-2.11 (m, 2H), 2.78-2.85 (m, 2H), 3.67 and 3.70 (2s, 3H), 4.23-4.29 (m, 2H), 4.89 and 4.90 (2s, 1H), 6.86-6.96 (m, 2H), 7.11-7.16 (m, 1H), 7.21 (d, J=7.6 Hz, 1H), 7.36 (t, J=7.6 Hz, 1H), 7.62 (d, J=7.6 Hz, 1H).

MS m/z ([M+NH4]$^+$) 474.

Step 2: Preparation of 2-(tert-butoxy)-2-[3-(3,4-dihydro-2H-1-benzopyran-6-yl)-4-methyl-1,1-dioxo-1$\lambda^6$-benzothiophen-2-yl]acetic acid Using the procedure described in example 18, step 8, the intermediate methyl 2-(tert-butoxy)-2-[3-(3,4-dihydro-2H-1-benzopyran-6-yl)-4-methyl-1,1-dioxo-1$\lambda^6$-benzothiophen-2-yl] acetate (55 mg, 0.12 mmol) is converted, without purification, to 2-(tert-butoxy)-2-[3-(3,4-dihydro-2H-1-benzopyran-6-yl)-4-methyl-1,1-dioxo-1$\lambda^6$-benzothiophen-2-yl]acetic acid (example 24) (39 mg, 0.09 mmol, 73%) as a white solid.

$^1$H NMR (400 MHz, CDCl$_3$) δ 1.25 (s, 9H), 1.81 (s, 3H), 2.02-2.11 (m, 2H), 2.78-2.90 (m, 2H), 4.21-4.31 (m, 2H), 4.83 and 4.87 (2s, 1H), 6.88-6.96 (m, 2H), 7.23 (d, J=7.5 Hz, 1H), 7.38 (m, 2H), 7.60 (d, J=7.5 Hz, 1H).

MS m/z ([M+NH4]$^+$) 460.

Example 25

Synthesis of 2-(tert-butoxy)-2-[3-(3,4-dihydro-2H-1-benzopyran-6-yl)imidazo[1,2-a]pyridin-2-yl]acetic acid

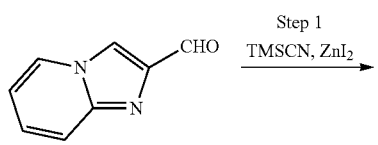

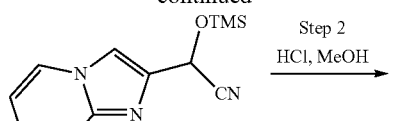

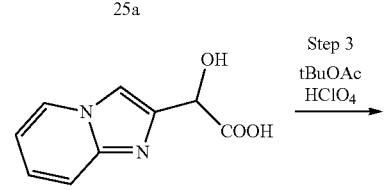

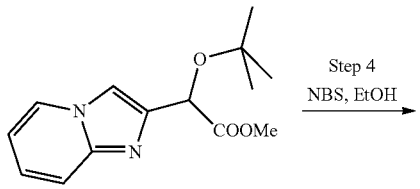

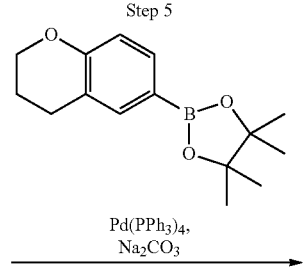

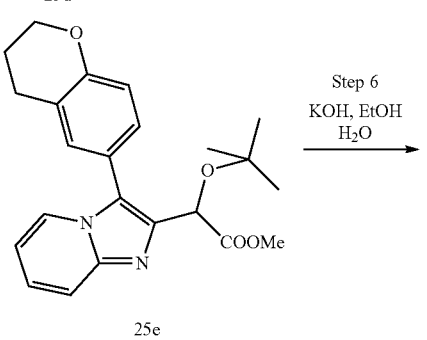

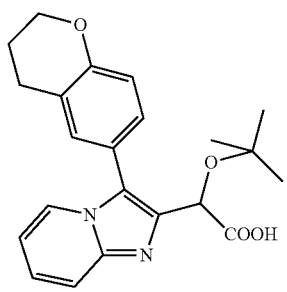

Example 25

Step 1: Preparation of intermediate of 2-{imidazo[1,2-a]pyridin-2-yl}-2-[(trimethylsilyl)oxy]acetonitrile (25a)

To a solution of imidazo[1,2-a]pyridine-2-carboxaldehyde (150 mg, 1.03 mmol) in anhydrous dichloromethane (10 mL) at 0° C. under nitrogen atmosphere were successively added zinc iodide (39 mg, 0.12 mmol) and trimethylsilyl cyanide (0.19 mL, 1.54 mmol). The mixture was stirred at room temperature overnight. A saturated solution of sodium hydrogencarbonate (10 mL) was added. Layers were separated and the aqueous layer was extracted with dichloromethane (10 mL). The organic layers were dried over sodium sulfate and concentrated in vacuo to provide the desired product (25a) (240 mg, 0.978 mmol, 95%) as a yellow solid which was used without further purification.

$^1$H NMR (400 MHz, CDCl$_3$) δ 0.27 (s, 6H), 5.73 (s, 1H), 6.83 (dt, J=1.0 Hz, 6.8 Hz, 1H), 7.22-7.28 (m, 1H), 7.60 (d, J=9.0 Hz, 1H), 7.73 (s, 1H), 8.10 (d, J=6.8 Hz, 1H).

Step 2: Preparation of intermediate methyl 2-hydroxy-2-{imidazo[1,2-a]pyridin-2-yl}acetate (25b)

Acetyl chloride (0.79 mL, 11.1 mmol) was added to anhydrous methanol (7 mL) at 0° C. under nitrogen atmosphere. The mixture was stirred for 10 minutes before adding 2-{imidazo[1,2-a]pyridin-2-yl}-2-[(trimethylsilyl)oxy]acetonitrile (25a) (227 mg, 0.93 mmol). The mixture was stirred 45 minutes at reflux then 1 hour at room temperature. The solution was concentrated in vacuo. The saturated solution of sodium hydrogencarbonate (10 mL) was added to the residue. The aqueous layer was extracted with dichloromethane (2×10 mL). The organic layer was dried over sodium sulfate and concentrated in vacuo to provide the desired ester (25b) (153 mg, 0.74 mmol, 80%) as a yellow solid which was used without further purification.

$^1$H NMR (300 MHz, CDCl$_3$) δ 3.81 (s, 3H), 5.44 (s, 1H), 6.78 (dt, J=1.1 Hz, 6.8 Hz, 1H), 7.16 (ddd, J=1.1 Hz, 6.8 Hz, 9.1 Hz, 1H), 7.59 (d, J=9.1 Hz, 1H), 7.63 (s, 1H), 8.07 (td, J=1.1 Hz, J=6.8 Hz, 1H).

MS m/z ([M+H]$^+$) 207.

Step 3: Preparation of intermediate methyl 2-(tert-butoxy)-2-{imidazo[1,2-a]pyridin-2-yl}acetate (25c)

To a solution of methyl 2-hydroxy-2-{imidazo[1,2-a]pyridin-2-yl}acetate (25b) (153 mg, 0.74 mmol) in tert-butyl acetate (12 mL) at 0° C. was added perchloric acid (1.5 mL). The mixture was stirred at 0° C. for 15 minutes and at room temperature for 45 minutes before being poured into a saturated aqueous solution of sodium hydrogencarbonate (50 mL). The layers were separated and the aqueous layer was extracted with ethyl acetate (2×20 mL). The organic layers were dried over sodium sulfate and concentrated in vacuo. The residue was purified by flash chromatography on silica gel (dichloromethane/ethyl acetate 50/50) to provide the desired product (25c) (108 mg, 0.41 mmol, 55%) as a colorless oil.

$^1$H NMR (300 MHz, CD$_3$OD) δ 1.27 (s, 9H), 3.75 (s, 3H), 5.36 (s, 1H), 6.88 (dt, J=1.1 Hz, 6.8 Hz, 1H), 7.28 (ddd, J=1.1 Hz, 6.8 Hz, 9.0 Hz, 1H), 7.48 (d, J=9.1 Hz, 1H), 7.82 (s, 1H), 8.07 (td, J=1.1 6.8 Hz, 1H).

MS m/z ([M+H]$^+$) 263.

Step 4: Preparation of intermediate methyl 2-{3-bromoimidazo[1,2-a]pyridin-2-yl}-2-(tert-butoxy)acetate (25d)

To a solution of methyl 2-(tert-butoxy)-2-{imidazo[1,2-a]pyridin-2-yl}acetate (25c) (108 mg, 0.41 mmol) in ethanol (5 mL) at 0° C. was added N-bromosuccinimide (76 mg, 0.43 mmol) portionwise. The mixture was stirred at 0° C. for 15 minutes and concentrated in vacuo. The residue was dissolved in ethyl acetate (5 mL) and washed with a saturated solution of sodium hydrogencarbonate (2×5 mL). The organic layer was dried over sodium sulfate and concentrated in vacuo to provide the desired product (25d) (127 mg, 0.37 mmol, 90%) as a yellow oil which was used without further purification.

$^1$H NMR (300 MHz, CDCl$_3$) δ 1.30 (s, 9H), 3.76 (s, 3H), 5.38 (s, 1H), 6.88 (dt, J=1.0 Hz, 6.8 Hz, 1H), 7.22 (ddd, J=1.2 Hz, 6.8 Hz, 9.0 Hz, 1H), 7.60 (td, J=1.0 Hz, J=9.1 Hz, 1H), 8.10 (td, J=1.1 Hz, J=6.8 Hz, 1H).

MS m/z ([M+H]$^+$) 341/343.

Step 5: Preparation of intermediate methyl 2-(tert-butoxy)-2-[3-(3,4-dihydro-2H-1-benzopyran-6-yl)imidazo[1,2-a]pyridin-2-yl]acetate (25e)

To a solution of methyl 2-{3-bromoimidazo[1,2-a]pyridin-2-yl}-2-(tert-butoxy)acetate (25d) (60 mg, 0.175 mmol), sodium carbonate (75 mg, 0.70 mmol), 6-(4,4,5,5-tetramethyl-1,3,2-dioxaborolan-2-yl)chroman (82 mg, 0.32 mmol) and palladium tetrakis(triphenylphosphine) (20 mg, 0.018 mmol) in a mixture of toluene (1.1 mL), water (0.55 mL) and ethanol (0.48 mL) was heated at 85° C. overnight. After cooling to room temperature, the mixture was poured into water (10 mL). The aqueous layer was extracted with ethyl acetate (2×5 mL). The organic layer was washed with brine (10 mL), dried over sodium sulfate and concentrated in vacuo. The residue was purified by flash chromatography on silica gel (dichloromethane/ethyl acetate 50/50). The residue containing target compound was dissolved in ethyl acetate (5 mL) and washed with 1M hydrochloric acid aqueous solution (5 mL). The acidic layer was basified with a saturated solution of sodium hydrogenocarbonate and extracted with ethyl acetate (2×5 mL). The organic layer was dried over sodium sulfate and concentrated in vacuo to provide the desired product (25e) (31 mg, 0.078 mmol, 45%).

$^1$H NMR (300 MHz, CDCl$_3$) δ 1.10 (s, 9H), 2.02-2.09 (m, 2H), 2.76-2.92 (m, 2H), 3.70 (s, 3H), 4.23-4.26 (m, 2H), 5.27 (s, 1H), 6.68 (t, J=6.8 Hz, 1H), 6.92 (d, J=9.0 Hz, 1H), 7.08-7.14 (m, 1H), 7.19-7.23 (m, 2H), 7.60 (d, J=9.1 Hz, 1H), 7.94 (d, J=6.9 Hz, 1H).

MS m/z ([M+H]$^+$) 395.

Step 6: Preparation of 2-(tert-butoxy)-2-[3-(3,4-dihydro-2H-1-benzopyran-6-yl)imidazo[1,2-a]pyridin-2-yl]acetic acid A mixture of methyl 2-(tert-butoxy)-2-[3-(3,4-dihydro-2H-1-benzopyran-6-yl)imidazo[1,2-a]pyridin-2-yl]acetate (25e) (31 mg, 0.079 mmol) and potassium hydroxide (18 mg, 0.37 mmol) in a mixture of ethanol (3 mL) and water (1 mL) was refluxed for 1 hour. The mixture was concentrated in vacuo. Water (1 mL) was added to the residue and the aqueous layer was extracted with ethyl acetate (5 mL). The aqueous layer was acidified with 1M hydrochloric acid until pH 7 and extracted with dichloromethane (2×5 mL). The organic layer was concentrated in vacuo to provide the desired acid (17 mg, 0.044 mmol, 56%) as a beige solid.

$^1$H NMR (400 MHz, CD$_3$OD) δ 1.07 (s, 9H), 2.03-2.07 (m, 2H), 2.82-2.96 (m, 2H), 4.26 (t, J=5.2 Hz, 2H), 5.15 (s, 1H), 6.97 (d, J=8.4 Hz, 1H), 7.11 (t, J=7.0 Hz, 1H), 7.34-7.38 (m, 2H), 7.56-7.60 (m, 1H), 7.71 (d, J=8.8 Hz, 1H), 8.26 (d, J=7.0 Hz, 1H).

MS m/z ([M+H]$^+$) 381.

MS m/z ([M−H]$^−$) 379.

Example 26

Synthesis of 2-(tert-butoxy)-2-[3-(3,4-dihydro-2H-1-benzopyran-6-yl)-4-methyl-1-benzofuran-2-yl]acetic acid

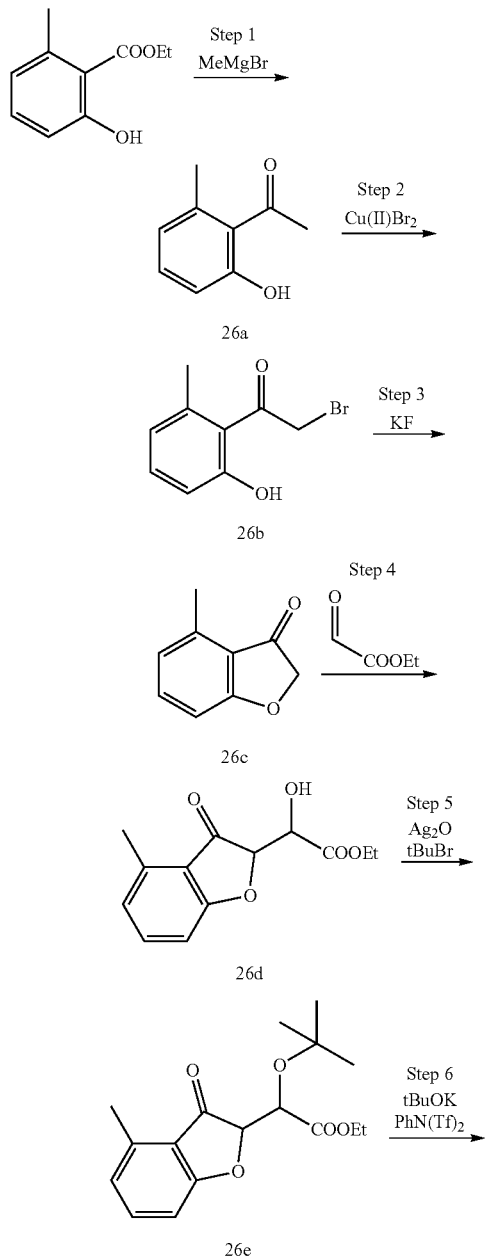

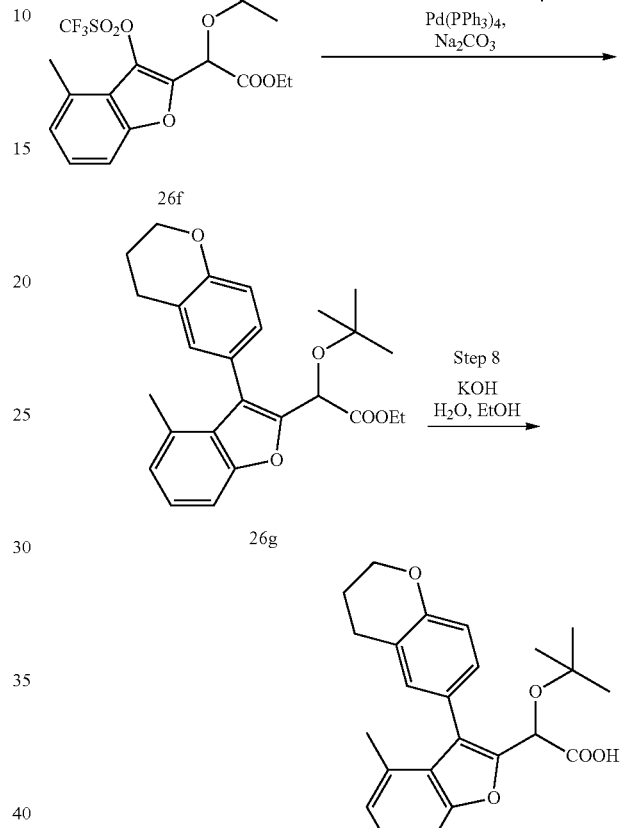

Step 1: Preparation of intermediate 1-(2-hydroxy-6-methylphenyl)ethan-1-one (26a)

A solution of methyl magnesium bromide 3M in diethyl ether (18.5 mL, 55.5 mmol) and triethylamine (6.0 mL, 44.4 mmol) in anhydrous toluene (14 mL) was cooled to 0° C. 6-methylsalicylic acid ethyl ester (2.0 g, 11.1 mmol) in anhydrous toluene (14 mL) was added dropwise and the reaction mixture was stirred at room temperature for 16 hours. A saturated solution of ammonium chloride (10 mL) was added and the mixture was filtered over Celite®. The filtrate was diluted with ethyl acetate (20 mL) and water (10 mL) and layers were separated. The organic layer was washed with brine (10 mL), dried over sodium sulfate and evaporated to dryness. The residue was purified by flash chromatography on silica gel (cyclohexane/ethyl acetate: 9/1) to provide the desired ketone (26a) (1.21 g, 8.0 mmol, 72%).

$^1$H NMR (300 MHz, CDCl$_3$) δ 2.60 (s, 3H), 2.67 (s, 3H), 6.72 (d, J=7.6 Hz, 1H), 6.84 (d, J=8.2 Hz, 1H), 7.28 (dd, J=7.6 Hz, 8.2 Hz, 1H), 12.29 (s, 1H).

Step 2: Preparation of intermediate 2-bromo-1-(2-hydroxy-6-methylphenyl)ethan-1-one (26b)

1-(2-hydroxy-6-methylphenyl)ethan-1-one (26a) (1.2 g, 8.0 mmol) was dissolved in a mixture of ethyl acetate (15 mL) and dichloromethane (15 mL) before being treated with copper (II) bromide (3.57 g, 16.0 mmol). The mixture was refluxed for 40 hours. After cooling to room temperature, the mixture was filtered and washed with ethyl acetate (5 mL). The filtrate was concentrated in vacuo and the residue was purified by flash chromatography on silica gel (cyclohexane/ethyl acetate 90/10) to provide the desired product (26b) (1.5 g, 6.5 mmol, 82%).

$^1$H NMR (300 MHz, CDCl$_3$) δ 2.60 (s, 3H), 4.58 (s, 2H), 6.82 (d, J=7.5 Hz, 1H), 6.92 (d, J=8.2 Hz, 1H), 7.44 (dd, J=7.5 Hz, 8.2 Hz, 1H).

Step 3: Preparation of intermediate 4-methyl-2,3-dihydro-1-benzofuran-3-one (26c)

Potassium fluoride (0.85 g, 14.7 mmol) was added to a solution of 2-bromo-1-(2-hydroxy-6-methylphenyl)ethan-1-one (26b) (1.5 g, 6.5 mmol) in anhydrous dimethylformamide (25 mL). The reaction mixture was stirred at room temperature for 4 days. Ethyl acetate (75 mL) was added and the mixture was washed with brine (3×100 mL). The organic layer was dried over sodium sulfate and evaporated to dryness. The residue was purified by flash chromatography on silica gel (cyclohexane/ethyl acetate 95/5 to 80/20) to provide the desired benzofuran-3-one (26c) (450 mg, 3.04 mmol, 46%).

$^1$H NMR (300 MHz, CDCl$_3$) δ 2.60 (s, 3H), 4.58 (s, 2H), 6.82 (d, J=7.4 Hz, 1H), 6.93 (d, J=8.3 Hz, 1H), 7.45 (dd, J=7.4 Hz, 8.3 Hz, 1H).

Steps 4 to 6: Preparation of intermediate ethyl 2-(tert-butoxy)-2-{4-methyl-3-[(trifluoromethane)sulfonyloxy]-1-benzofuran-2-yl}acetate (26f)

A solution of 4-methyl-2,3-dihydro-1-benzofuran-3-one (26c) (200 mg, 1.35 mmol) in ethyl glyoxylate 50% in toluene (0.40 mL, 2.02 mmol) was heated at 100° C. for 16 hours. The mixture was concentrated under reduced pressure and the residue was purified by flash chromatography on silica gel (cyclohexane/ethyl acetate: 95/5 to 80/20) to provide ethyl 2-hydroxy-2-(4-methyl-3-oxo-2,3-dihydro-1-benzofuran-2-yl)acetate (26d) (200 mg, 0.8 mmol) which was dissolved in a mixture of cyclohexane (2 mL) and dichloromethane (0.5 mL) before adding silver oxide (560 mg, 2.4 mmol) and tert-butyl bromide (0.54 mL, 4.8 mmol). The mixture was stirred at room temperature for 60 hours, with addition of silver oxide and tert-butyl bromide every hour of working day until the reaction stopped evolution. The mixture was filtered over Celite®, and the filtrate was concentrated in vacuo. The residue was purified by flash chromatography on silica gel (cyclohexane/ethyl acetate 90/10) to provide ethyl 2-(tert-butoxy)-2-(4-methyl-3-oxo-2,3-dihydro-1-benzofuran-2-yl)acetate (26e) (73 mg, 0.238 mmol) which was dissolved in a mixture of dimethylformamide (1.5 mL) and tetrahydrofuran (0.2 mL) under argon atmosphere. This mixture was cooled at −78° C. and a 1.0 M solution of potassium t-butoxide in tetrahydrofuran (0.26 mL, 0.262 mmol) was added. After 1 hour stirring at −78° C., a solution of N-phenyl-bis(trifluoromethanesulfonimide) (98 mg, 0.274 mmol) in dimethylformamide (0.07 mL) and tetrahydrofuran (0.3 mL) was slowly added and the mixture was further stirred at the same temperature for 90 minutes. The reaction was quenched by addition of saturated sodium carbonate solution (5 mL) and the mixture was extracted with ethyl acetate (2×10 mL). The combined organic layers were washed with brine, dried over sodium sulfate, and concentrated in vacuo. The residue was purified by preparative TLC (cyclohexane/ethyl acetate 80/20) to provide ethyl 2-(tert-butoxy)-2-{4-methyl-3-[(trifluoromethane)sulfonyloxy]-1-benzofuran-2-yl}acetate (26f) (60 mg, 0.137 mmol, 17% over 3 steps).

$^1$H NMR (400 MHz, CDCl$_3$) δ 1.24 (t, J=7.2 Hz, 3H), 1.29 (s, 9H), 2.62 (s, 3H), 4.18-4.29 (m, 2H), 5.42 (s, 1H), 7.08 (d, J=7.4 Hz, 1H), 7.27 (dd, J=7.4 Hz, 8.3 Hz, 1H), 7.38 (d, J=8.3 Hz, 1H).

Step 7: Preparation of intermediate ethyl 2-(tert-butoxy)-2-[3-(3,4-dihydro-2H-1-benzopyran-6-yl)-4-methyl-1-benzofuran-2-yl]acetate (26g)

A solution of ethyl 2-(tert-butoxy)-2-{4-methyl-3-[(trifluoromethane)sulfonyloxy]-1-benzofuran-2-yl}acetate (26f) (60 mg, 0.137 mmol), sodium carbonate (58 mg, 0.246 mmol), and 6-(4,4,5,5-tetramethyl-1,3,2-dioxaborolan-2-yl)chroman (64 mg, 0.246 mmol) in a mixture of toluene (0.6 mL), ethanol (0.3 mL) and water (0.3 mL) was bubbled with nitrogen for 5 minutes. Palladium tetrakis(triphenylphosphine) (8 mg, 0.007 mmol) was added and the reaction mixture was heated a 95° C. overnight. Water (3 mL) was added and aqueous layer was extracted with toluene (2×5 mL). The combined organic layers were washed with brine (5 mL), dried over sodium sulfate, and concentrated in vacuo. The residue was purified by preparative TLC (cyclohexane/ethyl acetate 80/20) to provide the desired product (26g) (30 mg, 0.07 mmol, 52%).

$^1$H NMR (400 MHz, CDCl$_3$) δ 1.10 (s, 9H), 1.21-1.30 (m, 3H), 2.02-2.11 (m, 2H), 2.15 (s, 3H), 2.76-2.89 (m, 2H), 4.16-4.26 (m, 2H), 4.26 (t, J=5.2 Hz, 2H), 5.06 (s, 1H), 6.81-6.90 (m, 1H), 6.94 (d, J=7.3 Hz, 1H), 7.05-7.16 (m, 1H), 7.13-7.21 (m, 2H), 7.38 (d, J=8.2 Hz, 1H).

Step 8: Preparation of 2-(tert-butoxy)-2-[3-(3,4-dihydro-2H-1-benzopyran-6-yl)-4-methyl-1-benzofuran-2-yl]acetic acid A mixture of ethyl 2-(tert-butoxy)-2-[3-(3,4-dihydro-2H-1-benzopyran-6-yl)-4-methyl-1-benzofuran-2-yl]acetate (26g) (30 mg, 0.07 mmol) and potassium hydroxide (34.6 mg, 0.28 mmol) in a mixture of ethanol (1 mL) and water (3 mL) was refluxed for 1 hour. The mixture was concentrated in vacuo. Water (2 mL) was added to the residue and the aqueous layer was washed with diethyl ether (2 mL). The aqueous layer was acidified with 1M hydrochloric acid until pH 2 and extracted with diethyl ether (2×3 mL). The organic layer was dried over sodium sulfate and concentrated in vacuo to provide the desired acid (example 26) (22 mg, 0.05 mmol, 79%).

$^1$H NMR (400 MHz, CDCl$_3$) δ 1.10 (s, 9H), 2.02-2.10 (m, 2H), 2.16 (s, 3H), 2.76-2.89 (m, 2H), 4.26 (t, J=5.2 Hz, 2H), 5.09 and 5.12 (s, 1H), 6.82-6.91 (m, 1H), 6.96 (d, J=7.4 Hz, 1H), 7.03-7.11 (m, 1H), 7.20 (dd, J=7.4 Hz, 8.1 Hz, 1H), 7.26-7.32 (m, 1H), 7.34 (d, J=8.1 Hz, 1H).

MS m/z ([M−H]$^−$) 393.

Example 27

Synthesis of 2-(tert-butoxy)-2-[5-(3,4-dihydro-2H-1-benzopyran-6-yl)-1,3-dimethyl-1H-pyrazol-4-yl] acetic acid

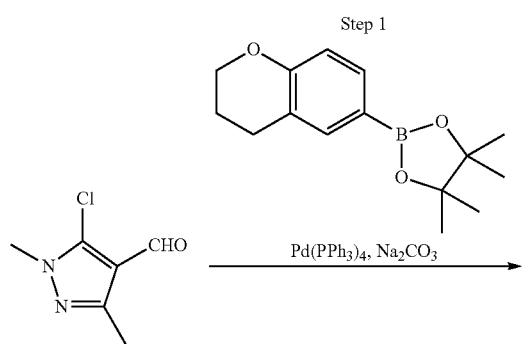

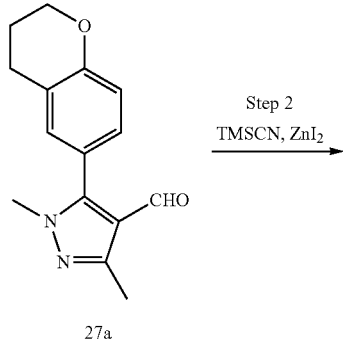

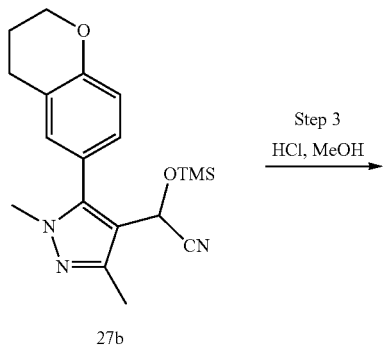

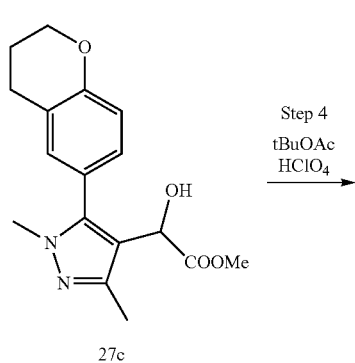

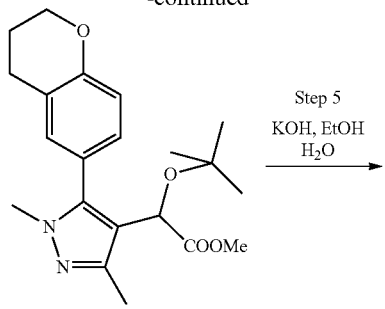

Step 1: Preparation of intermediate of 5-(3,4-dihydro-2H-1-benzopyran-6-yl)-1,3-dimethyl-1H-pyrazole-4-carbaldehyde (27a)

A solution of 5-chloro-1,3-dimethyl-1H-pyrazole-4-carboxaldehyde (200 mg, 1.26 mmol), sodium carbonate (282 mg, 2.66 mmol), 6-(4,4,5,5-tetramethyl-1,3,2-dioxaborolan-2-yl)chroman (426 mg, 1.64 mmol) and palladium tetrakis (triphenylphosphine) (73 mg, 0.063 mmol) in a mixture of dimethoxyethane (4 mL) and water (1.35 mL) was heated at 85° C. for 24 hours. After cooling to room temperature, the mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 80/20 then 50/50) to provide the desired product (27a) (110 mg, 0.43 mmol, 34%) as a beige solid.

$^1$H NMR (400 MHz, CDCl$_3$) δ 2.03-2.09 (m, 2H), 2.51 (s, 3H), 2.84 (t, J=6.4 Hz, 2H), 3.72 (s, 3H), 4.25-4.27 (m, 2H), 6.91 (d, J=8.3 Hz, 1H), 7.05-7.10 (m, 2H), 9.61 (s, 1H).

MS m/z ([M+H]$^+$) 257.

Step 2: Preparation of intermediate 2-[5-(3,4-dihydro-2H-1-benzopyran-6-yl)-1,3-dimethyl-1H-pyrazol-4-yl]-2-[(trimethylsilyl)oxy]acetonitrile (27b)

To a solution of 5-(3,4-dihydro-2H-1-benzopyran-6-yl)-1,3-dimethyl-1H-pyrazole-4-carbaldehyde (27a) (110 mg, 0.43 mmol) in anhydrous dichloromethane (5 mL) at 0° C. under nitrogen atmosphere were successively added zinc iodide (16 mg, 0.052 mmol) and trimethylsilyl cyanide (81 μL, 0.64 mmol). The mixture was stirred at room temperature overnight. A saturated solution of sodium hydrogencarbonate (10 mL) was added. Layers were separated and the aqueous layer was extracted with dichloromethane (2×10 mL). The organic layers were dried over sodium sulfate and concentrated in vacuo to provide the desired product (27b) (147 mg, 0.41 mmol, 96%) as a yellow oil which was used without further purification.

$^1$H NMR (300 MHz, CDCl$_3$) δ 0.09 (s, 9H), 2.02-2.10 (m, 2H), 2.44 (s, 3H), 2.83 (t, J=6.4 Hz, 2H), 3.66 (s, 3H), 4.24-4.27 (m, 2H), 5.17 (s, 1H), 6.89 (d, J=8.4 Hz, 1H), 6.95-7.01 (m, 2H).

Step 3: Preparation of intermediate methyl 2-[5-(3,4-dihydro-2H-1-benzopyran-6-yl)-1,3-dimethyl-1H-pyrazol-4-yl]-2-hydroxyacetate (27c)

Acetyl chloride (0.35 mL, 4.96 mmol) was added to anhydrous methanol (3 mL) at 0° C. under nitrogen atmosphere. The mixture was stirred for 20 minutes before adding 2-[5-(3,4-dihydro-2H-1-benzopyran-6-yl)-1,3-dimethyl-1H-pyrazol-4-yl]-2-[(trimethylsilyl)oxy]acetonitrile (27b) (147 mg, 0.41 mmol). The mixture was stirred at room temperature for 1 hour then at 50-60° C. for 5 hours. The solution was concentrated in vacuo. A saturated solution of sodium hydrogencarbonate (10 mL) was added to the residue. The aqueous layer was extracted with ethyl acetate (2×10 mL). The organic layer was washed with brine (10 mL), dried over sodium sulfate and concentrated in vacuo. The residue was purified by flash chromatography on silica gel (dichloromethane/ethyl acetate 40/60) to provide the desired hydroxyl-ester (27c) (72 mg, 0.227 mmol, 55%) as a colorless oil.

$^1$H NMR (300 MHz, CDCl$_3$) δ 1.99-2.07 (m, 2H), 2.21 (s, 3H), 2.81 (t, J=6.6 Hz, 2H), 3.30 (bs, 1H), 3.65 (s, 3H), 3.67 (s, 3H), 4.20-4.24 (m, 2H), 4.95 (d, J=3.0 Hz, 1H), 6.85 (d, J=8.4 Hz, 1H), 7.02-7.06 (m, 2H).

MS m/z ([M+H]$^+$) 317.

Step 4: Preparation of intermediate methyl 2-(tert-butoxy)-2-[5-(3,4-dihydro-2H-1-benzopyran-6-yl)-1,3-dimethyl-1H-pyrazol-4-yl]acetate (27d)

To a solution of methyl 2-[5-(3,4-dihydro-2H-1-benzopyran-6-yl)-1,3-dimethyl-1H-pyrazol-4-yl]-2-hydroxyacetate (27c) (72 mg, 0.227 mmol) in tert-butyl acetate (6 mL) at 0° C. was added perchloric acid (0.75 mL). The mixture was stirred at 0° C. for 3 hours at room temperature before being poured into a saturated aqueous solution of sodium carbonate (30 mL). The layers were separated and the aqueous layer was extracted with ethyl acetate (2×20 mL). The organic layers were dried over sodium sulfate and concentrated in vacuo. The residue was purified by flash chromatography on silica gel (cyclohexane/ethyl acetate: 50/50) to provide the desired product (27d) (51 mg, 0.137 mmol, 60%) as a colorless oil.

$^1$H NMR (400 MHz, CDCl$_3$) δ 1.02 (s, 9H), 2.02-2.08 (m, 2H), 2.32 (s, 3H), 2.76-2.89 (m, 2H), 3.62 (s, 3H), 3.65 (s, 3H), 4.23 (t, J=5.2 Hz, 2H), 4.78 (s, 1H), 6.86 (d, J=8.0 Hz, 1H), 7.03-7.07 (m, 2H).

MS m/z ([M+H]$^+$) 373.

Step 5: Preparation of 2-(tert-butoxy)-2-[5-(3,4-dihydro-2H-1-benzopyran-6-yl)-1,3-dimethyl-1H-pyrazol-4-yl]acetic acid A mixture of methyl 2-(tert-butoxy)-2-[5-(3,4-dihydro-2H-1-benzopyran-6-yl)-1,3-dimethyl-1H-pyrazol-4-yl]acetate (51 mg, 0.14 mmol) and potassium hydroxide (31 mg, 0.55 mmol) in a mixture of ethanol (3 mL) and water (1 mL) was refluxed for 30 minutes. The mixture was concentrated in vacuo. Water (2 mL) was added to the residue and the aqueous layer was extracted with diethyl ether (5 mL). The aqueous layer was acidified with 1M hydrochloric acid until pH 2.5 and extracted with diethyl ether (2×5 mL). The organic layer was dried over sodium sulfate and concentrated in vacuo to provide the desired acid (example 27) (34 mg, 0.094 mmol, 69%) as a white solid.

$^1$H NMR (300 MHz, CDCl$_3$) δ 1.05 (s, 9H), 2.01-2.09 (m, 2H), 2.28 (s, 3H), 2.81-2.86 (m, 2H), 3.65 (s, 3H), 4.25 (t, J=5.1 Hz, 2H), 4.83 (s, 1H), 6.87 (d, J=9.0 Hz, 1H), 7.10-7.13 (m, 2H).

MS m/z ([M+H]$^+$) 359.

MS m/z ([M−H]$^-$) 357.

Example 28

Synthesis of 2-(tert-butoxy)-2-(2,5-dimethyl-4-phenylthiophen-3-yl)acetic acid

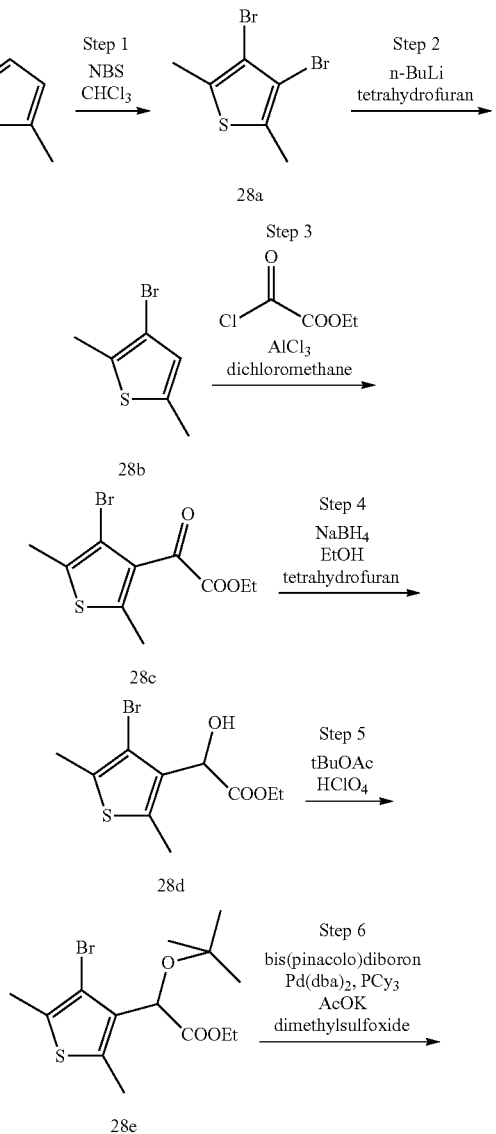

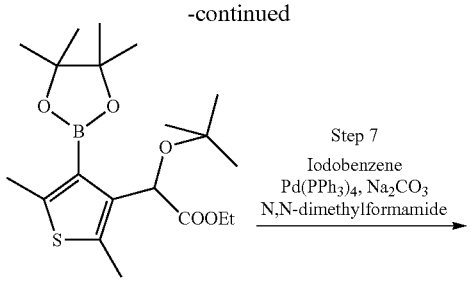

28f

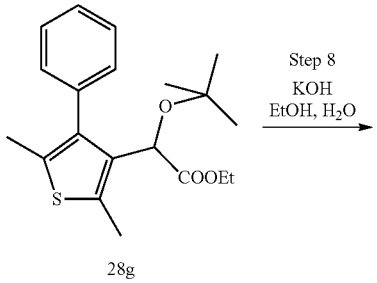

28g

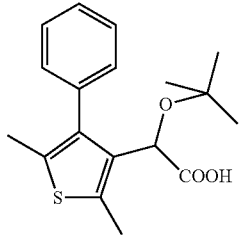

Example 28

Step 1: Preparation of intermediate 3,4-dibromo-2,5-dimethylthiophene (28a)

Under a nitrogen atmosphere, N-bromosuccinimide (9.52 g, 53.4 mmol) was added at 0° C. per portion to a solution of 2,5-dimethylthiophene (3 g, 26.7 mmol) in chloroform (150 mL) in an amber round bottom flask. After 30 minutes, the reaction mixture was warmed to room temperature and stirred for 7 hours more. Water was then added and the both layers were separated. The organic layer was washed with a saturated aqueous solution of sodium bicarbonate, water, brine, dried over sodium sulfate, filtered, and evaporated under reduced pressure. The residue was purified by flash chromatography on silica gel (cyclohexane) to afford a mixture of dibrominated (28a)/monobrominated (92/8) products as a white solid (6 g, 20.5 mmol, 77%).

$^1$H NMR (400 MHz, CDCl$_3$) δ 2.40 (s, 6H).

Step 2: Preparation of intermediate 3-bromo-2,5-dimethylthiophene (28b)

Under a nitrogen atmosphere, at −78° C., a solution of n-butyllithium (3.71 mL, 5.94 mmol, 1.6M in hexane) was added to a solution of 3,4-dibromo-2,5-dimethylthiophene (28a) (1.65 g, 5.94 mmol). The mixture was stirred at −78° C. for 1 hour. Water was then added and the mixture was stirred at room temperature. It was partitioned between ethyl acetate and water. The organic layer was washed with water, brine, dried over sodium sulfate, filtered, and concentrated under reduced pressure to give the desired product (28b) (886 mg, 4.6 mmol, 76%).

$^1$H NMR (400 MHz, CDCl$_3$) δ 2.32 (s, 3H), 2.40 (s, 3H), 6.56 (s, 6H).

Step 3: Preparation of intermediate ethyl 2-(4-bromo-2,5-dimethylthiophen-3-yl)-2-oxoacetate (28c)

Under a nitrogen atmosphere, ethyl chlorooxoacetate (1.04 mL, 9.27 mmol) and aluminum chloride (per 3 portions) (2.47 g, 18.54 mmol) was added successively at −5° C. to a solution of 3-bromo-2,5-dimethylthiophene (28b) (886 mg, 4.64 mmol) in dichloromethane (20 mL). After 3 hours at −5° C., the reaction mixture was slowly hydrolyzed at 0° C. with water. The organic layer was separated, washed with water, brine, dried over sodium sulfate, filtered, and evaporated under reduced pressure. The residue was purified by flash chromatography on silica gel (cyclohexane/ethyl acetate 95/5) to give the desired keto-ester (28c) (725 mg, 2.50 mmol, 50%).

$^1$H NMR (400 MHz, CDCl$_3$) δ 1.40 (t, J=7.2 Hz, 3H), 2.35 (s, 3H), 2.61 (s, 3H), 4.40 (q, J=7.2 Hz, 2H).

MS m/z ([M+H]$^+$) 291/293.

Step 4: Preparation of intermediate ethyl 2-(4-bromo-2,5-dimethylthiophen-3-yl)-2-hydroxyacetate (28d)

To a solution of ethyl 2-(4-bromo-2,5-dimethylthiophen-3-yl)-2-oxoacetate (28c) (1 g, 3.56 mmol) in tetrahydrofuran (22.5 mL) and ethanol (5.6 mL) cooled to 0° C. is added sodium tetraborohydride (121.2 mg, 3.20 mmol). The mixture is stirred at 0° C. for 1 hour. The mixture is quenched with HCl (1N) and extracted with ethyl acetate. The organic extract is washed with brine, dried over sodium sulfate, filtered and concentrated to afford the desired alcohol (28d) as a white solid (836 mg, 2.85 mmol, 89%) which was used without further purification.

$^1$H NMR (400 MHz, CDCl$_3$) δ 1.26 (t, J=7.1 Hz, 3H), 2.32 (s, 3H), 2.41 (s, 3H), 4.20-4.29 (m, 2H), 5.28 (s, 1H).

MS m/z ([M+H]$^+$) 275/277.

Step 5: Preparation of intermediate ethyl 2-(4-bromo-2,5-dimethylthiophen-3-yl)-2-(tert-butoxy)acetate (28e)

To a suspension of ethyl 2-(4-bromo-2,5-dimethylthiophen-3-yl)-2-hydroxyacetate (28d) (830 mg, 2.83 mmol) in tert-butylacetate (29 mL) at −10° C. was added perchloric acid (1 mL). The mixture was stirred at −5° C. for 1 hour. The mixture was then basified with a saturated aqueous solution of sodium bicarbonate until pH 8. The aqueous layer was extracted with ethyl acetate. The organic layer was washed with brine, dried over sodium sulfate, filtered and concentrated under reduced pressure. The residue was purified by flash chromatography on silica gel (cyclohexane/ethyl acetate 90/10) to afford the desired product (28e) as a colorless oil (870 g, 2.49 mmol, 88%).

$^1$H NMR (400 MHz, CDCl$_3$) δ 1.25 (s, 9H), 2.36 (s, 3H), 2.53 (s, 3H), 4.06-4.21 (m, 2H), 5.28 (s, 1H).

MS m/z ([M+Na]$^+$) 371/373.

Step 6: Preparation of intermediate ethyl 2-(tert-butoxy)-2-[2,5-dimethyl-4-(tetramethyl-1,3,2-dioxaborolan-2-yl)thiophen-3-yl]acetate (28f)

Under argon atmosphere, a mixture of bis(dibenzylideneacetone)palladium (98.8 mg, 0.172 mmol) and tricyclohexylphosphine (115.6 mg, 0.412 mmol) in dimethylsulfoxide (26 mL) was stirred for 30 minutes at room temperature. Then potassium acetate (1.68 g, 17.2 mmol), bis(pinacolo)diboron (2.18 g, 8.59 mmol) and the solution of ethyl 2-(4-bromo-2,5-dimethylthiophen-3-yl)-2-(tert-butoxy)acetate (28e, 2 g, 5.73 mmol) in dimethylsulfoxide was added successively. The mixture was stirred at 100° C. for 16 hours. The reaction was cooled to room temperature, diluted with ethyl acetate and filtered through Celite® (with ethyl acetate washings). The filtrate was concentrated. The mixture was extracted with ethyl acetate and the combined organic layers were washed with water, brine, dried over sodium sulfate, filtered and concentrated under reduced pressure. The residue was purified by flash chromatography on silica gel (cyclohexane/ethyl acetate 95/5) to afford the desired product (28f) (1.26 g, 3.18 mmol, 56%).

$^1$H NMR (400 MHz, CDCl$_3$) δ 1.20 (t, J=7.1 Hz, 3H), 1.24 (s, 9H), 1.32 (s, 6H), 1.33 (s, 6H), 2.50 (s, 3H), 2.58 (s, 3H), 3.96-4.19 (m, 2H), 5.93 (s, 1H). MS m/z ([M−OtBu])$^+$322/323.

Step 7: Preparation of intermediate ethyl 2-(tert-butoxy)-2-(2,5-dimethyl-4-phenylthiophen-3-yl)acetate (28g)

Under argon atmosphere, sodium carbonate (18 mg, 0.169 mmol), water (1.1 mL) and iodobenzene (19 μL, 0.17 mmol) were added to a solution of ethyl 2-(tert-butoxy)-2-[2,5-dimethyl-4-(tetramethyl-1,3,2-dioxaborolan-2-yl)thiophen-3-yl]acetate (28f) (70 mg, 0.16 mmol) in N,N-dimethylformamide (3.4 mL). The solution was degassed under argon and palladium tetrakis(triphenylphosphine) (37 mg, 0.032 mmol) was added. The mixture was heated at 100° C. for 3 hours. The mixture was then cooled at room temperature, water was added and the aqueous layer was extracted with ethyl acetate. The organic layer was washed with brine, dried over sodium sulfate, filtered and evaporated under reduced pressure. The residue was purified by preparative TLC (cyclohexane/ethyl acetate 90/10) to afford the desired product ethyl (28g) (42 mg, 0.121 mmol, 75%).

$^1$H NMR (400 MHz, CDCl$_3$) δ 0.97 (s, 9H), 1.23 (t, J=7.1 Hz, 3H), 2.19 (s, 3H), 2.51 (s, 3H), 4.09-4.17 (m, 2H), 4.77 (s, 1H), 7.28-7.43 (m, 5H). MS m/z ([M−Na]$^+$) 369.

Step 8: Preparation of 2-(tert-butoxy)-2-(2,5-dimethyl-4-phenylthiophen-3-yl)acetic acid Potassium hydroxide (6.5 mg, 0.115 mmol) was added to a solution of ethyl 2-(tert-butoxy)-2-(2,5-dimethyl-4-phenylthiophen-3-yl)acetate (28g) (20 mg, 0.058 mmol) in a mixture of ethanol (0.7 mL) and water (1.45 mL). The mixture was heated at 100° C. for 3 hours. The mixture was concentrated to evaporate ethanol in vacuo. The aqueous layer was acidified with a 1N hydrochloric acid solution and extracted with dichloromethane twice. The organic layer was washed with brine, dried over sodium sulfate, filtered and concentrated in vacuo. The residue was purified by preparative TLC (dichloromethane/methanol 95/5) to give the desired acid (example 28) (6 mg, 0.02 mmol, 33% yield).

$^1$H NMR (400 MHz, CDCl$_3$) δ 0.97 (s, 9H), 2.21 (s, 3H), 2.41 (s, 3H), 4.89 (s, 1H), 7.32-7.42 (m, 5H).

MS m/z ([M+Na]$^+$) 341.

Example 29

Synthesis of 2-(tert-butoxy)-2-[4-(cyclohex-1-en-1-yl)-2,5-dimethyl thiophen-3-yl]acetic acid

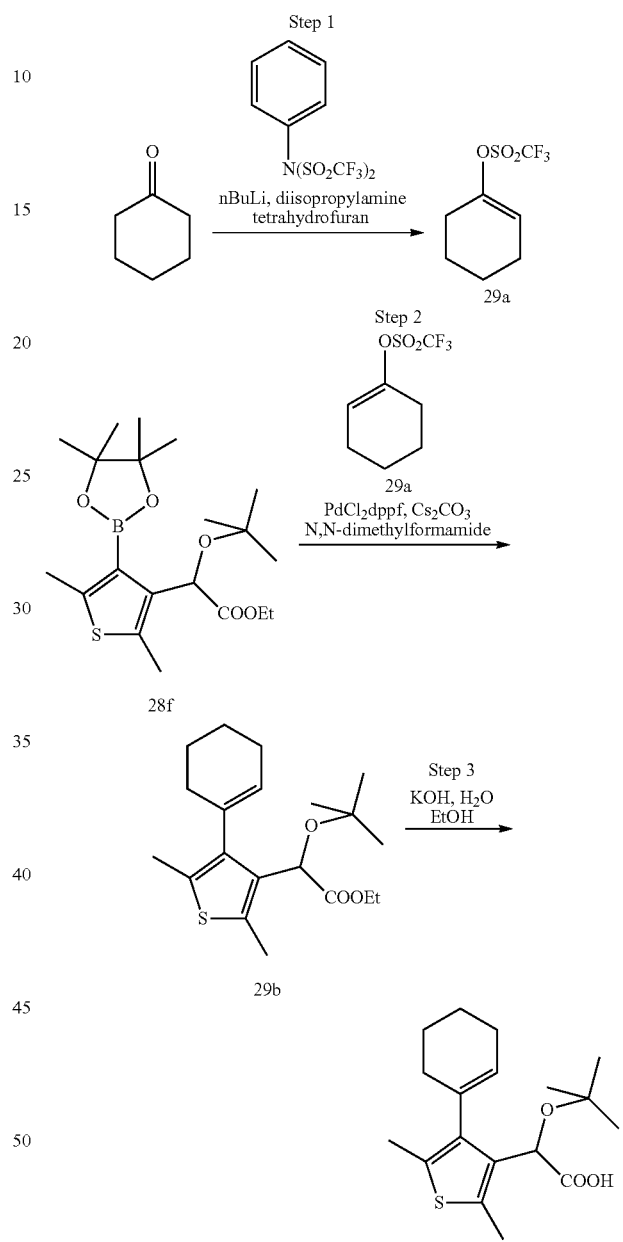

Step 1: Preparation of intermediate cyclohex-1-en-1-yl trifluoromethanesulfonate (29a)

At −78° C., n-butyllithium (1.6 M in hexanes, 1.40 mL, 2.24 mmol) was added to a solution of diisopropylamine (314 μL, 2.24 mmol) in tetrahydrofuran (4.8 mL). The solution was stirred for 20 minutes, and then a solution of cyclohexanone (200 mg, 2.04 mmol) in tetrahydrofuran (3 mL) was added. After stirring at −78° C. for 1 hour, a solution of N-phenyltrifluoromethanesulfonimide (779 mg, 2.18 mmol) in tetrahydrofuran (3 mL) was added. The reaction was stirred at −78° C. for 1.5 hours and it was warmed at room temperature. After 2.5 hours, the mixture was concentrated under reduced pressure. Then it was partitioned between diethyl ether and an aqueous saturated solution of sodium bicarbonate. The organic layer was washed with water, brine, dried over sodium sulfate, filtered, and concentrated under reduced pressure. The crude material was purified by flash chromatography on silica gel (cyclohexane/ethyl acetate 98/2) to provide the desired (208 mg, 0.903 mmol, 44%) as a colorless oil.

$^1$H NMR (400 MHz, CDCl$_3$) δ 1.57-1.66 (m, 2H), 1.78-1.85 (m, 2H), 2.19-2.23 (m, 2H), 2.33-2.37 (m, 2H), 5.77-5.79 (m, 1H).

Step 2: Preparation of intermediate ethyl 2-(tert-butoxy)-2-[4-(cyclohex-1-en-1-yl)-2,5-dimethylthiophen-3-yl]acetate (29b)

Under argon atmosphere, ethyl 2-(tert-butoxy)-2-[2,5-dimethyl-4-(tetramethyl-1,3,2-dioxaborolan-2-yl)thiophen-3-yl]acetate (28f) (50 mg, 0.114 mmol), cyclohex-1-en-1-yl trifluoromethanesulfonate (29a) (27.7 mg, 0.120 mmol) and cesium carbonate (112.2 mg, 0.344 mmol) was dissolved in dry N,N-dimethylformamide (570 μL). The solution was degassed under argon and PdCl$_2$(dppf) (5.6 mg, 0.007 mmol) was added. The reaction was heated and shaken at 100° C., for 6.5 hours. The mixture was filtered through Celite®, rinsed with ethyl acetate and dichloromethane. The solution was concentrated in vacuo and partitioned between ethyl acetate and water. The organic layer was washed with brine, dried over sodium sulfate, filtered, and concentrated under reduced pressure. The crude material was purified by preparative TLC (cyclohexane/ethyl acetate 90/01) to provide the desired product (30 mg, 0.09 mmol, 75%).

$^1$H NMR (400 MHz, CDCl$_3$) δ 1.21 (s, 9H), 1.24 (t, J=7.1 Hz, 3H), 1.68-1.80 (m, 4H), 1.99-2.34 (m, 7H), 2.50 (s, 3H), 4.14 (dq, J=7.1 Hz, 3.1 Hz, 2H), 5.00 (s, 1H), 5.60 (5, 1H).

MS m/z ([M+Na]$^+$) 373

Step 3: Preparation of 2-(tert-butoxy)-2-[4-(cyclohex-1-en-1-yl)-2,5-dimethylthiophen-3-yl]acetic acid Potassium hydroxide (9 mg, 0.16 mmol) was added to a solution of ethyl 2-(tert-butoxy)-2-[4-(cyclohex-1-en-1-yl)-2,5-dimethylthiophen-3-yl]acetate (29b) (28 mg, 0.08 mmol) in a mixture of ethanol (1 mL) and water (2.1 mL). The mixture was heated at 90° C. for 4 hours. The mixture was concentrated to evaporate ethanol in vacuo. The aqueous layer was acidified with a 1N hydrochloric acid solution and extracted with ethyl acetate twice. The organic layer was washed with brine, dried over sodium sulfate, filtered and concentrated in vacuo. The residue was purified by preparative TLC (dichloromethane/methanol 95/5) to give the desired acid (example 29) (13 mg, 0.04 mmol, 50% yield).

$^1$H NMR (400 MHz, CDCl$_3$) δ 1.25 (s, 9H), 1.68-1.80 (m, 4H), 2.01-2.18 (m, 3H), 2.26 (s, 3H), 2.32-2.38 (m, 1H), 2.42 (s, 3H), 5.07 (s, 1H), 5.62 (s, 1H).

MS m/z ([M−H]$^−$) 321.

Example 30

Synthesis of 2-(tert-butoxy)-2-[4-(3,6-dihydro-2H-pyran-4-yl)-2,5-dimethyl thiophen-3-yl]acetic acid

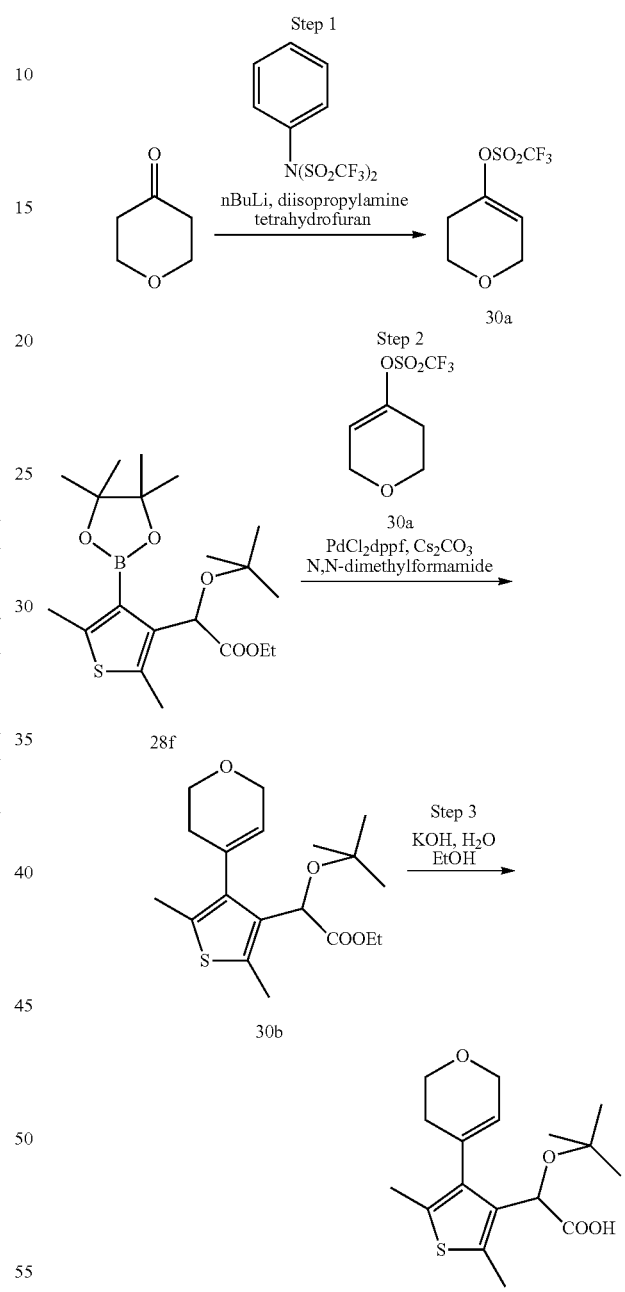

Example 30

Step 1: Preparation of intermediate 3,6-dihydro-2H-pyran-4-yl trifluoromethanesulfonate (30a)

Using the procedure described in example 29, step 1, tetrahydro-pyran-4-one (200 mg, 2.0 mmol) is converted, after purification by flash chromatography on silica gel (cyclohexane/ethyl acetate 90/01), to 3,6-dihydro-2H-pyran-4-yl trifluoromethanesulfonate (30a) (0.221 g, 0.60 mmol, 98%) as a colorless oil.

$^1$H NMR (400 MHz, CDCl$_3$) δ 2.46 (m, 2H), 3.89 (m, 2H), 4.26 (m, 2H), 5.82 (m, 1H).

Step 2: Preparation of intermediate ethyl 2-(tert-butoxy)-2-[4-(3,6-dihydro-2H-pyran-4-yl)-2,5-dimethylthiophen-3-yl]acetate (30b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (50 mg, 0.105 mmol) is converted, by reaction with 3,6-dihydro-2H-pyran-4-yl trifluoromethanesulfonate (30a) and after purification by flash chromatography on silica gel (cyclohexane/ethyl acetate 90/10), to ethyl 2-(tert-butoxy)-2-[4-(3,6-dihydro-2H-pyran-4-yl)-2,5-dimethylthiophen-3-yl]acetate (30b) (26 mg, 0.07 mmol, 70%).

$^1$H NMR (400 MHz, CDCl$_3$) δ 1.18-1.21 (m, 12H), 2.15-2.25 (m, 4H), 2.43-2.47 (m, 4H), 3.91 (t, J=5.5 Hz, 2H), 4.03-4.08 (m, 2H), 4.27-4.31 (m, 2H), 5.00 (s, 1H), 5.63 (s, 1H).

MS m/z ([M+Na]$^+$) 375.

Step 3: Preparation of 2-(tert-butoxy)-2-[4-(3,6-dihydro-2H-pyran-4-yl)-2,5-dimethylthiophen-3-yl]acetic acid Using the procedure described in example 29, step 3, ethyl 2-(tert-butoxy)-2-[4-(3,6-dihydro-2H-pyran-4-yl)-2,5-dimethylthiophen-3-yl]acetate (30b) (23 mg, 0.07 mmol) is converted, after purification by flash chromatography on silica gel (dichloromethane/methanol 90/10), to 2-(tert-butoxy)-2-[4-(3,6-dihydro-2H-pyran-4-yl)-2,5-dimethylthiophen-3-yl] acetic acid (example 30) (12 mg, 0.04 mmol, 59%).

$^1$H NMR (400 MHz, CDCl$_3$) δ 1.23 (s, 9H), 2.15-2.25 (m, 4H), 2.41-2.49 (m, 4H), 3.83-3.92 (m, 2H), 4.26-4.27 (m, 2H), 5.04 (s, 1H), 5.64 (s, 1H).

MS m/z ([M−H]$^-$) 323.

Example 31

Synthesis of 2-(tert-butoxy)-2-[4-(cyclohept-1-en-1-yl)-2,5-dimethyl thiophen-3-yl]acetic acid

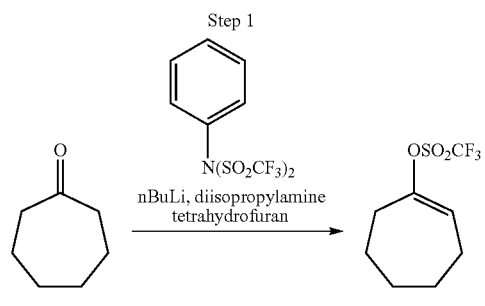

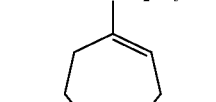

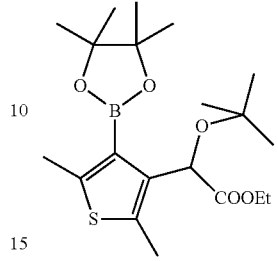

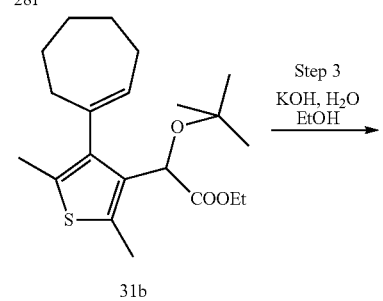

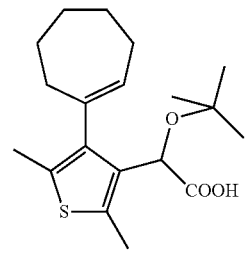

Example 31

Step 1: Preparation of intermediate cyclohept-1-en-1-yl trifluoromethanesulfonate (31a)

Using the procedure described in example 29, step 1, cycloheptanone (150 mg, 1.34 mmol) is converted, after purification by flash chromatography on silica gel (cyclohexane/ethyl acetate 95/5), to cyclohept-1-en-1-yl trifluoromethanesulfonate (31a) (114 mg, 0.47 mmol, 34%) as a colorless oil.

$^1$H NMR (400 MHz, CDCl$_3$) δ 1.61-1.76 (m, 6H), 2.14-2.18 (m, 2H), 2.51-2.53 (m, 2H), 5.88 (t, J=6.5 Hz, 1H).

Step 2: Preparation of intermediate ethyl 2-(tert-butoxy)-2-[4-(cyclohept-1-en-1-yl)-2,5-dimethylthiophen-3-yl]acetate (31b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (50 mg, 0.105 mmol) is converted, by reaction with cyclohept-1-en-1-yl trifluoromethanesulfonate (31a) and after purification by flash chromatography on silica gel (cyclohexane/ethyl acetate 80/20), to ethyl 2-(tert-butoxy)-2-[4-(cyclohept-1-en-1-yl)-2,5-dimethylthiophen-3-yl]acetate (31b) (23 mg, 0.06 mmol, 50%).

$^1$H NMR (400 MHz, CDCl$_3$) δ 1.17-1.20 (m, 12H), 1.60-1.85 (m, 6H), 2.24-2.47 (m, 10H), 4.05-4.16 (m, 2H), 4.96 (s, 1H), 5.70 (s, 1H).

Step 3: Preparation of 2-(tert-butoxy)-2-[4-(cyclohept-1-en-1-yl)-2,5-dimethylthiophen-3-yl]acetic acid (example 31)

Using the procedure described in example 29, step 3, ethyl 2-(tert-butoxy)-2-[4-(cyclohept-1-en-1-yl)-2,5-dimethylthiophen-3-yl]acetate (28f) (23 mg, 0.06 mmol) is converted, after purification by flash chromatography on silica gel (dichloromethane/methanol 90/10), to 2-(tert-butoxy)-2-[4-(cyclohept-1-en-1-yl)-2,5-dimethylthiophen-3-yl]acetic acid (example 31) (11 mg, 0.03 mmol, 52%).

$^1$H NMR (300 MHz, CDCl$_3$) δ 1.20 (s, 9H), 1.55-1.86 (m, 6H), 2.22-2.37 (m, 10H), 4.98 (s, 1H), 5.67 (s, 1H).

MS m/z ([M−H]$^-$) 335

Example 32

Synthesis of 2-(tert-butylsulfanyl)-2-[4-(3,4-dihydro-2H-1-benzopyran-6-yl)-2,5-dimethylthiophen-3-yl]acetic acid

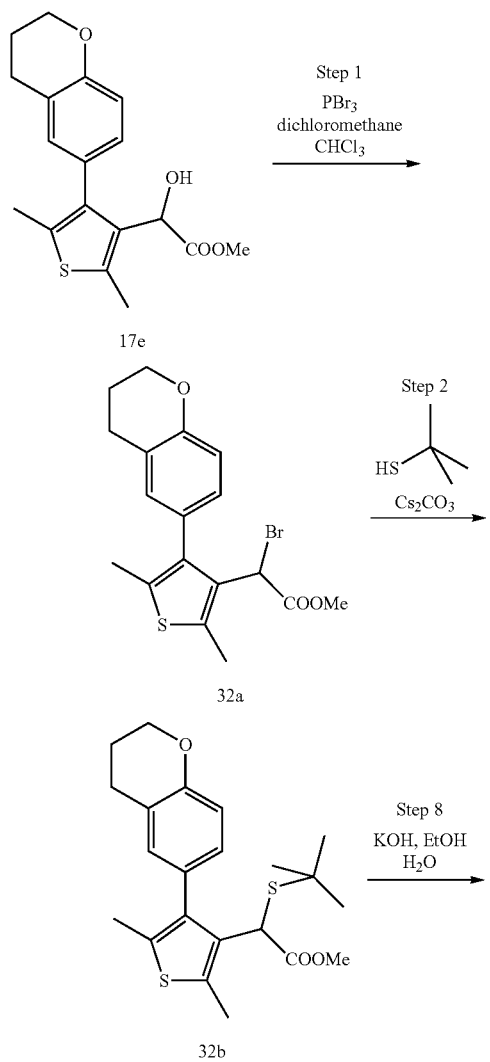

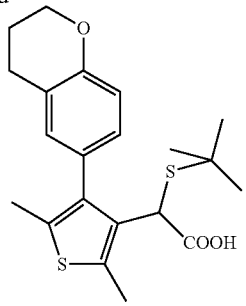

Example 32

Step 1: Preparation of intermediate methyl 2-bromo-2-[4-(3,4-dihydro-2H-1-benzopyran-6-yl)-2,5-dimethylthiophen-3-yl]acetate (32a)

Under a nitrogen atmosphere, phosphorus tribromide 1N in dichloromethane (0.98 mL, 0.98 mmol) was added to a solution of methyl 2-[4-(3,4-dihydro-2H-1-benzopyran-6-yl)-2,5-dimethylthiophen-3-yl]-2-hydroxyacetate (17e) (650 mg, 1.96 mmol) in chloroform (3 mL). After 3 hours stirring, dichloromethane (5 mL) was added and the reaction mixture was washed with water (2×10 mL). The organic layer was separated, dried over sodium sulfate and concentrated in vacuo to provide the desired brominated product (32a) (694 mg, 1.75 mmol, 89%) which was used without further purification.

$^1$H NMR (300 MHz, CDCl$_3$) δ 1.99-2.10 (m, 2H), 2.20 (s, 3H), 2.43 (s, 3H), 2.82 (t, J=6.5 Hz, 2H), 3.69 (s, 3H), 4.23 (t, J=5.2 Hz, 2H), 5.39 (s, 1H), 6.80-6.86 (m, 1H), 6.93-7.00 (m, 2H).

Step 2: Preparation of intermediate methyl 2-(tert-butylsulfanyl)-2-[4-(3,4-dihydro-2H-1-benzopyran-6-yl)-2,5-dimethylthiophen-3-yl]acetate (32b)

A mixture of methyl 2-bromo-2-[4-(3,4-dihydro-2H-1-benzopyran-6-yl)-2,5-dimethylthiophen-3-yl]acetate (32a) (50 mg, 0.126 mmol), cesium carbonate (82 mg, 0.253 mmol) and 2-methyl-2-propanethiol (23 mg, 0.253 mmol) in N,N-dimethylformamide (2 mL) was stirred at room temperature for 5 hours. The reaction mixture was quenched with water (6 mL) and extracted with ethyl acetate (4×5 mL). The organic layer was washed with brine (10 mL), dried over sodium sulfate and concentrated in vacuo. The residue was purified by preparative TLC (cyclohexane/ethyl acetate 80/20) to provide the desired thio-ether (32b) (28 mg, 0.07 mmol, 55%) as a clear yellow oil.

$^1$H NMR (400 MHz, CDCl$_3$) δ 1.09 (s, 9H), 1.99-2.08 (m, 2H), 2.20 (s, 3H), 2.49 (s, 3H), 2.73-2.88 (m, 2H), 3.70 (s, 3H), 4.19-4.25 (m, 2H), 4.54 (s, 1H), 6.80-6.88 (m, 1H), 6.92-7.03 (m, 2H).

Step 3: Preparation of 2-(tert-butylsulfanyl)-2-[4-(3,4-dihydro-2H-1-benzopyran-6-yl)-2,5-dimethylthiophen-3-yl]acetic acid A mixture of methyl 2-(tert-butylsulfanyl)-2-[4-(3,4-dihydro-2H-1-benzopyran-6-yl)-2,5-dimethylthiophen-3-yl]acetate (32b) (26 mg, 0.064 mmol) and potassium hydroxide (31 mg, 0.257 mmol) in a mixture of ethanol (0.5 mL), water (1.5 mL) and few drops of tetrahydrofuran was refluxed for 4 hours. The mixture was concentrated in vacuo. Water (2 mL) was added to the residue and the aqueous layer was washed with diethyl ether (2 mL). The aqueous layer was acidified with 1M hydrochloric acid until pH 2 and extracted with diethyl ether (2×3 mL). The organic layer was dried over sodium sulfate and concentrated in vacuo to provide the desired acid (example 32) (20 mg, 0.051 mmol, 80%).

¹H NMR (400 MHz, CDCl₃) δ 1.11 (s, 9H), 1.98-2.08 (m, 2H), 2.20 (s, 3H), 2.46 (s, 3H), 2.71-2.87 (m, 2H), 4.19-4.25 (m, 2H), 4.58 (s, 1H), 6.79-6.87 (m, 1H), 6.90-7.05 (m, 2H).

MS m/z ([M−H]⁻) 389.

Example 33

Synthesis of (4-1-Benzopyran-6-yl-3-methyl-2-oxo-2,3-dihydro-thiazol-5-yl)-tert-butoxy-acetic acid

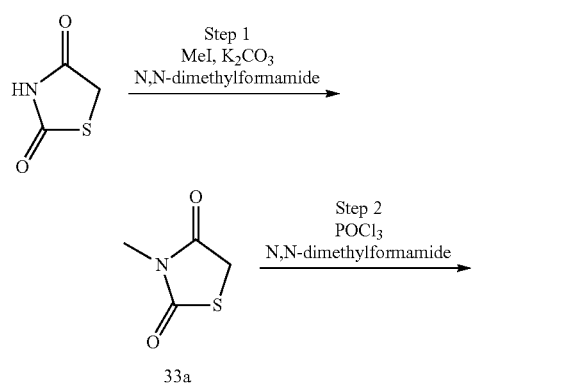

33a

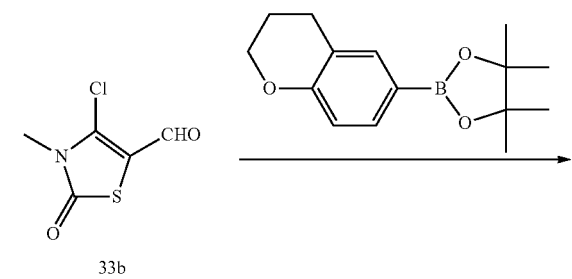

33b

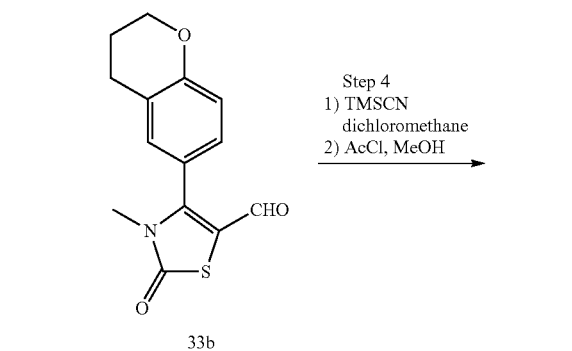

33b

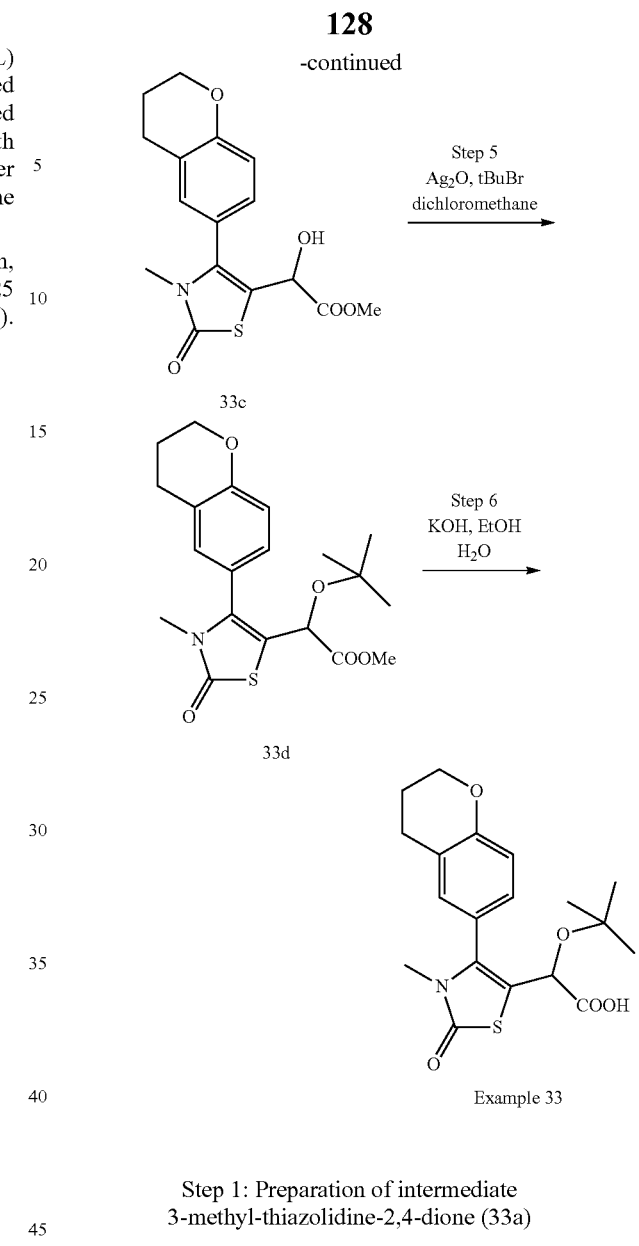

Example 33

Step 1: Preparation of intermediate 3-methyl-thiazolidine-2,4-dione (33a)

A solution of thiazolidine-2,4-dione (2 g, 17.1 mmol), potassium carbonate (3.55 g, 27.7 mmol) and methyl iodide (1.87 mL, 30 mmol) in N,N-dimethylformamide (16 mL) was stirred at 75° C. for 3 hours. The mixture was then filtered and concentrated. The residue was diluted with water (30 mL) and ethyl acetate (30 mL). The organic layer was washed with water (2×10 mL), brine (30 mL), dried over sodium sulfate, filtered and evaporated under reduced pressure to give, after purification by flash chromatography on silica gel (dichloromethane), the desired product (33a) as a white solid (1.77 g, 13.5 mmol, 79%).

¹H NMR (400 MHz, CDCl₃) δ 3.19 (s, 3H), 3.95 (s, 2H). MS m/z ([M+H]⁺) 132.

Step 2: Preparation of intermediate 4-chloro-3-methyl-2-oxo-2,3-dihydro-thiazole-5-carbaldehyde (33b)

At 0° C., N,N-dimethylformamide (2 mL, 27 mmol) was added to a solution of 3-methyl-thiazolidine-2,4-dione (33a) (1.77 g, 13.5 mmol) in phosphorus oxychloride (3.77 mL, 40.5 mmol). The reaction mixture was stirred at 110° C. for 3 hours, cooled to room temperature and quenched with a mixture of ice and ethyl acetate. The organic layer was washed with water (30 mL), brine (30 mL), dried over sodium sulfate, filtered, and evaporated under reduced pressure to give the desired aldehyde (33b) as a yellow solid (1.9 g, 10.7 mmol, 79%).

$^1$H NMR (400 MHz, CDCl$_3$) δ 3.46 (s, 3H), 9.84 (s, 1H).
MS m/z ([M+H]$^+$) 178/180.

Step 3: Preparation of intermediate 4-1-benzopyran-6-yl-3-methyl-2-oxo-2,3-dihydro-thiazole-5-carbaldehyde (33c)

Under a nitrogen atmosphere, a solution of 4-chloro-3-methyl-2-oxo-2,3-dihydro-thiazole-5-carbaldehyde (33b) (500 mg, 2.82 mmol), potassium carbonate (390 mg, 2.82 mmol), palladium diacetate (100 mg, 0.48 mmol), 6-(4,4,5,5-tetramethyl-1,3,2-dioxaborolan-2-yl)chroman (732 mg, 2.82 mmol) and tetrabutylammonium bromide (910 mg, 2.82 mmol) in ethanol (7 mL) and water (10 mL) was stirred at 70° C. for 3 hours. The mixture was then cooled at room temperature and diluted with ethyl acetate (30 mL) and water (30 mL). The organic layer was washed with water (30 mL), brine (30 mL), dried over sodium sulfate, filtered, and evaporated under reduced pressure. The residue was purified by flash chromatography on silica gel (cyclohexane/ethyl acetate 80/20) to afford the desired product as a white solid (270 mg, 0.98 mmol, 35%).

$^1$H NMR (400 MHz, CDCl$_3$) δ 2.03-2.11 (m, 2H), 2.84 (t, J=6.4 Hz, 2H), 3.22 (s, 3H), 4.25-4.30 (m, 2H), 6.93 (d, J=8.4 Hz, 1H), 7.08-7.14 (m, 2H), 9.36 (s, 1H).
MS m/z ([M+H]$^+$) 276.

Step 4: Preparation of intermediate methyl (4-1-benzopyran-6-yl-3-methyl-2-oxo-2,3-dihydro-thiazol-5-yl)-hydroxy-acetate (33d)

Using the procedure described in example 23, steps 6 and 7, the intermediate 4-1-benzopyran-6-yl-3-methyl-2-oxo-2,3-dihydro-thiazole-5-carbaldehyde (33c) (270 mg, 0.98 mmol) is converted, after purification by flash chromatography on silica gel (dichloromethane/ethyl acetate 90/10), to methyl (4-1-benzopyran-6-yl-3-methyl-2-oxo-2,3-dihydro-thiazol-5-yl)-hydroxy-acetate (33d) (134 mg, 0.4 mmol, 41%) as a white solid.

$^1$H NMR (400 MHz, CDCl$_3$) δ 2.00-2.09 (m, 2H), 2.82 (t, J=6.4 Hz, 2H), 3.08 (s, 3H), 3.81 (s, 3H), 4.21-4.27 (m, 2H), 5.00 (s, 1H), 6.88 (d, J=8.4 Hz, 1H), 7.03-7.09 (m, 2H).
MS m/z ([M+H]$^+$) 336.

Step 5: Preparation of intermediate methyl (4-1-benzopyran-6-yl-3-methyl-2-oxo-2,3-dihydro-thiazol-5-yl)-tert-butoxy-acetate (33e)

At room temperature, a solution of methyl (4-1-benzopyran-6-yl-3-methyl-2-oxo-2,3-dihydro-thiazol-5-yl)-hydroxy-acetate (33d) (84 mg, 0.25 mmol) and silver oxide (580 mg, 2.5 mmol) in dichloromethane (500 μL) and tert-butyl bromide (5 mL) was stirred for 8 hours. The mixture was then filtered and concentrated. The crude product was purified by flash chromatography on silica gel (dichloromethane/ethyl acetate 90/10) to afford the desired product (33e) as a white solid (29 mg, 0.073 mmol, 29%).

$^1$H NMR (400 MHz, CDCl$_3$) δ 1.05 (s, 9H), 2.01-2.09 (m, 2H), 2.75-2.89 (m, 2H), 3.03 (s, 3H), 3.73 (s, 3H), 4.21-4.28 (m, 2H), 4.85 (s, 1H), 6.87 (d, J=8.4 Hz, 1H), 6.95-7.05 (m, 2H).
MS m/z ([M+H]$^+$) 392.

Step 6: Preparation of intermediate (4-1-benzopyran-6-yl-3-methyl-2-oxo-2,3-dihydro-thiazol-5-yl)-tert-butoxy-acetic acid Using the procedure described in example 18, step 2, the intermediate methyl (4-1-benzopyran-6-yl-3-methyl-2-oxo-2,3-dihydro-thiazol-5-yl)-tert-butoxy-acetate (33e) (29 mg, 0.073 mmol) is converted, without purification, to (4-1-benzopyran-6-yl-3-methyl-2-oxo-2,3-dihydro-thiazol-5-yl)-tert-butoxy-acetic acid (example 33) (22 mg, 0.058 mmol, 80%) as a white solid.

$^1$H NMR (400 MHz, CDCl$_3$) δ 1.01 (s, 9H), 2.01-2.09 (m, 2H), 2.76-2.90 (m, 2H), 3.06 (s, 3H), 4.21-4.28 (m, 2H), 4.88 (s, 1H), 6.85-6.95 (m, 2H), 7.25-7.35 (m, 1H).
MS m/z ([M−H]$^-$) 376.

Example 34

Synthesis of 2-(tert-butoxy)-2-(4-{1,4-dioxaspiro[4.5]dec-7-en-8-yl}-2,5-dimethylthiophen-3-yl)acetic acid

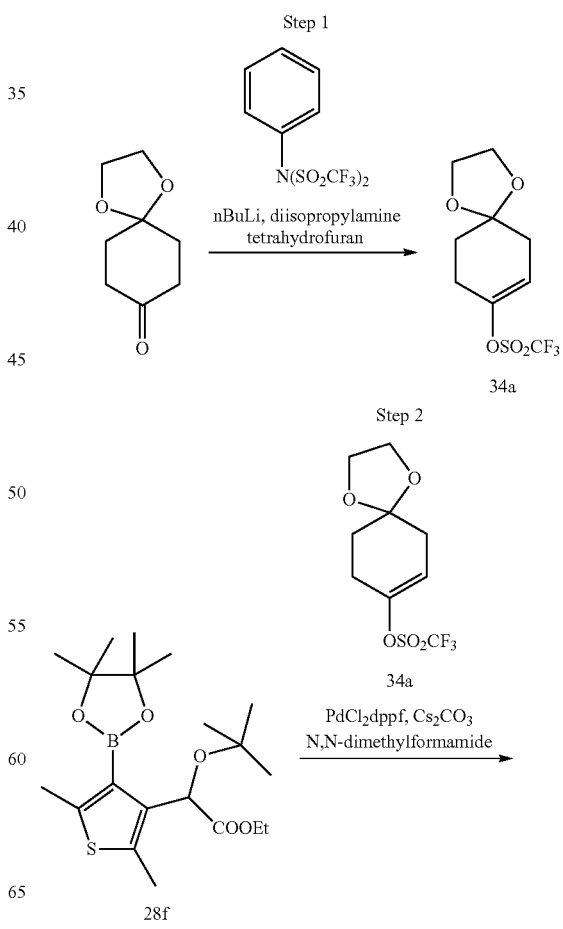

-continued

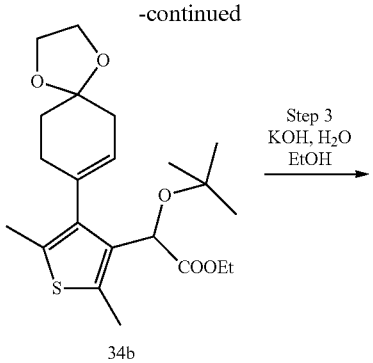

34b

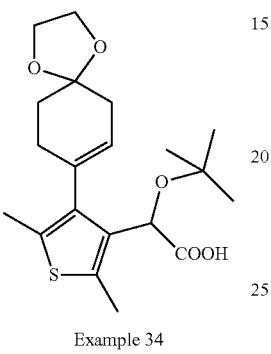

Example 34

Step 1: Preparation of intermediate 1,4-dioxaspiro[4.5]dec-7-en-8-yl trifluoromethane sulfonate (34a)

Using the procedure described in example 29, step 1, 1,4-dioxaspiro[4.5]decan-8-one (200 mg, 1.28 mmol) is converted, after purification by flash chromatography on silica gel (cyclohexane/ethyl acetate 95/5), to 1,4-dioxaspiro[4.5]dec-7-en-8-yltrifluoromethane sulfonate (34a) (148 mg, 0.513 mmol, 40%) as a colorless oil.

$^1$H NMR (300 MHz, CDCl$_3$) δ 1.90 (t, J=6.6 Hz, 2H), 2.40-2.42 (m, 2H), 2.51-2.57 (m, 2H), 3.96-4.01 (m, 4H), 5.65-5.68 (m, 1H).
MS m/z ([M+H]$^+$) 289.

Step 2: Preparation of intermediate ethyl 2-(tert-butoxy)-2-[4-(cyclohept-1-en-1-yl)-2,5-dimethylthiophen-3-yl]acetate (34b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (100 mg, 0,246 mmol) is converted, by reaction with 1,4-dioxaspiro[4.5]dec-7-en-8-yl trifluoromethanesulfonate (34a) and after purification by flash chromatography on silica gel (cyclohexane/ethyl acetate 90/10), to ethyl 2-(tert-butoxy)-2-(4-{1,4-dioxaspiro[4.5]dec-7-en-8-yl}-2,5-dimethylthiophen-3-yl)acetate (34b) (39 mg, 0.10 mmol, 39%).

$^1$H NMR (400 MHz, CDCl$_3$) δ 1.18-1.22 (m, 12H), 1.82-1.94 (m, 2H), 2.24-2.57 (m, 10H), 3.99-4.03 (m, 4H), 4.05-4.18 (m, 2H), 4.97 (s, 1H), 5.46 (s, 1H).

Step 3: Preparation of 2-(tert-butoxy)-2-(4-{1,4-dioxaspiro[4.5]dec-7-en-8-yl}-2,5-dimethyl thiophen-3-yl)acetic acid Using the procedure described in example 29, step 3, ethyl 2-(tert-butoxy)-2-(4-{1,4-dioxaspiro[4.5]dec-7-en-8-yl}-2, 5-dimethylthiophen-3-yl)acetate (34b) (38 mg, 0.09 mmol) is converted, after purification by flash chromatography on silica gel (dichloromethane/methanol 90/10), to 2-(tert-butoxy)-2-(4-{1,4-dioxaspiro[4.5]dec-7-en-8-yl}-2,5-dimethylthiophen-3-yl)acetic acid (example 34) (19 mg, 0.05 mmol, 53%).

$^1$H NMR (400 MHz, CDCl$_3$) δ 1.23 (s, 9H), 1.84-1.88 (m, 2H), 2.22-2.41 (m, 10H), 3.99-4.03 (m, 4H), 5.02 (s, 1H), 5.40 (s, 1H).
MS m/z ([M−H]$^-$) 379.

Example 35

Synthesis of 2-(tert-butoxy)-2-[2,5-dimethyl-4-(3-oxo-3,4-dihydro-2H-1,4-benzoxazin-6-yl)thiophen-3-yl]acetic acid Step 1

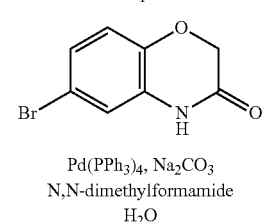

28f

Pd(PPh$_3$)$_4$, Na$_2$CO$_3$
N,N-dimethylformamide
H$_2$O

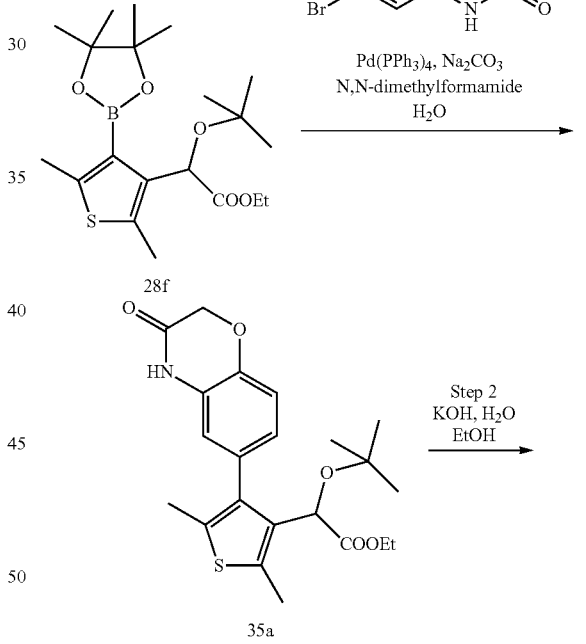

35a

Step 2
KOH, H$_2$O
EtOH

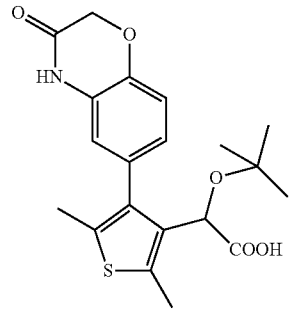

Example 35

Step 1: Preparation of intermediate ethyl 2-(tert-butoxy)-2-[2,5-dimethyl-4-(3-oxo-3,4-dihydro-2H-1,4-benzoxazin-6-yl)thiophen-3-yl]acetate (35a)

Under argon atmosphere, sodium carbonate (11.2 mg, 0.11 mmol), water (0.7 mL), and 6-bromo-3,4-dihydro-2H-1,4-benzoxazin-3-one (24.2 mg, 0.11 mmol) were added to a solution of ethyl 2-(tert-butoxy)-2-[2,5-dimethyl-4-(tetramethyl-1,3,2-dioxaborolan-2-yl)thiophen-3-yl]acetate (28f) (48 mg, 0.10 mmol) in N,N-dimethylformamide (2.1 mL). The solution was degassed under argon and palladium tetrakis(triphenylphosphine) (23.4 mg, 0.02 mmol) was added. The mixture was heated at 100° C. for 15 hours. The mixture was then cooled at room temperature, water was added and the aqueous layer was extracted with ethyl acetate. The organic layer was washed with brine, dried over sodium sulfate, filtered, and evaporated under reduced pressure. The residue was purified by preparative TLC (cyclohexane/ethyl acetate 70/30) to afford the desired product (35a) (14 mg, 0.03 mmol, 33%).

$^1$H NMR (400 MHz, CDCl$_3$) δ 1.02 (s, 9H), 1.23 (t, J=7.1 Hz, 3H), 2.17 (s, 3H), 2.50 (s, 3H), 4.08-4.16 (m, 2H), 4.68 (s, 2H), 4.76 (s, 1H), 6.76-7.08 (m, 3H).

MS m/z ([M−OtBu]$^+$) 344.

Step 2: Preparation of 2-(tert-butoxy)-2-[2,5-dimethyl-4-(3-oxo-3,4-dihydro-2H-1,4-benzoxazin-6-yl)thiophen-3-yl]acetic acid Using the procedure described in example 29, step 3, the intermediate ethyl 2-(tert-butoxy)-2-[2,5-dimethyl-4-(3-oxo-3,4-dihydro-2H-1,4-benzoxazin-6-yl)thiophen-3-yl]acetate (35a) (30 mg, 0.072 mmol) is converted, after purification by flash chromatography on silica gel (dichloromethane/methanol 95/5), to 2-(tert-butoxy)-2-[2,5-dimethyl-4-(3-oxo-3,4-dihydro-2H-1,4-benzoxazin-6-yl)thiophen-3-yl]acetic acid (example 35) (10 mg, 0.03 mmol, 35%).

$^1$H NMR (400 MHz, CDCl$_3$) δ 1.01 (s, 9H), 2.19 (s, 3H), 2.47 (s, 3H), 4.67 (s, 2H), 4.84 (s, 1H), 6.86-7.04 (m, 3H).

MS m/z ([M−H]$^-$) 388.

Example 36

Synthesis of 2-(tert-butoxy)-2-[4-(isoquinolin-4-yl)-2,5-dimethylthiophen-3-yl]acetic acid Step 1

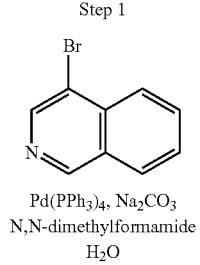

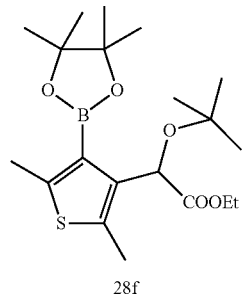

28f

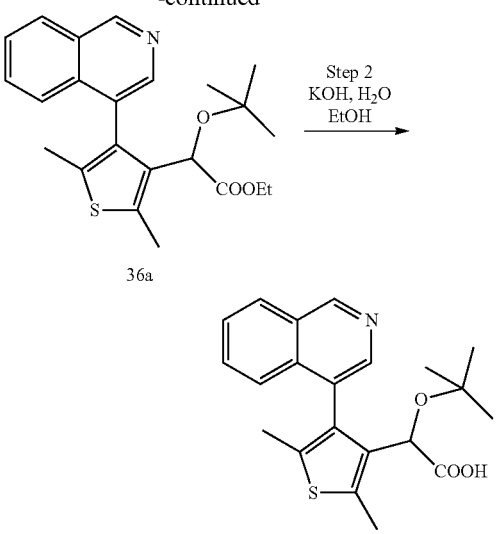

36a

Example 36

Step 1: Preparation of intermediate ethyl 2-(tert-butoxy)-2-[4-(isoquinolin-4-yl)-2,5-dimethylthiophen-3-yl]acetate (36a)

Using the procedure described in example 35, step 1, the intermediate ethyl 2-(tert-butoxy)-2-[2,5-dimethyl-4-(tetramethyl-1,3,2-dioxaborolan-2-yl)thiophen-3-yl]acetate (28f) (100 mg, 0.25 mmol) is converted, by reaction with 4-bromoisoquinoline and after purification by flash chromatography on silica gel (cyclohexane/ethyl acetate 70/30), to ethyl 2-(tert-butoxy)-2-[4-(isoquinolin-4-yl)-2,5-dimethylthiophen-3-yl]acetate (36a) (65 mg, 0.16 mmol, 66%).

$^1$H NMR (400 MHz, CDCl$_3$) δ 0.91 (s, 9H), 0.97 (t, J=7.1 Hz, 3H), 2.0 (s, 3H), 2.58 (s, 3H), 3.81-4.0 (m, 2H), 4.58-4.65 (m, 1H), 7.56-7.70 (m, 3H), 8.07-8.10 (m, 1H), 8.34 (s, 1H), 9.32 (s, 1H).

MS m/z ([M+H]$^+$) 398.

Step 2: Preparation of intermediate 2-(tert-butoxy)-2-[4-(isoquinolin-4-yl)-2,5-dimethylthiophen-3-yl]acetic acid Using the procedure described in example 29, step 3, the intermediate ethyl 2-(tert-butoxy)-2-[4-(isoquinolin-4-yl)-2,5-dimethylthiophen-3-yl]acetate (36a) (65 mg, 0.16 mmol) is converted, after purification by flash chromatography on silica gel (dichloromethane/methanol 95/5), to 2-(tert-butoxy)-2-[4-(isoquinolin-4-yl)-2,5-dimethylthiophen-3-yl]acetic acid (example 36) (14 mg, 0.04 mmol, 23%).

$^1$H NMR (400 MHz, CDCl$_3$) δ 0.78 (s, 9H), 2.0 (s, 3H), 2.57 (s, 3H), 4.71-4.89 (m, 1H), 7.63-7.74 (m, 3H), 8.06 (d, J=8.1 Hz, 1H), 8.38 (s, 1H), 9.34 (s, 1H).

MS m/z ([M−H]$^-$) 368.

Example 37

Synthesis of 2-(tert-butoxy)-2-[4-(1H-inden-2-yl)-2,5-dimethylthiophen-3-yl]acetic acid

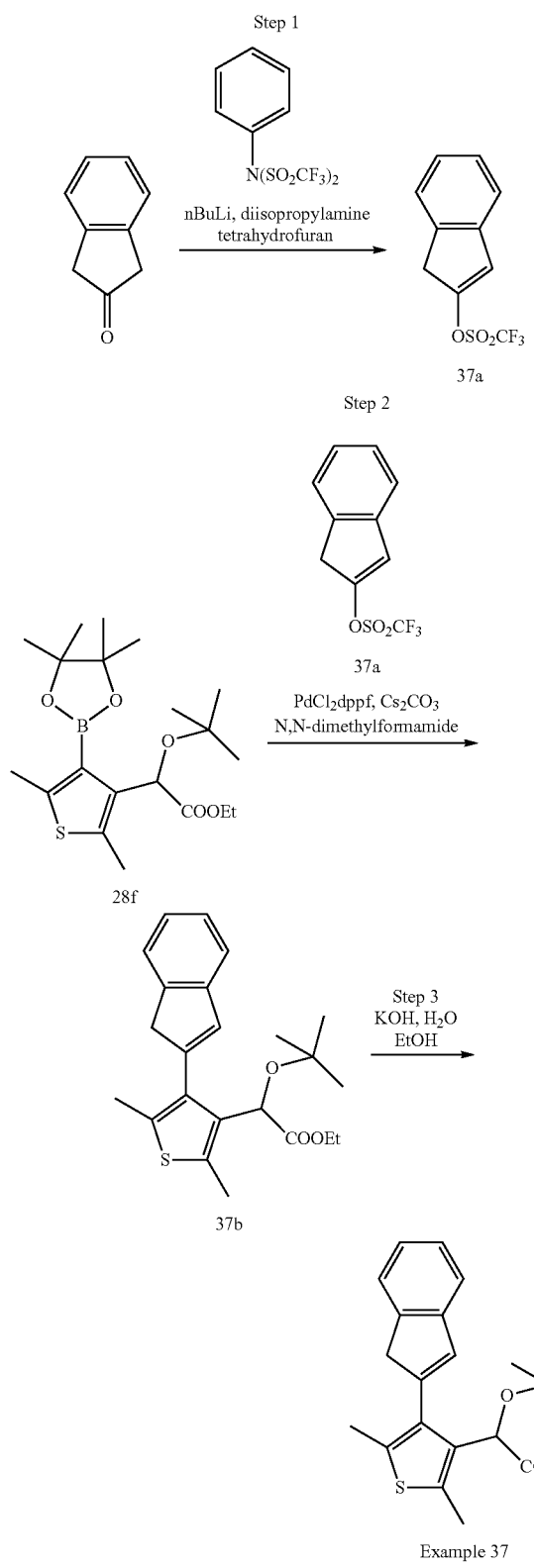

Step 1: Preparation of intermediate 1H-inden-2-yl trifluoromethanesulfonate (37a)

Using the procedure described in example 29, step 1, 2-indanone (200 mg, 1.51 mmol) is converted, after purification by flash chromatography on silica gel (cyclohexane/ethyl acetate 90/10), to 1H-inden-2-yl trifluoromethanesulfonate (37a) (263 mg, 1 mmol, 66%).

$^1$H NMR (300 MHz, CDCl$_3$) δ 3.67 (s, 2H), 6.70 (s, 1H), 7.24-7.40 (m, 4H).

Step 2: Preparation of intermediate ethyl 2-(tert-butoxy)-2-[4-(1H-inden-2-yl)-2,5-dimethylthiophen-3-yl]acetate (37b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (50 mg, 0.123 mmol) is converted, by reaction with 1H-inden-2-yl trifluoromethanesulfonate (37a) and after purification by flash chromatography on silica gel (cyclohexane/ethyl acetate 90/10), to ethyl 2-(tert-butoxy)-2-[4-(1H-inden-2-yl)-2,5-dimethylthiophen-3-yl]acetate (37b) (50 mg, 0.13 mmol, 75%).

$^1$H NMR (300 MHz, CDCl$_3$) δ 1.01 (s, 9H), 1.18 (t, J=7.1 Hz, 3H), 2.27 (s, 3H), 2.51 (s, 3H), 3.49 (d, J=22.4 Hz, 1h), 3.93 (d, J=22.4 Hz, 1H), 4.09 (q, J=7.1 Hz, 2H), 4.98 (s, 1H), 6.77 (s, 1H), 7.19-7.50 (m, 4H).

Step 3: Preparation of 2-(tert-butoxy)-2-[4-(1H-inden-2-yl)-2,5-dimethylthiophen-3-yl]acetic acid Using the procedure described in example 29, step 3, 2-(tert-butoxy)-2-[4-(1H-inden-2-yl)-2,5-dimethylthiophen-3-yl]acetate (37b) (50 mg, 0.13 mmol) is converted, after purification by flash chromatography on silica gel (dichloromethane/methanol 95/5), to 2-(tert-butoxy)-2-[4-(1H-inden-2-yl)-2,5-dimethylthiophen-3-yl]acetic acid (example 37) (24 mg, 0.07 mmol, 52%).

$^1$H NMR (400 MHz, CDCl$_3$) δ 1.13 (s, 9H), 2.28 (s, 3H), 2.44 (s, 3H), 3.49 (d, J=22.6 Hz, 1H), 3.89 (d, J=22.7 Hz, 1H), 5.08 (s, 1H), 6.84 (s, 1H), 7.20-7.33 (m, 2H), 7.43-7.48 (m, 2H).

MS m/z ([M−H]$^-$) 355.

Example 38

Synthesis of 2-(tert-butoxy)-2-[4-(3,4-dihydronaphthalen-2-yl-2,5-dimethylthiophen-3-yl]acetic acid

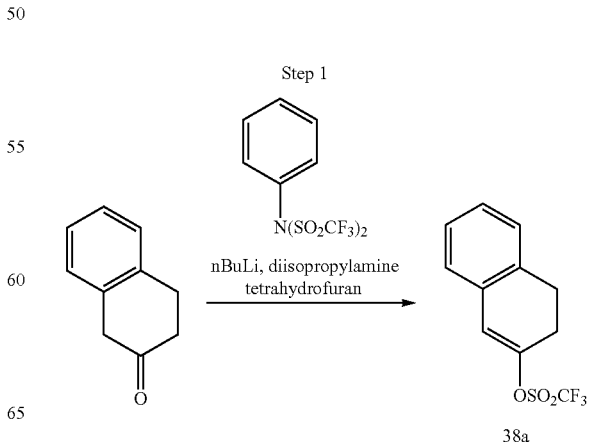

-continued

Step 2

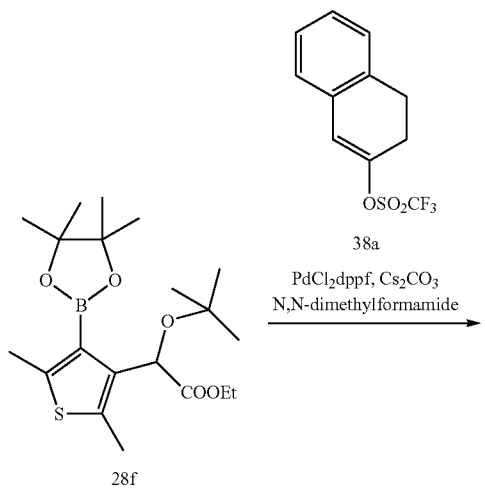

Step 1: Preparation of intermediate 3,4-dihydronaphthalen-2-yl trifluoromethanesulfonate (38a)

Using the procedure described in example 29, step 1, 1,2,3,4-tetrahydronaphthalen-2-one (200 mg, 1.37 mmol) is converted, after purification by flash chromatography on silica gel (cyclohexane), to 3,4-dihydronaphthalen-2-yl trifluoromethanesulfonate (38a) (217 mg, 0.78 mmol, 57%).

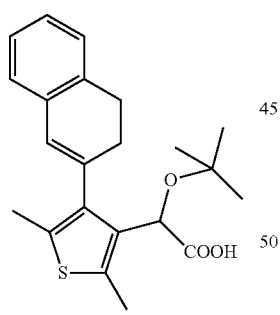

Example 38

¹H NMR (300 MHz, CDCl₃) δ 2.70 (t, J=8.6 Hz, 2H), 3.06 (t, J=8.3 Hz, 2H), 6.48 (s, 1H), 7.05-7.22 (m, 4H).

Step 2: Preparation of intermediate ethyl 2-(tert-butoxy)-2-[4-(3,4-dihydronaphthalen-2-yl)-2,5-dimethylthiophen-3-yl]acetate (38b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (50 mg, 0.105 mmol) is converted, by reaction with 3,4-dihydronaphthalen-2-yl trifluoromethanesulfonate (38a) and after purification by flash chromatography on silica gel (cyclohexane/ethyl acetate 90/10), to ethyl 2-(tert-butoxy)-2-[4-(3,4-dihydronaphthalen-2-yl)-2,5-dimethylthiophen-3-yl]acetate (38b) (33 mg, 0.08 mmol, 48%).

¹H NMR (300 MHz, CDCl₃) δ 1.16-1.22 (m, 12H), 2.17-2.69 (m, 8H), 2.87-3.05 (m, 2H), 4.05-4.16 (m, 2H), 5.05 (s, 1H), 6.39 (s, 1H), 7.05-7.07 (m, 1H), 7.17-7.19 (m, 3H).

MS m/z ([M−OtBu]⁺) 325.

Step 3: Preparation of intermediate 2-(tert-butoxy)-2-[4-(3,4-dihydronaphthalen-2-yl)-2,5-dimethylthiophen-3-yl]acetic acid Using the procedure described in example 29, step 3, ethyl 2-(tert-butoxy)-2-[4-(3,4-dihydronaphthalen-2-yl)-2,5-dimethylthiophen-3-yl]acetate (38b) (32 mg, 0.08 mmol) is converted, after purification by flash chromatography on silica gel (dichloromethane/methanol 95/5), to 2-(tert-butoxy)-2-[4-(3,4-dihydronaphthalen-2-yl)-2,5-dimethylthiophen-3-yl]acetic acid (example 38) (15 mg, 0.04 mmol, 50% yield).

¹H NMR (400 MHz, CDCl₃) δ 1.20 (s, 9H), 2.28 (s, 3H), 2.37-2.45 (m, 4H), 2.63-2.71 (m, 1H), 2.91-2.95 (m, 2H), 5.13 (s, 1H), 6.44 (s, 1H), 7.08-7.10 (m, 1H), 7.16-7.20 (m, 3H).

MS m/z ([M−H]⁻) 369.

Example 39

Synthesis of 2-(tert-butoxy)-2-[2,5-dimethyl-4-(5,6,7,8-tetrahydronaphthalen-2-yl)thiophen-3-yl]acetic acid Step 1

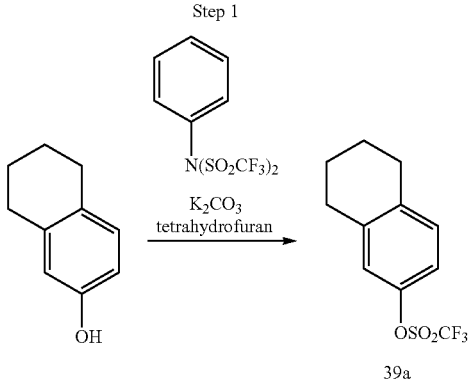

Step 2

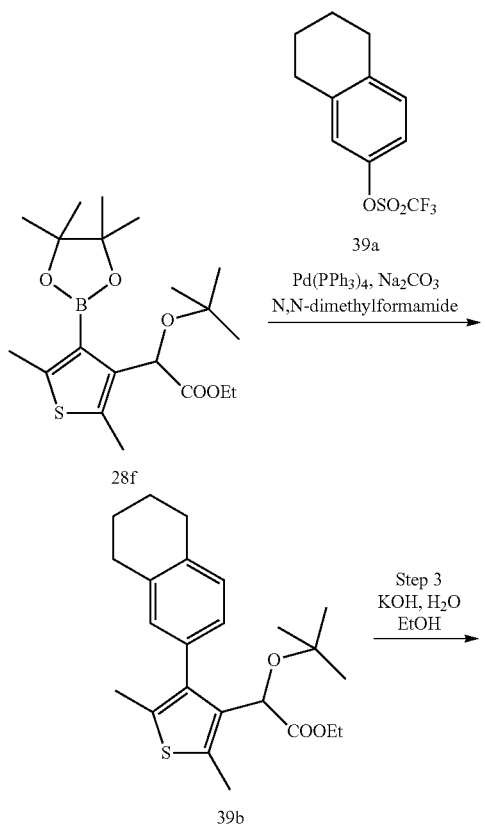

Step 1: Preparation of intermediate 5,6,7,8-tetrahydronaphthalen-2-yl trifluoromethanesulfonate (39a)

5,6,7,8-Tetrahydro-2-naphthol (200 mg, 1.35 mmol), N-Phenylbis(trifluoromethansulfonimide) (530.3 mg, 1.48 mmol) and potassium bicarbonate (280 mg, 2.02 mmol) in tetrahydrofuran (2.5 mL) were mixed in a microwave tube and immediately heated at 120° C. for 12 minutes (initial irradiation power 100 W). After complete conversion and cooling to room temperature, water and saturated aqueous sodium bicarbonate solution were added. The mixture was extracted twice with diethyl ether. The combined organic layers was washed with water and brine, dried over sodium sulfate, and concentrated in vacuo. The crude material was purified by flash chromatography on silica gel (cyclohexane) to provide 5,6,7,8-tetrahydronaphthalen-2-yl trifluoromethanesulfonate (39a) (364 mg, 1.30 mmol, 96%) as a colorless oil.

$^1$H NMR (300 MHz, CDCl$_3$) δ 1.79-1.82 (m, 4H), 2.77-2.79 (m, 4H), 6.96-6.99 (m, 2H), 7.10 (d, J=8.4 Hz, 1H).

Step 2: Preparation of intermediate ethyl 2-(tert-butoxy)-2-[2,5-dimethyl-4-(5,6,7,8-tetrahydronaphthalen-2-yl)thiophen-3-yl]acetate (39b)

Under argon atmosphere, ethyl 2-(tert-butoxy)-2-[2,5-dimethyl-4-(tetramethyl-1,3,2-dioxaborolan-2-yl)thiophen-3-yl]acetate (28f) (50 mg, 0.12 mmol), 5,6,7,8-tetrahydronaphthalen-2-yl trifluoromethanesulfonate (39a) (41.4 mg, 0.15 mmol) and sodium carbonate (13.7 mg, 0.13 mmol) were dissolved in dimethylformamide (2.5 mL) and water (0.85 mL). The solution was degassed under argon for 10 minutes and Tetrakis(triphenylphosphine)palladium (28.5 mg, 0.02 mmol) was added. The reaction was heated and shaken at 100° C. for 4 hours. After cooling at room temperature, water was added and the mixture was partitioned between ethyl acetate and water. The organic layer was washed with brine, dried over sodium sulfate, filtered, and concentrated under reduced pressure. The crude material was purified by preparative TLC (cyclohexane/ethyl acetate: 9/1) to provide the desired product (39b) (40 mg, 0.1 mmol, 77%).

$^1$H NMR (400 MHz, CDCl$_3$) δ 1.00 (s, 9H), 1.22 (t, J=7.1 Hz, 3H), 1.82-1.84 (m, 4H), 2.19 (s, 3H), 2.51 (s, 3H), 2.76-2.81 (m, 4H), 4.06-4.15 (m, 2H), 4.79 (s, 1H), 6.96-7.08 (m, 3H).

MS m/z ([M+Na]$^+$) 423.

Step 3: Preparation of intermediate 2-(tert-butoxy)-2-[2,5-dimethyl-4-(5,6,7,8-tetrahydro naphthalen-2-yl)thiophen-3-yl]acetic acid Using the procedure described in example 29, step 3, ethyl 2-(tert-butoxy)-2-[2,5-dimethyl-4-(5,6,7,8-tetrahydronaphthalen-2-yl)thiophen-3-yl]acetate (39b) (40 mg, 0.1 mmol) is converted, after purification by preparative TLC (dichloromethane/methanol 95/5), to 2-(tert-butoxy)-2-[2,5-dimethyl-4-(5,6,7,8-tetrahydronaphthalen-2-yl)thiophen-3-yl]acetic acid (example 39) (12 mg, 0.03 mmol, 32%).

$^1$H NMR (300 MHz, CDCl$_3$) δ 1.02 (s, 9H), 1.78-1.84 (m, 4H), 2.21 (s, 3H), 2.42 (s, 3H), 2.77-2.80 (m, 4H), 4.94 (s, 1H), 7.01-7.03 (m, 3H).

MS m/z ([M−H]$^-$) 371.

Example 40

Synthesis of 2-(tert-butoxy)-2-[2,5-dimethyl-4-(naphthalen-2-yl)thiophen-3-yl]acetic acid

Step 1

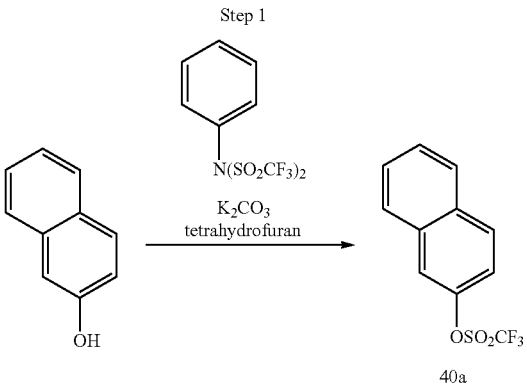

-continued

Step 2

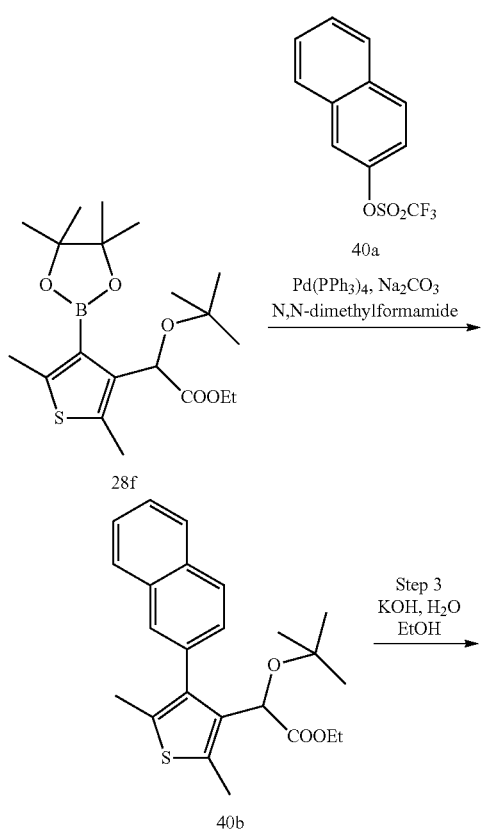

Step 1: Preparation of intermediate Naphthalen-2-yl trifluoromethanesulfonate (40a)

Using the procedure described in example 39, step 1, 2-naphthol (200 mg, 1.38 mmol) is converted, after purification by flash chromatography on silica gel (cyclohexane), to naphthalen-2-yl trifluoromethanesulfonate (40a) (380 mg, 1.37 mmol, 99%) as a colorless oil.

$^1$H NMR (300 MHz, CDCl$_3$) δ 7.38 (dd, J=2.5 Hz, 9.0 Hz, 1H), 7.55-7.61 (m, 2H), 7.76 (d, J=2.5 Hz, 1H), 7.86-7.94 (m, 3H).

Step 2: Preparation of intermediate ethyl 2-(tert-butoxy)-2-[2,5-dimethyl-4-(naphthalen-2-yl)thiophen-3-yl]acetate (40b)

Using the procedure described in example 39, step 2, ethyl 2-(tert-butoxy)-2-[2,5-dimethyl-4-(tetramethyl-1,3,2-dioxaborolan-2-yl)thiophen-3-yl]acetate (28f) (50 mg, 0.12 mmol) is converted, by reaction with naphthalen-2-yl trifluoromethanesulfonate (40a) and after purification by preparative TLC (cyclohexane/ethyl acetate 90/10), to ethyl 2-(tert-butoxy)-2-[2,5-dimethyl-4-(naphthalen-2-yl)thiophen-3-yl]acetate (40b) (45 mg, 0.11 mmol, 92%).

$^1$H NMR (400 MHz, CDCl$_3$) δ 0.97 (s, 9H), 1.24 (t, J=7.1 Hz, 3H), 2.21 (s, 3H), 2.55 (s, 3H), 4.10-4.17 (m, 2H), 4.82 (s, 1H), 7.40-7.44 (m, 1H), 7.49-7.53 (m, 2H), 7.77-7.92 (m, 4H).

Step 3: Preparation of 2-(tert-butoxy)-2-[2,5-dimethyl-4-(naphthalen-2-yl)thiophen-3-yl]acetic acid Using the procedure described in example 29, step 3, ethyl 2-(tert-butoxy)-2-[2,5-dimethyl-4-(naphthalen-2-yl)thiophen-3-yl]acetate (40b) (42 mg, 0.11 mmol) is converted, without further purification, to 2-(tert-butoxy)-2-[2,5-dimethyl-4-(naphthalen-2-yl)thiophen-3-yl]acetic acid (example 40) (25 mg, 0.07 mmol, 64%).

$^1$H NMR (300 MHz, CDCl$_3$) δ 0.98 (s, 9H), 2.24 (s, 3H), 2.46 (s, 3H), 4.97 (s, 1H), 7.48-7.53 (m, 3H), 7.86-7.90 (m, 4H).

MS m/z ([M−H$^-$]) 367.

Example 41

Synthesis of 2-(tert-butoxy)-2-{2,5-dimethyl-4-[4-(trifluoromethyl)cyclohex-1-en-1-yl]thiophen-3-yl}acetic acid

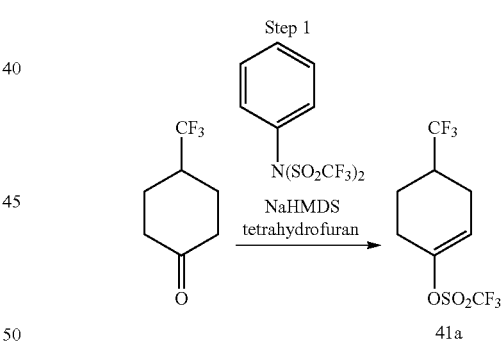

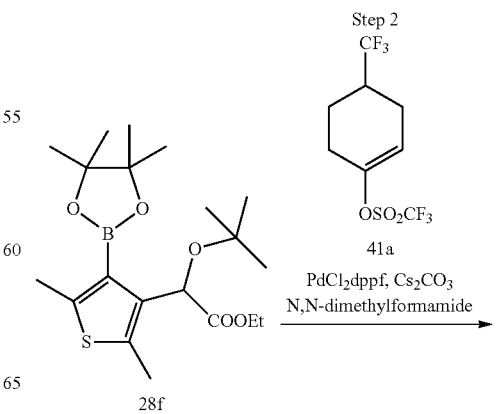

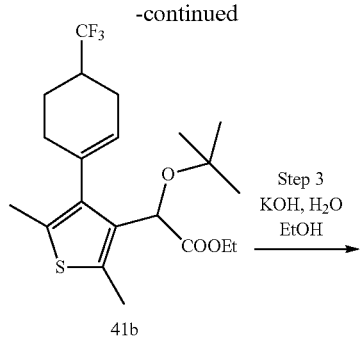

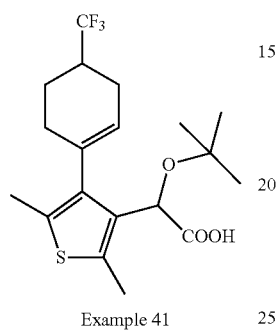

Example 41

Step 1: Preparation of intermediate 4-(trifluoromethyl)cyclohex-1-en-1-yl trifluoro methanesulfonate (41a)

Using the procedure described in example 29, step 1, 4-trifluoromethylcyclohexanone (150 mg, 0.902 mmol) is converted, after purification by flash chromatography on silica gel (cyclohexane), to 4-(trifluoromethyl)cyclohex-1-en-1-yl trifluoromethanesulfonate (41a) (42 mg, 0.142 mmol, 16%) as a colorless oil.

$^1$H NMR (300 MHz, CDCl$_3$) δ 1.72-1.82 (m, 1H), 2.12-2.19 (m, 1H), 2.27-2.50 (m, 5H), 5.78-5.79 (m, 1H).

Step 2: Preparation of intermediate ethyl 2-(tert-butoxy)-2-{2,5-dimethyl-4-[4-(trifluoromethyl)cyclohex-1-en-1-yl]thiophen-3-yl}acetate (41b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (60 mg, 0,148 mmol) is converted, by reaction with 4-(trifluoromethyl)cyclohex-1-en-1-yl trifluoromethanesulfonate (41a) and after purification by preparative TLC (cyclohexane/ethyl acetate 90/10), to 2-(tert-butoxy)-2-{2,5-dimethyl-4-[4-(trifluoromethyl)cyclohex-1-en-1-yl]thiophen-3-yl}acetate (41b) (31 mg, 0.07 mmol, 50%).

$^1$H NMR (400 MHz, CDCl$_3$) δ 1.18-1.23 (m, 12H), 1.62-1.77 (m, 1H), 2.04-2.51 (m, 12H), 4.03-4.16 (m, 2H), 4.90-4.91 (m, 1H), 5.53 (s, 1H).

Step 3: Preparation of 2-(tert-butoxy)-2-{2,5-dimethyl-4-[4-(trifluoromethyl)cyclohex-1-en-1-yl]thiophen-3-yl}acetic acid Using the procedure described in example 29, step 3, ethyl 2-(tert-butoxy)-2-{2,5-dimethyl-4-[4-(trifluoromethyl)cyclohex-1-en-1-yl]thiophen-3-yl}acetate (41b) (31 mg, 0.07 mmol) is converted, after purification by preparative TLC (dichloromethane/methanol 95/5), to 2-(tert-butoxy)-2-{2,5-dimethyl-4-[4-(trifluoromethyl)cyclohex-1-en-1-yl]thiophen-3-yl}acetic acid (example 41) (17 mg, 0.04 mmol, 58%).

$^1$H NMR (400 MHz, CDCl$_3$) δ 81.22 and 1.23 (2s, 9H), 1.46-1.72 (m, 1H), 2.04-2.19 (m, 2H), 2.20 (s, 3H), 2.21-2.39 (m, 3H), 2.40 (s, 3H), 2.41-2.52 (m, 1H), 4.97 and 5.02 (2s, 1H), 5.54-5.64 (m, 1H).

MS m/z ([M−H]$^−$) 389.

Example 42

Synthesis of 2-[4-(3,4-dihydro-2H-1-benzopyran-6-yl)-2,5-dimethyl thiophen-3-yl]-4,4-dimethylpentanoic acid

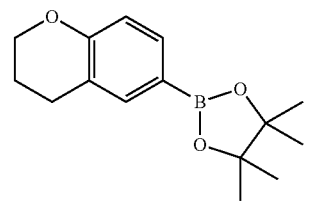

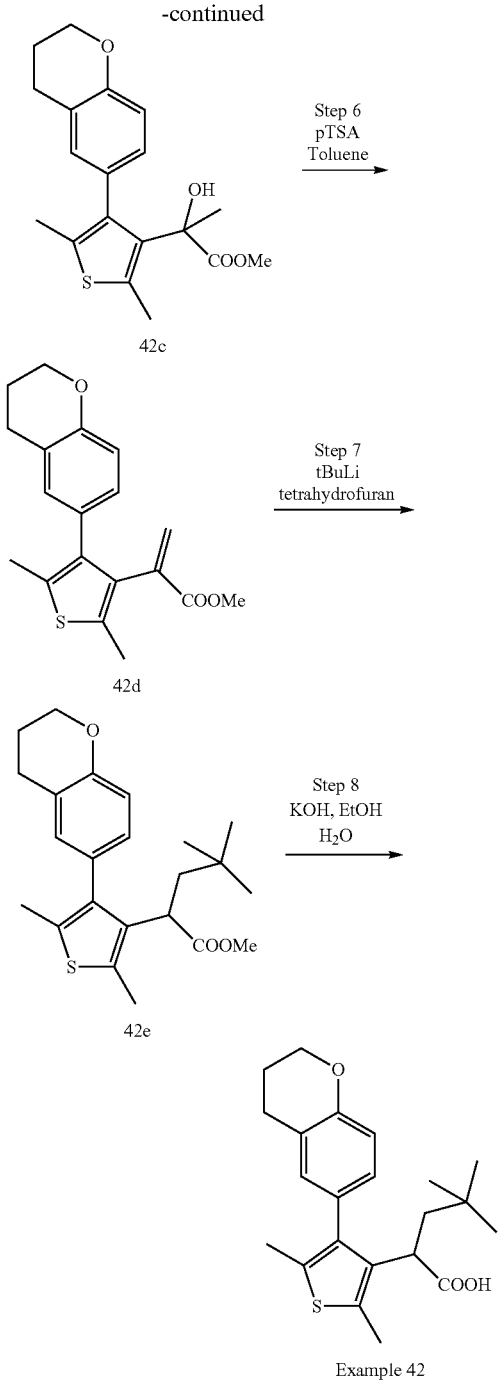

Step 1: Preparation of intermediate 2-[4-(3,4-dihydro-2H-1-benzopyran-6-yl)-2,5-dimethyl thiophen-3-yl]-2-oxoacetic acid (42a)

A solution of ethyl 2-(4-bromo-2,5-dimethylthiophen-3-yl)-2-oxoacetate (17c) (1.0 g, 3.43 mmol), sodium carbonate (1.46 g, 13.7 mmol), and 6-(4,4,5,5-tetramethyl-1,3,2-dioxaborolan-2-yl)chroman (1.16 g, 4.46 mmol) in a mixture of toluene (9 mL), ethanol (3 mL) and water (3.5 mL) was bubbled with nitrogen for 5 minutes. Palladium tetrakis(triphenylphosphine) (0.2 g, 0.17 mmol) was added and the reaction mixture was heated at 95° C. overnight. Water (5 mL) was added and the organic layer was extracted with 1N sodium hydroxide (5 mL). The combined aqueous layers were washed with ethyl acetate (10 mL), acidified with 1M hydrochloric acid until pH 2 and extracted with dichloromethane (2×10 mL). The organic layer was dried over sodium sulfate and concentrated in vacuo to provide the desired product (42a) (1.09 g, 3.43 mmol, 100%) which was used without further purification.

$^1$H NMR (400 MHz, CDCl$_3$) δ 1.95-2.02 (m, 2H), 2.28 (s, 3H), 2.64 (s, 3H), 2.71-2.76 (m, 2H), 4.17 (t, J=5.2 Hz, 2H), 6.75 (d, J=8.3 Hz, 1H), 6.80 (d, J=1.8 Hz, 1H), 6.88 (dd, J=1.8 8.3 Hz, 1H).

Step 2: Preparation of intermediate methyl 2-[4-(3,4-dihydro-2H-1-benzopyran-6-yl)-2,5-dimethylthiophen-3-yl]-2-oxoacetate (42b)

A solution of 2-[4-(3,4-dihydro-2H-1-benzopyran-6-yl)-2,5-dimethylthiophen-3-yl]-2-oxoacetic acid (42a) (1.09 g, 3.43 mmol) in methanol (10 mL) was cooled to 0° C. Trimethylsilyldiazomethane 2N in diethyl ether (6.89 mL, 13.7 mmol) was added dropwise and the reaction mixture was stirred at room temperature for 3 hours. The precipitate was filtered off and washed with cooled methanol (5 mL). The filtrate was concentrated in vacuo and the residue was dissolved in a minimum of methanol. The solution was sonicated for a few seconds and the precipitate was filtered and washed with cooled methanol. The precipitates were combined to provide the desired ester (42b) (820 mg, 2.48 mmol, 72% over two steps) as a beige solid, which was used without further purification.

$^1$H NMR (400 MHz, CDCl$_3$) δ 1.98-2.05 (m, 2H), 2.26 (s, 3H), 2.64 (s, 3H), 2.77 (t, J=6.5 Hz, 2H), 3.30 (s, 3H), 4.20 (t, J=5.1 Hz, 2H), 6.77-6.82 (m, 2H), 6.90-6.95 (m, 1H).

Step 3: Preparation of intermediate methyl 2-[4-(3,4-dihydro-2H-1-benzopyran-6-yl)-2,5-dimethylthiophen-3-yl]-2-hydroxypropanoate (42b)

Under a nitrogen atmosphere, a solution of methyl 2-[4-(3,4-dihydro-2H-1-benzopyran-6-yl)-2,5-dimethylthiophen-3-yl]-2-oxoacetate (360 mg, 1.09 mmol) in anhydrous diethyl ether (5 mL) was cooled to 0° C. Methyl magnesium bromide 3.0 M in diethyl ether (0.73 mL, 2.18 mmol) was added dropwise and the reaction mixture was stirred at 0° C. for 15 minutes, before being quenched with a minimum of water. Ethyl acetate (8 mL) was added and the mixture was dried over sodium sulfate, filtered and concentrated in vacuo. The residue was purified by flash chromatography on silica gel (cyclohexane/ethyl acetate 100/0 to 80/20) to provide the desired alcohol (42b) (206 mg, 0.59 mmol, 55%) as a colorless oil.

$^1$H NMR (300 MHz, CDCl$_3$) δ 1.60 and 1.62 (s, 3H), 1.97-2.07 (m, 5H), 2.50 and 2.52 (s, 3H), 2.77 (t, J=6.3 Hz, 2H), 3.16 and 3.20 (s, 1H), 3.52 and 3.53 (s, 3H), 4.21 (t, J=5.2 Hz, 2H), 6.72-6.81 (m, 2H), 6.85-6.92 (m, 1H).

Step 4: Preparation of intermediate methyl 2-[4-(3,4-dihydro-2H-1-benzopyran-6-yl)-2,5-dimethylthiophen-3-yl]prop-2-enoate (42c)

A mixture of methyl 2-[4-(3,4-dihydro-2H-1-benzopyran-6-yl)-2,5-dimethylthiophen-3-yl]-2-hydroxypropanoate (42b) (130 mg, 0.38 mmol), p-toluenesulfonic acid monohydrate (357 mg, 1.88 mmol) and a spoon of sodium sulfate, in anhydrous toluene (3 mL) was refluxed for 16 hours. After cooling to room temperature, the reaction mixture was filtered and the filtrate was successively washed with a saturated solution of sodium bicarbonate (2×5 mL) and brine (5 mL). The organic layer was dried over sodium sulfate and concentrated in vacuo to provide the desired product (42c) (114 mg, 0.35 mmol, 93%) which was used without further purification.

$^1$H NMR (300 MHz, CDCl$_3$) δ 1.96-2.04 (m, 2H), 2.29 (s, 3H), 2.33 (s, 3H), 2.75 (t, J=6.5 Hz, 2H), 3.46 (s, 3H), 4.18 (t, J=5.2 Hz, 2H), 5.54 (d, J=1.8 Hz, 1H), 6.41 (d, J=1.8 Hz, 1H), 6.73 (d, J=8.3 Hz, 1H), 6.79 (d, J=2.0 Hz, 1H), 6.84 (dd, J=8.3 2.0 Hz, 1H).

MS m/z ([M+H]$^+$) 329.

Step 5: Preparation of intermediate methyl 2-[4-(3,4-dihydro-2H-1-benzopyran-6-yl)-2,5-dimethylthiophen-3-yl]-4,4-dimethylpentanoate (42d)

Under a nitrogen atmosphere, a solution of methyl 2-[4-(3,4-dihydro-2H-1-benzopyran-6-yl)-2,5-dimethylthiophen-3-yl]prop-2-enoate (42c) (114 mg, 0.35 mmol) in anhydrous tetrahydrofuran (5 mL) was cooled to −78° C. tert-Butyllithium 1.6M in pentane (0.24 mL, 0.38 mmol) was added dropwise and the reaction mixture was stirred at −78° C. for 20 minutes before being quenched with brine (3 mL). The mixture was extracted with dichloromethane (2×6 mL). The organic layer was dried over sodium sulfate and concentrated in vacuo. The residue was purified by preparative TLC (cyclohexane/ethyl acetate 70/30) to provide the desired product (42d) (102 mg, 0.26 mmol, 76%) as a light yellow oil.

$^1$H NMR (400 MHz, CDCl$_3$) δ 0.64 (s, 9H), 1.36-1.44 (m, 1H), 1.99-2.08 (m, 2H), 2.18 (s, 3H), 2.29 (dd, J=14.0 8.2 Hz, 1H), 2.40 (s, 3H), 2.72-2.86 (m, 2H), 3.57 (dd, J=8.2 4.0 Hz, 1H), 3.63 (s, 3H), 4.19-4.25 (m, 2H), 6.72-7.12 (m, 3H).

MS m/z ([M+H]$^+$) 387.

Step 8: Preparation of 2-[4-(3,4-dihydro-2H-1-benzopyran-6-yl)-2,5-dimethylthiophen-3-yl]-4,4-dimethylpentanoic acid A mixture of methyl 2-[4-(3,4-dihydro-2H-1-benzopyran-6-yl)-2,5-dimethylthiophen-3-yl]-4,4-dimethylpentanoate (42d) (30 mg, 0.08 mmol) and sodium hydroxide (38 mg, 0.31 mmol) in a mixture of ethanol (0.5 mL), water (1.5 mL) was refluxed for 4 hours. Water (2 mL) was added to the residue and the aqueous layer was extracted with diethyl ether (2×2 mL). The organic layer was dried over sodium sulfate and concentrated in vacuo. The residue was purified by preparative TLC (dichloromethane/methanol 90/15) to provide the desired acid (example 42) (15 mg, 0.04 mmol, 50%).

$^1$H NMR (300 MHz, CDCl$_3$) δ 0.66 (s, 9H), 1.43 (dd, J=14.0 4.3 Hz, 1H), 1.97-2.07 (m, 2H), 2.18 (s, 3H), 2.23 (dd, J=14.0 7.6 Hz, 1H), 2.41 (s, 3H), 2.69-2.87 (m, 2H), 3.62 (dd, J=7.6 4.3 Hz, 1H), 4.18-4.25 (m, 2H), 6.75-7.07 (m, 3H).

MS m/z ([M−H]$^-$) 371.
MS m/z ([M+H]$^+$) 373.

Example 43

Synthesis of 2-(tert-butoxy)-2-[4-(6,6-dimethylcyclohex-1-en-1-yl)-2,5-dimethylthiophen-3-yl]acetic acid

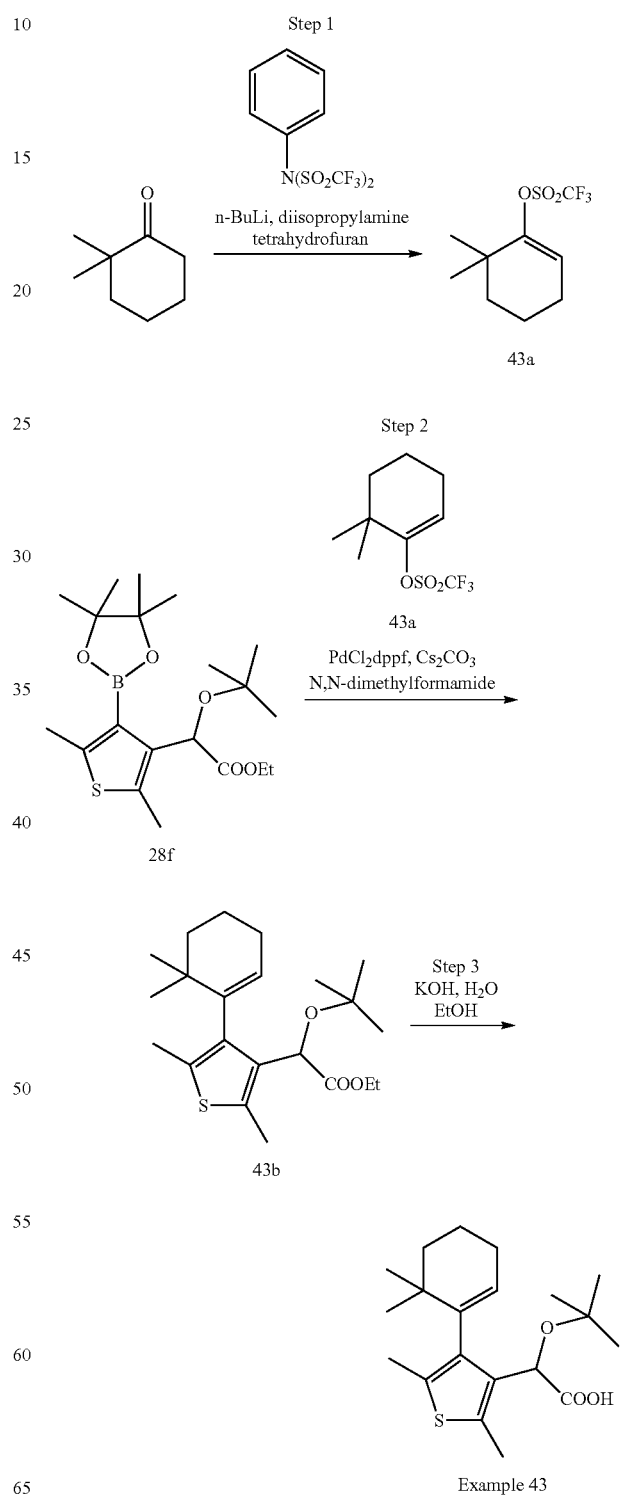

Step 1: Preparation of intermediate 6,6-dimethylcyclohex-1-en-1-yl trifluoromethanesulfonate (43a)

Using the procedure described in example 29, step 1, 2,2-dimethylcyclohexanone (200 mg, 1.58 mmol) is converted, after purification by flash chromatography on silica gel (cyclohexane/ethyl acetate 95/5), to 6,6-dimethylcyclohex-1-en-1-yl trifluoromethane sulfonate (43a) (176 mg, 0.68 mmol, 43%).

$^1$H NMR (300 MHz, CDCl$_3$) δ 1.14 (s, 6H), 1.63-1.65 (m, 4H), 2.14-2.20 (m, 2H), 5.66 (t, J=4.1 Hz, 1H).

Step 2: Preparation of intermediate ethyl 2-(tert-butoxy)-2-[4-(6,6-dimethylcyclohex-1-en-1-yl)-2,5-dimethylthiophen-3-yl]acetate (43b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (100 mg, 0,252 mmol) is converted, by reaction with 6,6-dimethylcyclohex-1-en-1-yl trifluoromethanesulfonate (43a) and after purification by preparative TLC (cyclohexane/ethyl acetate 9/1), to ethyl 2-(tert-butoxy)-2-[4-(6,6-dimethylcyclohex-1-en-1-yl)-2,5-dimethylthiophen-3-yl]acetate (43b) (36 mg, 0.09 mmol, 38%).

$^1$H NMR (400 MHz, CDCl$_3$) δ 0.97-1.01 (m, 3H), 1.05-1.16 (m, 9H), 1.18-1.25 (m, 6H), 1.58-1.61 (m, 2H), 1.73-1.80 (m, 2H), 2.09-2.16 (m, 2H), 2.21 (s, 3H), 2.43-2.61 (m, 3H), 3.98-4.18 (m, 2H), 4.90-4.93 (m, 1H), 5.35-5.42 (m, 1H).

Step 3: Preparation of 2-(tert-butoxy)-2-[4-(6,6-dimethylcyclohex-1-en-1-yl)-2,5-dimethyl thiophen-3-yl]acetic acid Using the procedure described in example 29, step 3, ethyl 2-(tert-butoxy)-2-[4-(6,6-dimethylcyclohex-1-en-1-yl)-2,5-dimethylthiophen-3-yl]acetate (43b) (36 mg, 0.09 mmol) is converted, after purification by preparative TLC (dichloromethane/methanol 95/5), to 2-(tert-butoxy)-2-[4-(6,6-dimethylcyclohex-1-en-1-yl)-2,5-dimethylthiophen-3-yl]acetic acid (example 43) (13 mg, 0.04 mmol, 39%).

$^1$H NMR (400 MHz, CDCl$_3$) δ 0.95-1.01 (m, 3H), 1.18-1.27 (m, 12H), 1.56-1.60 (m, 2H), 1.74-1.81 (m, 2H), 2.12-2.19 (m, 2H), 2.22 (s, 3H), 2.34-2.52 (m, 3H), 5.02-5.03 (m, 1H), 5.43-5.52 (m, 1H).

MS m/z ([M−H]$^−$) 349.

Example 44

Synthesis of 2-(tert-butoxy)-2-[5-chloro-4-(3,4-dihydro-2H-1-benzopyran-6-yl)-2-methylthiophen-3-yl]acetic acid

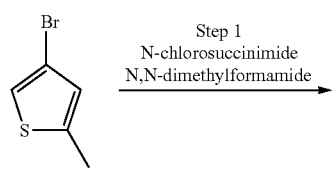

Step 1
N-chlorosuccinimide
N,N-dimethylformamide

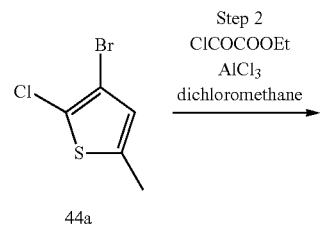

Step 2
ClCOCOOEt
AlCl$_3$
dichloromethane

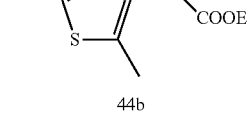

44b

Step 3
NaBH$_4$
tetrahydrofuran
MeOH

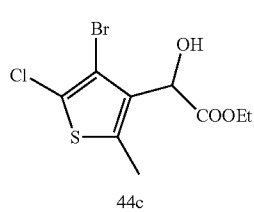

44c

Step 4
tBuOAc
HClO$_4$

Step 5

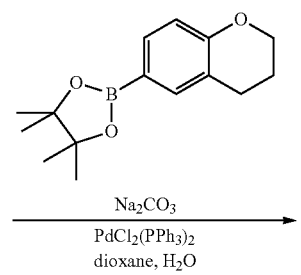

Na$_2$CO$_3$
PdCl$_2$(PPh$_3$)$_2$
dioxane, H$_2$O

44d

Step 6
KOH
MeOH, H$_2$O

44e

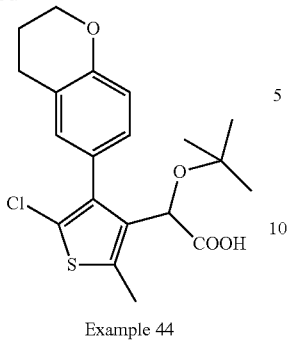

Example 44

Step 1: Preparation of intermediate 3-bromo-2-chloro-5-methylthiophene (44a)

Under argon atmosphere, N-chlorosuccinimide (1.51 g, 11.3 mmol) was added at −5° C. per portion to a solution of 4-bromo-2-methylthiophene (2 g, 11.3 mmol) in N,N-dimethylformamide (6 mL) in an amber round bottom flask. After 1 hour at 0° C., the reaction mixture was warmed to room temperature and stirred for 3 hours more. Water was then added at 0° C. and the mixture was extracted with dichloromethane twice. The organic layer was washed with brine, dried over sodium sulfate, filtered, and evaporated under reduced pressure. The residue was purified by flash chromatography on silica gel (cyclohexane) to afford the desired product (44a) as yellow oil (1.71 g, 8.1 mmol, 71%).

$^1$H NMR (400 MHz, CDCl$_3$) δ □2.40 (d, J=1.1 Hz, 3H), 6.58 (d, J=1.1 Hz, 1H).

Step 2: Preparation of intermediate ethyl 2-(4-bromo-5-chloro-2-methylthiophen-3-yl)-2-oxoacetate (44b)

Under a nitrogen atmosphere, ethyl chlorooxoacetate (898 μL, 8.04 mmol) and aluminum chloride (III) (2.14 g, 16.07 mmol) were added successively at −10° C. to a solution of 3-bromo-2-chloro-5-methylthiophene (44a) (1.7 g, 8.04 mmol) in dichloromethane (84 mL). After 1 hour at 0° C., the mixture was stirred at room temperature for 8 hours. The reaction mixture was slowly hydrolyzed at 0° C. with water. The organic layer was separated, washed with hydrochloric acid 1 N, brine, dried over sodium sulfate, filtered, and evaporated under reduced pressure. The residue was purified by flash chromatography on silica gel (cyclohexane/ethyl acetate 90/10) to give the desired keto-ester (44b) as an orange solid (1.44 g, 4.6 mmol, 56%).

$^1$H NMR (400 MHz, CDCl$_3$) δ 1.41 (t, J=7.2 Hz, 3H), 2.61 (s, 3H), 4.41 (q, J=7.2 Hz, 2H).

Step 3: Preparation of intermediate ethyl 2-(4-bromo-5-chloro-2-methylthiophen-3-yl)-2-hydroxyacetate (44c)

To a mixture of compound ethyl 2-(4-bromo-5-chloro-2-methylthiophen-3-yl)-2-oxoacetate (44b) (340 mg, 1.09 mmol), tetrahydrofuran (7 mL) and ethanol (1.7 mL) was added sodium tetraborohydride (37.2 mg, 0.98 mmol) at 0° C. The mixture was stirred at 0° C. for 2 hours. The mixture was quenched with hydrochloric acid 1N and extracted with ethyl acetate twice. The organic extract was washed with brine twice, dried over sodium sulfate, filtered and concentrated in vacuo to afford the crude alcohol (44c) as a colorless oil (335 mg, 1.07 mmol, 98%).

$^1$H NMR (400 MHz, CDCl$_3$) ε□1.27 (t, J=7.1 Hz, 3H), 2.42 (s, 3H), 4.23-4.32 (m, 2H), 5.27 (s, 1H).

Step 4: Preparation of intermediate ethyl 2-(4-bromo-5-chloro-2-methylthiophen-3-yl)-2-(tert-butoxy)acetate (44d)

To a suspension of ethyl 2-(4-bromo-5-chloro-2-methylthiophen-3-yl)-2-hydroxyacetate (44c) (334 mg, 1.065 mmol) in tert-butylacetate (10.9 mL) at −5° C. was added perchloric acid (70%, 0.4 mL). The mixture was stirred at −5° C. for 1 hour then at 0° C. for 30 minutes more. The mixture was stirred at room temperature for 1 hour more and was basified with a saturated aqueous solution of sodium bicarbonate until pH 8. The aqueous layer was extracted with ethyl acetate. The organic layer was washed with brine, dried over sodium sulfate, filtered and concentrated in vacuo. The residue was purified by flash chromatography on silica gel (cyclohexane/ethyl acetate 95/5) to afford the desired product (44d) as a colorless oil (324 mg, 0.88 mmol, 82%).

$^1$H NMR (400 MHz, CDCl$_3$) ε □1.20-1.23 (m, 12H), 2.51 (s, 3H), 4.08-4.21 (m, 2H), 5.22 (s, 1H).

Step 5: Preparation of intermediate ethyl 2-(tert-butoxy)-2-[5-chloro-4-(3,4-dihydro-2H-1-benzopyran-6-yl)-2-methylthiophen-3-yl]acetate (44e)

Under argon atmosphere, ethyl 2-(4-bromo-5-chloro-2-methylthiophen-3-yl)-2-(tert-butoxy)acetate (44d) (500 mg, 1.35 mmol), 6-(4,4,5,5-tetramethyl-1,3,2-dioxaborolan-2-yl)chroman (351.8 mg, 1.35 mmol), sodium carbonate (429 mg, 4.05 mmol) were dissolved in dioxane (28 mL) and water (4 mL). The solution was degassed under argon for 10 minutes and bis(triphenylphosphine)palladium (II) dichloride (142 mg, 0.20 mmol) was added. The reaction was heated and shaken at 85° C. for 8 hours. After cooling at room temperature, the mixture was filtered through celite, rinsed with methanol. The filtrate was concentrated in vacuo and partitioned between ethyl acetate and water. The organic layer was washed with brine, dried over sodium sulfate, filtered and concentrated under reduced pressure. The crude material was purified by flash chromatography on silica gel (cyclohexane/ethyl acetate 97/3) to give the desired product (44e) (308 mg, 0.73 mmol, 54%).

$^1$H NMR (400 MHz, CDCl$_3$) δ 1.00 (s, 9H), 1.24 (t, J=7.1 Hz, 3H), 2.03-2.08 (m, 2H), 2.50 (s, 3H), 2.79-2.84 (m, 2H), 4.09-4.18 (m, 2H), 4.24 (t, J=5.2 Hz, 2H), 4.80 (s, 1H), 6.84 (d, J=8.3 Hz, 1H), 7.04-7.06 (m, 2H).

Step 6: Preparation of 2-(tert-butoxy)-2-[5-chloro-4-(3,4-dihydro-2H-1-benzopyran-6-yl)-2-methylthiophen-3-yl]acetic acid Potassium hydroxide (6.6 mg, 0.12 mmol) was added to a solution of ethyl 2-(tert-butoxy)-2-[5-chloro-4-(3,4-dihydro-2H-1-benzopyran-6-yl)-2-methylthiophen-3-yl]acetate (44e) (25 mg, 0.06 mmol) in a mixture of methanol (0.8 mL) and water (0.95 mL). The mixture was sonicated for 10 minutes and then was heated at 100° C. for 2 hours. The mixture was concentrated to evaporate methanol in vacuo. The aqueous layer was acidified with hydrochloric acid 1N and extracted with ethyl acetate twice. The organic layer was washed with brine, dried over sodium sulfate, filtered and concentrated in vacuo. The residue was purified by preparative TLC (dichloromethane/methanol 90/10) to give the desired acid (example 44) (4 mg, 0.04 mmol, 17% yield).

$^1$H NMR (400 MHz, CDCl$_3$) δ 1.03 (s, 9H), 2.01-2.07 (m, 2H), 2.42 (s, 3H), 2.80-2.83 (m, 2H), 4.23 (t, J=5.2 Hz, 2H), 4.94 (s, 1H), 6.85 (d, J=8.4 Hz, 1H), 7.07-7.15 (m, 2H).

MS m/z ([M−H]$^−$) 393/395.

Example 45

Synthesis of tert-butoxy-[4-(3,5-dimethyl-cyclohex-1-enyl)-2,5-dimethyl-thiophen-3-yl]-acetic acid

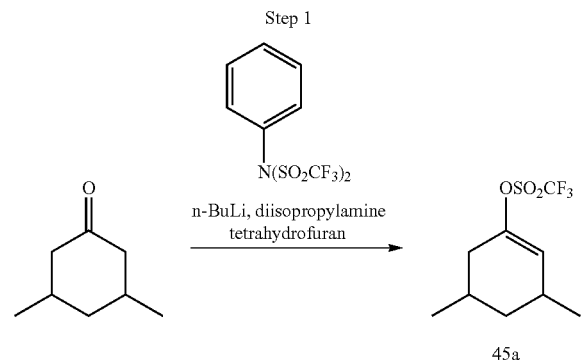

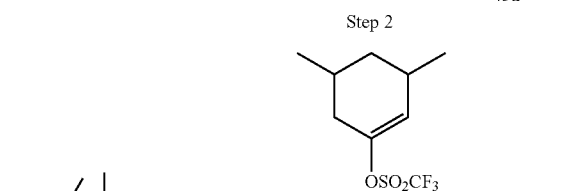

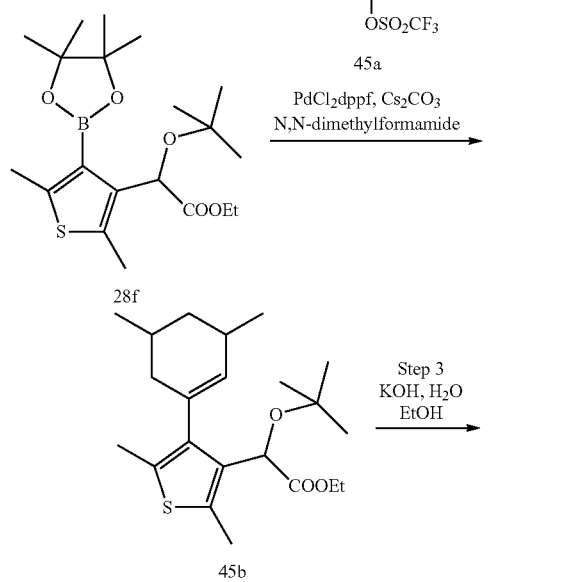

Step 1: Preparation of intermediate 3,5-dimethyl-cyclohex-1-enyltrifluoromethanesulfonate (45a)

Using the procedure described in example 29, step 1, 3,5-dimethylcyclohexanone (573 mg, 4.54 mmol) is converted, after purification by flash chromatography on silica gel (cyclohexane/ethyl acetate 90/10), to 3,5-dimethyl-cyclohex-1-enyltrifluoromethanesulfonate (45a) (509 mg, 1.97 mmol, 44%).

$^1$H NMR (300 MHz, CDCl$_3$) δ 0.78-0.90 (m, 1H), 0.99-1.07 (m, 6H), 1.72-2.03 (m, 3H), 2.25-2.32 (m, 1H), 2.37-2.47 (m, 1H), 5.57 (s, 1H).

Step 2: Preparation of intermediate ethyl tert-butoxy-[4-(3,5-dimethyl-cyclohex-1-enyl)-2,5-dimethyl-thiophen-3-yl]-acetate (45b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, after purification by flash chromatography on silica gel (cyclohexane/ethyl acetate 90/10), to ethyl tert-butoxy-[4-(3,5-dimethyl-cyclohex-1-enyl)-2,5-dimethyl-thiophen-3-yl]-acetate (45b) (122 mg, 0.32 mmol, 85%).

$^1$H NMR (300 MHz, CDCl$_3$) δ 0.85-0.92 (m, 1H), 0.96-1.06 (m, 6H), 1.17-1.24 (m, 12H), 1.55-1.68 (m, 1H), 1.78-1.85 (m, 2H), 1.94-1.97 (m, 1H), 2.21 and 2.22 (2s, 3H), 2.23-2.46 (m, 1H), 2.47 and 2.48 (2s, 3H), 3.99-4.23 (m, 2H), 4.95 and 4.98 (2s, 1H), 5.39-5.45 (m, 1H).

MS m/z ([M+H]$^+$) 379.

Step 3: Preparation of tert-butoxy-[4-(3,5-dimethyl-cyclohex-1-enyl)-2,5-dimethyl-thiophen-3-yl]-acetic acid Using the procedure described in example 29, step 3, ethyl tert-butoxy-[4-(3,5-dimethyl-cyclohex-1-enyl)-2,5-dimethyl-thiophen-3-yl]-acetate (45b) (122 mg, 0.32 mmol) is converted, after purification by flash chromatography on silica gel (dichloromethane/methanol 95/5), to tert-butoxy-[4-(3,5-dimethyl-cyclohex-1-enyl)-2,5-dimethyl-thiophen-3-yl]-acetic acid (1i) (60 mg, 0.17 mmol, 50%).

$^1$H NMR (300 MHz, CDCl$_3$) δ 0.79-1.36 (m, 16H), 1.53-1.88 (m, 3H), 1.97 (m, 1H), 2.20 (s, 3H), 2.22-2.35 (m, 2H), 2.39 (s, 3H), 4.98-5.03 (m, 1H), 5.38-5.44 (m, 1H).

MS m/z ([M−H]$^−$) 349.

Example 46

Synthesis of tert-butoxy-[4-(4-tert-butyl-cyclohex-1-enyl)-2,5-dimethyl-thiophen-3-yl]-acetic acid

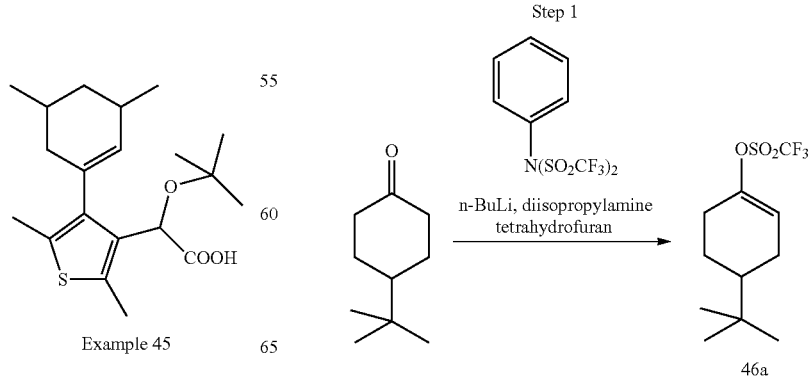

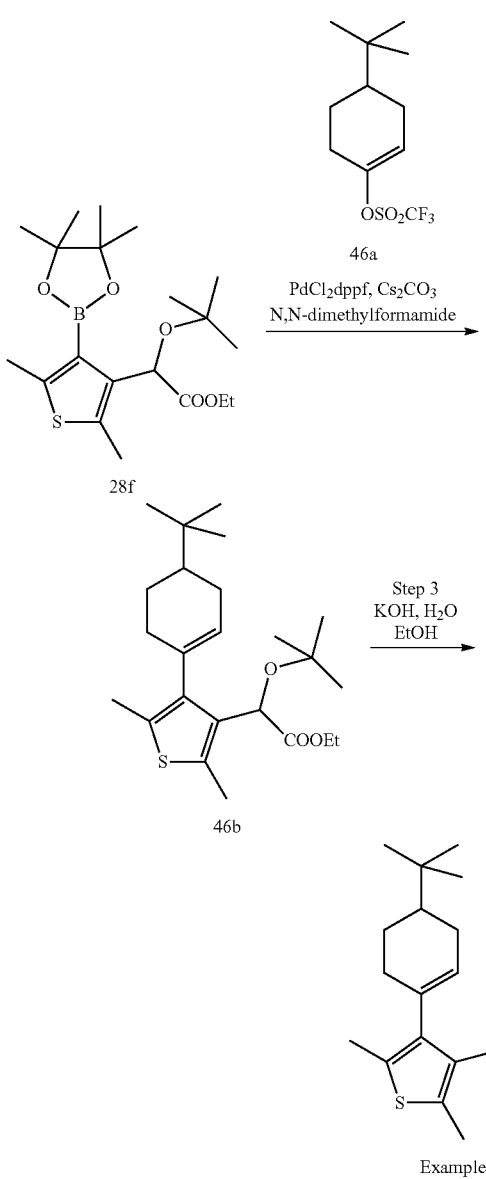

aborolan-2-yl)thiophen-3-yl]acetate (28f) (150 mg, 0.37 mmol) is converted, after purification by flash chromatography on silica gel (cyclohexane/ethyl acetate 90/10), to ethyl tert-butoxy-[4-(4-tert-butyl-cyclohex-1-enyl)-2,5-dimethyl-thiophen-3-yl]-acetate (46b) (70 mg, 0.17 mmol, 40%).

$^1$H NMR (300 MHz, CDCl$_3$) δ 0.92 (s, 9H), 1.17-1.42 (m, 14H), 1.87-2.20 (m, 4H), 2.25-2.35 (m, 1H), 2.21 (s, 3H), 2.47 (s, 3H), 4.04-4.22 (m, 2H), 4.93 and 4.97 (2s, 1H), 5.53-5.61 (m, 1H).

MS m/z ([M+H]$^+$) 407.

Step 3: Preparation of tert-butoxy-[4-(4-tert-butyl-cyclohex-1-enyl)-2,5-dimethyl-thiophen-3-yl]-acetic acid Using the procedure described in example 29, step 3, ethyl tert-butoxy-[4-(4-tert-butyl-cyclohex-1-enyl)-2,5-dimethyl-thiophen-3-yl]-acetate (46b) (70 mg, 0.17 mmol) is converted, after purification by flash chromatography on silica gel (dichloromethane/methanol 95/5), to tert-butoxy-[4-(3,5-dimethyl-cyclohex-1-enyl)-2,5-dimethyl-thiophen-3-yl]-acetic acid (example 46) (57 mg, 0.15 mmol, 88%).

$^1$H NMR (300 MHz, CDCl$_3$) δ 0.90 (s, 9H), 1.20 (s, 9H), 1.21-1.41 (m, 2H), 1.86-2.15 (m, 4H), 2.21 (s, 3H), 2.32-2.38 (m, 1H), 2.39 (s, 3H), 4.99 and 5.05 (2s, 1H), 5.57-5.63 (m, 1H).

MS m/z ([M−H]$^−$) 377.

Example 47

Synthesis of tert-butoxy-[2,5-dimethyl-4-(2-phenyl-cyclohex-1-enyl)-thiophen-3-yl]-acetic acid Step 1

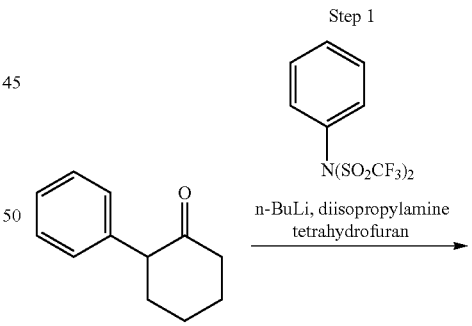

Step 1: Preparation of intermediate 4-tert-butyl-cyclohex-1-enyltrifluoromethanesulfonate (46a)

Using the procedure described in example 29, step 1, 4-tert-butylcyclohexanone (500 mg, 3.24 mmol) is converted, after purification by flash chromatography on silica gel (cyclohexane/ethyl acetate 90/10), to 4-tert-butyl-cyclohex-1-enyltrifluoromethanesulfonate (46a) (610 mg, 2.13 mmol, 66%).

$^1$H NMR (300 MHz, CDCl$_3$) δ 0.80 (s, 9H), 1.26-1.43 (m, 2H), 1.88-2.00 (m, 2H), 2.16-2.45 (m, 3H), 5.72-5.76 (m, 1H).

Step 2: Preparation of intermediate ethyl tert-butoxy-[4-(4-tert-butyl-cyclohex-1-enyl)-2,5-dimethyl-thiophen-3-yl]-acetate (46b)

Using the procedure described in example 29, step 2, ethyl 2-(tert-butoxy)-2-[2,5-dimethyl-4-(tetramethyl-1,3,2-diox-

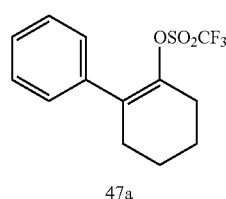

-continued

Step 2

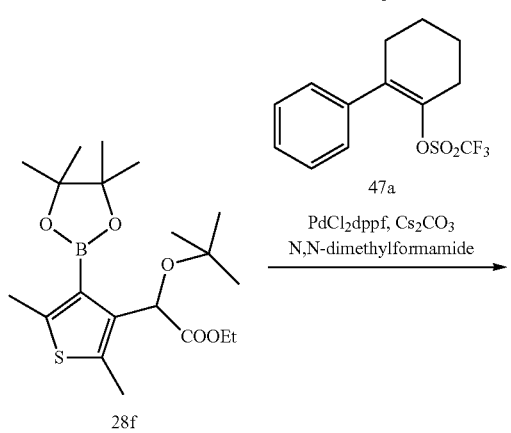

Step 3
KOH, H₂O
EtOH

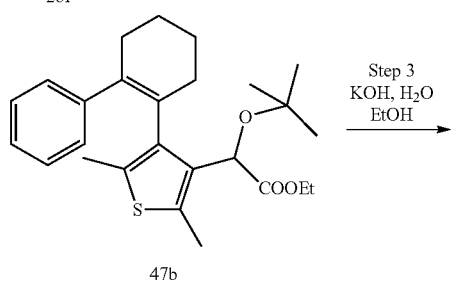

47b

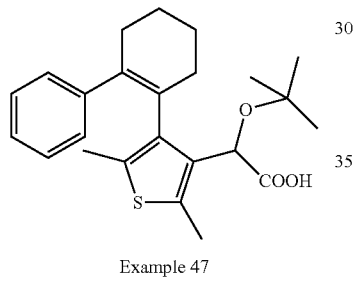

Example 47

Step 1: Preparation of intermediate 2-phenyl-cyclohex-1-enyltrifluoromethanesulfonate (47a)

Using the procedure described in example 29, step 1, 2-phenylcyclohexanone (500 mg, 2.87 mmol) is converted, after purification by flash chromatography on silica gel (cyclohexane/ethyl acetate 90/10), to 2-phenyl-cyclohex-1-enyl-trifluoromethanesulfonate (47a) (679 mg, 2.22 mmol, 77%).

$^1$H NMR (300 MHz, CDCl$_3$) δ 1.75-1.92 (m, 4H), 2.45-2.51 (m, 4H), 7.23-7.38 (m, 5H).

Step 2: Preparation of intermediate ethyl tert-butoxy-[2,5-dimethyl-4-(2-phenyl-cyclohex-1-enyl)-thiophen-3-yl]-acetate (47b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, after purification by flash chromatography on silica gel (cyclohexane/ethyl acetate 90/10), to ethyl tert-butoxy-[2,5-dimethyl-4-(2-phenyl-cyclohex-1-enyl)-thiophen-3-yl]-acetate (47b) (94 mg, 0.22 mmol, 58%).

$^1$H NMR (300 MHz, CDCl$_3$) δ 1.12-1.25 (m, 12H), 1.76-1.92 (m, 6H), 2.03-2.16 (m, 1H), 2.35-2.53 (m, 5H), 2.55-2.68 (m, 2H), 3.88-4.22 (m, 2H), 4.93 and 4.94 (2s, 1H), 7.00-7.16 (m, 3H), 7.23-7.38 (m, 2H).

MS m/z ([M+H]$^+$) 427.

Step 3: Preparation of tert-butoxy-[2,5-dimethyl-4-(2-phenyl-cyclohex-1-enyl)-thiophen-3-yl]-acetic acid (example 47)

Using the procedure described in example 29, step 3, ethyl tert-butoxy-[2,5-dimethyl-4-(2-phenyl-cyclohex-1-enyl)-thiophen-3-yl]-acetate (47a) (94 mg, 0.22 mmol) is converted, after purification by flash chromatography on silica gel (dichloromethane/methanol 95/5), to tert-butoxy-[4-(3,5-dimethyl-cyclohex-1-enyl)-2,5-dimethyl-thiophen-3-yl]-acetic acid (example 47) (58 mg, 0.14 mmol, 66%).

$^1$H NMR (300 MHz, CDCl$_3$) δ 1.07 and 1.16 (2s, 9H), 1.71-1.91 (m, 4H), 2.04-2.74 (m, 10H), 4.91 (s, 1H), 6.99-7.18 (m, 5H).

MS m/z ([M−H]$^-$) 397.

Example 48

Synthesis of tert-butoxy-[4-(3,4-dihydro-naphthalen-1-yl)-2,5-dimethyl-thiophen-3-yl]-acetic acid

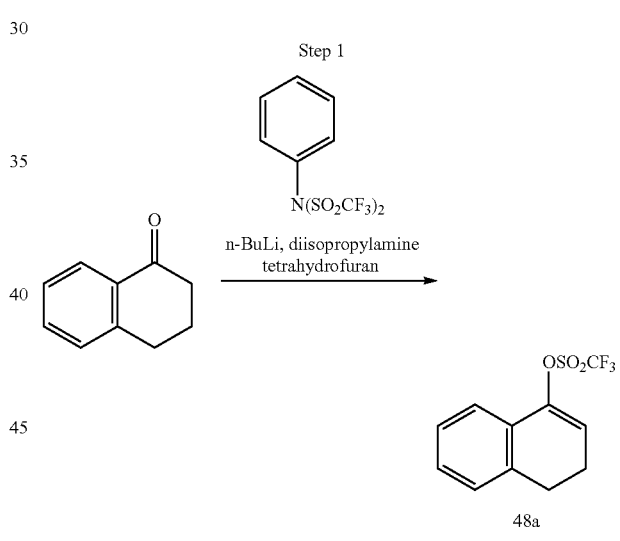

Step 1

Step 2

48a

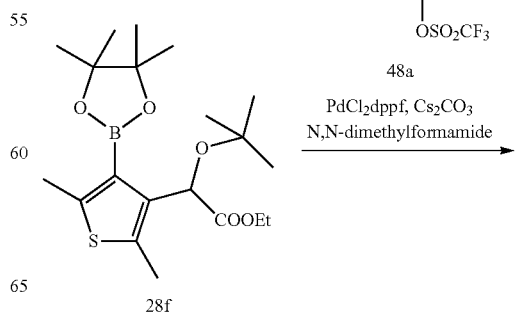

28f

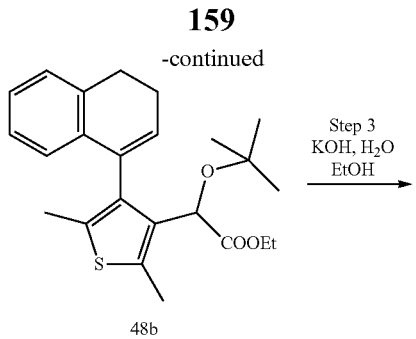

48b

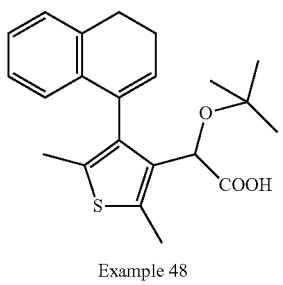

Example 48

Step 1: Preparation of intermediate 3,4-dihydro-naphthalen-1-yltrifluoromethanesulfonate (48a)

Using the procedure described in example 29, step 1, 3,4-dihydro-2H-naphthalen-1-one (664 mg, 4.54 mmol) is converted, after purification by flash chromatography on silica gel (cyclohexane/ethyl acetate 90/10), to 3,4-dihydro-naphthalen-1-yltrifluoromethanesulfonate (48a) (400 mg, 1.44 mmol, 32%).

$^1$H NMR (300 MHz, CDCl$_3$) δ 2.50-2.57 (m, 2H), 2.90 (t, J=8.2 Hz, 2H), 6.04 (t, J=4.7 Hz, 1H), 7.19-7.23 (m, 1H), 7.26-7.32 (m, 2H), 7.35-7.39 (m, 1H).

Step 2: Preparation of intermediate ethyl tert-butoxy-[4-(3,4-dihydro-naphthalen-1-yl)-2,5-dimethyl-thiophen-3-yl]-acetate (48b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with 3,4-dihydro-naphthalen-1-yltrifluoromethanesulfonate (48a) and after purification by flash chromatography on silica gel (cyclohexane/ethyl acetate 90/10), to ethyl tert-butoxy-[4-(3,4-dihydro-naphthalen-1-yl)-2,5-dimethyl-thiophen-3-yl]-acetate (48b) (102 mg, 0.25 mmol, 68%).

$^1$H NMR (300 MHz, CDCl$_3$) δ 0.91 and 1.10 (2s, 9H), 0.96 and 1.20 (2t, J=7.1 Hz, 3H), 2.14 and 2.15 (2s, 3H), 2.41-2.49 (m, 2H), 2.52 and 2.54 (2s, 3H), 2.83-2.94 (m, 2H), 3.71-4.11 (m, 2H), 4.80 and 4.83 (2s, 1H), 5.90 and 6.03 (2t, J=4.6 Hz, 1H), 6.67-6.74 (m, 1H), 7.01-7.17 (m, 3H).
MS m/z ([M+H]$^+$) 399.

Step 3: Preparation of tert-butoxy-[4-(3,4-dihydro-naphthalen-1-yl)-2,5-dimethyl-thiophen-3-yl]-acetic acid Using the procedure described in example 29, step 3, ethyl tert-butoxy-[4-(3,4-dihydro-naphthalen-1-yl)-2,5-dimethyl-thiophen-3-yl]-acetate (48b) (102 mg, 0.25 mmol) is converted, after purification by flash chromatography on silica gel (dichloromethane/methanol 95/5), to tert-butoxy-[4-(3,4-dihydro-naphthalen-1-yl)-2,5-dimethyl-thiophen-3-yl]-acetic acid (example 48) (60 mg, 0.16 mmol, 63%).

$^1$H NMR (300 MHz, CDCl$_3$) δ 0.91 and 1.01 (2s, 9H), 2.09 and 2.16 (2s, 3H), 2.36-2.47 (m, 5H), 2.81-2.89 (m, 2H), 4.92 and 5.06 (2s, 1H), 5.82 and 6.25 (2t, J=4.4 Hz, 1H), 6.76 (t, J=7.5 Hz, 1H), 7.02-7.17 (m, 3H).
MS m/z ([M−H]$^−$) 369.

Example 49

Synthesis of 2-[1-benzyl-5-(3,4-dihydro-2H-1-benzopyran-6-yl)-3-(trifluoro methyl)-1H-pyrazol-4-yl]-2-(tert-butoxy)acetic acid

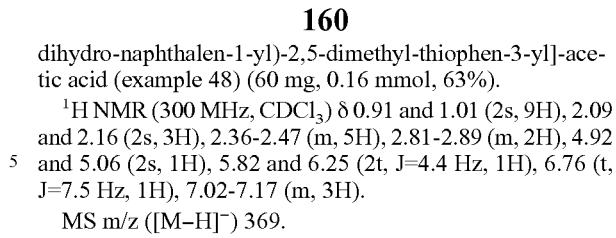

9a

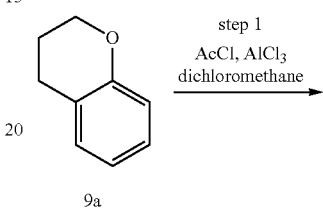

49a

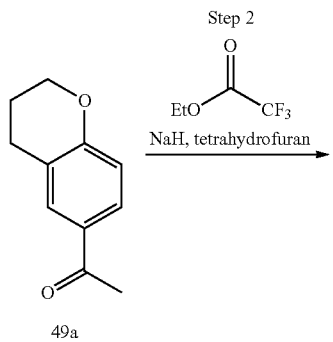

49b

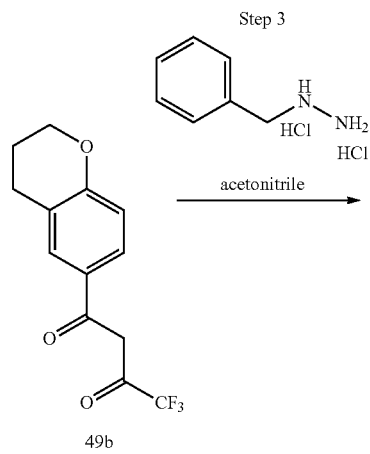

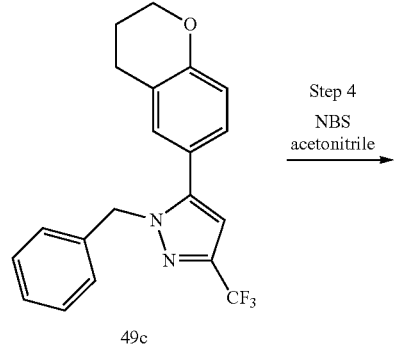

49c

-continued

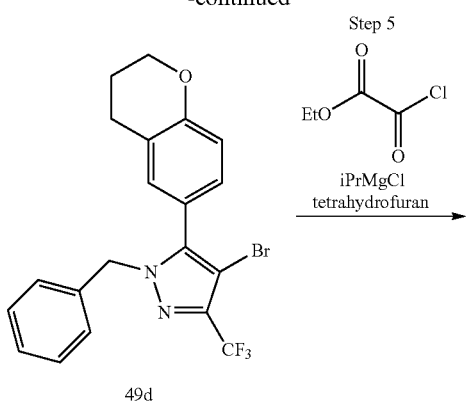

Step 5
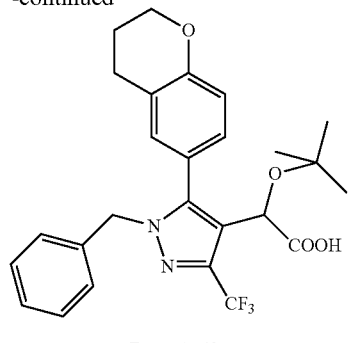
iPrMgCl
tetrahydrofuran

49d

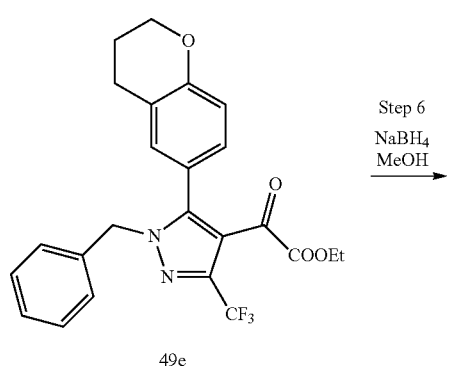

Step 6
NaBH₄
MeOH

49e

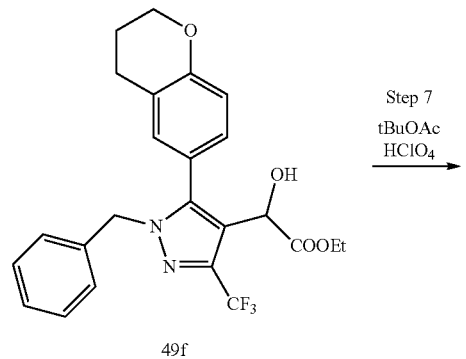

Step 7
tBuOAc
HClO₄

49f

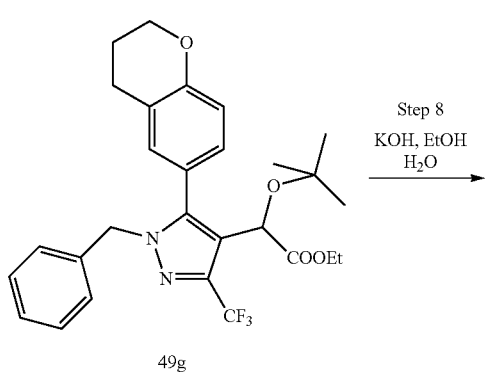

Step 8
KOH, EtOH
H₂O

49g

-continued

Example 49

Step 1: Preparation of intermediate 1-(3,4-dihydro-2H-1-benzopyran-6-yl)ethan-1-one (49a)

Aluminium chloride (1.19 g, 8.9 mmol) was added portionwise to a stirred solution of acetyl chloride (1.21 mL, 17.0 mmol) in dry dichloromethane (20 mL), previously cooled to −10° C., until homogeneous (5 min). The solution was added, via cannula, to a solution of 3,4-dihydro-2H-1-benzopyran (9a) (1.20 g, 8.9 mmol) in dry dichloromethane (17 mL) at −10° C. The mixture was stirred at the same temperature for 30 minutes before being poured into ice/concentrated hydrochloric acid (5:1, v/v, 126 mL). The stirring was maintained at room temperature for 2 hours and the solution was extracted with dichloromethane (3×50 mL). The organic layer was dried over sodium sulfate and concentrated in vacuo to provide 1-(3,4-dihydro-2H-1-benzopyran-6-yl)ethan-1-one (49a) (1.55 g, 8.8 mmol, 99%) which was used without further purification.

$^1$H NMR (300 MHz, CDCl$_3$) δ 1.97-2.07 (m, 2H), 2.53 (s, 3H), 2.82 (t, J=6.4 Hz, 2H), 4.24 (t, J=5.2 Hz, 2H), 6.81 (d, J=9.2 Hz, 1H), 7.67-7.74 (m, 2H).

MS m/z ([M+H]$^+$) 177.

Step 2: Preparation of intermediate 1-(3,4-dihydro-2H-1-benzopyran-6-yl)-4,4,4-trifluorobutane-1,3-dione (49b)

Under a nitrogen atmosphere, 1-(3,4-dihydro-2H-1-benzopyran-6-yl)ethan-1-one (49a) (1.55 g, 8.8 mmol) was dissolved in anhydrous tetrahydrofuran (48 mL) and sodium hydride (60% in mineral oil, 0.42 g, 10.6 mmol) was added portionwise, maintaining the temperature between −5 and 0° C. After 30 minutes stirring at the same temperature, ethyl trifluoroacetate (1.5 mL, 10.6 mmol) was added and the reaction mixture was stirred at room temperature for 3 hours. Water (10 mL) was added and tetrahydrofuran was removed in vacuo. The resulting aqueous layer was extracted with ethyl acetate (2×20 mL). The organic layer was washed with brine (10 mL), dried over sodium sulfate and concentrated in vacuo to provide 1-(3,4-dihydro-2H-1-benzopyran-6-yl)-4,4,4-trifluorobutane-1,3-dione (49b) (2.39 g, 8.8 mmol, 100%) which was used without further purification.

$^1$H NMR (400 MHz, CDCl$_3$) δ 1.82-1.91 (m, 2H), 2.50-2.60 (m, 2H), 4.07-4.15 (m, 2H), 5.96 (s, 1H), 6.56 (d, J=8.4 Hz, 1H), 7.20 (bs, 1H), 7.33 (bs, 1H).

Step 3: Preparation of intermediate 1-benzyl-5-(3,4-dihydro-2H-1-benzopyran-6-yl)-3-(trifluoromethyl)-1H-pyrazole (49c)

A solution of benzylhydrazine dihydrochloride (394 mg, 2.03 mmol) and 1-(3,4-dihydro-2H-1-benzopyran-6-yl)-4,4, 4-trifluorobutane-1,3-dione (49b) (500 mg, 1.84 mmol) in acetonitrile (80 mL) was refluxed for 16 hours. The mixture was concentrated in vacuo and the residue was taken up in ethyl acetate (5 mL). The organic layer was successively washed with water (10 mL) and brine (10 mL) before being dried over sodium sulfate and concentrated in vacuo. The oil was purified by preparative TLC (cyclohexane/ethyl acetate 100/0 to 90/10) to provide the desired pyrazole (49c) (260 mg, 0.73 mmol, 39%).

$^1$H NMR (400 MHz, CDCl$_3$) δ 1.98-2.06 (m, 2H), 2.73 (t, J=6.5 Hz, 2H), 4.22 (t, J=5.2 Hz, 2H), 5.34 (s, 2H), 6.52 (s, 1H), 6.80 (d, J=8.4 Hz, 1H), 6.92 (d, J=2.2 Hz, 1H), 6.98 (dd, J=8.4 Hz, J=2.2 Hz, 1H), 7.04-7.13 (m, 2H), 7.24-7.34 (m, 3H).

MS m/z ([M+H]$^+$) 359.

Step 4: Preparation of intermediate 1-benzyl-4-bromo-5-(3,4-dihydro-2H-1-benzopyran-6-yl)-3-(trifluoromethyl)-1H-pyrazole (49d)

A solution 1-benzyl-5-(3,4-dihydro-2H-1-benzopyran-6-yl)-3-(trifluoromethyl)-1H-pyrazole (49c) (260 mg, 0.73 mmol) and N-bromosuccinimide (157 mg, 0.88 mmol) in acetonitrile (5 mL) was refluxed for 45 minutes. Water (5 mL) was added, and the aqueous layer was extracted with dichloromethane (2×5 mL). The combined organics layers were dried over sodium sulfate and concentrated in vacuo. The residue was purified by preparative TLC (cyclohexane/ethyl acetate 100/0 to 90/10) to provide the 1-benzyl-4-bromo-5-(3,4-dihydro-2H-1-benzopyran-6-yl)-3-(trifluoromethyl)-1H-pyrazole (49d) (200 mg, 0.46 mmol, 63%).

$^1$H NMR (400 MHz, CDCl$_3$) δ 1.99-2.08 (m, 2H), 2.74 (t, J=6.5 Hz, 2H), 4.24 (t, J=5.2 Hz, 2H), 5.26 (s, 2H), 6.83-6.87 (m, 2H), 6.95 (dd, J=8.4 Hz, J=2.2 Hz, 1H), 7.01-7.07 (m, 2H), 7.26-7.32 (m, 3H).

MS m/z ([M+H]$^+$) 437/439.

Step 5: Preparation of intermediate ethyl 2-[1-benzyl-5-(3,4-dihydro-2H-1-benzopyran-6-yl)-3-(trifluoromethyl)-1H-pyrazol-4-yl]-2-oxoacetate (49e)

Under nitrogen, isopropyl magnesium chloride 2M in tetrahydrofuran (0.30 mL, 0.59 mmol) was added dropwise to a solution of 1-benzyl-4-bromo-5-(3,4-dihydro-2H-1-benzopyran-6-yl)-3-(trifluoromethyl)-1H-pyrazole (49d) (200 mg, 0.46 mmol) in anhydrous tetrahydrofuran (1.0 mL), previously cooled to −20° C. After 2 hour stirring at the same temperature, ethyl chlorooxoacetate (87 μL, 0.78 mmol) was dropwise added. The mixture was stirred at −20° C. for 60 minutes before being poured in water (2 mL). The mixture was extracted with ethyl acetate (2×3 mL) and the organic layer was dried over sodium sulfate and concentrated in vacuo. The residue was purified by preparative TLC (cyclohexane/ethyl acetate 75/25) to provide the desired keto-ester (49e) (80 mg, 0.17 mmol, 38%)

$^1$H NMR (400 MHz, CDCl$_3$) δ 1.10 (t, J=7.2 Hz, 3H), 1.97-2.07 (m, 2H), 2.72 (t, J=6.5 Hz, 2H), 3.77 (q, J=7.2 Hz, 2H), 4.23 (t, J=5.2 Hz, 2H), 5.21 (s, 2H), 6.80-6.85 (m, 2H), 6.93 (dd, J=8.4 Hz, J=2.2 Hz, 1H), 7.00-7.08 (m, 2H), 7.27-7.33 (m, 3H).

MS m/z ([M+H]$^+$) 459.

Step 6: Preparation of intermediate ethyl 2-[1-benzyl-5-(3,4-dihydro-2H-1-benzopyran-6-yl)-3-(trifluoromethyl)-1H-pyrazol-4-yl]-2-hydroxyacetate (49f)

Under a nitrogen atmosphere, sodium borohydride (6.44 mg, 0.17 mmol) was added portionwise to a solution of ethyl 2-[1-benzyl-5-(3,4-dihydro-2H-1-benzopyran-6-yl)-3-(trifluoromethyl)-1H-pyrazol-4-yl]-2-oxoacetate (49e) (78 mg, 0.17 mmol) in anhydrous methanol (2 mL). After 2 hours stirring, water was added (3 mL). The methanol was removed under reduced pressure, and the aqueous layer was extracted with ethyl acetate (2×5 mL). The organic layer was successively washed with water (3 mL) and brine (3 mL), before being dried over sodium sulfate and concentrated in vacuo to provide the desired alcohol (49f) (70 mg, 0.17 mmol, 89%) which was used without further purification.

$^1$H NMR (400 MHz, CDCl$_3$) δ 1.21 (t, J=7.1 Hz, 3H), 1.98-2.06 (m, 2H), 2.71 (t, J=6.4 Hz, 2H), 3.37 (bs, 1H), 4.07-4.20 (m, 2H), 4.23 (t, J=5.2 Hz, 2H), 5.02 (s, 1H), 5.16 (d, J=15.4 Hz, 1H), 5.27 (d, J=15.4 Hz, 1H), 6.81 (d, J=8.4 Hz, 1H), 6.85 (d, J=2.0 Hz, 1H), 6.94 (dd, J=8.4 Hz, J=2.0 Hz, 1H), 6.99-7.05 (m, 2H), 7.24-7.31 (m, 3H).

MS m/z ([M+H]$^+$) 461.

Step 7: Preparation of intermediate ethyl 2-[1-benzyl-5-(3,4-dihydro-2H-1-benzopyran-6-yl)-3-(trifluoromethyl)-1H-pyrazol-4-yl]-2-(tert-butoxy)acetate (49g)

To a solution of ethyl 2-[1-benzyl-5-(3,4-dihydro-2H-1-benzopyran-6-yl)-3-(trifluoromethyl)-1H-pyrazol-4-yl]-2-hydroxyacetate (49f) (70 mg, 0.152 mmol) in tert-butyl acetate (2.9 mL) at 0° C. was added perchloric acid (0.347 mL). The mixture was stirred for 1 hour at room temperature before being slowly quenched with a saturated solution of potassium carbonate (10 mL). The layers were separated and the aqueous layer was extracted with ethyl acetate (2×10 mL). The organic layers were dried over sodium sulfate and concentrated in vacuo. The residue was purified by preparative TLC (cyclohexane/ethyl acetate 75/25) to provide the desired ether (49g) (22 mg, 0.04 mmol, 28%) as a clear yellow oil.

$^1$H NMR (300 MHz, CDCl$_3$) δ 1.06 (s, 9H), 1.18 (t, J=7.1 Hz, 3H), 1.96-2.08 (m, 2H), 2.70 (t, J=6.4 Hz, 2H), 4.01-4.14 (m, 2H), 4.23 (t, J=5.2 Hz, 2H), 4.93 (s, 1H), 5.12 (d, J=15.4 Hz, 1H), 5.25 (d, J=15.4 Hz, 1H), 6.78 (d, J=8.3 Hz, 1H), 6.86 (d, J=2.0 Hz, 1H), 6.92 (dd, J=8.3 Hz, J=2.0 Hz, 1H), 6.95-7.03 (m, 2H), 7.22-7.31 (m, 3H).

Step 8: Preparation of 2-[1-benzyl-5-(3,4-dihydro-2H-1-benzopyran-6-yl)-3-(trifluoromethyl)-1H-pyrazol-4-yl]-2-(tert-butoxy)acetic acid A mixture of ethyl 2-[1-benzyl-5-(3,4-dihydro-2H-1-benzopyran-6-yl)-3-(trifluoromethyl)-1H-pyrazol-4-yl]-2-(tert-butoxy)acetate (49g) (22 mg, 0.04 mmol) and potassium hydroxide (21 mg, 0.17 mmol) in a mixture of ethanol (0.3 mL) and water (0.3 mL) was refluxed for 7 hours. The mixture was concentrated in vacuo. Water (2 mL) was added to the residue and the aqueous layer was washed with diethyl ether (2 mL), acidified with 1M hydrochloric acid until pH 2 and extracted with diethyl ether (2×3 mL). The organic layer was dried over sodium sulfate and concentrated in vacuo to provide the desired acid (example 49) (19 mg, 0.04 mmol, 91%).

$^1$H NMR (300 MHz, CDCl$_3$) δ 1.07 (s, 9H), 1.97-2.09 (m, 2H), 2.72 (t, J=6.3 Hz, 2H), 4.24 (t, J=5.2 Hz, 2H), 4.86 (s, 1H), 5.11 (d, J=15.4 Hz, 1H), 5.28 (d, J=15.4 Hz, 1H), 6.82 (d, J=8.4 Hz, 1H), 6.93-7.06 (m, 4H), 7.23-7.33 (m, 3H).

MS m/z ([M−H]$^−$) 487.

MS m/z ([M+H]$^+$) 489.

Example 50

Synthesis of tert-butoxy-[4-(4-chloro-phenyl)-2,5-dimethyl-thiophen-3-yl]-acetic acid

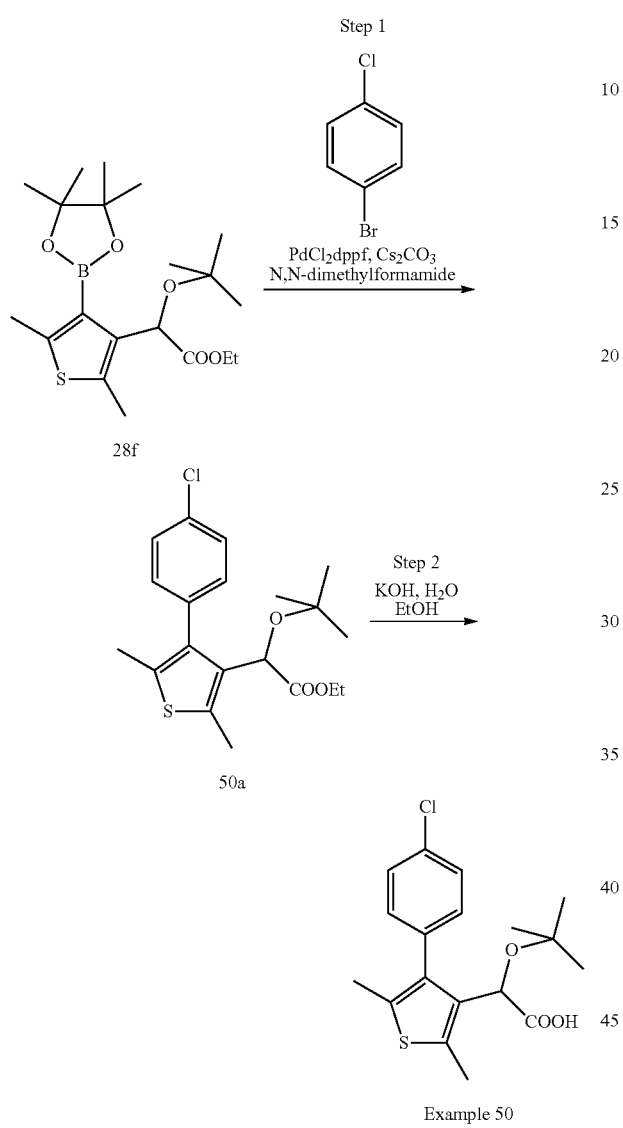

Example 50

Step 1: Preparation of intermediate ethyl tert-butoxy-[4-(4-chloro-phenyl)-2,5-dimethyl-thiophen-3-yl]-acetate (50a)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with 1-bromo-4-chlorobenzene and after purification by flash chromatography on silica gel (cyclohexane/ethyl acetate 90/10), to ethyl tert-butoxy-[4-(4-chloro-phenyl)-2,5-dimethyl-thiophen-3-yl]-acetate (50a) (80 mg, 0.21 mmol, 56%).

$^1$H NMR (300 MHz, CDCl$_3$) δ 0.99 (s, 9H), 1.22 (t, J=7.2 Hz, 3H), 2.17 (s, 3H), 2.50 (s, 3H), 4.07-4.20 (m, 2H), 4.72 (s, 1H), 7.23 (d, J=8.7 Hz, 2H), 7.39 (d, J=8.7 Hz, 2H).

MS m/z ([M+H]$^+$) 381/383.

Step 2: Preparation of tert-butoxy-[4-(4-chloro-phenyl)-2,5-dimethyl-thiophen-3-yl]-acetic acid Using the procedure described in example 29, step 3, ethyl tert-butoxy-[4-(4-chloro-phenyl)-2,5-dimethyl-thiophen-3-yl]-acetate (50a) (131 mg, 0.34 mmol) is converted, after purification by flash chromatography on silica gel (dichloromethane/methanol 95/5), to tert-butoxy-[4-(4-chloro-phenyl)-2,5-dimethyl-thiophen-3-yl]-acetic acid (example 50) (107 mg, 0.30 mmol, 89%).

$^1$H NMR (300 MHz, CDCl$_3$) δ 1.00 (s, 9H), 2.19 (s, 3H), 2.41 (s, 3H), 4.84 (s, 1H), 7.26-7.40 (m, 4H).

MS m/z ([M−H]$^−$) 351/353.

Example 51

Synthesis of tert-butoxy-[4-(2-chloro-phenyl)-2,5-dimethyl-thiophen-3-yl]-acetic acid

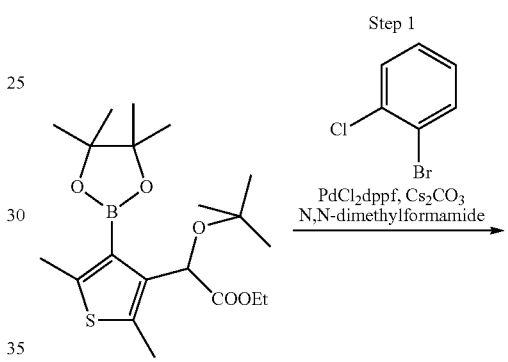

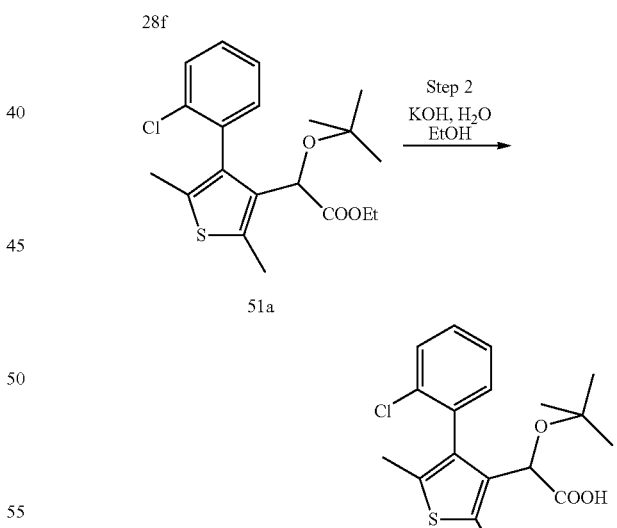

Example 51

Step 1: Preparation of intermediate ethyl tert-butoxy-[4-(2-chloro-phenyl)-2,5-dimethyl-thiophen-3-yl]-acetate (51a)

Using the procedure described in example 29, step 1, ethyl 2-(tert-butoxy)-2-[2,5-dimethyl-4-(tetramethyl-1,3,2-dioxaborolan-2-yl)thiophen-3-yl]acetate (28f) (300 mg, 0.75 mmol) is converted, by reaction with 1-bromo-2-chlorobenzene and after purification by flash chromatography on silica gel (cyclohexane/ethyl acetate 90/10), to ethyl tert-butoxy-[4-(2-chloro-phenyl)-2,5-dimethyl-thiophen-3-yl]-acetate (51a) (110 mg, 0.29 mmol, 38%).

$^1$H NMR (300 MHz, CDCl$_3$) δ 1.02 and 1.08 (2s, 9H), 1.15 and 1.22 (2t, J=7.2 Hz, 3H), 2.09 and 2.12 (2s, 3H), 2.53 and 2.57 (2s, 3H), 3.97-4.12 (m, 2H), 4.60 and 4.63 (2s, 1H), 7.16-7.38 (m, 3H), 7.44-7.49 (m, 1H).

MS m/z ([M+H]$^+$) 381/383.

Step 2: Preparation of tert-butoxy-[4-(2-chloro-phenyl)-2,5-dimethyl-thiophen-3-yl]-acetic acid Using the procedure described in example 29, step 2, ethyl tert-butoxy-[4-(2-chloro-phenyl)-2,5-dimethyl-thiophen-3-yl]-acetate (28f) (110 mg, 0.29 mmol) is converted, after purification by flash chromatography on silica gel (dichloromethane/methanol 95/5), to tert-butoxy-[4-(2-chloro-phenyl)-2,5-dimethyl-thiophen-3-yl]-acetic acid (example 51) (67 mg, 0.19 mmol, 67%).

$^1$H NMR (300 MHz, CDCl$_3$) δ 1.04 and 1.11 (2s, 9H), 2.07 and 2.15 (2s, 3H), 2.42 and 2.50 (2s, 3H), 4.73 and 4.94 (2s, 1H), 7.07-7.35 (m, 2H), 7.41-7.62 (m, 2H).

MS m/z ([M−H]$^-$) 351/353.

Example 52

Synthesis of tert-butoxy-[4-(4,4-dimethyl-cyclohex-1-enyl)-2,5-dimethyl-thiophen-3-yl]-acetic acid

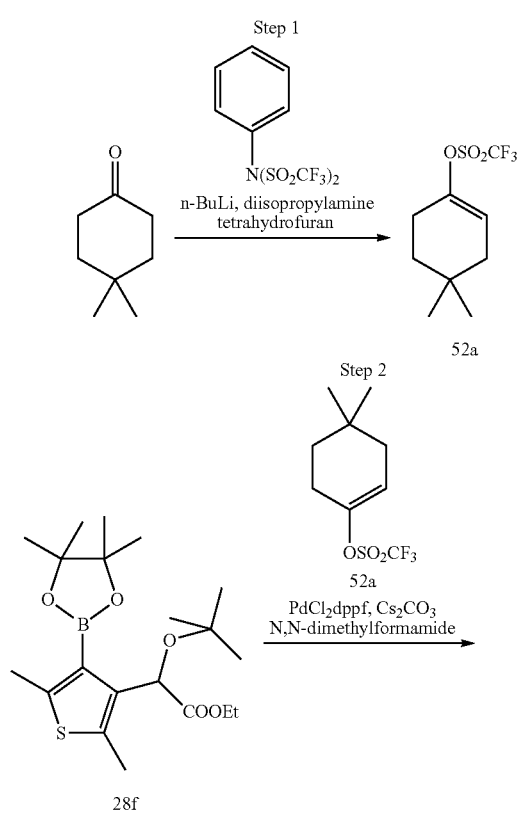

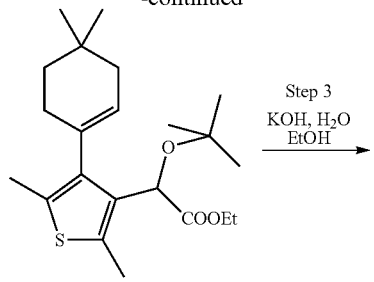

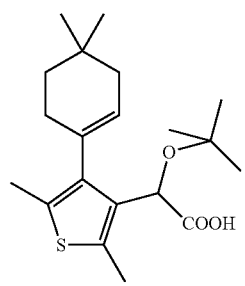

Example 52

Step 1: Preparation of intermediate 4,4-dimethylcyclohexen-1-yltrifluoromethanesulfonate (52a)

Using the procedure described in example 29, step 1, 4,4-dimethylcyclohexanone (500 mg, 5.1 mmol) is converted, after purification by flash chromatography on silica gel (cyclohexane/ethyl acetate 90/10), to 4,4-dimethylcyclohexen-1-yltrifluoromethanesulfonate (52a) (195 mg, 0.85 mmol, 17%).

$^1$H NMR (300 MHz, CDCl$_3$) δ 0.97 (s, 6H), 1.53 (t, J=6.5 Hz, 2H), 1.96-1.99 (m, 2H), 2.30-2.36 (m, 2H), 5.55-5.59 (m, 1H).

Step 2: Preparation of intermediate ethyl tert-butoxy-[4-(4,4-dimethyl-cyclohex-1-enyl)-2,5-dimethyl-thiophen-3-yl]-acetate (52b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with 4,4-dimethylcyclohexen-1-yltrifluoromethanesulfonate (52a) and after purification by flash chromatography on silica gel (cyclohexane/ethyl acetate 90/10), to ethyl tert-butoxy-[4-(4,4-dimethyl-cyclohex-1-enyl)-2,5-dimethyl-thiophen-3-yl]-acetate (52b) (107 mg, 0.28 mmol, 76%).

$^1$H NMR (300 MHz, CDCl$_3$) δ 1.02 (s, 3H), 1.03 (s, 3H), 1.17 (s, 9H), 1.20 (t, J=7.1 Hz, 3H), 1.46 (m, 2H), 1.88-2.08 (m, 3H), 2.21 (s, 3H), 2.24-2.39 (m, 1H), 2.48 (s, 3H), 4.00-4.20 (m, 2H), 4.96 (s, 1H), 5.47 (m, 1H).

MS m/z ([M+H]$^+$) 379.

Step 3: Preparation of tert-butoxy-[4-(4,4-dimethyl-cyclohex-1-enyl)-2,5-dimethyl-thiophen-3-yl]-acetic acid Using the procedure described in example 29, step 3, ethyl tert-butoxy-[4-(4,4-dimethyl-cyclohex-1-enyl)-2,5-dimethyl-thiophen-3-yl]-acetate (52b) (107 mg, 0.28 mmol) is converted, after purification by flash chromatography on silica gel (dichloromethane/methanol 95/5), to tert-butoxy-[4-(4,4-dimethyl-cyclohex-1-enyl)-2,5-dimethyl-thiophen-3-yl]-acetic acid (example 52) (68 mg, 0.19 mmol, 69%).

$^1$H NMR (300 MHz, CDCl$_3$) δ 1.00 (s, 6H), 1.20 (s, 9H), 1.46 (t, J=6.1 Hz, 2H), 1.89-2.11 (m, 3H), 2.21 (s, 3H), 2.34-2.46 (m, 4H), 5.01 (s, 1H), 5.50 (m, 1H).

MS m/z ([M−H]$^−$) 349.

Example 53

Synthesis of tert-butoxy-[4-(2,6-dimethyl-cyclohex-1-enyl)-2,5-dimethyl-thiophen-3-yl]-acetic acid

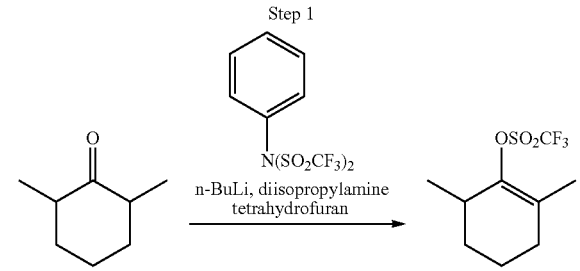

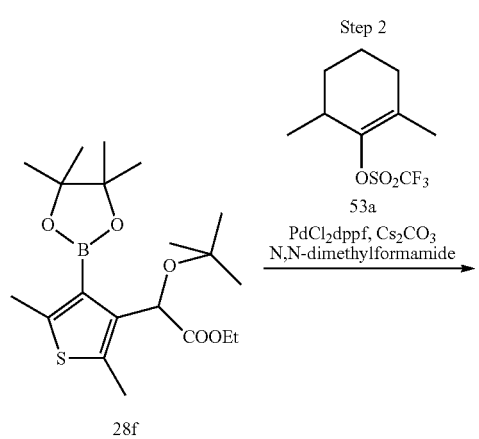

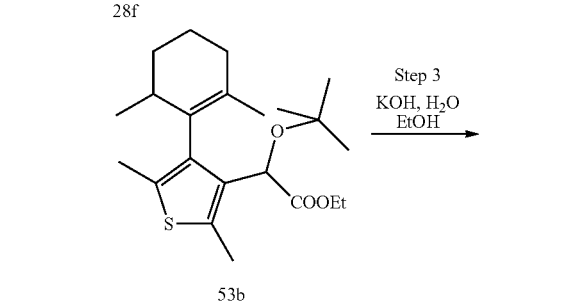

Example 53

Step 1: Preparation of intermediate 2,6-dimethyl-cyclohex-1-enyltrifluoromethanesulfonate (53a)

Using the procedure described in example 29, step 1, 2,6-dimethylcyclohexanone (573 mg, 4.54 mmol) is converted, after purification by flash chromatography on silica gel (cyclohexane/ethyl acetate 90/10), to 2,6-dimethyl-cyclohex-1-enyltrifluoromethanesulfonate (53a) (250 mg, 0.97 mmol, 21%).

$^1$H NMR (300 MHz, CDCl$_3$) δ 1.10 and 1.12 (2s, 3H), 1.37-1.48 (m, 1H), 1.50-1.72 (m, 2H), 1.75 (s, 3H), 1.87-1.97 (m, 1H), 2.03-2.21 (m, 2H), 2.52-2.61 (m, 1H).

Step 2: Preparation of intermediate ethyl tert-Butoxy-[4-(2,6-dimethyl-cyclohex-1-enyl)-2,5-dimethyl-thiophen-3-yl]-acetate (53b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with 6-dimethyl-cyclohex-1-enyltrifluoromethanesulfonate (53a) and after purification by flash chromatography on silica gel (cyclohexane/ethyl acetate 90/10), to ethyl tert-butoxy-[4-(2,6-dimethyl-cyclohex-1-enyl)-2,5-dimethyl-thiophen-3-yl]-acetate (53b) (90 mg, 0.24 mmol, 64%).

$^1$H NMR (300 MHz, CDCl$_3$) δ 0.80-0.97 (m, 3H), 1.14-1.36 (m, 15H), 1.40-1.56 (m, 1H), 1.59-1.71 (m, 1H), 1.73-1.90 (m, 1H), 1.97-2.31 (m, 6H), 2.45 and 2.52 and 2.55 and 2.62 (4s, 3H), 3.94-4.19 (m, 2H), 4.79 and 4.82 and 4.85 and 4.86 (4s, 1H).

MS m/z ([M+H]$^+$) 379.

Step 3: Preparation of tert-Butoxy-[4-(2,6-dimethyl-cyclohex-1-enyl)-2,5-dimethyl-thiophen-3-yl]-acetic acid Using the procedure described in example 29, step 3, ethyl tert-butoxy-[4-(2,6-dimethyl-cyclohex-1-enyl)-2,5-dimethyl-thiophen-3-yl]-acetate (53b) (90 mg, 0.24 mmol) is converted, after purification by flash chromatography on silica gel (dichloromethane/methanol 95/5), to tert-butoxy-[4-(4,4-dimethyl-cyclohex-1-enyl)-2,5-dimethyl-thiophen-3-yl]-acetic acid (example 53) (21 mg, 0.06 mmol, 25%).

$^1$H NMR (300 MHz, CDCl$_3$) δ 0.81-0.86 (m, 3H), 1.21-1.51 (m, 13H), 1.55-1.70 (m, 1H), 1.71-1.86 (m, 2H), 1.99-2.08 (m, 2H), 2.11 and 2.13 (2s, 3H), 2.16-2.29 (m, 1H), 2.40 and 2.45 and 2.46 and 2.56 (4s, 3H), 4.91 and 4.93 and 4.94 and 4.97 (4s, 1H).

MS m/z ([M−H]$^−$) 349.

Example 54

Synthesis of 2-[1-benzyl-5-(3,4-dihydro-2H-1-benzopyran-6-yl)-3-(trifluoro methyl)-1H-pyrazol-4-yl]-2-(tert-butoxy)acetic acid

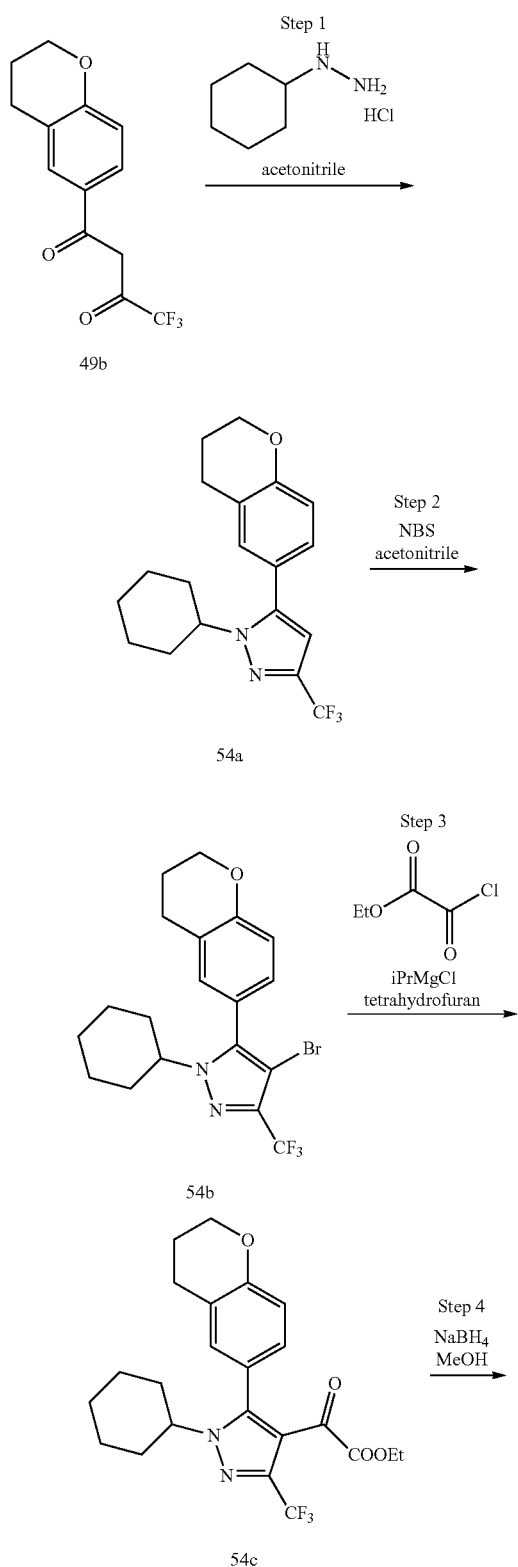

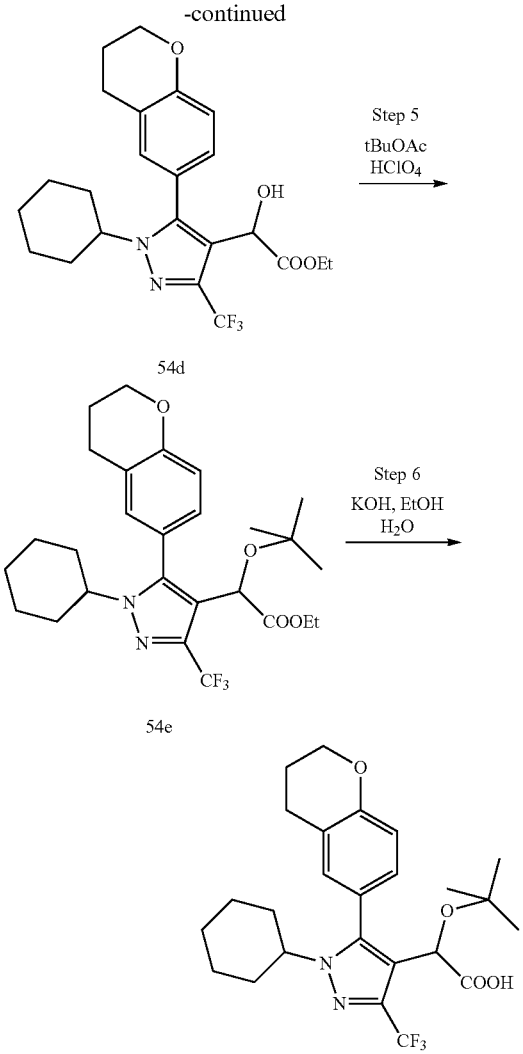

Example 54

Step 1: Preparation of intermediate 1-cyclohexyl-5-(3,4-dihydro-2H-1-benzopyran-6-yl)-3-(trifluoromethyl)-1H-pyrazole (54a)

Using the procedure described in example 49, step 3, the intermediate 1-(3,4-dihydro-2H-1-benzopyran-6-yl)-4,4,4-trifluorobutane-1,3-dione (49b) (200 mg, 0.73 mmol) is converted, after purification by preparative TLC (cyclohexane/ethyl acetate 80/20), to provide the desired pyrazole (54a) (180 mg, 0.51 mmol, 70%).

$^1$H NMR (400 MHz, CDCl$_3$) δ 1.18-1.35 (m, 3H), 1.53-1.73 (m, 1H), 1.78-1.96 (m, 4H), 1.96-2.11 (m, 4H), 2.84 (t, J=6.5 Hz, 2H), 4.06-4.17 (m, 1H), 4.25 (t, J=5.2 Hz, 2H), 6.39 (s, 1H), 6.87 (d, J=8.3 Hz, 1H), 7.00-7.07 (m, 2H).

MS m/z ([M+H]$^+$) 351.

Step 2: Preparation of intermediate 4-bromo-1-cyclohexyl-5-(3,4-dihydro-2H-1-benzopyran-6-yl)-3-(trifluoromethyl)-1H-pyrazole (54b)

Using the procedure described in example 49, step 3, the intermediate 1-cyclohexyl-5-(3,4-dihydro-2H-1-benzopyran-6-yl)-3-(trifluoromethyl)-1H-pyrazole (54a) (180 mg, 0.51 mmol) is converted to 4-bromo-1-cyclohexyl-5-(3,4-dihydro-2H-1-benzopyran-6-yl)-3-(trifluoromethyl)-1H-pyrazole (54b) (220 mg, 0.51 mmol, 100%) which was used without further purification.

¹H NMR (300 MHz, CDCl₃) δ 1.13-1.33 (m, 3H), 1.53-1.70 (m, 1H), 1.77-2.02 (m, 6H), 2.02-2.13 (m, 2H), 2.85 (t, J=6.5 Hz, 2H), 3.94-4.08 (m, 1H), 4.27 (t, J=5.2 Hz, 2H), 6.88-6.94 (m, 1H), 6.99-7.06 (m, 2H).

MS m/z ([M+H]⁺) 429/431.

Step 3: Preparation of intermediate ethyl 2-[1-cyclohexyl-5-(3,4-dihydro-2H-1-benzopyran-6-yl)-3-(trifluoromethyl)-1H-pyrazol-4-yl]-2-oxoacetate (54c)

Under nitrogen, isopropyl magnesium chloride 2M in tetrahydrofuran (0.47 mL, 0.94 mmol) was dropwise added to a solution of 4-bromo-1-cyclohexyl-5-(3,4-dihydro-2H-1-benzopyran-6-yl)-3-(trifluoromethyl)-1H-pyrazole (54b) (134 mg, 0.31 mmol) in anhydrous tetrahydrofuran (1.0 mL), previously cooled to −20° C. After 90 minutes stirring at the same temperature, ethyl chlorooxoacetate (70 μL, 0.62 mmol) was added dropwise. The mixture was stirred at −20° C. for 40 minutes before being poured in water (2 mL). The mixture was extracted with ethyl acetate (2×3 mL) and the organic layer was dried over sodium sulfate and concentrated in vacuo. The residue was purified by preparative TLC (cyclohexane/ethyl acetate 75/25) to provide the desired ketoester (54c) (104 mg, 0.23 mmol, 74%).

¹H NMR (400 MHz, CDCl₃) δ 1.12 (t, J=7.2 Hz, 3H), 1.20-1.30 (m, 3H), 1.61-1.69 (m, 1H), 1.78-1.90 (m, 4H), 1.94-2.11 (m, 4H), 2.82 (t, J=6.4 Hz, 2H), 3.77 (q, J=7.2 Hz, 2H), 3.89-3.99 (m, 1H), 4.25 (t, J=5.2 Hz, 2H), 6.89 (d, J=8.3 Hz, 1H), 6.95 (d, J=2.1 Hz, 1H), 7.01 (dd, J=8.3 Hz, J=2.1 Hz, 1H).

MS m/z ([M+H]⁺) 451.

Step 4: Preparation of intermediate ethyl 2-[1-cyclohexyl-5-(3,4-dihydro-2H-1-benzopyran-6-yl)-3-(trifluoromethyl)-1H-pyrazol-4-yl]-2-hydroxyacetate (54d)

Using the procedure described in example 49, step 6, the intermediate ethyl 2-[1-cyclohexyl-5-(3,4-dihydro-2H-1-benzopyran-6-yl)-3-(trifluoromethyl)-1H-pyrazol-4-yl]-2-oxoacetate (54c) (104 mg, 0.23 mmol) is converted to ethyl 2-[1-cyclohexyl-5-(3,4-dihydro-2H-1-benzopyran-6-yl)-3-(trifluoromethyl)-1H-pyrazol-4-yl]-2-hydroxyacetate (54d) (104 mg, 0.23 mmol, 100%) which was used without further purification.

¹H NMR (400 MHz, CDCl₃) δ 1.16-1.27 (m, 5H), 1.52-1.68 (m, 2H), 1.75-1.91 (m, 4H), 1.91-2.10 (m, 4H), 2.82 (t, J=6.4 Hz, 2H), 3.33 (bs, 1H), 3.88-3.98 (m, 1H), 4.09-4.19 (m, 2H), 4.25 (t, J=5.2 Hz, 2H), 4.99 (s, 1H), 6.87 (d, J=8.7 Hz, 1H), 6.98-7.04 (m, 2H).

MS m/z ([M+H]⁺) 453.

Step 5: Preparation of intermediate ethyl 2-(tert-butoxy)-2-[1-cyclohexyl-5-(3,4-dihydro-2H-1-benzopyran-6-yl)-3-(trifluoromethyl)-1H-pyrazol-4-yl]acetate (54e)

Using the procedure described in example 49, step 7, the intermediate ethyl 2-[1-cyclohexyl-5-(3,4-dihydro-2H-1-benzopyran-6-yl)-3-(trifluoromethyl)-1H-pyrazol-4-yl]-2-hydroxyacetate (54d) (104 mg, 0.23 mmol) is converted, after purification by preparative TLC (cyclohexane/ethyl acetate 75/25), to ethyl 2-(tert-butoxy)-2-[1-cyclohexyl-5-(3,4-dihydro-2H-1-benzopyran-6-yl)-3-(trifluoromethyl)-1H-pyrazol-4-yl]acetate (54e) (41 mg, 0.08 mmol, 35%).

¹H NMR (300 MHz, CDCl₃) δ 1.05 (s, 9H), 1.17 (t, J=7.1 Hz, 3H), 1.18-1.32 (m, 2H), 1.53-1.66 (m, 2H), 1.68-1.97 (m, 6H), 1.98-2.12 (m, 2H), 2.82 (t, J=6.5 Hz, 2H), 3.81-3.95 (m, 1H), 3.98-4.11 (m, 2H), 4.26 (t, J=5.2 Hz, 2H), 4.90 (s, 1H), 6.86 (d, J=8.3 Hz, 1H), 6.96-7.07 (m, 2H).

MS m/z ([M+H]⁺) 509.

Step 6: Preparation of 2-(tert-butoxy)-2-[1-cyclohexyl-5-(3,4-dihydro-2H-1-benzopyran-6-yl)-3-(trifluoromethyl)-1H-pyrazol-4-yl]acetic acid A mixture of ethyl 2-(tert-butoxy)-2-[1-cyclohexyl-5-(3,4-dihydro-2H-1-benzopyran-6-yl)-3-(trifluoromethyl)-1H-pyrazol-4-yl]acetate (54e) (40 mg, 0.08 mmol) and potassium hydroxide (38 mg, 0.31 mmol) in a mixture of ethanol (0.5 mL) and water (1.5 mL) was refluxed for 7 hours. The mixture was concentrated in vacuo. Water (2 mL) was added to the residue and the aqueous layer was washed with diethyl ether (2 mL), acidified with 1M hydrochloric acid until pH 2 and extracted with diethyl ether (2×3 mL). The organic layer was dried over sodium sulfate and concentrated in vacuo to provide the desired acid (example 54) (35 mg, 0.07 mmol, 93%).

¹H NMR (400 MHz, CDCl₃) δ 1.05 (s, 9H), 1.22-1.30 (m, 2H), 1.58-1.67 (m, 1H), 1.68-2.13 (m, 9H), 2.84 (t, J=6.5 Hz, 2H), 3.87-3.98 (m, 1H), 4.27 (t, J=5.2 Hz, 2H), 4.84 (s, 1H), 6.90 (d, J=8.3 Hz, 1H), 6.91-7.24 (m, 2H).

MS m/z ([M−H]⁻) 479.
MS m/z ([M+H]⁺) 481.

Example 55

Synthesis of tert-butoxy-[4-(2,4-dichloro-phenyl)-2,5-dimethyl-thiophen-3-yl]-acetic acid

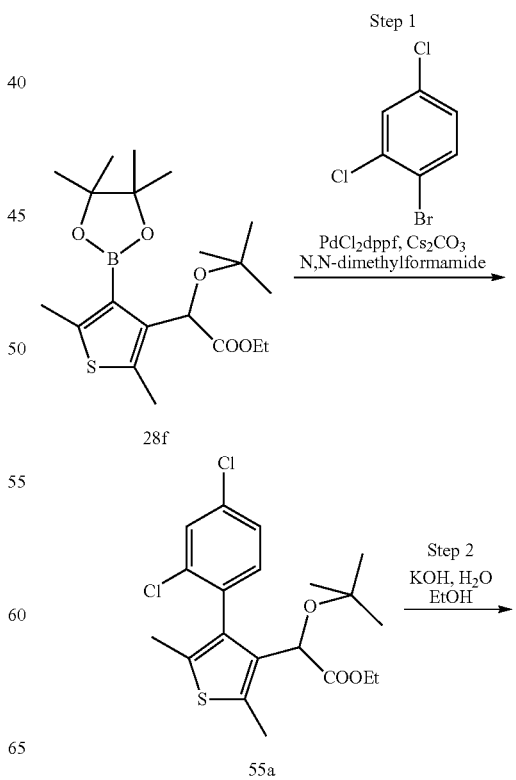

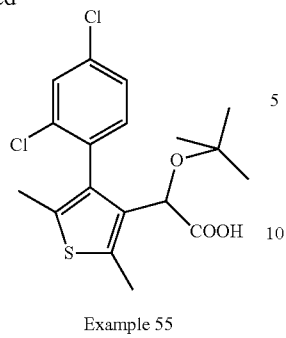

Example 55

Step 1: Preparation of intermediate ethyl tert-butoxy-[4-(2,4-dichloro-phenyl)-2,5-dimethyl-thiophen-3-yl]-acetate (55a)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (320 mg, 0.81 mmol) is converted, by reaction with 1-bromo-2,4-dichlorobenzene and after purification by flash chromatography on silica gel (cyclohexane/ethyl acetate 90/10), to ethyl tert-butoxy-[4-(2,4-dichloro-phenyl)-2,5-dimethyl-thiophen-3-yl]-acetate (55a) (41 mg, 0.10 mmol, 12%).

$^1$H NMR (300 MHz, CDCl$_3$) δ 1.05 and 1.09 (2s, 9H), 1.14-1.25 (m, 3H), 2.07 and 2.10 (2s, 3H), 2.52 and 2.55 (2s, 3H), 4.01-4.15 (m, 2H), 4.59 and 4.64 (2s, 1H), 7.09-7.31 (m, 2H), 7.47-7.49 (m, 1H).

MS m/z ([M+H]$^+$) 414/416/418.

Step 2: Preparation of tert-butoxy-[4-(2,4-dichlorophenyl)-2,5-dimethyl-thiophen-3-yl]-acetic acid Using the procedure described in example 29, step 3, ethyl tert-butoxy-[4-(2,4-dichloro-phenyl)-2,5-dimethyl-thiophen-3-yl]-acetate (55a) (41 mg, 0.10 mmol) is converted, after purification by flash chromatography on silica gel (dichloromethane/methanol 95/5), to tert-butoxy-[4-(2,4-dichloro-phenyl)-2,5-dimethyl-thiophen-3-yl]-acetic acid (example 55) (25 mg, 0.06 mmol, 64%).

$^1$H NMR (300 MHz, CDCl$_3$) δ☐☐1.08 and 1.13 (2s, 9H), 2.06 and 2.13 (2s, 3H), 2.44 and 2.55 (2s, 3H), 4.71 and 4.94 (2s, 1H), 7.01-7.33 (m, 2H), 7.45-7.52 (m, 2H).

MS m/z ([M−H]$^−$) 385/387/389.

Example 56

Synthesis of (4-bicyclo[2.2.1]hept-2-en-2-yl-2,5-dimethyl-thiophen-3-yl)-tert-butoxy-acetic acid Step 1

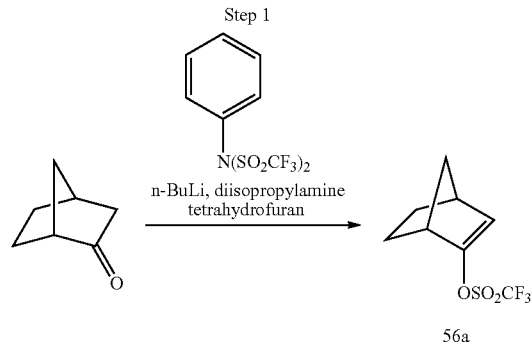

Step 2

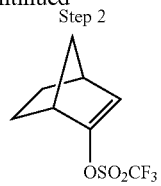

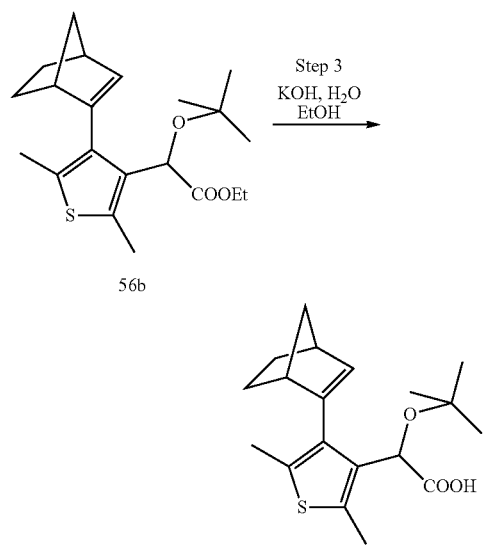

Example 56

Step 1: Preparation of intermediate Bicyclo[2.2.1]hept-2-en-2-yltrifluoromethanesulfonate (56a)

Using the procedure described in example 29, step 1, bicyclo[2.2.1]heptan-2-one (500 mg, 4.54 mmol) is converted, after purification by flash chromatography on silica gel (cyclohexane/ethyl acetate 90/10), to bicyclo[2.2.1]hept-2-en-2-yltrifluoromethanesulfonate (56a) (420 mg, 1.73 mmol, 38%).

$^1$H NMR (300 MHz, CDCl$_3$) δ 1.15-1.25 (m, 2H), 1.37-1.40 (m, 1H), 1.64-1.69 (m, 1H), 1.72-1.85 (m, 2H), 2.94-3.02 (m, 2H), 5.67 (d, J=3.4 Hz, 1H).

Step 2: Preparation of intermediate ethyl (4-bicyclo[2.2.1]hept-2-en-2-yl-2,5-dimethyl-thiophen-3-yl)-tert-butoxy-acetate (56b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with bicyclo[2.2.1]hept-2-en-2-yltrifluoromethanesulfonate (56a) and after purification by flash chromatography on silica gel (cyclohexane/ethyl acetate 90/10), to ethyl (4-bicyclo[2.2.1]hept-2-en-2-yl-2,5-dimethyl-thiophen-3-yl)-tert-butoxy-acetate (56b) (82 mg, 0.23 mmol, 61%).

¹H NMR (300 MHz, CDCl₃) δ 1.13 and 1.17 (2s, 9H), 1.17-1.43 (m, 6H), 1.61-1.84 (m, 3H), 2.21 and 2.25 (2s, 3H), 2.47 and 2.50 (2s, 3H), 2.94-3.23 (m, 2H), 4.02-4.23 (m, 2H), 4.97 and 5.04 (2s, 1H), 5.96-5.98 (m, 1H).

MS m/z ([M+H]⁺) 363.

Step 3: Preparation of (4-bicyclo[2.2.1]hept-2-en-2-yl-2,5-dimethyl-thiophen-3-yl)-tert-butoxy-acetic acid Using the procedure described in example 29, step 2, ethyl (4-bicyclo[2.2.1]hept-2-en-2-yl-2,5-dimethyl-thiophen-3-yl)-tert-butoxy-acetate (56b) (82 mg, 0.23 mmol) is converted, after purification by flash chromatography on silica gel (dichloromethane/methanol 95/5), to (4-bicyclo[2.2.1]hept-2-en-2-yl-2,5-dimethyl-thiophen-3-yl)-tert-butoxy-acetic acid (example 56) (55 mg, 0.16 mmol, 71%).

¹H NMR (300 MHz, CDCl₃) δ ☐1.08-1.27 (m, 11H), 1.35-1.46 (m, 1H), 1.55-1.84 (m, 3H), 2.20 and 2.30 (2s, 3H), 2.36 and 2.38 (2s, 3H), 2.94-3.29 (m, 2H), 5.05 and 5.20 (2s, 1H), 5.98-6.07 (m, 1H).

MS m/z ([M−H]⁻) 333.

Example 57

Synthesis of tert-butoxy-(4-cyclopent-1-enyl-2,5-dimethyl-thiophen-3-yl)-acetic acid

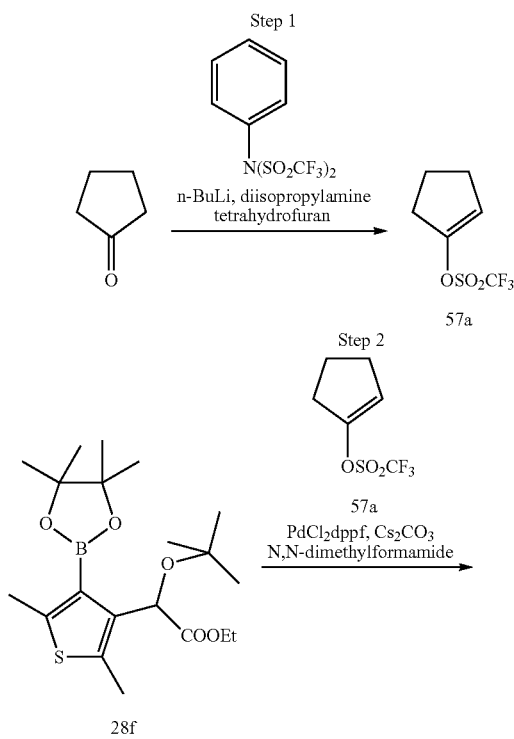

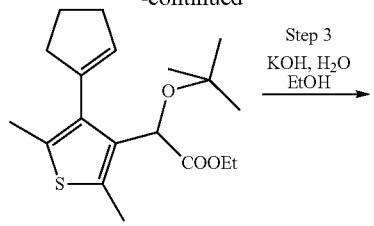

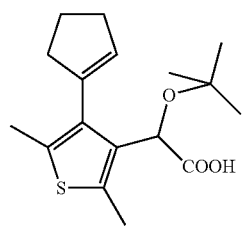

Example 57

Step 1: Preparation of intermediate cyclopent-1-enyltrifluoromethanesulfonate (57a)

Using the procedure described in example 29, step 1, cyclopentanone (500 mg, 4.94 mmol) is converted, after purification by flash chromatography on silica gel (cyclohexane/ethyl acetate 90/10), to cyclopent-1-enyltrifluoromethanesulfonate (57a) (320 mg, 1.48 mmol, 25%).

¹H NMR (300 MHz, CDCl₃) δ 1.98-2.08 (m, 2H), 2.38-2.45 (m, 2H), 2.53-2.62 (m, 2H), 5.61-5.66 (m, 1H).

Step 2: Preparation of intermediate ethyl tert-butoxy-(4-cyclopent-1-enyl-2,5-dimethyl-thiophen-3-yl)-acetate (57b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with cyclopent-1-enyltrifluoromethanesulfonate (57a) and after purification by flash chromatography on silica gel (cyclohexane/ethyl acetate 90/10), to ethyl tert-butoxy-(4-cyclopent-1-enyl-2,5-dimethyl-thiophen-3-yl)-acetate (57b) (105 mg, 0.31 mmol, 84%).

¹H NMR (300 MHz, CDCl₃) δ ☐1.15 (s, 9H), 1.21 (t, J=7.1 Hz, 3H), 1.94-2.05 (m, 2H), 2.23 (s, 3H), 2.46 (s, 3H), 2.34-2.60 (m, 3H), 2.62-2.75 (m, 1H), 4.02-4.21 (m, 2H), 4.98 (s, 1H), 5.64-5.68 (m, 1H).

MS m/z ([M+H]⁺) 337.

Step 3: Preparation of tert-butoxy-(4-cyclopent-1-enyl-2,5-dimethyl-thiophen-3-yl)-acetic acid Using the procedure described in example 29, step 3, ethyl tert-butoxy-(4-cyclopent-1-enyl-2,5-dimethyl-thiophen-3-yl)-acetate (57b) (105 mg, 0.31 mmol) is converted, after purification by flash chromatography on silica gel (dichloromethane/methanol 95/5), to tert-butoxy-(4-cyclopent-1-enyl-2,5-dimethyl-thiophen-3-yl)-acetic acid (example 57) (52 mg, 0.17 mmol, 54%).

¹H NMR (300 MHz, CDCl₃) δ =0.19 (s, 9H), 1.97 (m, 2H), 2.23 (s, 3H), 2.38 (s, 3H), 2.39-2.53 (m, 3H), 2.63-2.77 (m, 1H), 5.07 (s, 1H), 5.69-5.74 (m, 1H).

MS m/z ([M−H]⁻) 307.

Example 58

Synthesis of tert-butoxy-[4-(3,4-dihydro-2H-pyrano[3,2-b]pyridin-6-yl)-2,5-dimethyl-thiophen-3-yl]-acetic acid

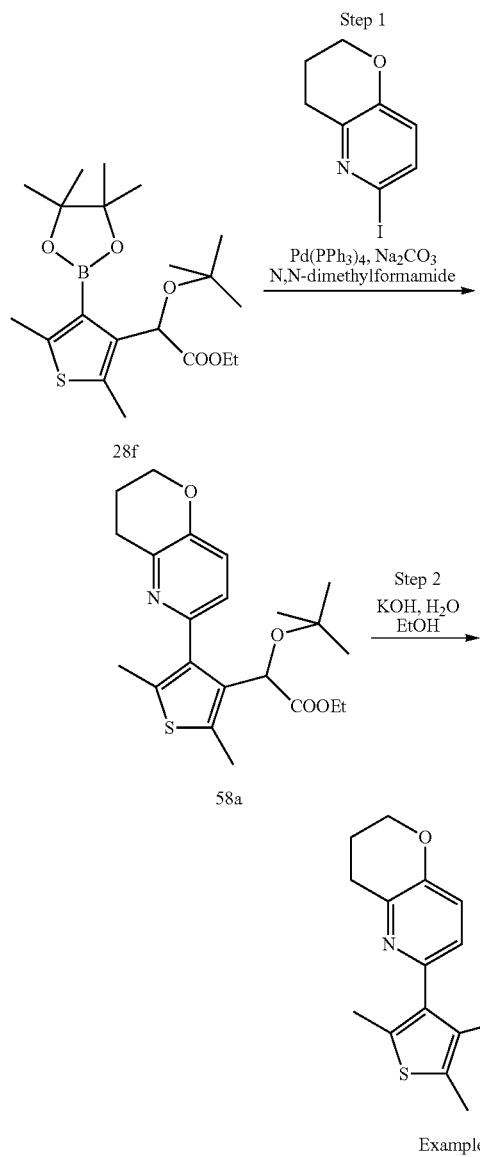

Step 1: Preparation of intermediate ethyl tert-butoxy-[4-(3,4-dihydro-2H-pyrano[3,2-b]pyridin-6-yl)-2,5-dimethyl-thiophen-3-yl]-acetate (58a)

Using the procedure described in example 28, step 7, ethyl 2-(tert-butoxy)-2-[2,5-dimethyl-4-(tetramethyl-1,3,2-dioxaborolan-2-yl)thiophen-3-yl]acetate (28f) (100 mg, 0.25 mmol) is converted, by reaction with 6-Iodo-3,4-dihydro-2H-pyrano[3,2-b]pyridine and after purification by preparative TLC (cyclohexane/ethyl acetate 80/20), to ethyl tert-butoxy-[4-(3,4-dihydro-2H-pyrano[3,2-b]pyridin-6-yl)-2,5-dimethyl-thiophen-3-yl]-acetate (58a) (56 mg, 0.14 mmol, 55%).

$^1$H NMR (300 MHz, CDCl$_3$) δ 1.09 (s, 9H), 1.25 (t, J=7.0 Hz, 3H), 2.13-2.18 (m, 2H), 2.26 (s, 3H), 2.51 (s, 3H), 2.94-3.02 (m, 2H), 4.00-4.12 (m, 2H), 4.21-4.27 (m, 2H), 5.13 (s, 1H), 7.07 (d, J=8.0 Hz, 1H), 7.13 (d, J=8.0 Hz, 1H).

MS m/z ([M+H]$^+$) 404.

Step 2: Preparation of tert-butoxy-[4-(3,4-dihydro-2H-pyrano[3,2-b]pyridin-6-yl)-2,5-dimethyl-thiophen-3-yl]-acetic acid Using the procedure described in example 28, step 8, ethyl tert-butoxy-[4-(3,4-dihydro-2H-pyrano[3,2-b]pyridin-6-yl)-2,5-dimethyl-thiophen-3-yl]-acetate (58a) (56 mg, 0.14 mmol) is converted, without further purification, to tert-butoxy-[4-(3,4-dihydro-2H-pyrano[3,2-b]pyridin-6-yl)-2,5-dimethyl-thiophen-3-yl]-acetic acid (example 58) (52 mg, 0.14 mmol, 100%).

$^1$H NMR (300 MHz, CDCl$_3$) δ 80.98 (s, 9H), 2.13-2.24 (m, 2H), 2.38 (s, 3H), 2.51 (s, 3H), 3.04-3.17 (m, 2H), 4.29 (t, J=5.3 Hz, 2H), 5.12 (s, 1H), 7.22 (d, J=8.5 Hz, 1H), 7.36 (d, J=8.5 Hz, 1H).

MS m/z ([M+H]$^+$) 376.

MS m/z ([M−H]$^−$) 374.

Example 59

Synthesis of tert-butoxy-[4-(3,4-dihydro-2H-pyrano[2,3-b]pyridin-6-yl)-2,5-dimethyl-thiophen-3-yl]-acetic acid

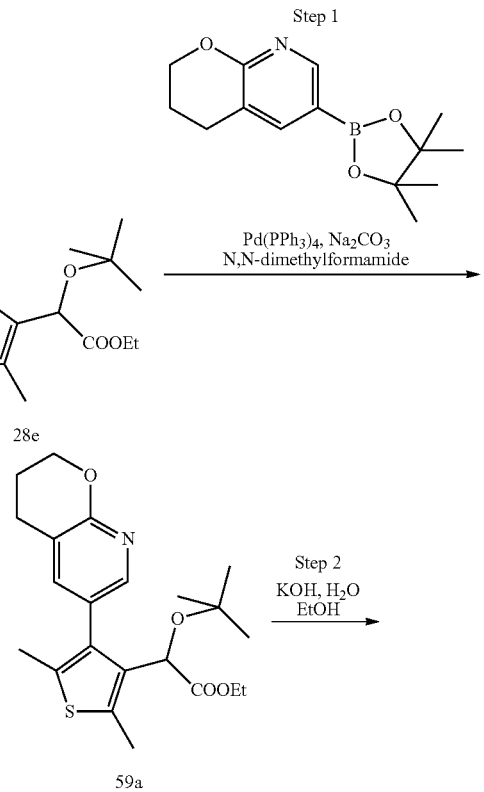

Example 60

Synthesis of (4-bicyclo[2.2.2]oct-2-en-2-yl-2,5-dimethyl-thiophen-3-yl)-tert-butoxy-acetic acid

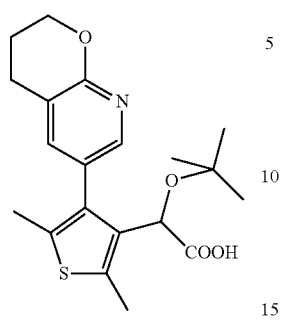

Example 59

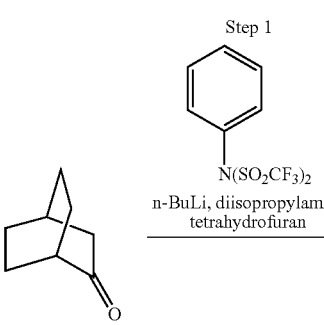

Step 1: Preparation of intermediate ethyl tert-butoxy-[4-(3,4-dihydro-2H-pyrano[2,3-b]pyridin-6-yl)-2,5-dimethyl-thiophen-3-yl]-acetate (59a)

Using the procedure described in example 28, step 7, ethyl (4-bromo-2,5-dimethyl-thiophen-3-yl)-tert-butoxy-acetate (28e) (100 mg, 0.29 mmol) is converted, by reaction with 6-(4,4,5,5-tetramethyl-1,3,2-dioxaborolan-2-yl)-3,4-dihydro-2H-pyrano[2,3-b]pyridine and after purification by preparative TLC (dichloromethane/ethyl acetate 80/20), to ethyl tert-butoxy-[4-(3,4-dihydro-2H-pyrano[2,3-b]pyridin-6-yl)-2,5-dimethyl-thiophen-3-yl]-acetate (59a) (40 mg, 0.1 mmol, 39%).

¹H NMR (400 MHz, CDCl₃) δ □1.04 (s, 9H), 1.21 (t, J=7.1 Hz, 3H), 2.04-2.11 (m, 2H), 2.18 (s, 3H), 2.50 (s, 3H), 2.80-2.87 (m, 2H), 4.02-4.16 (m, 2H), 4.43 (t, J=5.3 Hz, 2H), 4.74 (s, 1H), 7.41-7.50 (m, 1H), 7.96 (d, J=2.0 Hz, 1H).

MS m/z ([M+H]⁺) 404.

Step 2: Preparation of tert-butoxy-[4-(3,4-dihydro-2H-pyrano[2,3-b]pyridin-6-yl)-2,5-dimethyl-thiophen-3-yl]-acetic acid Using the procedure described in example 28, step 8, ethyl tert-Butoxy-[4-(3,4-dihydro-2H-pyrano[2,3-b]pyridin-6-yl)-2,5-dimethyl-thiophen-3-yl]-acetate (59a) (56 mg, 0.14 mmol) is converted, without further purification, to tert-butoxy-[4-(3,4-dihydro-2H-pyrano[2,3-b]pyridin-6-yl)-2,5-dimethyl-thiophen-3-yl]-acetic acid (example 59) (33 mg, 0.088 mmol, 88%).

¹H NMR (400 MHz, CDCl₃) δ 1.07 (s, 9H), 2.02-2.08 (m, 2H), 2.17 (s, 3H), 2.45 (s, 3H), 2.83 (t, J=6.4 Hz, 2H), 4.39 (t, J=5.3 Hz, 2H), 4.83 (s, 1H), 7.45 (s, 1H), 7.98 (s, 1H).

MS m/z ([M+H]⁺) 376.
MS m/z ([M-H]⁻) 374.

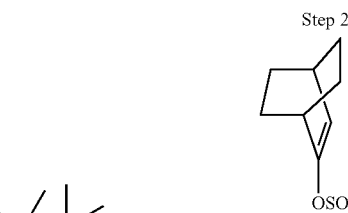

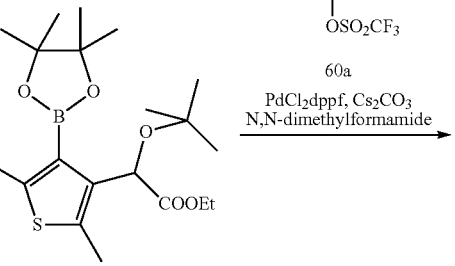

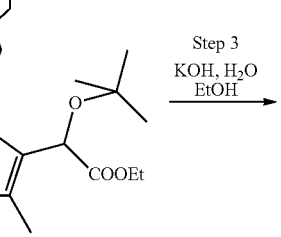

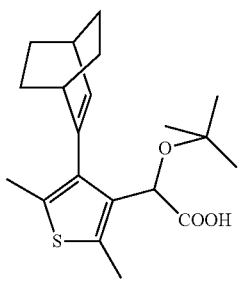

Example 60

Step 1: Preparation of intermediate bicyclo[2.2.2]oct-2-en-2-yltrifluoromethanesulfonate (60a)

Using the procedure described in example 29, step 1, bicyclo[2.2.2]octan-2-one (500 mg, 4.03 mmol) is converted, after purification by flash chromatography on silica gel (cyclohexane/ethyl acetate 90/10), to bicyclo[2.2.2]oct-2-en-2-yltrifluoromethanesulfonate (60a) (323 mg, 1.26 mmol, 31%).

$^1$H NMR (300 MHz, CDCl$_3$) δ 1.25-1.39 (m, 2H), 1.49-1.64 (m, 6H), 2.67-2.73 (m, 1H), 2.74-2.82 (m, 1H), 6.02 (dd, J=2.6 and 7.5 Hz, 1H).

Step 2: Preparation of intermediate ethyl (4-bicyclo[2.2.2]oct-2-en-2-yl-2,5-dimethyl-thiophen-3-yl)-tert-butoxy-acetate (60b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with bicyclo[2.2.2]oct-2-en-2-yltrifluoromethanesulfonate (60a) and after purification by flash chromatography on silica gel (cyclohexane/ethyl acetate 90/10), to ethyl (4-bicyclo[2.2.2]oct-2-en-2-yl-2,5-dimethyl-thiophen-3-yl)-tert-butoxy-acetate (60b) (85 mg, 0.22 mmol, 56%).

$^1$H NMR (300 MHz, CDCl$_3$) δ 1.14 (s, 9H), 1.21 (t, J=7.1 Hz, 3H), 1.33-1.74 (m, 8H), 2.25 (s, 3H), 2.49 (s, 3H), 2.59-2.72 (m, 2H), 4.02-4.23 (m, 2H), 4.97 (s, 1H), 6.17-6.20 (dd, J=1.5 and 6.7 Hz, 1H).
MS m/z ([M+H]$^+$) 377.

Step 3: Preparation of (4-bicyclo[2.2.2]oct-2-en-2-yl-2,5-dimethyl-thiophen-3-yl)-tert-butoxy-acetic acid Using the procedure described in example 29, step 3, ethyl (4-bicyclo[2.2.2]oct-2-en-2-yl-2,5-dimethyl-thiophen-3-yl)-tert-butoxy-acetate (60b) (85 mg, 0.22 mmol) is converted, after purification by flash chromatography on silica gel (dichloromethane/methanol 95/5), to (4-bicyclo[2.2.2]oct-2-en-2-yl-2,5-dimethyl-thiophen-3-yl)-tert-butoxy-acetic acid (example 60) (67 mg, 0.19 mmol, 86%).

$^1$H NMR (300 MHz, CDCl$_3$) δ 1.15 (s, 9H), 1.29-1.45 (m, 3H), 1.54-1.71 (m, 5H), 2.26 (s, 3H), 2.37 (s, 3H), 2.63-2.70 (m, 1H), 2.72-2.80 (m, 1H), 5.07 (s, 1H), 6.24-6.34 (d, J=6.5 Hz, 1H).
MS m/z ([M−H]$^-$) 347.

Example 61

Synthesis of (4-bicyclo[2.2.2]octa-2,5-dien-2-yl-2,5-dimethyl-thiophen-3-yl)-tert-butoxy-acetic acid

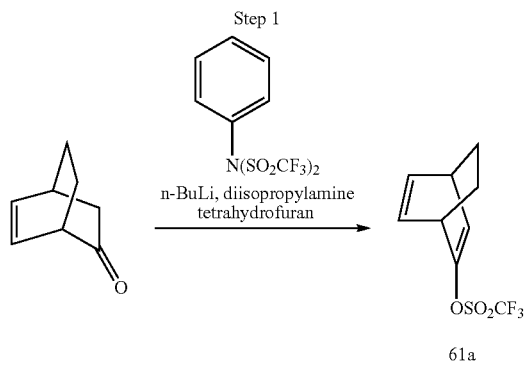

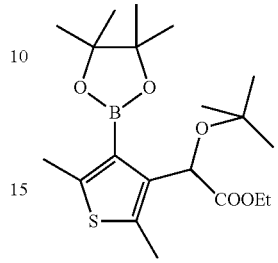

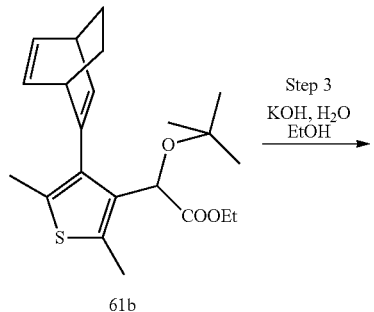

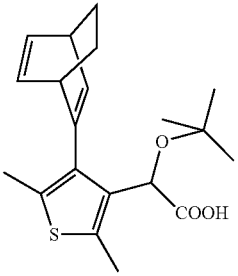

Example 61

Step 1: Preparation of intermediate bicyclo[2.2.2]octa-2,5-dien-2-yltrifluoromethanesulfonate (61a)

Using the procedure described in example 29, step 1, bicyclo[2.2.2]oct-5-en-2-one (500 mg, 4.09 mmol) is converted, after purification by flash chromatography on silica gel (cyclohexane/ethyl acetate 90/10), to bicyclo[2.2.2]octa-2,5-dien-2-yltrifluoromethane sulfonate (61a) (427 mg, 1.68 mmol, 41%).

$^1$H NMR (300 MHz, CDCl$_3$) δ 1.34-1.48 (m, 3H), 1.65-1.74 (m, 1H), 3.59-3.55 (m, 1H), 3.66-3.74 (m, 1H), 6.03 (dd, J=2.7 and 7.1 Hz, 1H), 6.29-6.39 (m, 2H).

Step 2: Preparation of intermediate ethyl (4-bicyclo[2.2.2]octa-2,5-dien-2-yl-2,5-dimethyl-thiophen-3-yl)-tert-butoxy-acetate (61b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with bicyclo[2.2.2]octa-2,5- dien-2-yltrifluoromethanesulfonate (61a) and after purification by flash chromatography on silica gel (cyclohexane/ethyl acetate 90/10), to ethyl (4-bicyclo[2.2.2]octa-2,5-dien-2-yl-2,5-dimethyl-thiophen-3-yl)-tert-butoxy-acetate (61b) (26 mg, 0.07 mmol, 18%).

$^1$H NMR (300 MHz, CDCl$_3$) δ 1.05 and 1.15 (2s, 9H), 1.17-1.51 (m, 7H), 2.17 and 2.19 and 2.21 (3s, 3H), 2.46 and 2.48 and 2.51 (3s, 3H), 3.55-3.83 (m, 2H), 4.00-4.29 (m, 2H), 4.74 and 4.77 and 4.86 (3s, 1H), 6.18 (dd, J=1.7 and 6.2 Hz, 1H), 6.36-6.51 (m, 2H).

MS m/z ([M+H]$^+$) 375.

Step 3: Preparation of (4-bicyclo[2.2.2]octa-2,5-dien-2-yl-2,5-dimethyl-thiophen-3-yl)-tert-butoxy-acetic acid Using the procedure described in example 29, step 3, ethyl (4-bicyclo[2.2.2]octa-2,5-dien-2-yl-2,5-dimethyl-thiophen-3-yl)-tert-butoxy-acetate (61b) (26 mg, 0.07 mmol) is converted, after purification by flash chromatography on silica gel (dichloromethane/methanol 95/5), to (4-bicyclo[2.2.2] octa-2,5-dien-2-yl-2,5-dimethyl-thiophen-3-yl)-tert-butoxy-acetic acid (example 61) (11 mg, 0.03 mmol, 45%).

$^1$H NMR (300 MHz, CDCl$_3$) δ 1.10 and 1.11 (2s, 9H), 1.25-1.76 (m, 4H), 2.21 and 2.23 (2s, 3H), 2.35 and 2.36 (2s, 3H), 3.60-3.97 (m, 2H), 4.86 and 4.96 (2s, 1H), 6.18-6.49 (m, 3H).

MS m/z ([M–H]$^-$) 345.

Example 62

Synthesis of 2-(tert-butoxy)-2-[2,5-dimethyl-4-(4-methylphenyl)thiophen-3-yl]acetic acid

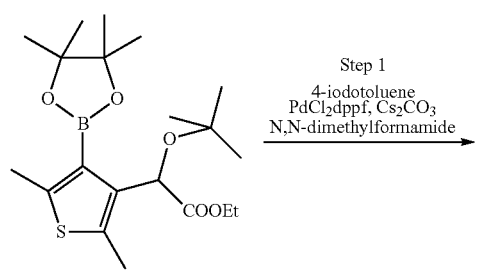

28f

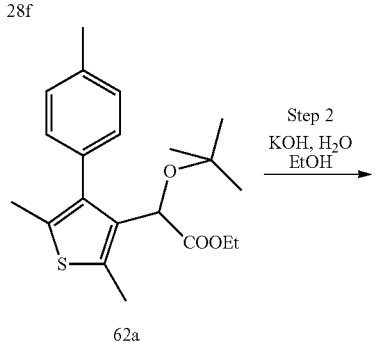

62a

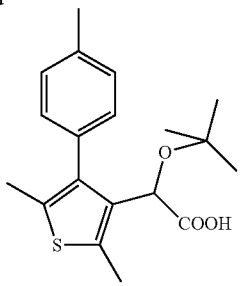

Example 62

Step 1: Preparation of intermediate ethyl 2-(tert-butoxy)-2-[2,5-dimethyl-4-(4-methylphenyl)thiophen-3-yl]acetate (62a)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.38 mmol) is converted, by reaction with 4-iodotoluene and after purification by flash chromatography on silica gel (cyclohexane/ethyl acetate 90/10), to ethyl 2-(tert-butoxy)-2-[2,5-dimethyl-4-(4-methylphenyl)thiophen-3-yl]acetate (62a) (136 mg, 0.37 mmol, 99%).

$^1$H NMR (300 MHz, CDCl$_3$) δ 0.98 (s, 9H), 1.23 (t, J=7.1 Hz, 3H), 2.18 (s, 3H), 2.40 (s, 3H), 2.50 (s, 3H), 4.08-4.18 (m, 2H), 4.77 (s, 1H), 7.13-7.24 (m, 4H).

MS m/z ([M+H]$^+$) 361.

Step 2: Preparation of 2-(tert-butoxy)-2-[2,5-dimethyl-4-(4-methylphenyl)thiophen-3-yl]acetic acid Using the procedure described in example 29, step 3, ethyl tert-Butoxy-(2,5-dimethyl-4-p-tolyl-thiophen-3-yl)-acetate (62a) (136 mg, 0.37 mmol) is converted, after purification by flash chromatography on silica gel (dichloromethane/methanol: 95/5), to tert-Butoxy-(2,5-dimethyl-4-p-tolyl-thiophen-3-yl)-acetic acid (example 62) (105 mg, 0.31 mmol, 83%).

$^1$H NMR (300 MHz, CDCl$_3$) δ 0.98 (s, 9H), 2.20 (s, 3H), 2.39 (s, 3H), 2.42 (s, 3H), 4.90 (s, 1H), 7.15-7.25 (m, 4H).

MS m/z ([M–H]$^-$) 331.

Example 63

Synthesis of tert-butoxy-[4-(4-methyl-cyclohex-1-enyl)-2,5-dimethyl-thiophen-3-yl]-acetic acid

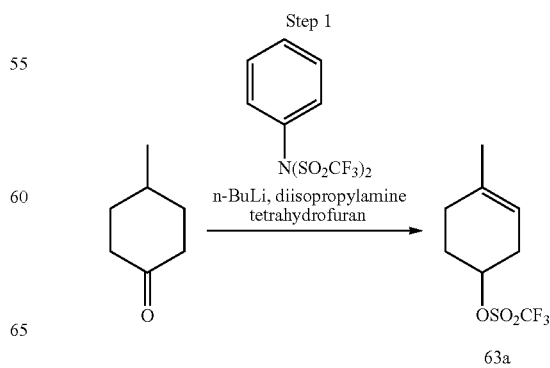

63a

-continued

Step 2

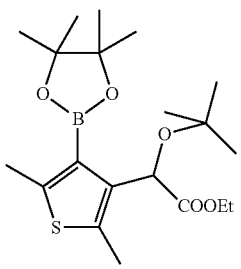

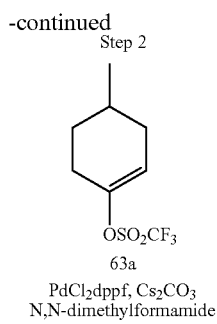

28f

PdCl₂dppf, Cs₂CO₃
N,N-dimethylformamide

Step 3
KOH, H₂O
EtOH

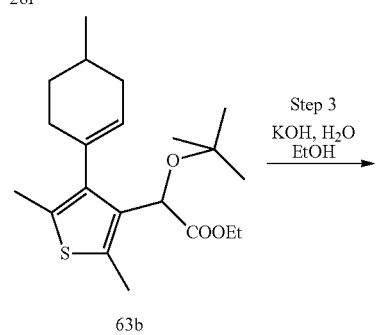

63b

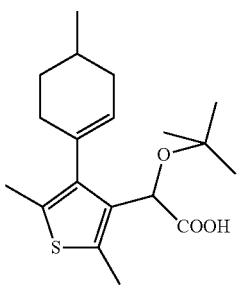

Example 63

Step 1: Preparation of intermediate 4-methyl-cyclohex-1-enyltrifluoromethanesulfonate (63a)

Using the procedure described in example 29, step 1, cyclohexanone (500 mg, 4.45 mmol) is converted, after purification by flash chromatography on silica gel (cyclohexane/ethyl acetate 90/10), to 4-methyl-cyclohex-1-enyltrifluoromethanesulfonate (63a) (400 mg, 1.63 mmol, 37%) as mixture of diastereoisomers (1/1).

$^1$H NMR (300 MHz, CDCl₃) δ 0.98 and 1.00 (s, 3H), 1.37-1.52 (m, 1H), 1.67-1.88 (m, 3H), 2.18-2.46 (m, 3H), 5.69-5.74 (m, 1H).

Step 2: Preparation of intermediate ethyl tert-butoxy-[4-(4-methyl-cyclohex-1-enyl)-2,5-dimethyl-thiophen-3-yl]-acetate (63b)

Using the procedure described in example 29, step 2, ethyl 2-(tert-butoxy)-2-[2,5-dimethyl-4-(tetramethyl-1,3,2-dioxaborolan-2-yl)thiophen-3-yl]acetate (28f) (150 mg, 0.37 mmol) is converted, by reaction with 4-methyl-cyclohexen-1-yltrifluoromethanesulfonate (63a) and after purification by flash chromatography on silica gel (cyclohexane/ethyl acetate 90/10), to ethyl tert-butoxy-[4-(4-methyl-cyclohex-1-enyl)-2,5-dimethyl-thiophen-3-yl]-acetate (63b) (105 mg, 0.29 mmol, 75%) as mixture of diastereoisomers (1/1).

$^1$H NMR (300 MHz, CDCl₃) δ 1.02-1.05 (m, 3H), 1.17 (s, 9H), 1.18-1.23 (m, 3H), 1.28-1.48 (m, 1H), 1.72-1.87 (m, 3H), 1.93-2.15 (m, 1H), 2.21 (s, 3H), 2.22-2.43 (m, 2H), 2.47 (s, 3H), 4.01-4.19 (m, 2H), 4.94 and 4.96 (2s, 1H), 5.49-5.55 (m, 1H).

MS m/z ([M+H]⁺) 365.

Step 3: Preparation of intermediate tert-butoxy-[4-(4-methyl-cyclohex-1-enyl)-2,5-dimethyl-thiophen-3-yl]-acetic acid Using the procedure described in example 29, step 3, ethyl tert-butoxy-[4-(4-methyl-cyclohex-1-enyl)-2,5-dimethyl-thiophen-3-yl]-acetate (63b) (105 mg, 0.29 mmol) is converted, after purification by flash chromatography on silica gel (dichloromethane/methanol 95/5), to tert-butoxy-[4-(4-methyl-cyclohex-1-enyl)-2,5-dimethyl-thiophen-3-yl]-acetic acid (example 63) (89 mg, 0.26 mmol, 91%) as mixture of diastereoisomers (1/1).

$^1$H NMR (300 MHz, CDCl₃) δ 1.00 and 1.02 (2s, 3H), 1.20 (s, 9H), 1.25-1.41 (m, 1H), 1.68-1.87 (m, 3H), 1.95-2.17 (m, 1H), 2.21 (s, 3H), 2.24-2.37 (m, 2H), 2.39 (s, 3H), 5.00 and 5.04 (2s, 1H), 5.50-5.62 (m, 1H).

MS m/z ([M−H]⁻) 335.

Antiviral Activity

The antiviral activity, particularly against HIV, of compounds according to the invention is evaluated by the protocol described below.

Preparation of Virus stock of the NL4-3 strain of HIV-1 (Adachi et al, J Virol, 1986, 59(2):284-91).

The virus was prepared as described in Lopez et al (Lopez et al, Proc Natl Acad Sci USA., 2006, 103(40):14947-52, by transfecting 2×10⁶ 293T cells (CRL-1573, ATCC) with following modifications: 6 μg of NL4-3 proviral DNA molecular clone were mixed with Fugene 6 transfection reagent from Roche, and used according to manufacturer's instructions. Forty eight hours later, transfected cell supernatants were harvested, filtered through 0.45-μm-pore-size filters, quantified for HIV-1 p24 antigen by using a Innotest HIV antigen mAb assay (Ingen) according to manufacturer's instructions, and used in infection experiments.

Preparation of Compounds:

Serial dilutions of compounds to be tested were prepared in complete RPMI medium from 10 mM DMSO stock solutions, and distributed in a volume of 20 μl in 96 well Falcon 353072 Microtest™ tissue culture plate, in order to get 0.5% DMSO final concentration in each well, after the addition of infected cells. Control wells contained also 0.5% DMSO final concentration but no compound.

Infection of Cells:

MT4 cells (from the NIH AIDS Research and Reference Reagent Program) in RPMI complete medium were counted (10×10⁶ cells per well in Falcon 353047 Multiwell™ 24 well) and infected for 2 hours at 37°, at a multiplicity of infection (moi) of 0.0001-0.00001. Cells were then centrifuged 3 min at 3000 rpm, and washed two times in 1 ml PBS to remove viruses that have not entered in cells. Infected cells were resuspended in complete RPMI at 1.25×10⁶ cells/ml, and 800 of infected cells were distributed in each well containing compounds to be tested or control wells. The plates were then incubated at 37° for 5 days.

Assay used to measure the inhibition of HIV replication by the compounds (according to Gregg S. Jones et al., Antimicrobial Agents and Chemotherapy, 2009, 53 (3): 1194-1203).

After 5 days of incubation, 50 μl of CellTiter-Glo reagent (Promega Biosciences, Inc., Madison Wis., USA) were added to each well. Cell lysis was carried out at room temperature during 10 min, 150 μl of lysates were transferred in Packard Optiplate 96 well, and luminescence was read on a Fluoroskan (Thermo Scientific).

The EC50, or effective concentration 50, is the concentration of compound leading to 50% of cyto-protection in a Cell-Titer-Glo® viability assay based on MT4 cells infected with NL4.3 virus.

| Example number | EC50 (μM) |
|---|---|
| 17 | 26 |
| 18 | 34 |
| 23 | 23 |
| 24 | 11 |
| 29 | 33 |
| 31 | 29 |
| 32 | 26 |
| 39 | 41 |
| 44 | 16 |
| 50 | 44 |
| 51 | 41 |
| 52 | 33 |
| 54 | 2.2 |

The results show that the compounds according to the invention can inhibit the HIV replication and thus can be used as anti-HIV compounds.

The invention claimed is:

1. A compound according to formula (D1),

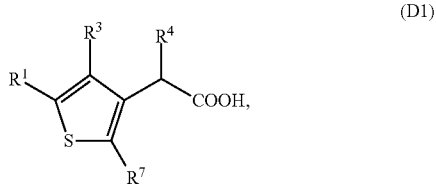

(D1)

wherein:
W represents a substituted aromatic heterocycle;
$R^1$ and $R^7$ each independently represent hydrogen, —CN, —OH, —O-cycloalkyl, —O-cycloalkenyl, —O-cycloalkynyl, —NH$_2$, —NR$^{11}$-cycloalkyl, —NR$^{11}$-cycloalkenyl, —NR$^{11}$-cycloalkynyl, —S-cycloalkyl, —S-cycloalkenyl, —S-cycloalkynyl, —COOH, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{11}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{11}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, non-substituted or substituted by at least one T$^1$,
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form a C=O, C=S, N=O, N=S, S=O or S(O)$_2$,
and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;
and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, or heterocyclyl-alkynyl group can include one or more heteroatoms, selected from O, S and N, in the alkyl, alkenyl, or alkynyl moiety;
$R^3$ represents —O-cycloalkyl, —O-cycloalkenyl, —O-cycloalkynyl, —NR$^{11}$-cycloalkyl, —NR$^{11}$-cycloalkenyl, —NR$^{11}$-cycloalkynyl, —S-cycloalkyl, —S-cycloalkenyl, —S-cycloalkynyl, C$_4$-C$_{20}$ alkyl, C$_4$-C$_{20}$ alkenyl, C$_4$-C$_{20}$ alkynyl, heteroalkyl, heteroalkenyl, heteroalkynyl, aryl, —O-aryl, —NR$^{11}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{11}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, non-substituted or substituted by at least one T$^1$,
wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form a C=O, C=S, N=O, N=S, S=O or S(O)$_2$,
wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be fused with at least one further cycle,
and wherein said alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, or heterocyclyl-alkynyl group can include one or more heteroatoms, selected from O, S and N, in the alkyl, alkenyl, or alkynyl moiety;
$R^4$ represents —CN, —O-cycloalkyl, —O-cycloalkenyl, —O-cycloalkynyl, —S-cycloalkyl, —S-cycloalkenyl, —S-cycloalkynyl, C$_3$-C$_{20}$ alkyl, alkenyl, alkynyl, heteroalkyl, heteroalkenyl, heteroalkynyl, aryl, —O-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, non-substituted or substituted by at least one T$^2$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form a $C=O$, $C=S$, $N=O$, $N=S$, $S=O$ or $S(O)_2$, and wherein said alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, or heterocyclyl-alkynyl group can include one or more heteroatoms, selected from O, S and N, in the alkyl, alkenyl, or alkynyl moiety;

$R^{11}$ represents hydrogen, alkyl or aryl, wherein a carbon atom of said alkyl or aryl can be oxidized to form a $C=O$, $C=S$, $N=O$, $N=S$, $S=O$ or $S(O)_2$;

$T^1$ represents hydrogen, halogen, $-OT^3$, $-OCF_3$, $=O$, $-ST^3$, $=S$, $-S(O)T^4$, $-S(O)_2T^4$, $-S(O)_2NT^5T^6$, $-CF_3$, $-NO_2$, $-NT^5T^6$, $-NT^3S(O)_2T^4$, $CN$, $-NT^3C(O)T^4$, $-NT^3C(O)NT^5T^6$, $-C(O)OT^3$, $-C(O)NT^5T^6$, $-C(O)T^4$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be substituted with one or more $T^7$, and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form a $C=O$, $C=S$, $N=O$, $N=S$, $S=O$ or $S(O)_2$;

$T^2$ represents hydrogen, halogen, $-OT^8$, $-OCF_3$, $=O$, $-ST^8$, $=S$, $-S(O)T^9$, $-S(O)_2T^9$, $-S(O)_2NT^{10}T^{11}$, $-CF_3$, $-NO_2$, $-NT^{10}T^{11}$, $-NT^8S(O)_2T^9$, $-CN$, $-NT^8C(O)T^9$, $-NT^8C(O)NT^{10}T^{11}$, $-C(O)OT^8$, $-C(O)NT^{10}T^{11}$, $-C(O)T^9$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be substituted with one or more $T^7$, and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form a $C=O$, $C=S$, $N=O$, $N=S$, $S=O$ or $S(O)_2$;

$T^3$ represents hydrogen, alkyl, alkenyl, alkynyl, heteroalkyl, heteroalkenyl, heteroalkynyl, aryl, or heterocycle, wherein said alkyl, alkenyl, alkynyl, heteroalkyl, heteroalkenyl, heteroalkynyl, aryl, or heterocycle can be substituted or non substituted with one or more $-OH$, $=O$, halogen, $=S$, $-CF_3$, $-O$-alkyl, $-OCF_3$, $-CN$, $-NO_2$, $-C(O)OH$, $-NH_2$ or $C(O)NH_2$, and wherein a carbon atom or heteroatom of said alkyl, alkenyl, alkynyl, heteroalkyl, heteroalkenyl, heteroalkynyl, aryl, or heterocycle can be oxidized to form a $C=O$, $C=S$, $N=O$, $N=S$, $S=O$ or $S(O)_2$;

$T^4$ represents $-OH$, alkyl, alkenyl, alkynyl, heteroalkyl, heteroalkenyl, heteroalkynyl, aryl, or heterocycle, wherein said alkyl, alkenyl, alkynyl, heteroalkyl, heteroalkenyl, heteroalkynyl, aryl, or heterocycle, can be substituted or non substituted with one or more $-OH$, $=O$, halogen, $-SH$, $=S$, $-CF_3$, $-O$-alkyl, $-OCF_3$, $-CN$, $-NO_{22}$, $-C(O)OH$, $-NH_2$ or $C(O)NH_2$, and wherein a carbon atom or heteroatom of said alkyl, alkenyl, alkynyl, heteroalkyl, heteroalkenyl, heteroalkynyl aryl, or heterocycle can be oxidized to form a $C=O$, $C=S$, $N=O$, $N=S$, $S=O$ or $S(O)_2$;

$T^5$ and $T^6$ each independently represent hydrogen, alkyl, alkenyl, alkynyl, heteroalkyl, heteroalkenyl, heteroalkynyl, aryl, or heterocycle wherein said alkyl, alkenyl, alkynyl, heteroalkyl, heteroalkenyl, heteroalkynyl, aryl, or heterocycle can be substituted or non substituted with one or more $-OH$, $=O$, halogen, $-SH$, $=S$, $-CF_3$, $-O$-alkyl, $-OCF_3$, $-CN$, $-NO_2$, $-C(O)OH$, $-NH_2$ or $C(O)NH_2$, and wherein a carbon atom or heteroatom of said alkyl, alkenyl, alkynyl, heteroalkyl, heteroalkenyl, heteroalkynyl aryl, or heterocycle can be oxidized to form a $C=O$, $C=S$, $N=O$, $N=S$, $S=O$ or $S(O)_2$, or $T^5$ and $T^6$ can be taken together to form a 4, 5, 6 or 7 membered heterocycle substituted or non substituted with an alkyl, alkenyl, alkynyl, heteroalkyl, heteroalkenyl, heteroalkynyl, $-OH$, halogen, $-SH$, $-CF_3$, $-O$-alkyl, $-OCF_3$, $-CN$, $-NO_2$, $-C(O)OH$, $-NH_2$ or $-C(O)NH_2$;

$T^7$ represents an alkyl, alkenyl, alkynyl, heteroalkyl, heteroalkenyl, heteroalkynyl, $-OH$, $=O$, halogen, $-SH$, $=S$, $-CF_3$, $-CN$, $-NO_2$, $-COOH$, $-NH_2$, or $-C(O)NH_2$;

$T^8$ represents hydrogen, alkyl, alkenyl, alkynyl, heteroalkyl, heteroalkenyl, or heteroalkynyl, wherein said alkyl, alkenyl, alkynyl, heteroalkyl, heteroalkenyl, or heteroalkynyl, can be substituted or non substituted with one or more $-OH$, $=O$, halogen, $-SH$, $=S$, $-CF_3$, $-O$-alkyl, $-OCF_3$, $-CN$, $-NO_2$, $-C(O)OH$, $-NH_2$ or $-C(O)NH_2$, and wherein a carbon atom or heteroatom of said alkyl, alkenyl, alkynyl, heteroalkyl, heteroalkenyl, or heteroalkynyl can be oxidized to form a C=O, C=S, N=O, N=S, S=O or S(O)$_2$;

$T^9$ represents —OH, alkyl, alkenyl, alkynyl, heteroalkyl, heteroalkenyl, or heteroalkynyl, wherein said alkyl, alkenyl, alkynyl, heteroalkyl, heteroalkenyl, or heteroalkynyl; can be substituted or non substituted with one or more —OH, =O, halogen, —SH, =S, —CF$_3$, —O-alkyl, —OCF$_3$, —CN, —NO$_2$, —C(O)OH, —NH$_2$ or —C(O)NH$_2$, and wherein a carbon atom or heteroatom of said alkyl, alkenyl, alkynyl, heteroalkyl, heteroalkenyl, or heteroalkynyl can be oxidized to form a C=O, C=S, N=O, N=S, S=O or S(O)$_2$; and $T^{10}$ or $T^{11}$ each independently represent hydrogen, alkyl, alkenyl, alkynyl, heteroalkyl, heteroalkenyl, or heteroalkynyl, wherein said alkyl, alkenyl, alkynyl, heteroalkyl, heteroalkenyl, or heteroalkynyl, can be substituted or non substituted with one or more —OH, =O, halogen, —SH, =S, —CF$_3$, —O-alkyl, —OCF$_3$, —CN, —NO$_2$, —C(O)OH, —NH$_2$ or —C(O)NH$_2$, and wherein a carbon atom or heteroatom of said alkyl, alkenyl, alkynyl, heteroalkyl, heteroalkenyl, or heteroalkynyl can be oxidized to form a C=O, C=S, N=O, N=S, S=O or S(O)$_2$, or $T^{10}$ and $T^{11}$ can be taken together to form a 4, 5, 6 or 7 membered heterocycle substituted or non substituted with an alkyl, alkenyl, alkynyl, heteroalkyl, heteroalkenyl, heteroalkynyl, —OH, halogen, —SH, —CF$_3$, O-alkyl, —OCF$_3$, —CN, —NO2$_2$, —C(O)OH, —NH$_2$ or —C(O)NH$_2$;

and a racemate, enantiomer, isomer, atropisomer or diastereoisomer or a pharmaceutically acceptable salt thereof.

2. A pharmaceutical composition comprising a compound according to claim 1 as an active ingredient and a pharmaceutically acceptable carrier.

3. The pharmaceutical composition according to claim 2 further comprising a further antiviral agent.

4. A method of treatment of a viral infection comprising administering a compound according to claim 1 to a patient in need thereof.

5. The method according to claim 4 wherein said viral infection is a retroviral infection.

6. The method according to claim 5 wherein said retroviral infection is HIV.

7. A method for the treatment of an HIV infection in a mammal being infected comprising administering the pharmaceutical composition according to claim 2.

8. A method of inhibiting the replication of HIV comprising exposing said HIV to an effective amount of a compound according to claim 1 under conditions where replication of HIV is inhibited.

* * * * *